(12) United States Patent
Abad et al.

(10) Patent No.: US 10,301,643 B2
(45) Date of Patent: May 28, 2019

(54) GENES AND USES FOR PLANT IMPROVEMENT

(71) Applicant: Monsanto Technology LLC, St Louis, MO (US)

(72) Inventors: Mark Scott Abad, Webster Groves, MO (US); Barry S. Goldman, St. Louis, MO (US); Balasulojini Karunanandaa, Creve Coeur, MO (US); Angela Ferguson, Morrisville, NC (US); Erin Naymark, Carmichael, CA (US); Mahmood Sayed, Durham, NC (US); Daniel Riggsbee, Durham, NC (US); Maria McDonald, Garner, NC (US); Bettina Darveaux, Hillsborough, NC (US); Jaclyn Cleveland, Durham, NC (US)

(73) Assignee: Monsanto Technology LLC, St. Louis, MO (US)

( * ) Notice: Subject to any disclaimer, the term of this patent is extended or adjusted under 35 U.S.C. 154(b) by 15 days.

(21) Appl. No.: 15/731,003

(22) Filed: Apr. 6, 2017

(65) Prior Publication Data
US 2017/0292131 A1 Oct. 12, 2017

Related U.S. Application Data

(60) Continuation of application No. 14/121,854, filed on Oct. 24, 2014, which is a continuation of application No. 11/982,700, filed on Nov. 1, 2007, now Pat. No. 9,115,368, which is a division of application No. 11/188,298, filed on Jul. 22, 2005.

(60) Provisional application No. 60/592,978, filed on Jul. 31, 2004.

(51) Int. Cl.
| | | |
|---|---|---|
| *C12N 15/82* | (2006.01) | |
| *C07K 14/415* | (2006.01) | |
| *C12N 9/02* | (2006.01) | |

(52) U.S. Cl.
CPC ........ *C12N 15/8273* (2013.01); *C07K 14/415* (2013.01); *C12N 9/0008* (2013.01); *C12N 15/8261* (2013.01); *C12N 15/8271* (2013.01); *C12Y 102/01024* (2013.01); *C12Y 102/01016* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 6,025,545 A | 2/2000 | Lundquist et al. | |
| 6,162,965 A | 12/2000 | Hansen | |
| 9,115,368 B2 | 8/2015 | Abad et al. | |
| 9,777,287 B2 | 10/2017 | Nadzan et al. | |
| 2002/0170093 A1* | 11/2002 | He .................. | C07K 14/415 |
| | | | 800/288 |
| 2003/0233675 A1 | 12/2003 | Cao et al. | |
| 2004/0034888 A1 | 2/2004 | Liu et al. | |
| 2006/0075522 A1 | 4/2006 | Cleveland et al. | |
| 2006/0107345 A1 | 5/2006 | Alexandrov et al. | |
| 2006/0150283 A1 | 7/2006 | Alexandrov et al. | |
| 2007/0214517 A1 | 9/2007 | Alexandrov et al. | |
| 2008/0090998 A1 | 4/2008 | Abad et al. | |
| 2009/0265815 A1* | 10/2009 | Alexandrov ......... | C07K 14/415 |
| | | | 800/298 |
| 2015/0135367 A1 | 5/2015 | Abad et al. | |
| 2015/0259699 A1* | 9/2015 | Nadzan ............... | C12N 15/8271 |
| | | | 800/267 |

FOREIGN PATENT DOCUMENTS

| | | | | |
|---|---|---|---|---|
| CA | 2300692 A1 | 8/2000 | | |
| EP | 1033405 A2 * | 9/2000 | ........... | C07K 14/415 |
| EP | 1033405 A2 | 9/2000 | | |
| EP | 1586645 A2 | 10/2005 | | |
| WO | WO-2000044221 A1 | 8/2000 | | |
| WO | WO-2002016655 A2 | 2/2002 | | |

OTHER PUBLICATIONS

Smith et al. (Nature Biotechnology, 15:1222-1223, 1997).*
Bork et al. (TIG, 12:425-427, 1996).*
Doerks et al., (TIG, 14:248-250, 1998).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
"SAUR-AC-like protein (small auxin up RNA) [*Arabidopsis thaliana*]", NCBI, GenBank, Sequence Accession No. AAM66977,1, (Jan. 27, 2006), 1 pg.
"SAUR-AC-like protein (small auxin up RNA) [*Arabidopsis thaliana*]", NCBI, GenBank, Sequence Accession No. CAB36843.1, (Jul. 26, 2016), 1 pg.
"SAUR-AC-like protein (small auxin up RNA) [*Arabidopsis thaliana*]", NCBI, GenBank, Sequence Accession No. CAB78421.1, (Jul. 26, 2016), 1 pg.
"U.S. Appl. No. 11/188,298, Final Office Action dated Jun. 1, 2007", 14 pgs.

(Continued)

*Primary Examiner* — Vinod Kumar
(74) *Attorney, Agent, or Firm* — Schwegman Lundberg & Woessner, P.A.

(57) ABSTRACT

Transgenic seed for crops with improved traits are provided by trait-improving recombinant DNA where plants grown from such transgenic seed exhibit one or more improved traits as compared to a control plant. Also provided are methods of making transgenic plants with recombinant DNA and the one or more improved traits and methods of using those plants.

7 Claims, No Drawings

Specification includes a Sequence Listing.

(56) References Cited

OTHER PUBLICATIONS

"U.S. Appl. No. 11/188,298, Non Final Office Action dated Sep. 8, 2006", 21 pgs.
"U.S. Appl. No. 11/188,298, Response filed Mar. 8, 2007 to Non Final Office Action dated Sep. 8, 2006", 14 pgs.
"U.S. Appl. No. 11/188,298, Response filed Jun. 21, 2006 to Restriction Requirement dated Mar. 21, 2006", 7 pgs.
"U.S. Appl. No. 11/188,298, Restriction Requirement dated Mar. 21, 2006", 8 pgs.
"U.S. Appl. No. 11/982,700, Advisory Action dated Aug. 24, 2009", 14 pgs.
"U.S. Appl. No. 11/982,700, Advisory Action dated Sep. 11, 2014", 3 pgs.
"U.S. Appl. No. 11/982,700, Appeal Brief filed Apr. 5, 2010", 21 pgs.
"U.S. Appl. No. 11/982,700, Appeal Brief filed Dec. 7, 2009", 24 pgs.
"U.S. Appl. No. 11/982,700, Decision on Appeal mailed Jun. 15, 2011", 7 pgs.
"U.S. Appl. No. 11/982,700, Declaration Under 37 CFR 1.132 from Anil Neelam dated Aug. 4, 2009", (Aug. 4, 2009), 3 pgs.
"U.S. Appl. No. 11/982,700, Examiner Interview Summary dated Nov. 3, 2009", 1 pg.
"U.S. Appl. No. 11/982,700, Examiners Answer dated Jun. 25, 2010", 28 pgs.
"U.S. Appl. No. 11/982,700, Final Office Action dated Apr. 30, 2014", 10 pgs.
"U.S. Appl. No. 11/982,700, Final Office Action dated May 7, 2009", 23 pgs.
"U.S. Appl. No. 11/982,700, Non Final Office Action dated Dec. 6, 2013", 7 pgs.
"U.S. Appl. No. 11/982,700, Non Final Office Action dated Dec. 15, 2008", 20 pgs.
"U.S. Appl. No. 11/982,700, Notice of Allowance dated Nov. 21, 2014", 8 pgs.
"U.S. Appl. No. 11/982,700, PTO Response to Rule 312 Communication dated Mar. 11, 2015", 2 pgs.
"U.S. Appl. No. 11/982,700, Response filed Mar. 4, 2014 to Non Final Office Action dated Dec. 6, 2013", 6 pgs.
"U.S. Appl. No. 11/982,700, Response filed Apr. 15, 2009 to Non Final Office Action dated Dec. 15, 2008", 13 pgs.
"U.S. Appl. No. 11/982,700, Response filed Aug. 7, 2009 to Final Office Action dated May 7, 2009", 16 pgs.
"U.S. Appl. No. 11/982,700, Response filed Aug. 12, 2011 to Decision on Appeal mailed Jun. 15, 2011", 6 pgs.
"U.S. Appl. No. 11/982,700, Response filed Sep. 2, 2014 to Final Office Action dated Apr. 30, 2014", 4 pgs.
"U.S. Appl. No. 11/982,700, Response filed Sep. 23, 2008 to Restriction Requirement dated May 23, 2008", 5 pgs.
"U.S. Appl. No. 11/982,700, Response filed Sep. 24, 2009 to Advisory Action dated Aug. 24, 2009", 2 pgs.
"U.S. Appl. No. 11/982,700, Response filed Sep. 30, 2014 to Advisory Action dated Jul. 11, 2014", 5 pgs.
"U.S. Appl. No. 11/982,700, Restriction Requirement dated May 23, 2008", 8 pgs.
"U.S. Appl. No. 14/121,854, Non Final Office Action dated Dec. 6, 2016", 30 pgs.
"U.S. Appl. No. 14/121,854, Preliminary Amendment filed Jan. 23, 2015", 4 pgs.
"U.S. Appl. No. 14/121,854, Response filed Oct. 17, 2016 to Restriction Requirement dated Aug. 17, 2016", 8 pgs.
"U.S. Appl. No. 14/121,854, Restriction Requirement dated Aug. 17, 2016", 9 pgs.
"U.S. Appl. No. 14/121,854, Supplemental Preliminary Amendment filed Dec. 16, 2015", 7 pgs.
"AT3g26280/MTC11_19 [*Arabidopsis thaliana*]", NCBI, GenBank, Sequence Accession No. AAL90915.1, [Online]. Retrieved from the Internet: <URL: https://www.ncbi.nlm.nih.gov/protein/AAL90915, (Mar. 24, 2002), 2 pgs.

"At3g26280/MTC11_19 [*Arabidopsis thaliana*]", NCBI, GenBank, Sequence Accession No. AAN31105.1, [Online]. Retrieved from the Internet: <URL: https://www.ncbi.nlm.nih.gov/protein/AAN31105, (Oct. 5, 2002), 2 pgs.
"Cytochrome P450 [*Arabidopsis thaliana*]", NCBI, GenBank, Sequence Accession No. BAB02451.1, [Online]. Retrieved from the Internet: <URL: https://www.ncbi.nlm.nih.gov/protein/BAB02451, (Feb. 14, 2004), 2 pgs.
"Cytochrome P450 monooxygenase [*Arabidopsis thaliana*]", NCBI, GenBank, Sequence Accession No. BAA28535.1, [Online]. Retrieved from the Internet: <URL: https://www.ncbi.nlm.nih.gov/protein/BAA28535 1/, (Aug. 8, 2007), 1 pg.
"European Application Serial No. 05106786.6, Reply filed Apr. 2, 2007 to Office Action dated Sep. 22, 2006".
"European Application Serial No. 05106786.6, Extended European Search Report dated Dec. 13, 2005", 7 pgs.
"European Application Serial No. 05106786.6, Office Action dated May 23, 2008", 4 pgs.
"European Application Serial No. 05106786.6, Office Action dated Jul. 20, 2009", 3 pgs.
"European Application Serial No. 05106786.6, Office Action dated Sep. 22, 2006", 3 pgs.
"European Application Serial No. 05106786.6, Office Action dated Sep. 23, 2010", 4 pgs.
"European Application Serial No. 05106786.6, Preliminary Amendment dated Jul. 29, 2006", 3 pgs.
"European Application Serial No. 05106786.6, Reply filed Nov. 30, 2009 to Office Action dated Jul. 20, 2009", 6 pgs.
"European Application Serial No. 05106786.6, Reply filed Dec. 2, 2008 to Office Action dated May 23, 2008", 7 pgs.
"European Application Serial No. 10179338.8, European Search Report dated Oct. 14, 2011", 8 pgs.
"European Application Serial No. 10179338.8,Partial European Search Report dated Jun. 28, 2011", 6.
Bork, P., et al., "Go hunting in sequence databases but watch out for the traps.", Trends Genet., 12(10), (Oct. 1996), 426-427.
Bouche, N., et al., "GABA in plants: just a metabolite?", Trends Plant Sci., 9(3), (Mar. 2004), 110-115.
Bouche, N., et al., "Mitochondrial succinic-semialdehyde dehydrogenase of the gamma-aminobutyrate shunt is required to restrict levels of reactive oxygen intermediates in plants", Proc Natl Acad Sci U S A., 100(11), (May 27, 2003), 6843-8.
Day, Christopher D., et al., "Transgene integration into the same chromosome location can produce alleles that express at a predictable level, or alleles that are differentially silenced", Genes & Development 14, (2000), 2869-2880.
Doerks, Tobias, et al., "Protein Annotation: detective work for function prediction", Trends in Genetics, vol. 14, No. 6, (1998), 248-250.
Galleschi, L., et al., "Succinic Semialdehyde Dehydrogenase in Higher Plants: Purification and Properties of the Enzyme from Triticum durum Embryos", Biochemie und Physiologie der Pflanzen, 178, (1983), 645-651.
Goodner, et al., NCBI, GenBank, Sequence Accession No. F98145 (contig accession No. AE008689), (Jan. 2002), 1 pg.
Guo, H. H, et al., "Protein tolerance to random amino acid change", Proc Natl Acad Sci U S A., 101(25), (2004), 9205-9210.
Inui, et al., "Herbicide Metabolism and Tolerance in the Transgenic Rice Plants Expressing Human CYP2C9 and CYP2C19", Pesticide Biochemistry and Physiology, (2001), 156-169.
Keskin, O., et al., "A new, structurally nonredundant, diverse data set of protein-protein interfaces and its implications.", Protein Sci.,13(4), (Apr. 2004), 1043-55.
Matzke, Marjori A., et al., "How and Why Do Plants Inactivate Homologous (Trans)genes?", Plant Physiol. 107, (1995), 679-685.
Mizutani, et al., Gen Bank Sequence Accession No. D78603, (May 28, 1998), 1-2.
Ngo, J. Thomas, et al., "In the Protein Folding Problem and Tertiary Structure Prediction", Merz, et al., (ed.), Birkhauser, Boston, MA, (1994), 492-495.
Smith, Temple F, et al., "The Challenges of Genome Sequence Annotation or "The Devil is in the Details"", Nature Biotechnology, 15(12), (Nov. 1997), 1222-1223.

(56) References Cited

OTHER PUBLICATIONS

Sunkar, R., et al., "Overexpression of a stress-inducible aldehyde dehydrogenase gene from *Arabidopsis thaliana* in transgenic plants improves stress tolerance", Plant J., 35(4), (Aug. 2003), 452-64.

Thornton, Janet M, et al., "From structure to function: approaches and limitations", Nat Struct Biol. 7(Suppl), (Nov. 2000), 991-4.

Valvekens, D., et al., "Agrobacterium tumefaciens-mediated transformation of *Arabidopsis thaliana* root explants by using kanamycin selection", Proc Natl Acad Sci U S A., 85(15), (Aug. 1988), 5536-40.

Wells, J. A., "Additivity of Mutational Effects in Proteins", Biochemistry 29(37), (1990), 8509-8517.

Yang, et al., "Cytochrome P450 Genes and Their Applications in Plant Improvement", Hereditas, w/English Translation, (Mar. 25, 2003), 237-240.

\* cited by examiner

GENES AND USES FOR PLANT IMPROVEMENT

CROSS REFERENCE TO RELATED APPLICATIONS

This application is a continuation of U.S. patent application Ser. No. 14/121,854, filed Oct. 24, 2014, which application is a continuation of U.S. application Ser. No. 11/982,700, filed Nov. 1, 2007, which application is a divisional of U.S. application Ser. No. 11/188,298, filed Jul. 22, 2005, which claims the benefit of priority to U.S. Provisional Application No. 60/592,978, filed Jul. 31, 2004, which applications are incorporated herein by reference and made a part hereof in their entirety, and the benefit of priority of each of which is claimed herein.

INCORPORATION OF SEQUENCE LISTING

Two copies of the sequence listing (Copy 1 and Copy 2) and a computer readable form (CRF) of the sequence listing, all on CD-ROMs, each containing the file named "3126.002US4 seq listing in text-crf (1379958x7ADA8). TXT", which is 70,686,720 bytes (measured in MS-WINDOWS) and was created on Apr. 5, 2017, are herein incorporated by reference.

FIELD OF THE INVENTION

Disclosed herein are inventions in the field of plant genetics and developmental biology. More specifically, this invention provides transgenic seeds for crops, wherein the genome of said seed comprises recombinant DNA, the expression of which results in the production of transgenic plants that have improved trait(s).

BACKGROUND OF THE INVENTION

Transgenic plants with improved traits, such as improved yield, environmental stress tolerance, pest resistance, herbicide tolerance, modified seed compositions, and the like are desired by both farmers and consumers. Although considerable efforts in plant breeding have provided significant gains in desired traits, the ability to introduce specific DNA into plant genomes provides further opportunities for generation of plants with improved and/or unique traits. The ability to develop transgenic plants with improved traits depends in part on the identification of genes that are useful in recombinant DNA constructs for production of transformed plants with improved properties.

SUMMARY OF THE INVENTION

This invention provides transgenic seeds, transgenic plants and DNA constructs with trait-improving recombinant DNA from a gene for a protein having an amino acid sequence with at least 90% identity to a consensus amino acid sequence in the group consisting of SEQ ID NO: 270 and its homologs through SEQ ID NO: 538, where the respective homolog proteins have amino acid sequences SEQ ID NO: 539 through SEQ ID NO: 22568, as indicated in Table 16. In some cases of trait improvement, the recombinant DNA encodes a protein; in other cases, the recombinant DNA suppresses endogenous protein expression. In a broad aspect this invention provides transgenic seeds for growing crop plants with improved traits, such crop plants with improved traits and the plant parts including transgenic seed produced by such crop plants. The improved traits provided by the recombinant DNA in the transgenic crop plant of this invention are identified by comparison to a control plant, i.e., a plant without the trait-improving recombinant DNA. In one aspect of the invention, transgenic crop plant grown from the transgenic seed has improved yield, as compared to the yield of a control plant, e.g., a plant without the recombinant DNA that produces the increased yield. Some plants of this invention exhibit increased yield by producing a yield increase under non-stress conditions. Other plants of this invention exhibit increased yield by producing a yield increase under one or more environmental stress conditions including, but not limited to, water deficit stress, cold stress, heat stress, high salinity stress, shade stress, and low nitrogen availability stress. Still other plants of this invention have other improved phenotypes, such as improved plant development, plant morphology, plant physiology or seed composition as compared to a corresponding trait of a control plant. The various aspects of this invention are especially useful for transgenic seed and transgenic plants having improved traits in corn (maize), soybean, cotton, canola (rape), wheat, sunflower, sorghum, alfalfa, barley, millet, rice, tobacco, fruit and vegetable crops, and turfgrass.

The invention also comprises recombinant DNA constructs. In one aspect, such recombinant DNA constructs useful for the transgenic seed and transgenic plants of this invention comprise a promoter functional in a plant cell operably linked to a DNA segment for expressing a protein associated with a trait in a model plant or a homologue. In another aspect the recombinant DNA constructs useful for the transgenic seed and transgenic plants of this invention comprise a promoter functional in a plant cell operably linked to a DNA segment for suppressing the level of an endogenous plant protein which is a homologue to a model-plant protein, the suppression of which is associated with an improved trait. Suppression can be effected by any of a variety of methods known in the art, e.g., post transcriptional suppression by anti-sense, sense, dsRNA and the like or by transcriptional suppression.

This invention also provides a method of producing a transgenic crop plant having at least one improved trait, wherein the method comprises providing to a grower of transgenic seeds comprising recombinant DNA for expression or suppression of a trait-improving gene provided herein, and growing transgenic plant from said transgenic seed. Such methods are used to generate transgenic crop plants having at least one improved trait under one or more environmental stress conditions including, but not limited to, water deficit stress, cold stress, heat stress, high salinity stress, shade stress, and low nitrogen availability stress. In another aspect, such methods are used to generate transgenic crop plants having improved plant development, plant morphology, plant physiology or seed component phenotype as compared to a corresponding phenotype of a control plant. Of particular interest are uses of such methods to generate transgenic crop plants having increased yield under non-stress condition, or under one or more stress conditions.

DETAILED DESCRIPTION OF THE INVENTION

This invention provides transgenic plant seed having in its genome trait-improving recombinant DNA and transgenic plants grown from such seed which exhibit an improved trait as compared a control plant. In one aspect, the invention provides transgenic plants where the improved trait is one or more of improved drought stress tolerance, improved heat stress tolerance, improved cold stress tolerance, improved high salinity stress tolerance, improved low nitrogen availability stress tolerance, improved shade stress tolerance, improved plant growth and development at the stages of seed imbibition through early vegetative phase, and improved plant growth and development at the stages of leaf development, flower production and seed maturity. Particular transgenic plants grown from transgenic seeds of this invention exhibit increased seed yield. Recombinant DNA constructs used in this invention comprise recombinant DNA disclosed herein which produces mRNA to modulate gene expression imparting improved traits to plants.

"Gene" means all or part of the DNA that encodes a protein or mRNA, e.g., chromosomal DNA, plasmid DNA, cDNA, or synthetic DNA, and includes DNA regions flanking the coding sequences, e.g., introns, 5'UTR, 3' UTR, promoters and other DNA involved in the regulation of expression.

"Transgenic seed" means plant seed having a genome altered by the incorporation of recombinant DNA, e.g., by transformation. "Transgenic plant" means a plant produced from an original transformation event, or progeny from later generations or crosses of a plant to a transformed plant, so long as the progeny contains the recombinant DNA in its genome. "Recombinant DNA" means a DNA molecule having a genetically engineered modification introduced through a combination of endogenous and/or exogenous DNA elements in a transcription unit, manipulation via mutagenesis, restriction enzymes, and the like or simply by inserting multiple copies of a native transcription unit. Recombinant DNA may comprise DNA segments obtained from different sources, or DNA segments obtained from the same source, but which have been manipulated to join DNA segments which do not naturally exist in the joined form. Recombinant DNA can exist outside of a cell, e.g., as a PCR fragment or in a plasmid, or can be integrated into a genome such as a plant genome.

"Trait" means a physiological, morphological, biochemical, or physical characteristic of a plant or particular plant material or cell. In some instances the characteristic is visible to the human eye, e.g., seed or plant size, or can be measured by biochemical techniques, e.g., detecting the protein, starch, or oil content of seed or leaves, or by observation of a metabolic or physiological process, e.g., by measuring uptake of carbon dioxide, or by the observation of the expression level of a gene or genes, e.g., by employing Northern analysis, RT-PCR, microarray gene expression assays, or reporter gene expression systems, or by agricultural observations such as stress tolerance, yield, or pathogen tolerance.

"Control plant" is a plant without trait-improving recombinant DNA. A control plant is used to measure and compare trait improvement in a transgenic plant with such trait-improving recombinant DNA. One suitable control plant is a non-transgenic plant of the parental line that was used to generate a transgenic plant. Another suitable control plant is a transgenic plant that comprises recombinant DNA without the specific trait producing DNA, e.g., simply a marker gene. Another suitable control plant is a negative segregant progeny of hemizygous transgenic plant. In certain demonstrations of trait improvement, e.g., in field conditions, the use of a limited number of control plants can cause a wide variation in the control dataset. To minimize the effect of the variation within the control dataset, a "reference" is used, i.e., a trimmed mean of all data from both transgenic and control plants grown under the same conditions and at the same developmental stage. The trimmed mean is calculated by eliminating a specific percentage, i.e., 20%, of the smallest and largest observation from the data set and then calculating the average of the remaining observation.

"Trait improvement" means a detectable and desirable difference in a characteristic in a transgenic plant relative to a control plant or a reference. In some cases, the trait improvement is measured quantitatively. For example, the trait improvement can entail at least a 2% desirable difference in an observed trait, at least a 5% desirable difference, at least about a 10% desirable difference, at least about a 20% desirable difference, at least about a 30% desirable difference, at least about a 50% desirable difference, at least about a 70% desirable difference, or at least about a 100% difference, or an even greater desirable difference. In other cases, the trait improvement is only measured qualitatively. It is known that there are natural variations in a trait. Therefore, the trait improvement observed entails a change of the normal distribution of the trait in the transgenic plant compared with the trait distribution observed in a control plant or a reference, which is evaluated by statistical methods provided herein. Trait improvement includes, but not limited to, yield increase, including increased yield under non-stress conditions and increased yield under environmental stress conditions. Stress conditions may include, for example, drought, shade, fungal disease, viral disease, bacterial disease, insect infestation, nematode infestation, cold temperature exposure, heat exposure, osmotic stress, reduced nitrogen nutrient availability, reduced phosphorus nutrient availability and high plant density. Many agronomic traits can affect "yield", including without limitation, plant height, pod number, pod position on the plant, number of internodes, incidence of pod shatter, grain size, efficiency of nodulation and nitrogen fixation, efficiency of nutrient assimilation, resistance to biotic and abiotic stress, carbon assimilation, plant architecture, resistance to lodging, percent seed germination, seedling vigor, and juvenile traits. Other traits that can affect yield include, efficiency of germination (including germination in stressed conditions), growth rate (including growth rate in stressed conditions), ear number, seed number per ear, seed size, composition of seed (starch, oil, protein) and characteristics of seed fill. Also of interest is the generation of transgenic plants that demonstrate desirable phenotypic properties that may or may not confer an increase in overall plant yield. Such properties include improved plant morphology, plant physiology or improved components of the mature seed harvested from the transgenic plant.

"Yield-limiting environment" means a condition under which a plant would have the limitation on yield including environmental stress conditions.

"Stress condition" means a condition unfavorable for a plant, which adversely affects plant metabolism, growth and/or development. A plant under the stress condition typically shows reduced germination rate, retarded growth and development, reduced photosynthesis rate, and eventually leading to reduction in yield. Specifically, "water deficit stress" means sub-optimal conditions for water and humidity needed for normal growth of natural plants. Relative water content (RWC) is one physiological measure of plant water deficit. RWC measures the effect of osmotic adjustment in plant water status, when a plant is under stressed conditions. RWC can result from heat, drought, high salinity and induced osmotic stress.

"Cold stress" means exposure of a plant to temperatures below, e.g., at least two or more degrees Celsius below, those temperatures that are normal for a particular species or particular strain of plant.

"Sufficient nitrogen growth condition" means a growth condition where the soil or growth medium contains or receives enough amounts of nitrogen nutrient to sustain a healthy plant growth and/or for a plant to reach its typical yield for a particular plant species or a particular strain. "Nitrogen nutrient" means any one or any mix of the nitrate salts commonly used as plant nitrogen fertilizer, including, but not limited to, potassium nitrate, calcium nitrate, sodium nitrate, ammonium nitrate. "Ammonium" means any one or any mix of the ammonium salts commonly used as plant nitrogen fertilizer, e.g., ammonium nitrate, ammonium chloride, ammonium sulfate, etc. Those skilled in the art know what constitutes such soil, media and fertilizer inputs for most plant species. "Low nitrogen availability stress" means a plant growth condition that does not contain sufficient nitrogen nutrient to maintain a healthy plant growth and/or for a plant to reach its typical yield under a sufficient nitrogen growth condition; a useful low nitrogen availability stress is a growth condition with 50% or less of the conventional nitrogen inputs.

"Shade stress" means a limited light availability that triggers the shade avoidance response in plant. Plants are subject to shade stress when localized at lower part of the canopy, or in close proximity of neighboring vegetation. Shade stress is exacerbated when the planting density exceeds the average prevailing density for a particular plant species. The average prevailing densities per acre of a few other examples of crop plants in the USA in the year 2000 were: wheat 1,000,000-1,500,000; rice 650,000-900,000; soybean 150,000-200,000, canola 260,000-350,000, sunflower 17,000-23,000 and cotton 28,000-55,000 plants per acre.

"Increased yield" of a transgenic plant of this invention is evidenced and measured in a number of ways, including test weight, seed number per plant, seed weight, seed number per unit area (i.e., seeds, or weight of seeds, per acre), bushels per acre, tons per acre, tons per acre, kilo per hectare. For example, corn yield is measured as production of shelled corn kernels per unit of production area, e.g., in bushels per acre or metric tons per hectare, often reported on a moisture adjusted basis, e.g., at 15.5% moisture. Increased yield is often achieved from improved utilization of key biochemical compounds, such as nitrogen, phosphorous and carbohydrate, or from improved responses to environmental stresses, such as cold, heat, drought, salt, and attack by pests or pathogens. Trait-improving recombinant DNA is used to provide transgenic plants having improved growth and development, and ultimately increased yield, as the result of modified expression of plant growth regulators or modification of cell cycle or photosynthesis pathways.

"Expression" means transcription of DNA to produce RNA. The resulting RNA includes mRNA encoding a protein, antisense RNA that is complementary to an mRNA encoding a protein, or an RNA transcript comprising a combination of sense and antisense gene regions, such as for use in RNAi gene suppression. Expression also means production of encoded protein from mRNA.

"Promoter" means a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. "Tissue preferred" promoters preferentially regulate expression in certain tissues, such as leaves, roots, or seeds. "Tissue specific" promoters predominately regulate expression only in certain tissues. "Cell type" specific promoter primarily regulate expression in certain cell types in one or more organs, for example, vascular cells in roots or leaves. "Inducible" and "repressible" promoters regulate expression under environmental influences, under the effect of anaerobic conditions, certain chemicals, or the presence of light. Tissue specific, tissue preferred, cell type specific, and inducible promoters constitute a class of "non-constitutive" promoters. "Constitutive" promoters are promoters which are active under most conditions. "Anti-sense orientation" refers to a DNA sequence that is operably linked to a promoter in an orientation where the anti-sense strand is transcribed. "Operably linked" refers to an association of two or more DNA elements in a single construct so that the function of one is affected by the other. For example, a promoter is operably linked with transcribable DNA when it is capable of affecting the expression of that DNA; that is, the coding DNA is under the transcriptional control of the promoter.

"Consensus sequence" means an artificial, amino acid sequence of conserved parts of the proteins encoded by homologous genes, e.g., as determined by a CLUSTALW alignment of amino acid sequence of homolog proteins.

"Homologs" means genes that produce functionally similar proteins, e.g., in the same organism or in different organisms. A gene can be related to a homolog gene by descent from a common ancestral DNA. Homologs include genes where the relationship is by speciation, e.g., often called orthologs, or by genetic duplication, e.g., often called paralogs. More specifically, "orthologs" include homologs in different species that evolved from a common ancestral gene by specification. Normally orthologs retain the same function in the course of evolution. "Paralogs" include homologs in the same species that have diverged from each other as a consequence of genetic duplication.

"Percent identity" means the extent to which two optimally aligned DNA or protein segments are invariant throughout a window of alignment of components, e.g., nucleotide sequence or amino acid sequence. An "identity fraction" for aligned segments of sequences is the number of identical components which are shared divided by the total number of sequence components in the segment used as a reference over a window of alignment which is the smaller of the sequences. "Percent identity" ("% identity") is the identity fraction times 100. "% identity" to a consensus amino acid sequence" is 100 times the identity fraction in a window of alignment of an amino acid sequence of a test protein optimally aligned to consensus amino acid sequence of this invention.

"*Arabidopsis*" means plants of *Arabidopsis thaliana*.

Recombinant DNA Constructs

This invention provides recombinant DNA constructs comprising DNA elements for imparting one or more improved traits to transgenic plant. Such constructs typically comprise a promoter operatively linked to DNA to provide for expression of a protein or RNA for gene suppression in a target plant. Recombinant DNA constructs can also include additional regulatory elements, such as 5' or 3' untranslated regions (UTRs) such as polyadenylation sites, introns, and transit or signal peptides. Such recombinant DNA constructs are assembled using methods known to those of ordinary skill in the art.

In certain embodiments, recombinant DNA constructs comprise sense-oriented, trait-imparting DNA operably linked to a promoter that is functional in a plant to provide for expression of the trait-imparting DNA in the sense orientation such that a desired protein is produced. In other embodiments at least a part of the trait-imparting DNA is in an anti-sense orientation for gene suppression activity.

Recombinant DNA constructs, especially for expressing proteins are typically prepared with a 3' UTR that a polyadenylation site and signal. Recombinant DNA constructs can also include a transit peptide for targeting of a gene target to a plant organelle, particularly to a chloroplast, leucoplast or other plastid organelle. For descriptions of the use of chloroplast transit peptides, see U.S. Pat. Nos. 5,188,642 and 5,728,925, incorporated herein by reference.

Table 1 provides a list of genes that can provide trait-imparting DNA for recombinant DNA constructs. DNA from each gene was used in a model plant (*Arabidopsis*) to discover associations with improved traits. The DNA was also used to identify homologs from which a consensus amino acid sequence is defined for characterizing the aspects of the invention where recombinant DNA is incorporated in the transgenic seeds, transgenic plants, DNA constructs and methods of this invention. With reference to Table 1:

"NUC SEQ ID NO" refers to a SEQ ID NO. for particular DNA sequence in the Sequence Listing.

"PEP SEQ ID NO" refers to a SEQ ID NO. in the Sequence Listing for the amino acid sequence of a protein cognate to a particular DNA "construct_id" refers to an arbitrary number used to identify a particular recombinant DNA construct comprising the particular DNA.

"gene" refers to an arbitrary name used to identify the particular DNA.

"orientation" refers to the orientation of the particular DNA in a recombinant DNA construct relative to the promoter.

"species" refers to the organism from which the particular DNA was derived.

TABLE 1

| Nuc SEQ ID | Pep SEQ ID | construct_id | Gene | orientation | Species |
| --- | --- | --- | --- | --- | --- |
| 1 | 270 | 14324 | CGPG1560 | SENSE | *Arabidopsis thaliana* |
| 2 | 271 | 17484 | CGPG2630 | SENSE | *Arabidopsis thaliana* |
| 3 | 272 | 19109 | CGPG1381 | ANTI-SENSE | *Arabidopsis thaliana* |
| 4 | 273 | 70423 | CGPG3165 | SENSE | *Arabidopsis thaliana* |
| 5 | 274 | 70424 | CGPG3180 | SENSE | *Arabidopsis thaliana* |
| 6 | 275 | 70480 | CGPG3833 | SENSE | *Arabidopsis thaliana* |
| 7 | 276 | 70509 | CGPG2420 | SENSE | *Arabidopsis thaliana* |
| 8 | 277 | 70647 | CGPG4334 | SENSE | *Arabidopsis thaliana* |
| 9 | 278 | 70675 | CGPG4519 | SENSE | *Arabidopsis thaliana* |
| 10 | 279 | 70829 | CGPG518 | SENSE | *Arabidopsis thaliana* |
| 11 | 280 | 70849 | CGPG596 | SENSE | *Arabidopsis thaliana* |
| 12 | 281 | 71627 | CGPG1270 | SENSE | *Arabidopsis thaliana* |
| 13 | 282 | 71934 | CGPG2294 | SENSE | *Arabidopsis thaliana* |
| 14 | 283 | 72615 | CGPG4829 | SENSE | *Arabidopsis thaliana* |
| 15 | 284 | 72927 | CGPG1477 | SENSE | *Arabidopsis thaliana* |
| 16 | 285 | 73014 | CGPG5692 | SENSE | *Xenorhabdus nematophilus* 85816 |
| 17 | 286 | 73559 | CGPG6535 | SENSE | *Bacillus subtilis* 168 |
| 18 | 287 | 74251 | CGPG5489 | SENSE | *Arabidopsis thaliana* |
| 19 | 288 | 19631 | CGPG3627 | SENSE | *Arabidopsis thaliana* |
| 20 | 289 | 70121 | CGPG2380 | SENSE | *Saccharomyces cerevisiae* |
| 21 | 290 | 70654 | CGPG4352 | SENSE | *Arabidopsis thaliana* |
| 22 | 291 | 70696 | CGPG4590 | SENSE | *Arabidopsis thaliana* |
| 23 | 292 | 70713 | CGPG1462 | ANTI-SENSE | *Arabidopsis thaliana* |
| 24 | 293 | 70740 | CGPG3700 | SENSE | *Arabidopsis thaliana* |
| 25 | 294 | 71321 | CGPG4418 | SENSE | *Arabidopsis thaliana* |
| 26 | 295 | 71835 | CGPG4634 | SENSE | *Arabidopsis thaliana* |
| 27 | 296 | 72934 | CGPG5798 | SENSE | *Saccharomyces cerevisiae* |
| 28 | 297 | 72945 | CGPG5787 | SENSE | *Saccharomyces cerevisiae* |
| 29 | 298 | 72980 | CGPG5773 | SENSE | *Saccharomyces cerevisiae* |
| 30 | 299 | 73504 | CGPG6480 | SENSE | *Synechocystis* sp. PCC 6803 |
| 31 | 300 | 73507 | CGPG6504 | SENSE | *Bacillus subtilis* 168 |
| 32 | 301 | 73573 | CGPG6462 | SENSE | *Agrobacterium tumefaciens* C58 |
| 33 | 302 | 73586 | CGPG6471 | SENSE | *Bacillus subtilis* 168 |
| 34 | 303 | 73770 | CGPG5435 | SENSE | *Arabidopsis thaliana* |
| 35 | 304 | 74105 | CGPG6574 | SENSE | *Xenorhabdus nematophilus* 86068 |
| 36 | 305 | 74111 | CGPG6622 | SENSE | *Escherichia coli* K-12 |
| 37 | 306 | 74136 | CGPG6632 | SENSE | *Synechocystis* |
| 38 | 307 | 74139 | CGPG6561 | SENSE | *Escherichia coli* K-12 |
| 39 | 308 | 74267 | CGPG5364 | SENSE | *Arabidopsis thaliana* |
| 40 | 309 | 74291 | CGPG5363 | SENSE | *Arabidopsis thaliana* |
| 41 | 310 | 74318 | CGPG5826 | SENSE | *Arabidopsis thaliana* |
| 42 | 311 | 74319 | CGPG5831 | SENSE | *Arabidopsis thaliana* |
| 43 | 312 | 74324 | CGPG5885 | SENSE | *Arabidopsis thaliana* |
| 44 | 313 | 74512 | CGPG32 | SENSE | *Arabidopsis thaliana* |
| 45 | 314 | 74583 | CGPG6649 | SENSE | *Ralstonia metallidurans* CH34 |
| 46 | 315 | 70427 | CGPG3067 | SENSE | *Arabidopsis thaliana* |
| 47 | 316 | 71811 | CGPG4426 | SENSE | *Arabidopsis thaliana* |
| 48 | 317 | 73463 | CGPG6384 | SENSE | *Ralstonia metallidurans* CH34 |
| 49 | 318 | 72081 | CGPG5279 | SENSE | *Glycine max* |
| 50 | 319 | 10139 | CGPG101 | ANTI-SENSE | *Arabidopsis thaliana* |
| 51 | 320 | 11410 | CGPG103 | SENSE | *Arabidopsis thaliana* |
| 52 | 321 | 11604 | CGPG48 | ANTI-SENSE | *Arabidopsis thaliana* |

TABLE 1-continued

| Nuc SEQ ID | Pep SEQ ID | construct_id | Gene | orientation | Species |
|---|---|---|---|---|---|
| 53 | 322 | 12368 | CGPG1006 | SENSE | *Arabidopsis thaliana* |
| 54 | 323 | 13502 | CGPG1354 | SENSE | *Arabidopsis thaliana* |
| 55 | 324 | 13745 | CGPG1576 | ANTI-SENSE | *Arabidopsis thaliana* |
| 56 | 325 | 13821 | CGPG1569 | SENSE | *Arabidopsis thaliana* |
| 57 | 326 | 14240 | CGPG1697 | SENSE | *Arabidopsis thaliana* |
| 58 | 327 | 14718 | CGPG1082 | SENSE | *Arabidopsis thaliana* |
| 59 | 328 | 17022 | CGPG1774 | SENSE | *Arabidopsis thaliana* |
| 60 | 329 | 17924 | CGPG2882 | SENSE | *Arabidopsis thaliana* |
| 61 | 330 | 18259 | CGPG3368 | SENSE | *Arabidopsis thaliana* |
| 62 | 331 | 19171 | CGPG2952 | SENSE | *Saccharomyces cerevisiae* |
| 63 | 332 | 19201 | CGPG2332 | SENSE | *Arabidopsis thaliana* |
| 64 | 333 | 19317 | CGPG3662 | SENSE | *Xanthomonas* |
| 65 | 334 | 70417 | CGPG3427 | SENSE | *Arabidopsis thaliana* |
| 66 | 335 | 70467 | CGPG3785 | SENSE | *Arabidopsis thaliana* |
| 67 | 336 | 70806 | CGPG712 | SENSE | *Arabidopsis thaliana* |
| 68 | 337 | 70818 | CGPG479 | SENSE | *Arabidopsis thaliana* |
| 69 | 338 | 70820 | CGPG655 | SENSE | *Arabidopsis thaliana* |
| 70 | 339 | 70919 | CGPG4029 | SENSE | *Glycine max* |
| 71 | 340 | 71623 | CGPG4696 | SENSE | *Arabidopsis thaliana* |
| 72 | 341 | 71662 | CGPG4679 | SENSE | *Glycine max* |
| 73 | 342 | 71693 | CGPG4652 | SENSE | *Glycine max* |
| 74 | 343 | 72384 | CGPG4639 | SENSE | *Saccharomyces cerevisiae* |
| 75 | 344 | 72439 | CGPG5075 | SENSE | *Arabidopsis thaliana* |
| 76 | 345 | 72619 | CGPG4835 | SENSE | *Arabidopsis thaliana* |
| 77 | 346 | 72624 | CGPG4842 | SENSE | *Arabidopsis thaliana* |
| 78 | 347 | 72715 | CGPG5521 | SENSE | *Saccharomyces cerevisiae* |
| 79 | 348 | 72754 | CGPG5548 | SENSE | *Saccharomyces cerevisiae* |
| 80 | 349 | 72819 | CGPG4989 | SENSE | *Arabidopsis thaliana* |
| 81 | 350 | 75516 | CGPG7689 | SENSE | *Glycine max* |
| 82 | 351 | 75701 | CGPG7856 | SENSE | *Glycine max* |
| 83 | 352 | 73515 | CGPG6473 | SENSE | *Bacillus subtilis* 168 |
| 84 | 353 | 74684 | CGPG6360 | SENSE | *Arabidopsis thaliana* |
| 85 | 354 | 19542 | CGPG3069 | SENSE | *Arabidopsis thaliana* |
| 86 | 355 | 19618 | CGPG3574 | SENSE | *Arabidopsis thaliana* |
| 87 | 356 | 19649 | CGPG3140 | SENSE | *Arabidopsis thaliana* |
| 88 | 357 | 19745 | CGPG3973 | SENSE | *Glycine max* |
| 89 | 358 | 19768 | CGPG4096 | SENSE | *Glycine max* |
| 90 | 359 | 19772 | CGPG3939 | SENSE | *Glycine max* |
| 91 | 360 | 19779 | CGPG4113 | SENSE | *Glycine max* |
| 92 | 361 | 19833 | CGPG4074 | SENSE | *Glycine max* |
| 93 | 362 | 19862 | CGPG3961 | SENSE | *Glycine max* |
| 94 | 363 | 19879 | CGPG4009 | SENSE | *Glycine max* |
| 95 | 364 | 70445 | CGPG3728 | SENSE | *Arabidopsis thaliana* |
| 96 | 365 | 70738 | CGPG3195 | SENSE | *Arabidopsis thaliana* |
| 97 | 366 | 71437 | CGPG4043 | SENSE | *Glycine max* |
| 98 | 367 | 71572 | CGPG4520 | SENSE | *Arabidopsis thaliana* |
| 99 | 368 | 71617 | CGPG1227 | SENSE | *Arabidopsis thaliana* |
| 100 | 369 | 72532 | CGPG4780 | SENSE | *Arabidopsis thaliana* |
| 101 | 370 | 72757 | CGPG5572 | SENSE | *Arabidopsis thaliana* |
| 102 | 371 | 73412 | CGPG6448 | SENSE | *Pseudomonas syringae* var tomato DC3000 |
| 103 | 372 | 74102 | CGPG6550 | SENSE | *Bacillus halodurans* C-125 |
| 104 | 373 | 72633 | CGPG4853 | SENSE | *Arabidopsis thaliana* |
| 105 | 374 | 72456 | CGPG4745 | SENSE | *Arabidopsis thaliana* |
| 106 | 375 | 72963 | CGPG1746 | SENSE | *Arabidopsis thaliana* |
| 107 | 376 | 70426 | CGPG3199 | SENSE | *Arabidopsis thaliana* |
| 108 | 377 | 70772 | CGPG4627 | SENSE | *Arabidopsis thaliana* |
| 109 | 378 | 71137 | CGPG125 | SENSE | *Arabidopsis thaliana* |
| 110 | 379 | 71529 | CGPG2808 | SENSE | *Arabidopsis thaliana* |
| 111 | 380 | 71601 | CGPG1858 | SENSE | *Arabidopsis thaliana* |
| 112 | 381 | 72362 | CGPG983 | SENSE | *Arabidopsis thaliana* |
| 113 | 382 | 72466 | CGPG4767 | SENSE | *Arabidopsis thaliana* |
| 114 | 383 | 72524 | CGPG4770 | SENSE | *Arabidopsis thaliana* |
| 115 | 384 | 73085 | CGPG5689 | SENSE | *Synechocystis* sp. PCC 6803 |
| 116 | 385 | 74241 | CGPG5457 | SENSE | *Arabidopsis thaliana* |
| 117 | 386 | 74247 | CGPG5475 | SENSE | *Arabidopsis thaliana* |
| 118 | 387 | 74284 | CGPG5413 | SENSE | *Arabidopsis thaliana* |
| 119 | 388 | 74652 | CGPG6168 | SENSE | *Arabidopsis thaliana* |
| 120 | 389 | 70437 | CGPG3706 | SENSE | *Arabidopsis thaliana* |
| 121 | 390 | 71633 | CGPG857 | SENSE | *Arabidopsis thaliana* |
| 122 | 391 | 72948 | CGPG5617 | SENSE | *Arabidopsis thaliana* |
| 123 | 392 | 72519 | CGPG4749 | SENSE | *Arabidopsis thaliana* |
| 124 | 393 | 10475 | CGPG399 | SENSE | *Arabidopsis thaliana* |
| 125 | 394 | 11120 | CGPG459 | ANTI-SENSE | *Arabidopsis thaliana* |
| 126 | 395 | 19736 | CGPG4129 | SENSE | *Glycine max* |
| 127 | 396 | 71606 | CGPG4715 | SENSE | *Arabidopsis thaliana* |
| 128 | 397 | 71840 | CGPG4353 | SENSE | *Arabidopsis thaliana* |
| 129 | 398 | 74240 | CGPG5454 | SENSE | *Arabidopsis thaliana* |
| 130 | 399 | 74331 | CGPG5834 | SENSE | *Arabidopsis thaliana* |

TABLE 1-continued

| Nuc SEQ ID | Pep SEQ ID | construct_id | Gene | orientation | Species |
|---|---|---|---|---|---|
| 131 | 400 | 74610 | CGPG6048 | SENSE | *Arabidopsis thaliana* |
| 132 | 401 | 75527 | CGPG7682 | SENSE | *Glycine max* |
| 133 | 402 | 70681 | CGPG4584 | SENSE | *Arabidopsis thaliana* |
| 134 | 403 | 71663 | CGPG4638 | SENSE | *Xanthomonas* |
| 135 | 404 | 72769 | CGPG5573 | SENSE | *Arabidopsis thaliana* |
| 136 | 405 | 71508 | CGPG1541 | SENSE | *Arabidopsis thaliana* |
| 137 | 406 | 74248 | CGPG5476 | SENSE | *Arabidopsis thaliana* |
| 138 | 407 | 72771 | CGPG2166 | SENSE | *Arabidopsis thaliana* |
| 139 | 408 | 72085 | CGPG5228 | SENSE | *Arabidopsis thaliana* |
| 140 | 409 | 72744 | CGPG5563 | SENSE | *Saccharomyces cerevisiae* |
| 141 | 410 | 73039 | CGPG810 | SENSE | *Arabidopsis thaliana* |
| 142 | 411 | 73054 | CGPG5754 | SENSE | *Saccharomyces cerevisiae* |
| 143 | 412 | 73501 | CGPG6456 | SENSE | *Agrobacterium tumefacians* C58 |
| 144 | 413 | 19707 | CGPG4179 | SENSE | *Glycine max* |
| 145 | 414 | 19951 | CGPG3941 | SENSE | *Glycine max* |
| 146 | 415 | 19967 | CGPG4032 | SENSE | *Glycine max* |
| 147 | 416 | 70543 | CGPG3815 | SENSE | *Arabidopsis thaliana* |
| 148 | 417 | 70707 | CGPG1273 | ANTI-SENSE | *Arabidopsis thaliana* |
| 149 | 418 | 70719 | CGPG1712 | ANTI-SENSE | *Arabidopsis thaliana* |
| 150 | 419 | 71134 | CGPG817 | SENSE | *Arabidopsis thaliana* |
| 151 | 420 | 71146 | CGPG2928 | SENSE | *Arabidopsis thaliana* |
| 152 | 421 | 71660 | CGPG4690 | SENSE | *Arabidopsis thaliana* |
| 153 | 422 | 72086 | CGPG5236 | SENSE | *Arabidopsis thaliana* |
| 154 | 423 | 72632 | CGPG4852 | SENSE | *Arabidopsis thaliana* |
| 155 | 424 | 72716 | CGPG5529 | SENSE | *Saccharomyces cerevisiae* |
| 156 | 425 | 72723 | CGPG1848 | SENSE | *Arabidopsis thaliana* |
| 157 | 426 | 72987 | CGPG1787 | SENSE | *Arabidopsis thaliana* |
| 158 | 427 | 74109 | CGPG6606 | SENSE | *Xenorhabdus nematophilus* 86068 |
| 159 | 428 | 74140 | CGPG6569 | SENSE | *Bacillus halodurans* C-125 |
| 160 | 429 | 74191 | CGPG6597 | SENSE | *Rhodobacter sphaeroides* 2.4.1 |
| 161 | 430 | 74265 | CGPG5356 | SENSE | *Arabidopsis thaliana* |
| 162 | 431 | 74369 | CGPG6076 | SENSE | *Arabidopsis thaliana* |
| 163 | 432 | 70217 | CGPG6 | SENSE | *Arabidopsis thaliana* |
| 164 | 433 | 72711 | CGPG1846 | SENSE | *Arabidopsis thaliana* |
| 165 | 434 | 70932 | CGPG4089 | SENSE | *Glycine max* |
| 166 | 435 | 73518 | CGPG6497 | SENSE | *Pseudomonas fluorescens* PfO-1 |
| 167 | 436 | 19771 | CGPG4011 | SENSE | *Glycine max* |
| 168 | 437 | 73549 | CGPG6460 | SENSE | *Xenorhabdus nematophilus* 85816 |
| 169 | 438 | 72994 | CGPG5803 | SENSE | *Saccharomyces cerevisiae* |
| 170 | 439 | 71928 | CGPG1617 | SENSE | *Arabidopsis thaliana* |
| 171 | 440 | 72903 | CGPG5584 | SENSE | *Arabidopsis thaliana* |
| 172 | 441 | 73017 | CGPG5733 | SENSE | *Saccharomyces cerevisiae* |
| 173 | 442 | 74587 | CGPG6774 | SENSE | *Agrobacterium tumefacians* C58 |
| 174 | 443 | 72453 | CGPG4735 | SENSE | *Arabidopsis thaliana* |
| 175 | 444 | 72967 | CGPG5742 | SENSE | *Saccharomyces cerevisiae* |
| 176 | 445 | 72961 | CGPG5591 | SENSE | *Arabidopsis thaliana* |
| 177 | 446 | 73070 | CGPG5627 | SENSE | *Arabidopsis thaliana* |
| 178 | 447 | 73475 | CGPG6385 | SENSE | *Rhodopseudomonas palustris* CGA009 |
| 179 | 448 | 72916 | CGPG1814 | SENSE | *Arabidopsis thaliana* |
| 180 | 449 | 72969 | CGPG5789 | SENSE | *Saccharomyces cerevisiae* |
| 181 | 450 | 74449 | CGPG6659 | SENSE | *Agrobacterium tumefaciens* |
| 182 | 451 | 16615 | CGPG2539 | SENSE | *Agrobacterium* |
| 183 | 452 | 19187 | CGPG3310 | SENSE | *Arabidopsis thaliana* |
| 184 | 453 | 19648 | CGPG3134 | SENSE | *Arabidopsis thaliana* |
| 185 | 454 | 70354 | CGPG3995 | SENSE | *Glycine max* |
| 186 | 455 | 70421 | CGPG2942 | SENSE | *Arabidopsis thaliana* |
| 187 | 456 | 70459 | CGPG3758 | SENSE | *Arabidopsis thaliana* |
| 188 | 457 | 70465 | CGPG3775 | SENSE | *Arabidopsis thaliana* |
| 189 | 458 | 70683 | CGPG4587 | SENSE | *Arabidopsis thaliana* |
| 190 | 459 | 70725 | CGPG2097 | ANTI-SENSE | *Arabidopsis thaliana* |
| 191 | 460 | 70852 | CGPG1465 | SENSE | *Arabidopsis thaliana* |
| 192 | 461 | 71112 | CGPG934 | SENSE | *Arabidopsis thaliana* |
| 193 | 462 | 71127 | CGPG945 | SENSE | *Arabidopsis thaliana* |
| 194 | 463 | 71132 | CGPG1561 | SENSE | *Arabidopsis thaliana* |
| 195 | 464 | 71217 | CGPG95 | SENSE | *Arabidopsis thaliana* |
| 196 | 465 | 71645 | CGPG4688 | SENSE | *Arabidopsis thaliana* |
| 197 | 466 | 71726 | CGPG3894 | SENSE | *Arabidopsis thaliana* |
| 198 | 467 | 72432 | CGPG4562 | SENSE | *Arabidopsis thaliana* |
| 199 | 468 | 72450 | CGPG4732 | SENSE | *Arabidopsis thaliana* |
| 200 | 469 | 72455 | CGPG4742 | SENSE | *Arabidopsis thaliana* |
| 201 | 470 | 72727 | CGPG5522 | SENSE | *Saccharomyces cerevisiae* |
| 202 | 471 | 72817 | CGPG4987 | SENSE | *Arabidopsis thaliana* |
| 203 | 472 | 72992 | CGPG5777 | SENSE | *Saccharomyces cerevisiae* |
| 204 | 473 | 73007 | CGPG5760 | SENSE | *Saccharomyces cerevisiae* |
| 205 | 474 | 73073 | CGPG5688 | SENSE | *Synechocystis* sp. PCC 6803 |
| 206 | 475 | 73506 | CGPG6496 | SENSE | *Pseudomonas fluorescens* PfO-1 |
| 207 | 476 | 74107 | CGPG6590 | SENSE | *Sinorhizobium meliloti* 1021 |
| 208 | 477 | 74117 | CGPG6575 | SENSE | *Xenorhabdus nematophilus* 86068 |

TABLE 1-continued

| Nuc SEQ ID | Pep SEQ ID | construct_id | Gene | orientation | Species |
|---|---|---|---|---|---|
| 209 | 478 | 74131 | CGPG6592 | SENSE | Synechocystis sp. PCC 6803 |
| 210 | 479 | 74344 | CGPG5929 | SENSE | Arabidopsis thaliana |
| 211 | 480 | 14320 | CGPG1229 | SENSE | Arabidopsis thaliana |
| 212 | 481 | 16756 | CGPG2117 | SENSE | Arabidopsis thaliana |
| 213 | 482 | 17448 | CGPG2673 | SENSE | Arabidopsis thaliana |
| 214 | 483 | 17633 | CGPG2839 | SENSE | Arabidopsis thaliana |
| 215 | 484 | 18876 | CGPG3096 | SENSE | Arabidopsis thaliana |
| 216 | 485 | 19120 | CGPG1976 | ANTI-SENSE | Arabidopsis thaliana |
| 217 | 486 | 19221 | CGPG2958 | SENSE | Arabidopsis thaliana |
| 218 | 487 | 70206 | CGPG4116 | SENSE | Glycine max |
| 219 | 488 | 70223 | CGPG53 | SENSE | Arabidopsis thaliana |
| 220 | 489 | 70347 | CGPG3147 | SENSE | Arabidopsis thaliana |
| 221 | 490 | 70406 | CGPG1687 | SENSE | Arabidopsis thaliana |
| 222 | 491 | 70469 | CGPG3791 | SENSE | Arabidopsis thaliana |
| 223 | 492 | 70564 | CGPG1864 | SENSE | Arabidopsis thaliana |
| 224 | 493 | 70601 | CGPG2917 | SENSE | Arabidopsis thaliana |
| 225 | 494 | 70612 | CGPG3721 | SENSE | Arabidopsis thaliana |
| 226 | 495 | 70720 | CGPG1358 | ANTI-SENSE | Arabidopsis thaliana |
| 227 | 496 | 70735 | CGPG2661 | SENSE | Arabidopsis thaliana |
| 228 | 497 | 70846 | CGPG377 | SENSE | Arabidopsis thaliana |
| 229 | 498 | 70923 | CGPG4020 | SENSE | Glycine max |
| 230 | 499 | 71149 | CGPG3457 | SENSE | Arabidopsis thaliana |
| 231 | 500 | 71608 | CGPG4687 | SENSE | Arabidopsis thaliana |
| 232 | 501 | 71739 | CGPG4345 | SENSE | Arabidopsis thaliana |
| 233 | 502 | 72014 | CGPG5230 | SENSE | Arabidopsis thaliana |
| 234 | 503 | 72051 | CGPG5241 | SENSE | Arabidopsis thaliana |
| 235 | 504 | 74259 | CGPG5343 | SENSE | Arabidopsis thaliana |
| 236 | 505 | 72463 | CGPG4760 | SENSE | Arabidopsis thaliana |
| 237 | 506 | 72902 | CGPG5597 | SENSE | Arabidopsis thaliana |
| 238 | 507 | 74572 | CGPG6640 | SENSE | Synechocystis |
| 239 | 508 | 73055 | CGPG5768 | SENSE | Saccharomyces cerevisiae |
| 240 | 509 | 74103 | CGPG6558 | SENSE | Escherichia coli K-12 |
| 241 | 510 | 72921 | CGPG5781 | SENSE | Saccharomyces cerevisiae |
| 242 | 511 | 72968 | CGPG5772 | SENSE | Saccharomyces cerevisiae |
| 243 | 512 | 19703 | CGPG4172 | SENSE | Glycine max |
| 244 | 513 | 19946 | CGPG4097 | SENSE | Glycine max |
| 245 | 514 | 19980 | CGPG3914 | SENSE | Glycine max |
| 246 | 515 | 70435 | CGPG3701 | SENSE | Arabidopsis thaliana |
| 247 | 516 | 71114 | CGPG1657 | SENSE | Arabidopsis thaliana |
| 248 | 517 | 72451 | CGPG4733 | SENSE | Arabidopsis thaliana |
| 249 | 518 | 72947 | CGPG5607 | SENSE | Glycine max |
| 250 | 519 | 73012 | CGPG5786 | SENSE | Saccharomyces cerevisiae |
| 251 | 520 | 73022 | CGPG5622 | SENSE | Arabidopsis thaliana |
| 252 | 521 | 73488 | CGPG6394 | SENSE | Bacillus subtilis 168 |
| 253 | 522 | 73901 | CGPG5237 | SENSE | Arabidopsis thaliana |
| 254 | 523 | 73964 | CGPG5804 | SENSE | Saccharomyces cerevisiae |
| 255 | 524 | 74019 | CGPG5706 | SENSE | Bacillus subtilis 168 |
| 256 | 525 | 74022 | CGPG5724 | SENSE | Arabidopsis thaliana |
| 257 | 526 | 74114 | CGPG6551 | SENSE | Agrobacterium tumefacians C58 |
| 258 | 527 | 74262 | CGPG5353 | SENSE | Arabidopsis thaliana |
| 259 | 528 | 74292 | CGPG5367 | SENSE | Arabidopsis thaliana |
| 260 | 529 | 74302 | CGPG5384 | SENSE | Arabidopsis thaliana |
| 261 | 530 | 74325 | CGPG5898 | SENSE | Arabidopsis thaliana |
| 262 | 531 | 74429 | CGPG6689 | SENSE | Bacillus subtilis 168 |
| 263 | 532 | 74440 | CGPG6682 | SENSE | Bacillus halodurans C-125 |
| 264 | 533 | 74462 | CGPG6668 | SENSE | Synechocystis |
| 265 | 534 | 74465 | CGPG6692 | SENSE | Bacillus subtilis 168 |
| 266 | 535 | 74474 | CGPG6669 | SENSE | Synechocystis |
| 267 | 536 | 74505 | CGPG6783 | SENSE | Escherichia coli K-12 |
| 268 | 537 | 74507 | CGPG6799 | SENSE | Xenorhabdus nematophilus 85816 |
| 269 | 538 | 74562 | CGPG6764 | SENSE | Bacillus subtilis 168 |

Recombinant DNA

Trait-imparting DNA for use in this invention for improved traits in plants is disclosed herein as having a DNA sequence of SEQ ID NO:1 through SEQ ID NO:269 and any of the respective homologs. A subset of the trait-imparting DNA includes fragments with less than the full DNA sequence, e.g., consisting of oligonucleotides of at least about 15 to 20 or more consecutive nucleotides from one of the disclosed sequences. Such oligonucleotides are fragments of the larger molecules having a sequence selected from the group consisting of SEQ ID NO: 1 through SEQ ID NO: 269, and find use, for example as probes and primers for detection of the polynucleotides of the invention or for cloning DNA for use in this invention.

Useful DNA includes variants of the disclosed DNA. Such variants include naturally occurring, including homologous DNA from genes of the same or a different species, or non-natural variants, for example DNA synthesized using chemical synthesis methods, or generated using recombinant DNA techniques. Degeneracy of the genetic code provides the possibility to substitute at least one nucleotide of a disclosed DNA without causing the amino acid sequence of the protein produced to be changed. Hence, useful DNA can have any base sequence that has been changed from the sequences provided herein by substitution in accordance with degeneracy of the genetic code.

Homologs of the trait-imparting DNA generally demonstrate significant identity with the DNA provided herein. Homologous DNA is substantially identical to a trait-imparting DNA if, when the nucleotide sequences are optimally aligned there is at least about 60% nucleotide identity, or higher, e.g., at least 70% or 80% or 85% or even 90% identity or higher, such as 95% or 98% identity over a comparison window of at least 50 to 100 nucleotides, and up to the entire length of the trait-imparting DNA. Optimal alignment of sequences for aligning a comparison window can be conducted by algorithms including computerized implementations of the algorithms (for example, the Wisconsin Genetics Software Package Release 7.0-10.0, Genetics Computer Group, 575 Science Dr., Madison, Wis.). The reference DNA sequence can represent a full-length coding sequence or a portion.

Proteins useful for imparting improved traits are entire proteins or at least a sufficient portion of the entire protein to impart the relevant biological activity of the protein. Proteins useful for generation of transgenic plants having improved traits include the proteins with an amino acid sequence provided herein as SEQ ID NO: 270 through SEQ ID NO: 538, as well as homologs of such proteins.

One method to identify homologs of the proteins useful in this invention is by comparison of the amino acid sequence of the trait-imparting protein to amino acid sequences of proteins from the same or different organisms, e.g., manually or by using known homology-based search algorithms such as those commonly known and referred to as BLAST, FASTA, and Smith-Waterman. In one method a local sequence alignment program, e.g., BLAST, is used to search a database of sequences to find similar sequences, and the summary Expectation value (E-value) is used to measure the sequence base similarity. As a protein hit with the best E-value for a particular organism may not necessarily be an ortholog or the only ortholog, a reciprocal BLAST search is used to filter hit sequences with significant E-values for ortholog identification. The reciprocal BLAST entails search of the significant hits against a database of amino acid sequences from the base organism that are similar to the sequence of the query protein. A hit is a likely ortholog, when the reciprocal BLAST's best hit is the query protein itself or a protein encoded by a duplicated gene after speciation. Thus, homolog is used herein to described proteins that are assumed to have functional similarity by inference from sequence base similarity. The relationship of homologs with amino acid sequences of SEQ ID NO: 539 through SEQ ID NO: 22568 to the proteins with amino acid sequences of SEQ ID NO: 270 through SEQ ID NO: 538 is found in Table 16.

Aspects of the invention also use DNA encoding functional homolog proteins which differ in one or more amino acids from those of protein encoded by disclosed trait-imparting DNA as the result of one or more of the well-known conservative amino acid substitutions, e.g., valine is a conservative substitute for alanine and threonine is a conservative substitute for serine. Conservative substitutions for an amino acid within the native sequence are selected from other members of a class to which the naturally occurring amino acid belongs. Representative amino acids within these various classes include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence are selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine. A further aspect of the invention uses DNA encoding proteins that differ in one or more amino acids from those of protein encoded from a described trait-imparting DNA as the result of deletion or insertion of one or more amino acids in a native sequence.

Homologs of the proteins encoded by disclosed trait-improving DNA will generally demonstrate significant sequence identity, e.g., at least 50% amino acid sequence identity or higher such as at least 70% identity or at least 80% or at least 90% identity with an amino acid sequence of SEQ ID NO:270 through SEQ ID NO:538. Identity of protein homologs is determined by optimally aligning the amino acid sequence of a putative protein homolog with a defined amino acid sequence of a protein encoded by a disclosed trait-imparting DNA and by calculating the percentage of identical and conservatively substituted amino acids over the window of comparison. The window of comparison for determining identity can be the entire amino acid sequence disclosed herein, e.g., the full sequence of any of SEQ ID NO:270 through SEQ ID NO:538.

Genes that are homologs to each other can be grouped into families and included in multiple sequence alignments to allow a consensus sequence to be derived. This analysis enables the derivation of conserved and class-(family) specific residues or motifs that are functionally important. These conserved residues and motifs can be further validated with 3D protein structure if available. A consensus sequence is used to define the full scope of the invention, e.g., to identify proteins with a homolog relationship and the corresponding trait-imparting DNA. Thus, this invention contemplates that protein homologs include proteins with an amino acid sequence that has at least 90% identity to such a consensus amino acid sequence.

Promoters

Numerous promoters that are active in plant cells have been described in the literature. These include promoters present in plant genomes as well as promoters from other sources, including nopaline synthase (NOS) promoter and octopine synthase (OCS) promoters carried on tumor-inducing plasmids of *Agrobacterium tumefaciens*, caulimovirus promoters such as the cauliflower mosaic virus or figwort mosaic virus promoters. For instance, see U.S. Pat. Nos. 5,858,742 and 5,322,938 which disclose versions of the constitutive promoter derived from cauliflower mosaic virus (CaMV35S), U.S. Pat. No. 5,378,619 which discloses a Figwort Mosaic Virus (FMV) 35S promoter, U.S. Pat. No. 6,437,217 which discloses a maize RS81 promoter, U.S. Pat. No. 5,641,876 which discloses a rice actin promoter, U.S.

Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Patent Application Publication 2002/0192813A1 which discloses 5', 3' and intron elements useful in the design of effective plant expression vectors, U.S. patent application Ser. No. 09/078,972 which discloses a coixin promoter, U.S. patent application Ser. No. 09/757,089 which discloses a maize chloroplast aldolase promoter, and U.S. patent application Ser. No. 10/739,565 which discloses water-deficit inducible promoters, all of which are incorporated herein by reference. These and numerous other promoters that function in plant cells are known to those skilled in the art and available for use in recombinant DNA to provide for expression of desired genes in transgenic plant cells.

It is well known in the art that promoters are usefully altered to contain multiple "enhancer sequences" to assist in elevating gene expression. By including an enhancer sequence with such constructs, expression is generally enhanced. These enhancers often are found 5' to the start of transcription in a promoter that functions in eukaryotic cells, and can also be inserted in the forward or reverse orientation 5' or 3' to the coding sequence. In some instances, 5' enhancing elements are introns. Particularly useful enhancers are the 5' introns of the rice actin 1 gene and the rice actin 2 gene. Other enhancers include elements from the CaMV 35S promoter, octopine synthase genes, the maize alcohol dehydrogenase gene, the maize shrunken 1 gene and promoters from non-plant eukaryotes.

In some aspects of the invention it is preferred that the promoter element in the DNA construct be capable of causing sufficient expression in water deficit conditions. Such promoters can be identified and isolated from the regulatory region of plant genes that are over expressed in water deficit conditions. Specific water-deficit-inducible promoters for use in this invention are derived from the 5' regulatory region of genes identified as a heat shock protein 17.5 gene (HSP17.5), an HVA22 gene (HVA22), a Rab17 gene and a cinnamic acid 4-hydroxylase (CA4H) gene (CA4H) of Zea maize. Such water-deficit-inducible promoters are disclosed in U.S. 2004-0123347 A1, incorporated herein by reference.

In other aspects of the invention, sufficient expression in plant seed tissues is desired to effect improvements in seed composition. Exemplary promoters for use for seed composition modification include promoters from seed genes such as napin (U.S. Pat. No. 5,420,034), maize L3 oleosin (U.S. Pat. No. 6,433,252), zein Z27 (Russell, et al., (1997) Transgenic Res. 6(2):157-166), globulin 1 (Belanger, et al., (1991) Genetics 129:863-872), glutelin 1 (Russell (1997) supra), and peroxiredoxin antioxidant (Per1) (Stacy, et al., (1996) Plant Mol Biol. 31(6):1205-1216).

In still other aspects of the invention, preferential expression in plant green tissues is desired. Promoters of interest for such uses include those from genes such as SSU (Fischhoff, et al., (1992) Plant Mol Biol. 20:81-93), aldolase and pyruvate orthophosphate dikinase (PPDK) (Taniguchi, et al., (2000) Plant Cell Physiol. 41(1):42-48).

Gene Overexpression

"Gene overexpression" means expression, e.g., of a gene at a level in its native host that exceeds levels of expression in a non-transgenic host. In many embodiments of the invention, a recombinant DNA construct provides gene overexpression, e.g., as identified in Table 1.

Gene Suppression

Gene suppression includes any of the well-known methods for suppressing expression, typically indicated by reduced levels of protein. Posttranscriptional gene suppression is mediated by transcription of integrated recombinant DNA to form double-stranded RNA (dsRNA) having homology to a gene targeted for suppression. This formation of dsRNA most commonly results from transcription of an integrated inverted repeat of an element of a target gene, and is a common feature of gene suppression methods known as anti-sense suppression, co-suppression and RNA interference (RNAi). Transcriptional suppression can be mediated by a transcribed dsRNA having homology to a promoter DNA sequence to effect what is called promoter trans suppression.

More particularly, posttranscriptional gene suppression by inserting a recombinant DNA construct with one or more copies of anti-sense oriented DNA to regulate gene expression in plant cells is disclosed in U.S. Pat. No. 5,107,065 (Shewmaker, et al.,) and U.S. Pat. No. 5,759,829 (Shewmaker, et Transgenic plants transformed using such anti-sense oriented DNA constructs for gene suppression can comprise integrated DNA arranged as an inverted repeats that result from insertion of the DNA construct into plants by Agrobacterium-mediated transformation, as disclosed by Redenbaugh, et al., in "Safety Assessment of Genetically Engineered Flavr Savr™ Tomato, CRC Press, Inc. (1992). Inverted repeat insertions can comprises a part or all of the T-DNA construct, e.g., an inverted repeat of a complete transcription unit or an inverted repeat of transcription terminator sequence. Screening for inserted DNA comprising inverted repeat elements can improve the efficiency of identifying transformation events effective for gene silencing whether the transformation construct is a simple anti-sense DNA construct which must be inserted in multiple copies or a complex inverted repeat DNA construct (e.g., an RNAi construct) which can be inserted as a single copy.

Posttranscriptional gene suppression by inserting a recombinant DNA construct with sense-oriented DNA to regulate gene expression in plants is disclosed in U.S. Pat. No. 5,283,184 (Jorgensen, et al.) and U.S. Pat. No. 5,231,020 (Jorgensen, et al.). Inserted T-DNA providing gene suppression in plants transformed with such sense constructs by Agrobacterium is organized predominately in inverted repeat structures, as disclosed by Jorgensen, et al., Mol. Gen. Genet., 207:471-477 (1987). See also Stam, et al., The Plant Journal, 12(1), 63-82 (1997) who used segregation studies to support Jorgensen's finding that gene silencing is mediated by multimeric transgene T-DNA loci in which the T-DNAs are arranged in inverted repeats. Screening for inserted DNA comprising inverted repeat elements can improve the gene silencing efficiency when transforming with simple sense-orientated DNA constructs. Gene silencing efficiency can also be improved by screening for single insertion events when transforming with an RNAi construct containing inverted repeat elements As disclosed by Redenbaugh, et al., gene suppression can be achieved by inserting into a plant genome recombinant DNA that transcribes dsRNA. Such a DNA insert can be transcribed to an RNA element having the 3' region as a double stranded RNA. RNAi constructs are also disclosed in EP 0426195 A1 (Goldbach, et al., —1991) where recombinant DNA constructs for transcription into hairpin dsRNA for providing transgenic plants with resistance to tobacco spotted wilt virus. Double-stranded RNAs were also disclosed in WO 94/01550 (Agrawal, et al.,) where anti-sense RNA was stabilized with a self-complementary 3' segment. Agrawal, et al., referred to U.S. Pat. No. 5,107,065 for using such self-stabilized anti-sense RNAs for regulating gene expression in plant cells; see International Publication No. 94/01550. Other double-stranded hairpin-forming elements in transcribed RNA are disclosed in International Publication No. 98/05770 (Werner, et al.,) where the anti-sense RNA is stabilized by hairpin forming repeats of poly(CG) nucleotides. See also U.S. Patent Application Publication No. 2003/0175965 A1 (Lowe, et al.,) which discloses gene suppression using and RNAi construct comprising a gene coding sequence preceded by inverted repeats of 5'UTR. See also U.S. Patent Application Publication No. 2002/0048814 A1 (Oeller) where RNAi constructs are transcribed to sense or anti-sense RNA which is stabilized by a poly(T)-poly(A) tail. See also U.S. Patent Application Publication No. 2003/0018993 A1 (Gutterson, et al.,) where sense or anti-sense RNA is stabilized by an inverted repeat of the 3' untranslated region of the NOS gene. See also U.S. Patent Application Publication No. 2003/0036197 A1 (Glassman, et al.,) where RNA having homology to a target is stabilized by two complementary RNA regions.

Gene silencing can also be affected by transcribing RNA from both a sense and an anti-sense oriented DNA, e.g., as disclosed by Shewmaker, et al., in U.S. Pat. No. 5,107,065 where in Example 1 a binary vector was prepared with both sense and anti-sense aroA genes. See also U.S. Pat. No. 6,326,193 where gene targeted DNA is operably linked to opposing promoters.

Gene silencing can also be affected by transcribing from contiguous sense and anti-sense DNA. In this regard see Sijen, et al., The Plant Cell, Vol. 8, 2277-2294 (1996) discloses the use of constructs carrying inverted repeats of a cowpea mosaic virus gene in transgenic plants to mediate virus resistance. Such constructs for posttranscriptional gene suppression in plants by double-stranded RNA are also disclosed in International Publication No. WO 99/53050 (Waterhouse, et al,), International Publication No. WO 99/49029 (Graham, et al.), U.S. 2004-0029283 A1 (Fillatti), U.S. Pat. No. 6,506,559 (Fire, et al,). See also U.S. 2004-0006792 A1 (Shewmaker, et al.,) that discloses constructs and methods for simultaneously expressing one or more recombinant genes while simultaneously suppressing one or more native genes in a transgenic plant. See also U.S. Pat. No. 6,448,473 (Mitsky, et al.,) that discloses multi-gene suppression vectors for use in plants. All of the above-described patents, applications and international publications disclosing materials and methods for posttranscriptional gene suppression in plants are incorporated herein by reference. Transcriptional suppression such as promoter trans suppression can be affected by a expressing a DNA construct comprising a promoter operably linked to inverted repeats of promoter DNA for a target gene. Constructs useful for such gene suppression mediated by promoter trans suppression are disclosed by Mette, et al., The EMBO Journal, Vol. 18, No. 1, pp. 241-148, 1999 and by Mette, et al., The EMBO Journal, Vol. 19, No. 19, pp. 5194-5201-148, 2000, both of which are incorporated herein by reference.

Suppression can also be achieved by insertion mutations created by transposable elements may also prevent gene function. For example, in many dicot plants, transformations with the T-DNA of *Agrobacterium* are readily achieved and large numbers of transformants can be rapidly obtained. Also, some species have lines with active transposable elements that are efficiently be used for the generation of large numbers of insertion mutations, while some other species lack such options. Mutant plants produced by *Agrobacterium* or transposon mutagenesis and having altered expression of a polypeptide of interest are identified using the polynucleotides of this invention. For example, a large population of mutated plants are screened to detect mutated plants having an insertion in the gene encoding the polypeptide of interest.

Gene Stacking

This invention also contemplates that the trait-improving recombinant DNA is used in combination with other recombinant DNA to create plants with a multiple desired traits. The combinations generated include multiple copies of any one or more of the recombinant DNA constructs. These stacked combinations are created by any method, including but not limited to cross breeding of transgenic plants, or multiple genetic transformation.

Plant Transformation Methods

Numerous methods for transforming plant cells with recombinant DNA are known in the art and are useful in producing the transgenic seeds of this invention. Two commonly used methods for plant transformation are *Agrobacterium*-mediated transformation and microprojectile bombardment. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn) and U.S. Pat. No. 6,153,812 (wheat) and *Agrobacterium*-mediated transformation is described in U.S. Pat. No. 5,159,135 (cotton); U.S. Pat. No. 5,824,877 (soybean); U.S. Pat. No. 5,591,616 (corn); and U.S. Pat. No. 6,384,301 (soybean), all of which are incorporated herein by reference. For *Agrobacterium tumefaciens* based plant transformation system, additional elements present on transformation constructs include T-DNA left and right border sequences to facilitate incorporation of the recombinant polynucleotide into the plant genome.

In general it is preferred to introduce heterologous DNA randomly, i.e., at a non-specific location, in the genome of a target plant line. In special cases it is useful to target heterologous DNA insertion in order to achieve site-specific integration, e.g., to replace an existing gene in the genome, to use an existing promoter in the plant genome, or to insert a recombinant polynucleotide at a predetermined site known to be active for gene expression. Several site specific recombination systems exist which are known to function implants include cre-lox as disclosed in U.S. Pat. No. 4,959,317 and FLP-FRT as disclosed in U.S. Pat. No. 5,527,695, both incorporated herein by reference.

Transformation methods of this invention are preferably practiced in tissue culture on media and in a controlled environment. "Media" means any of the numerous nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. It is contemplated that any cell from which a fertile plant is regenerated is useful as a recipient cell. Callus is initiated from tissue sources including, but not limited to, immature embryos, seedling apical meristems, microspores and the like. Cells capable of proliferating as callus are also recipient cells for genetic transformation. Practical transformation methods and materials for making transgenic plants of this invention, e.g., various media and recipient target cells, transformation of immature embryos and subsequent regeneration of fertile transgenic plants are disclosed in U.S. Pat. Nos. 6,194,636 and 6,232,526 and U.S. 2004-0216189 A1, which are incorporated herein by reference.

In practice DNA is introduced into only a small percentage of target cells in any one experiment. Marker genes are used to provide an efficient system for identification of those cells that are stably transformed by receiving and integrating a transgenic DNA construct into their genomes. Preferred marker genes provide selective markers that confer resistance to a selective agent, such as an antibiotic or herbicide. Potentially transformed cells are exposed to the selective agent. In the population of surviving cells are those cells where, generally, the resistance-conferring gene has been integrated and expressed at sufficient levels to permit cell survival. Cells are tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS). Examples of such selectable are illustrated in U.S. Pat. Nos. 5,550,318; 5,633,435; 5,780,708 and 6,118,047, all of which are incorporated herein by reference. Screenable markers which provide an ability to visually identify transformants are also often employed, e.g., a gene expressing a colored or fluorescent protein such as a luciferase or green fluorescent protein (GFP) or a gene expressing a beta-glucuronidase or uidA gene (GUS) for which various chromogenic substrates are known. It is also contemplated that combinations of screenable and selectable markers will be useful for identification of transformed cells. See PCT publication WO 99/61129 which discloses use of a gene fusion between a selectable marker gene and a screenable marker gene, e.g., an NPTII gene and a GFP gene.

Cells that survive exposure to the selective agent, or cells that have been scored positive in a screening assay, are cultured in regeneration media and allowed to mature into plants. Developing plantlets are transferred to soil less plant growth mix, and hardened off, e.g., in an environmentally controlled chamber at about 85% relative humidity, 600 ppm $CO_2$, and 25-250 microeinsteins $m^{-2}$ $s^{-1}$ of light, prior to transfer to a greenhouse or growth chamber for maturation. Plants are preferably matured either in a growth chamber or greenhouse. Plants are regenerated from about 6 wk to 10 months after a transformant is identified, depending on the initial tissue. During regeneration, cells are grown to plants on solid media at about 19 to 28 degrees C. After regenerating plants have reached the stage of shoot and root development, they are transferred to a greenhouse for further growth and testing. Plants are pollinated using conventional plant breeding methods known to those of skill in the art and seed produced.

Progeny are recovered from transformed plants and tested for expression of the exogenous recombinant polynucleotide. Useful assays include, for example, "molecular biological" assays, such as Southern and Northern blotting and PCR; "biochemical" assays, such as detecting the presence of RNA, e.g., double stranded RNA, or a protein product, e.g., by immunological means (ELISAs and Western blots) or by enzymatic function; plant part assays, such as leaf or root assays; and also, by analyzing the phenotype of the whole regenerated plant.

Discovery of Trait-Improving Recombinant DNA

To identify recombinant DNA that confer improved traits to plants, *Arabidopsis* plants were transformed with a large population of recombinant DNA constructs for expressing a large variety of distinct DNA. Transgenic plants were produced and screened to identify those plants having recombinant DNA constructs expressing trait-imparting DNA. A two-step screening process was employed which comprised two passes of trait characterization to ensure that the trait modification was dependent on expression of the recombinant DNA, but not due to the chromosomal location of the integration of the transgene. Twelve independent transgenic lines for each recombinant DNA construct were established and assayed for the transgene expression levels. Five transgenic lines with high transgene expression levels were used in the first pass screen to evaluate the transgene's function in T2 transgenic plants. Subsequently, three transgenic events, which had been shown to have one or more improved traits, were further evaluated in the second pass screen to confirm the transgene's ability to impart an improved trait. The following Table 2 summarizes the improved traits that have been confirmed as provided by a recombinant DNA construct.

In particular, Table 2 reports

"PEP SEQ ID" which is the amino acid sequence of the protein cognate to the DNA in the recombinant DNA construct corresponding to a protein sequence of a SEQ ID NO. in the Sequence Listing.

"construct_id" is an arbitrary name for the recombinant DNA describe more particularly in Table 1.

"annotation" refers to a description of the top hit protein obtained from an amino acid sequence query of each PEP SEQ ID NO to GenBank database of the National Center for Biotechnology Information (ncbi). More particularly, "gi" is the GenBank ID number for the top BLAST hit.

"description" refers to the description of the top BLAST hit.

"e-value" provides the expectation value for the BLAST hit.

"identity" refers to the percentage of identically matched amino acid residues along the length of the portion of the sequences which is aligned by BLAST between the sequence of interest provided herein and the hit sequence in GenBank.

"traits" identified by two letters codes the confirmed improvement in a transgenic plant provided by the recombinant DNA. The codes for improved traits are:

"CK" which indicates cold tolerance improvement identified under a cold shock tolerance screen;

"CS" which indicates cold tolerance improvement identified by a cold germination tolerance screen;

"DS" which indicates drought tolerance improvement identified by a soil drought stress tolerance screen;

"PEG" which indicates osmotic stress tolerance improvement identified by a PEG induced osmotic stress tolerance screen;

"HS" which indicates heat stress tolerance improvement identified by a heat stress tolerance screen;

"SS" which indicates high salinity stress tolerance improvement identified by a salt stress tolerance screen;

"LN" which indicates nitrogen use efficiency improvement identified by a limited nitrogen tolerance screen;

"LL" which indicates attenuated shade avoidance response identified by a shade tolerance screen under a low light condition;

"PP" which indicates improved growth and development at early stages identified by an early plant growth and development screen;

"SP" which indicates improved growth and development at late stages identified by a late plant growth and development screen provided herein.

TABLE 2

| Pep SEQ Id | construct id | gene | annotation | | | | traits | | | | |
|---|---|---|---|---|---|---|---|---|---|---|---|
| | | | e value | % identity | ncbi id | description | | | | | |
| 270 | 14324 | CGPG1560 | 1.00E−127 | 86 | gi|15232185| | ref|NP_191546.1|expressed protein [*Arabidopsis thaliana*]] | CK | SS | | | |
| 271 | 17484 | CGPG2630 | 0 | 93 | gi|15220912| | ref|NP_173239.1|zinc finger (C3HC4-type RING finger) family protein [*Arabidopsis thaliana*] | CK | | | | |
| 272 | 19109 | CGPG1381 | 9.00E−31 | 81 | gi|18404521| | ref|NP_565870.1|expressed protein [*Arabidopsis thaliana*] | CK | | | | |
| 273 | 70423 | CGPG3165 | 1.00E−134 | 96 | gi|30688808| | ref|NP_850953.1|MADS-box protein (AGL9) [*Arabidopsis thaliana*] gb|AAM65812.1| putative floral homeotic protein, AGL9 [*Arabidopsis thaliana*] | CK | CS | CK | HS | PP |
| 274 | 70424 | CGPG3180 | 1.00E−142 | 81 | gi|25405039| | pir||H96827protein F20B17.12 [imported] - *Arabidopsis thaliana* gb|AAF68121.1| F20B17.12 [*Arabidopsis thaliana*] | CK | | | | |
| 275 | 70480 | CGPG3833 | 1.00E−122 | 99 | gi|18411867| | ref|NP_565174.1|14-3-3 protein GF14 pi (GRF13) [*Arabidopsis thaliana*] | CK | | | | |
| 276 | 70509 | CGPG2420 | 1.00E−113 | 82 | gi|15225186| | ref|NP_180770.1|ovate protein-related [*Arabidopsis thaliana*] | CK | | | | |
| 277 | 70647 | CGPG4334 | 1.00E−171 | 94 | gi|15237269| | ref|NP_200093.1|ornithine cyclodeaminase/mu-crystallin family protein [*Arabidopsis thaliana*] dbj|BAB10429.1| | CK | | | | |
| 278 | 70675 | CGPG4519 | 0 | 100 | gi|15224730| | ref|NP_180115.1|2-oxoglutarate-dependent dioxygenase, putative [*Arabidopsis thaliana*] pir||E84648 probable dioxygenase] | CK | | | | |
| 279 | 70829 | CGPG518 | 0 | 92 | gi|15232841| | ref|NP_186854.1|potassium transporter (KUP3) [*Arabidopsis thaliana*] | CK | | | | |
| 280 | 70849 | CGPG596 | 1.00E−166 | 96 | gi|15224801| | ref|NP_179547.1|cytidine deaminase (CDD)/cytidine aminohydrolase [*Arabidopsis thaliana*] | CK | | | | |
| 281 | 71627 | CGPG1270 | 0 | 99 | gi|18398032| | ref|NP_566315.1|ABC1 family protein [*Arabidopsis thaliana*] | CK | | | | |
| 282 | 71934 | CGPG2294 | 1.00E−154 | 79 | gi|15233973| | ref|NP_195575.1|26S proteasome regulatory subunit S5A (RPN10) [*Arabidopsis thaliana*] sp|P55034|PSD4_ARATH 26S proteasome non-ATPase regulatory subunit 4 (26S proteasome regulatory | CK | | | | |
| 283 | 72615 | CGPG4829 | 2.00E−49 | 88 | gi|18422886| | ref|NP_568693.1|expressed protein [*Arabidopsis thaliana*] | CK | | | | |
| 284 | 72927 | CGPG1477 | 1.00E−114 | 81 | gi|15234815| | ref|NP_194797.1|MA3 domain-containing protein [*Arabidopsis thaliana*] pir||A85359 translation initiation factor-like protein | CK | | | | |
| 285 | 73014 | CGPG5692 | 1.00E−180 | 93 | gi|37528369| | ref|NP_931714.1|Fructose-1,6-bisphosphatase (D-fructose-1,6-bisphosphate 1-phosphohydrolase) (FBPase) [*Photorhabdus luminescens* subsp. *laumondii* TTO1] | CK | PP | | | |
| 286 | 73559 | CGPG6535 | 0 | 93 | gi|16078422| | ref|NP_389241.1|similar to aspartate aminotransferase | CK | | | | |

TABLE 2-continued

| Pep SEQ Id | construct id | gene | e value | % identity | ncbi id | description | traits | | |
|---|---|---|---|---|---|---|---|---|---|
| | | | | | | [*Bacillus subtilis*] sp\|O31665\|MTNE_BACSU Transaminase mtnE pir\|\|F69863 probable transaminase (EC 2.6.1.—) ykrV | | | |
| 287 | 74251 | CGPG5489 | 1.00E−171 | 87 | gi\|15238437\| | ref\|NP_200760.1\|zinc transporter (ZIP2) [*Arabidopsis thaliana*] sp\|Q9LTH9\|ZIP2_ARATH Zinc transporter 2 precursor (ZRT/IRT-like protein 2) | CK | SP | |
| 288 | 19631 | CGPG3627 | 1.00E−94 | 90 | gi\|18410249\| | ref\|NP_565053.1\|SNF7 family protein [*Arabidopsis thaliana*] pir\|\|G96755 developmental protein homolog DG1118 [imported] - *Arabidopsis thaliana* | CS | | |
| 289 | 70121 | CGPG2380 | 1.00E−111 | 100 | gi\|6323765\| | ref\|NP_013836.1\|Hypothetical ORF; Ymr118cp [*Saccharomyces cerevisiae*] sp\|Q04487\|YM07_YEAST Putative succinate dehydrogenase cytochrome B subunit, mitochondrial precursor | CS | | |
| 290 | 70654 | CGPG4352 | 2.00E−63 | 88 | gi\|18400941\| | ref\|NP_566531.1\|expressed protein [*Arabidopsis thaliana*] | CS | | |
| 291 | 70696 | CGPG4590 | 8.00E−92 | 87 | gi\|25408379\| | pir\|\|E84768hypothetical protein At2g35430 | CS | PP | |
| 292 | 70713 | CGPG1462 | 0 | 95 | gi\|30678679\| | ref\|NP_191966.2\|malate oxidoreductase, putative | CS | | |
| 293 | 70740 | CGPG3700 | 0 | 94 | gi\|18402759\| | ref\|NP_566667.1\|transcription factor jumonji (jmjC) domain-containing protein | CS | LL | PP |
| 294 | 71321 | CGPG4418 | 0 | 91 | gi\|13878402\| | sp\|Q9STL0\|C71N_ARATH Cytochrome P450 71A23 pir\|\|T06712 probable cytochrome P450 T29H11.180 | CS | | |
| 295 | 71835 | CGPG4634 | 0 | 100 | gi\|15234361\| | ref\|NP_192100.1\|DC1 domain-containing protein [*Arabidopsis thaliana*] pir\|\|E85024 probable CHP-rich zinc finger protein | CS | SP | |
| 296 | 72934 | CGPG5798 | 0 | 98 | gi\|6323512\| | ref\|NP_013583.1\|High-affinity inorganic phosphate (Pi) transporter and low-affinity manganese transporter; regulated by Pho4p and Spt7p; mutation confers resistance to arsenate; exit from the ER during maturation requires Pho86p; Pho84p [*Saccharomyces cerevisiae*] | CS | | |
| 297 | 72945 | CGPG5787 | 0 | 94 | gi\|6319991\| | ref\|NP_010071.1\|GABA-specific transport protein; Uga4p [*Saccharomyces cerevisiae*] sp\|P32837\|UGA4_YEAST GABA-specific permease (GABA-specific transport protein) | CS | | |
| 298 | 72980 | CGPG5773 | 0 | 89 | gi\|6321960\| | ref\|NP_012036.1\|Subunit of the anaphase-promoting complex/cyclosome (APC/C), which is a ubiquitin-protein ligase required for degradation of anaphase inhibitors, | CS | | |

TABLE 2-continued

| Pep SEQ Id | construct id | gene | e value | % identity | ncbi id | description | traits | | | |
|---|---|---|---|---|---|---|---|---|---|---|
| | | | | | | including mitotic cyclins, during the metaphase/anaphase transition; Cdc23p | | | | |
| 299 | 73504 | CGPG6480 | 1.00E−178 | 100 | gi|16330153| | ref|NP_440881.1|fructokinase [*Synechocystis* sp. PCC 6803] pir||S77227 fructokinase (EC 2.7.1.4) - *Synechocystis* sp (strain PCC 6803) | CS | PP | | |
| 300 | 73507 | CGPG6504 | 1.00E−178 | 100 | gi|16078547| | ref|NP_389366.1|similar to glutaminase [*Bacillus subtilis*] | CS | LL | PP | PEG |
| 301 | 73573 | CGPG6462 | 0 | 100 | gi|15890038| | ref|NP_355719 1|AGR_C_5 067p [*Agrobacterium tumefaciens* str. C58] ref|NP_533456.1| 3-isopropylmalate dehydrogenase | CS | PP | | |
| 302 | 73586 | CGPG6471 | 1.00E−177 | 100 | gi|16077684| | ref|NP_388498.1|similar to fructokinase [*Bacillus subtilis*] | CS | DS | PP | |
| 303 | 73770 | CGPG5435 | 2.00E−34 | 68 | gi|15235771| | ref|NP_193383.1|cysteine protease inhibitor family protein/cystatin family protein [*Arabidopsis thaliana*] | CS | PP | | |
| 304 | 74105 | CGPG6574 | 0 | 73 | gi|23059330| | ref|ZP_00084307.1|COG10 12: NAD-dependent aldehyde dehydrogenases [*Pseudomonas fluorescens* PfO-1] | CS | | | |
| 305 | 74111 | CGPG6622 | 0 | 99 | gi|16131442| | ref|NP_418028.1|alpha-amylase [*Escherichia coli* K12] | CS | | | |
| 306 | 74136 | CGPG6632 | 9.00E−81 | 99 | gi|16330993| | ref|NP_441721.1|unknown protein [*Synechocystis* sp. PCC 6803] | CS | CK | HS | |
| 307 | 74139 | CGPG6561 | 1.00E−180 | 95 | gi|24112825| | ref|NP_707335.1|glyceraldehyde-3-phosphate dehydrogenase A [*Shigella flexneri* 2a str. 301] | CS | LL | | |
| 308 | 74267 | CGPG5364 | 0 | 97 | gi|18399375| | ref|NP_566402.1|U-box domain-containing protein [*Arabidopsis thaliana*] | CS | | | |
| 309 | 74291 | CGPG5363 | 0 | 94 | gi|18401867| | ref|NP_565676.1|armadillo/beta-catenin repeat family protein/U-box domain-containing protein [*Arabidopsis thaliana*] | CS | | | |
| 310 | 74318 | CGPG5826 | 0 | 100 | gi|15219730| | ref|NP_176847.1|cell division protein kinase, putative [*Arabidopsis thaliana*] | CS | HS | | |
| 311 | 74319 | CGPG5831 | 0 | 96 | gi|15224359| | ref|NP_181907.1|mitogen-activated protein kinase, putative/MAPK, putative (MPK6) [*Arabidopsis thaliana*] | CS | | | |
| 312 | 74324 | CGPG5885 | 1.00E−174 | 95 | gi|42569304| | ref|NP_180094.2|protein kinase family protein [*Arabidopsis thaliana*] | CS | | | |
| 313 | 74512 | CGPG32 | 0 | 96 | gi|15217945| | ref|NP_176132.1|amino acid permease T(AAP1) [*Arabidopsis thaliana*] | CS | HS | SP | |
| 314 | 74583 | CGPG6649 | 1.00E−151 | 83 | gi|22978283| | ref|ZP_00024043.1|COG02 52: L-asparaginase/archaeal Glu-tRNAGln amidotransferase subunit D [*Ralstonia metallidurans*] | CS | PP | | |
| 315 | 70427 | CGPG3067 | 0 | 100 | gi|42572771| | ref|NP_974481.1|kelch repeat-containing F-box family protein [*Arabidopsis thaliana*] | CS | DS | | |

TABLE 2-continued

| Pep SEQ Id | construct id | gene | e value | % identity | ncbi id | description | traits | | | |
|---|---|---|---|---|---|---|---|---|---|---|
| 316 | 71811 | CGPG4426 | 0 | 97 | gi\|15223341\| | ref\|NP_171627.1\|cytochrome P450, putative [*Arabidopsis thaliana*] | CS | DS | LL | LN |
| 317 | 73463 | CGPG6384 | 0 | 100 | gi\|22977164\| | ref\|ZP_00022985.1\|COG05 38: Isocitrate dehydrogenases [*Ralstonia metallidurans*] | DS | | | |
| 318 | 72081 | CGPG5279 | 7.00E−66 | 77 | gi\|42570373\| | ref\|NP_850277.2\|CCAAT-box binding transcription factor, putative [*Arabidopsis thaliana*] | DS | PEG | | |
| 319 | 10139 | CGPG101 | 0 | 89 | gi\|15229877\| | ref\|NP_187154.1\|sodium proton exchanger, putative (NHX2) [*Arabidopsis thaliana*] | DS | | | |
| 320 | 11410 | CGPG103 | 0 | 82 | gi\|15236418\| | ref\|NP_192555.1\|homeobox protein knotted-1 like 1 (KNAT1) [*Arabidopsis thaliana*] | DS | | | |
| 321 | 11604 | CGPG48 | 0 | 92 | gi\|15233457\| | ref\|NP_194642.1\|hexokinase 1 (HXK1) [*Arabidopsis thaliana*] | DS | | | |
| 322 | 12368 | CGPG1006 | 1.00E−146 | 85 | gi\|15231451\| | ref\|NP_190238.1\|epsin N-terminal homology (ENTH) domain-containing protein/ clathrin assembly protein-related [*Arabidopsis thaliana*] | DS | | | |
| 323 | 13502 | CGPG1354 | 0 | 95 | gi\|15224557\| | ref\|NP_180632.1\|serine/threonine protein kinase, putative [*Arabidopsis thaliana*] | DS | PP | | |
| 324 | 13745 | CGPG1576 | 1.00E−112 | 84 | gi\|15222987\| | ref\|NP_177749.1\|hypothetical protein [*Arabidopsis thaliana*] gb\|AAF17642.1\| T23E18.15 [*Arabidopsis thaliana*] | DS | | | |
| 325 | 13821 | CGPG1569 | 1.00E−155 | 85 | gi\|18416499\| | ref\|NP_567716.1\|expressed protein [*Arabidopsis thaliana*] | DS | | | |
| 326 | 14240 | CGPG1697 | 0 | 94 | gi\|15241302\| | ref\|NP_197527.1\|expressed protein [*Arabidopsis thaliana*] | DS | | | |
| 327 | 14718 | CGPG1082 | 0 | 86 | gi\|18407200\| | ref\|NP_566090.1\|expressed protein [*Arabidopsis thaliana*] | DS | | | |
| 328 | 17022 | CGPG1774 | 1.00E−159 | 100 | gi\|15237803\| | ref\|NP_197755.1\|nodulin MtN3 family protein [*Arabidopsis thaliana*] | DS | | | |
| 329 | 17924 | CGPG2882 | 3.00E−92 | 100 | gi\|15233350\| | ref\|NP_192875.1\|zinc finger (C3HC4-type RING finger) family protein (RHA1b) [*Arabidopsis thaliana*] | DS | | | |
| 330 | 18259 | CGPG3368 | 2.00E−94 | 88 | gi\|30685085\| | ref\|NP_849549.1\|zinc finger protein (LSD1) [*Arabidopsis thaliana*] | DS | PP | | |
| 331 | 19171 | CGPG2952 | 0 | 91 | gi\|6320063\| | ref\|NP_010143.1\|plasma membrane glucose sensor; Rgt2p [*Saccharomyces cerevisiae*] | DS | | | |
| 332 | 19201 | CGPG2332 | 0 | 95 | gi\|15233948\| | ref\|NP_194205.1\|protein kinase (AFC2) [*Arabidopsis thaliana*] sp\|P51567\|AFC2_ARATH Protein kinase | DS | | | |
| 333 | 19317 | CGPG3662 | 1.00E−151 | 91 | gi\|21232858\| | ref\|NP_638775.1\|conserved hypothetical protein [*Xanthomonas campestris* pv. *campestris* str. ATCC 33913] | DS | | | |
| 334 | 70417 | CGPG3427 | 0 | 81 | gi\|18396278\| | ref\|NP_566180.1\|integral membrane family protein [*Arabidopsis thaliana*] | DS | PP | SP | |
| 335 | 70467 | CGPG3785 | 0 | 100 | gi\|15241416\| | ref\|NP_196953.1\|no apical meristem (NAM) family | DS | | | |

TABLE 2-continued

| Pep SEQ Id | construct id | gene | e value | % identity | ncbi id | description | traits | | |
|---|---|---|---|---|---|---|---|---|---|
| 336 | 70806 | CGPG712 | 0 | 100 | gi\|15218225\| | ref\|NP_173010.1\|cyclin, putative [*Arabidopsis thaliana*] | DS | | |
| 337 | 70818 | CGPG479 | 1.00E−157 | 92 | gi\|30691978\| | ref\|NP_568508.2\|bZIP transcription factor family protein [*Arabidopsis thaliana*] | DS | | |
| 338 | 70820 | CGPG655 | 0 | 93 | gi\|15224342\| | ref\|NP_181899.1\|acyl-[acyl-carrier-protein] desaturase/ stearoyl-ACP desaturase (SSI2) [*Arabidopsis thaliana*] | DS | | |
| 339 | 70919 | CGPG4029 | 1.00E−169 | 73 | gi\|6996560\| | emb\|CAB75429.1\|oligouridylate binding protein [*Nicotiana plumbaginifolia*] | DS | | |
| 340 | 71623 | CGPG4696 | 1.00E−150 | 95 | gi\|15236511\| | ref\|NP_192588.1\|mitogen-activated protein kinase, putative [*Arabidopsis thaliana*] pir\|\|T01835 serine/threonine-specific protein kinase ARA.KIN homolog T15F16.3-*Arabidopsis thaliana* | DS | | |
| 341 | 71662 | CGPG4679 | 1.00E−173 | 91 | gi\|5929964\| | gb\|AAD56659.1\|malate dehydrogenase [*Glycine max*] | DS | | |
| 342 | 71693 | CGPG4652 | 6.00E−86 | 56 | gi\|21553460\| | gb\|AAM62553.1\|snap25a [*Arabidopsis thaliana*] | DS | | |
| 343 | 72384 | CGPG4639 | 0 | 98 | gi\|1169548\| | sp\|P38604\|ERG7_YEASTLa-nosterol synthase (Oxidosqualene-lanosterol cyclase) (2,3-epoxysqualene--lanosterol cyclase) (OSC) gb\|AAA64377.1\| 2,3-oxidosqualene-lanosterol cyclase | DS | | |
| 344 | 72439 | CGPG5075 | 8.00E−57 | 90 | gi\|22331337\| | ref\|NP_683594.1\|NPR1/ NIM1-interacting protein 2 (NIMIN-2) | DS | | |
| 345 | 72619 | CGPG4835 | 6.00E−83 | 88 | gi\|15237317\| | ref\|NP_200108.1\|expressed protein [*Arabidopsis thaliana*] | DS | | |
| 346 | 72624 | CGPG4842 | 0 | 100 | gi\|15242148\| | ref\|NP_200558.1\|expressed protein [*Arabidopsis thaliana*] | DS | | |
| 347 | 72715 | CGPG5521 | 0 | 91 | gi\|6323933\| | ref\|NP_014004.1\|Carboxy-terminal domain (CTD) phosphatase, essential for dephosphorylation of the repeated C-terminal domain of the RNA polymerase II large subunit (Rpo21p); Fcp1p [*Saccharomyces cerevisiae*] | DS | SS | |
| 348 | 72754 | CGPG5548 | 1.00E−169 | 100 | gi\|728961\| | sp\|Q00618\|BET4_YEASTGe-ranylgeranyl transferase type II alpha subunit (Type II protein geranyl- | DS | | |
| 349 | 72819 | CGPG4989 | 0 | 100 | gi\|18417026\| | ref\|NP_567780.1\|pfkB-type carbohydrate kinase family protein [*Arabidopsis thaliana*] | DS | | |
| 350 | 75516 | CGPG7689 | 1.00E−138 | 70 | gi\|42568081\| | ref\|NP_197938.2\|zinc finger (C3HC4-type RING finger) family protein [*Arabidopsis thaliana*] | DS | | |
| 351 | 75701 | CGPG7856 | 8.00E−41 | 37 | gi\|15225413\| | ref\|NP_182037.1\|zinc finger (C2H2 type) family protein [*Arabidopsis thaliana*] | DS | LN | |
| 352 | 73515 | CGPG6473 | 1.00E−162 | 100 | gi\|16079626\| | ref\|NP_390450.1\|similar to 6-phosphogluconate | HS | CS | PEG |

TABLE 2-continued

| Pep SEQ Id | construct id | gene | e value | % identity | ncbi id | description | traits | | |
|---|---|---|---|---|---|---|---|---|---|
| | | | | | | dehydrogenase (pentose phosphate) [*Bacillus subtilis*] | | | |
| 353 | 74684 | CGPG6360 | 1.00E−64 | 100 | gi\|18390735\| | ref\|NP_563782.1\|expressed protein [*Arabidopsis thaliana*] | CS | HS | |
| 354 | 19542 | CGPG3069 | 0 | 90 | gi\|18403574\| | ref\|NP_564592.1\|F-box family protein [*Arabidopsis thaliana*] | HS | | |
| 355 | 19618 | CGPG3574 | 1.00E−121 | 100 | gi\|15218423\| | ref\|NP_177373.1\|trypsin and protease inhibitor family protein/Kunitz family protein [*Arabidopsis thaliana*] pir\|\|F96746 probable drought induced protein | HS | | |
| 356 | 19649 | CGPG3140 | 1.00E−141 | 87 | gi\|18412787\| | ref\|NP_567287.1\|vesicle-associated membrane family protein/VAMP family protein | HS | | |
| 357 | 19745 | CGPG3973 | 2.00E−60 | 46 | gi\|15239303\| | ref\|NP_201424.1\|expressed protein (*Arabidopsis thaliana*] | HS | | |
| 358 | 19768 | CGPG4096 | 1.00E−179 | 81 | gi\|25052804\| | gb\|AAN65180.1\|mitogen-activated protein kinase 4 [*Petroselinum crispum*] | HS | SS | |
| 359 | 19772 | CGPG3939 | 3.00E−82 | 79 | gi\|7488744\| | pir\|\|T09700MADS-box protein - alfalfa (fragment) gb\|AAB51377.1\| MADS-box protein [*Medicago sativa*] | HS | | |
| 360 | 19779 | CGPG4113 | 1.00E−153 | 89 | gi\|30681126\| | ref\|NP_196201.2\|phosphate translocator-related [*Arabidopsis thaliana*] | CS | HS | |
| 361 | 19833 | CGPG4074 | 1.00E−107 | 79 | gi\|6683777\| | gb\|AAF23363.1\|CAGL2 [*Cucumis sativus*] | CS | HS | PP |
| 362 | 19862 | CGPG3961 | 2.00E−89 | 56 | gi\|15229637\| | ref\|NP_188469.1\|no apical meristem (NAM) family protein [*Arabidopsis thaliana*] dbj\|BAB01106.1\| unnamed protein product [*Arabidopsis thaliana*] | HS | | |
| 363 | 19879 | CGPG4009 | 0 | 75 | gi\|18401703\| | ref\|NP_564504.1\|protein phosphatase 2C-related/ PP2C-related [*Arabidopsis thaliana*] | HS | CS | SS |
| 364 | 70445 | CGPG3728 | 2.00E−51 | 88 | gi\|30696602\| | ref\|NP_200357.2\|protease inhibitor/seed storage/lipid transfer protein (LTP) family protein [*Arabidopsis thaliana*] | HS | | |
| 365 | 70738 | CGPG3195 | 1.00E−96 | 100 | gi\|15234797\| | ref\|NP_194791.1\|expressed protein [*Arabidopsis thaliana*] | HS | PP | |
| 366 | 71437 | CGPG4043 | 1.00E−164 | 81 | gi\|15241535\| | ref\|NP_196433.1\|serine/ threonine protein kinase, putative [*Arabidopsis thaliana*] | HS | | |
| 367 | 71572 | CGPG4520 | 3.00E−83 | 92 | gi\|18403850\| | ref\|NP_565804.1\|expressed protein [*Arabidopsis thaliana*] | HS | | |
| 368 | 71617 | CGPG1227 | 0 | 100 | gi\|15236219\| | ref\|NP_195218.1\|1-phosphatidylinositol phosphodiesterase-related [*Arabidopsis thaliana*] | HS | CK | |
| 369 | 72532 | CGPG4780 | 1.00E−118 | 90 | gi\|15236659\| | ref\|NP_194120.1\|expressed protein [*Arabidopsis thaliana*] | HS | | |
| 370 | 72757 | CGPG5572 | 0 | 89 | gi\|15242402\| | ref\|NP_197088.1\|zinc finger protein CONSTANS (CO) [*Arabidopsis thaliana*] | HS | LL | PEG |
| 371 | 73412 | CGPG6448 | 0 | 99 | gi\|28867589\| | ref\|NP_790208.1\|glutamine synthetase, type I [*Pseudomonas syringae* pv. tomato str. DC3000] | HS | | |

TABLE 2-continued

| Pep SEQ Id | construct id | gene | e value | % identity | ncbi id | description | traits | | |
|---|---|---|---|---|---|---|---|---|---|
| 372 | 74102 | CGPG6550 | 1.00E−167 | 94 | gi|15614187| | ref|NP_242490.1|L-asparaginase [*Bacillus halodurans* C-125] | HS | | |
| 373 | 72633 | CGPG4853 | 1.00E−145 | 86 | gi|15238013| | ref|NP_199519.1|casein kinase II beta chain, putative [*Arabidopsis thaliana*] | CS | LL | PEG |
| 374 | 72456 | CGPG4745 | 1.00E−75 | 92 | gi|15239846| | ref|NP_196763.1|17.6 kDa class II heat shock protein (HSP17.6-CII) [*Arabidopsis thaliana*] | DS | LL | |
| 375 | 72963 | CGPG1746 | 1.00E−151 | 87 | gi|15222239| | ref|NP_172174.1|ovate family protein [*Arabidopsis thaliana*] | LL | LN | |
| 376 | 70426 | CGPG3199 | 8.00E−54 | 88 | gi|18397268| | ref|NP_564336.1|double-stranded DNA-binding family protein [*Arabidopsis thaliana*] | LL | | |
| 377 | 70772 | CGPG4627 | 1.00E−92 | 80 | gi|15220084| | ref|NP_173175.1|MADS-box protein (AGL100) [*Arabidopsis thaliana*] P | LL | | |
| 378 | 71137 | CGPG125 | 1.00E−111 | 90 | gi|15218957| | ref|NP_176202.1|two-component responsive regulator/response regulator 3 (ARR3) [*Arabidopsis thaliana*] | LL | | |
| 379 | 71529 | CGPG2808 | 1.00E−131 | 72 | gi|42562375| | ref|NP_174152.3|Dof-type zinc finger domain-containing protein [*Arabidopsis thaliana*] | LL | | |
| 380 | 71601 | CGPG1858 | 1.00E−168 | 92 | gi|15231425| | ref|NP_187378.1|transcriptional activator, putative [*Arabidopsis thaliana*] | LL | | |
| 381 | 72362 | CGPG983 | 1.00E−163 | 95 | gi|15242779| | ref|NP_200562.1|xyloglucan:xyloglucosyl transferase, putative/xyloglucan endotransglycosylase, putative/endo-xyloglucan transferase, putative [*Arabidopsis thaliana*] | LL | | |
| 382 | 72466 | CGPG4767 | 3.00E−60 | 83 | gi|15234046| | ref|NP_195030.1|glutaredoxin family protein [*Arabidopsis thaliana*] | CK | LL | PEG |
| 383 | 72524 | CGPG4770 | 1.00E−134 | 91 | gi|18412649| | ref|NP_567140.1|expressed protein [*Arabidopsis thaliana*] | CK | LL | |
| 384 | 73085 | CGPG5689 | 1.00E−134 | 100 | gi|16331347| | ref|NP_442075.1|triosephosphate isomerase [*Synechocystis* sp. PCC 6803] | LL | | |
| 385 | 74241 | CGPG5457 | 0 | 89 | gi|444790| | prf||1908224Anucleotide translocator | LL | | |
| 386 | 74247 | CGPG5475 | 1.00E−159 | 100 | gi|18411863| | ref|NP_565172.1|protein phosphatase 2C, putative/PP2C, putative [*Arabidopsis thaliana*] | LL | | |
| 387 | 74284 | CGPG5413 | 0 | 97 | gi|15230577| | ref|NP_190087.1|serine carboxypeptidase III, putative [*Arabidopsis thaliana*] | LL | | |
| 388 | 74652 | CGPG6168 | 1.00E−90 | 80 | gi|15235970| | ref|NP_194879.1|expressed protein [*Arabidopsis thaliana*] | LL | DS | |
| 389 | 70437 | CGPG3706 | 1.00E−172 | 100 | gi|30678824| | ref|NP_186983.2|short-chain dehydrogenase/reductase (SDR) family protein [*Arabidopsis thaliana*] | CK | LN | |
| 390 | 71633 | CGPG857 | 1.00E−100 | 86 | gi|6690274| | gb|AAF24061.1|v-SNARE AtVTI1a [*Arabidopsis thaliana*] | DS | LN | |
| 391 | 72948 | CGPG5617 | 0 | 94 | gi|15225456| | ref|NP_182059.1|leucine-rich repeat transmembrane protein kinase, putative [*Arabidopsis thaliana*] | LN | PEG | |

TABLE 2-continued

| Pep SEQ Id | construct id | gene | e value | % identity | ncbi id | description | traits | | | |
|---|---|---|---|---|---|---|---|---|---|---|
| 392 | 72519 | CGPG4749 | | | | | LN | SS | | |
| 393 | 10475 | CGPG399 | 1.00E−164 | 96 | gi|15240972| | ref|NP_195761.1|stress-responsive protein, putative [Arabidopsis thaliana] | LN | | | |
| 394 | 11120 | CGPG459 | 0 | 100 | gi|15227169| | ref|NP_179812.1|inositol-3-phosphate synthase isozyme 2/myo-inositol-1-phosphate synthase 2/MI-1-P synthase 2/IPS 2 [Arabidopsis thaliana] | LN | | | |
| 395 | 19736 | CGPG4129 | 2.00E−94 | 67 | gi|13346194| | gb|AAK19619.1|GHMYB9 [Gossypium hirsutum] | LN | | | |
| 396 | 71606 | CGPG4715 | 0 | 91 | gi|15218674| | ref|NP_171800.1|phototropic-responsive NPH3 family protein [Arabidopsis thaliana] | LN | | | |
| 397 | 71840 | CGPG4353 | 0 | 96 | gi|18401087| | ref|NP_566542.1|mitotic phosphoprotein N' end (MPPN) family protein [Arabidopsis thaliana] | DS | LL | LN | |
| 398 | 74240 | CGPG5454 | 1.00E−155 | 90 | gi|15233884| | ref|NP_194188.1|mitochondrial substrate carrier family protein [Arabidopsis thaliana] pir||T05577 uncoupling protein homolog F22K18.230 - Arabidopsis thaliana | CK | LN | | |
| 399 | 74331 | CGPG5834 | 0 | 94 | gi|15220416| | ref|NP_172003.1|protein kinase family protein [Arabidopsis thaliana] | LN | | | |
| 400 | 74610 | CGPG6048 | 1.00E−117 | 100 | gi|15217568| | ref|NP_172434.1|Ras-related GTP-binding protein, putative [Arabidopsis thaliana] sp|O04486|RB1C_ARATH Ras-related protein Rab11C | LL | LN | | |
| 401 | 75527 | CGPG7682 | 1.00E−55 | 65 | gi|15240946| | ref|NP_195750.1|phosphatidyl-ethanolamine-binding family protein [Arabidopsis thaliana] | LN | | | |
| 402 | 70681 | CGPG4584 | 9.00E−64 | 93 | gi|18411465| | ref|NP_567196.1|auxin-responsive family protein [Arabidopsis thaliana] | CK | PEG | | |
| 403 | 71663 | CGPG4638 | 0 | 93 | gi|21230153| | ref|NP_636070.1|conserved hypothetical protein [Xanthomonas campestris pv. campestris str. ATCC 33913] | CK | PEG | | |
| 404 | 72769 | CGPG5573 | 0 | 100 | gi|15225499| | ref|NP_182075.1|cytochrome P450, putative [Arabidopsis thaliana] | CK | PEG | | |
| 405 | 71508 | CGPG1541 | 2.00E−24 | 100 | gi|15241504| | sp|Q9SD80|OM05_ARATH Mitochondrial import receptor subunit TOM5 homolog (Translocase of outer membrane 5 kDa subunit homolog) | PEG | CS | SP | PEG |
| 406 | 74248 | CGPG5476 | 0 | 100 | gi|15226152| | ref|NP_180926.1|protein phosphatase 2C, putative/PP2C, putative [Arabidopsis thaliana] p | PEG | CS | | |
| 407 | 72771 | CGPG2166 | 5.00E−44 | 100 | gi|18395032| | ref|NP_564151.1|expressed protein [Arabidopsis thaliana] | PEG | CK | HS | SS |
| 408 | 72085 | CGPG5228 | 0 | 94 | gi|15241541| | ref|NP_199275.1|cytochrome P450 family protein [Arabidopsis thaliana] dbj|BAA98115.1|flavonoid 3',5'-hydroxylase-like; cytochrome P450 [Arabidopsis thaliana] | PEG | HS | | |
| 409 | 72744 | CGPG5563 | 1.00E−136 | 96 | gi|6321574| | ref|NP_011651.1|20S proteasome beta-type subunit; the only | HS | PEG | CK | |

TABLE 2-continued

| Pep SEQ Id | construct id | gene | e value | % identity | ncbi id | description | traits | | | |
|---|---|---|---|---|---|---|---|---|---|---|
| 410 | 73039 | CGPG810 | 0 | 96 | gi\|15242124\| | ref\|NP_197599.1\|molybdopterin biosynthesis CNX1 protein/molybdenum cofactor biosynthesis enzyme CNX1 (CNX1) [*Arabidopsis thaliana*] nonessential 20S subunit; Pre9p [*Saccharomyces cerevisiae*] | HS | PEG | | |
| 411 | 73054 | CGPG5754 | 2.00E−98 | 100 | gi\|6324827\| | ref\|NP_014896.1\|Nat5p [*Saccharomyces cerevisiae*] pir\|\|S67150 hypothetical protein YOR253w - yeast (*Saccharomyces cerevisiae*) | PEG | HS | SS | PEG |
| 412 | 73501 | CGPG6456 | 0 | 97 | gi\|15888752\| | ref\|NP_354433.1\|AGR_C_2 631p [*Agrobacterium tumefaciens* str. C58] sp\|Q8UFH1\|ENO_AGRT5 Enolase (2-phosphoglycerate dehydratase) (2-phospho-D-glycerate hydro-lyase) | HS | PEG | | |
| 413 | 19707 | CGPG4179 | 1.00E−86 | 49 | gi\|15236282\| | ref\|NP_195242.1\|O-methyltransferase family 2 protein [*Arabidopsis thaliana*] | PEG | CS | | |
| 414 | 19951 | CGPG3941 | 5.00E−91 | 54 | gi\|15221582\| | ref\|NP_177064.1\|basic helix-loop-helix (bHLH) family protein [*Arabidopsis thaliana*] | PEG | CK | | |
| 415 | 19967 | CGPG4032 | 1.00E−127 | 67 | gi\|4760710\| | dbj\|BAA77395.1\|SLL2-S9-protein [*Brassica rapa*] | PEG | | | |
| 416 | 70543 | CGPG3815 | 0 | 95 | gi\|15220994\| | ref\|NP_175222.1\|E2F transcription factor-2 (E2F2)/transcription factor E2Fc (E2Fc) [*Arabidopsis thaliana*] | PEG | CK | | |
| 417 | 70707 | CGPG1273 | 1.00E−108 | 100 | gi\|15219558\| | ref\|NP_177523.1\|Ssu72-like family protein [*Arabidopsis thaliana*] pir\|\|F96765 unknown protein F | PEG | | | |
| 418 | 70719 | CGPG1712 | 0 | 86 | gi\|18394560\| | ref\|NP_564043.1\|expressed protein [*Arabidopsis thaliana*] | PEG | | | |
| 419 | 71134 | CGPG817 | 8.00E−55 | 100 | gi\|15240471\| | ref\|NP_200327.1\|small ubiquitin-like modifier 2 (SUMO) [*Arabidopsis thaliana*] | PEG | HS | PP | |
| 420 | 71146 | CGPG2928 | 1.00E−86 | 92 | gi\|29165403\| | gb\|AAO65311.1\|MADS affecting flowering 3 variant II [*Arabidopsis thaliana*] | PEG | | | |
| 421 | 71660 | CGPG4690 | 3.00E−80 | 100 | gi\|18415773\| | ref\|NP_567637.1\|methionine sulfoxide reductase domain-containing protein/ SelR domain-containing protein [*Arabidopsis thaliana*] | PEG | | | |
| 422 | 72086 | CGPG5236 | 0 | 100 | gi\|15232215\| | ref\|NP_191556.1\|methylene-tetrahydrofolate reductase 1 (MTHFR1) [*Arabidopsis thaliana*] - | PEG | PP | PEG | |
| 423 | 72632 | CGPG4852 | 4.00E−99 | 90 | gi\|18425032\| | ref\|NP_569028.1\|expressed protein [*Arabidopsis thaliana*] | PEG | | | |
| 424 | 72716 | CGPG5529 | 2.00E−85 | 89 | gi\|6320196\| | ref\|NP_010276.1\|subunit of the Anaphase Promoting Complex; all known APC subunits co-immunoprecipitate with epitope-tagged Apc11p; Apc11p [*Saccharomyces cerevisiae*] | PEG | | | |

TABLE 2-continued

| Pep SEQ Id | construct id | gene | annotation e value | % identity | ncbi id | description | traits | | | | |
|---|---|---|---|---|---|---|---|---|---|---|---|
| 425 | 72723 | CGPG1848 | 0 | 97 | gi\|15237500\| | ref\|NP_199487.1\|human Rev interacting-like family protein/hRIP family protein [*Arabidopsis thaliana*] dbj\|BAB08919.1\| zinc finger protein Glo3-like [*Arabidopsis thaliana*] | PEG | | | | |
| 426 | 72987 | CGPG1787 | 5.00E−81 | 77 | gi\|15231568\| | ref\|NP_189282.1\|octicosa-peptide/Phox/Bem1p (PB1) domain-containing protein [*Arabidopsis thaliana*] | PEG | SP | | | |
| 427 | 74109 | CGPG6606 | 0 | 77 | gi\|37524479\| | ref\|NP_927823.1\|maltodextrin phosphorylase [*Photorhabdus luminescens* subsp. *laumondii* TTO1] | PEG | | | | |
| 428 | 74140 | CGPG6569 | 0 | 99 | gi\|15613102\| | ref\|NP_241405.1\|NADP-dependent aldehyde dehydrogenase [*Bacillus halodurans* C-125] | PEG | PP | PEG | | |
| 429 | 74191 | CGPG6597 | 0 | 96 | gi\|22960294\| | ref\|ZP_00007935.1\|COG1850: Ribulose 1,5-bisphosphate carboxylase, large subunit [*Rhodobacter sphaeroides*] | PEG | | | | |
| 430 | 74265 | CGPG5356 | 1.00E−117 | 100 | gi\|15237288\| | ref\|NP_197727.1\|GRAM domain-containing protein/ABA-responsive protein-related [*Arabidopsis thaliana*] | PEG | PP | PEG | | |
| 431 | 74369 | CGPG6076 | 2.00E−86 | 96 | gi\|18409647\| | ref\|NP_564994.1\|ubiquitin-conjugating enzyme family protein [*Arabidopsis thaliana*] | PEG | CK | PP | PEG | |
| 432 | 70217 | CGPG6 | 0 | 97 | gi\|15231536\| | ref\|NP_189259.1\|cytochrome P450 family protein [*Arabidopsis thaliana*] | CK | PP | SP | | |
| 433 | 72711 | CGPG1846 | 4.00E−75 | 79 | gi\|15221048\| | ref\|NP_175816.1\|transcription initiation factor IID (TFIID) 31 kDa subunit (TAFII-31) family protein [*Arabidopsis thaliana*] | CK | PP | SP | | |
| 434 | 70932 | CGPG4089 | 1.00E−129 | 56 | gi\|15223134\| | ref\|NP_177792.1\|expressed protein [*Arabidopsis thaliana*] | CS | HS | PP | | |
| 435 | 73518 | CGPG6497 | 1.00E−177 | 63 | gi\|22981996\| | ref\|ZP_00027327.1\|COG1012: NAD-dependent aldehyde dehydrogenases [*Burkholderia fungorum*] | CS | CK | PP | | |
| 436 | 19771 | CGPG4011 | 3.00E−90 | 80 | gi\|18418200\| | ref\|NP_568342.1\|rubredoxin family protein [*Arabidopsis thaliana*] dbj\|BAB10504.1\| gene_id: MKP11.2~unknown protein [*Arabidopsis thaliana*] g | PP | HS | SS | | |
| 437 | 73549 | CGPG6460 | 0 | 90 | gi\|37524978\| | ref\|NP_928322.1\|5-carboxymethyl-2-hydroxymuconate semialdehyde dehydrogenase [*Photorhabdus luminescens* subsp. *laumondii* TTO1] | HS | DS | PP | | |
| 438 | 72994 | CGPG5803 | 0 | 83 | gi\|6322702\| | ref\|NP_012776.1\|Vacuolar transporter, exports large neutral amino acids from the vacuole; member of a family of seven *S. cerevisiae* genes (AVT1-7) related to vesicular GABA-glycine transporters; Avt3p [*Saccharomyces cerevisiae*] | CK | PEG | CS | PP | PEG |
| 439 | 71928 | CGPG1617 | 0 | 100 | gi\|18394888\| | ref\|NP_564120.1\|catalase 3 (SEN2) [*Arabidopsis thaliana*] | CS | PEG | CK | PP | PEG |

TABLE 2-continued

| Pep SEQ Id | construct id | gene | e value | % identity | ncbi id | description | traits | | | | | |
|---|---|---|---|---|---|---|---|---|---|---|---|---|
| 440 | 72903 | CGPG5584 | 0 | 91 | gi\|6322293\| | ref\|NP_012367.1\|Histone methyltransferase with a role in transcriptional elongation, methylates a lysine residue of histone H3; associates with the C-terminal domain of Rpo21p; histone methylation activity is regulated by phosphorylation status of Rpo21p; Set2p [*Saccharomyces cerevisiae*] sp\|P46995\|SET2_YEAST SET domain protein 2 | PEG | PP | SS | | | |
| 441 | 73017 | CGPG5733 | 0 | 94 | gi\|6325368\| | ref\|NP_015436.1\|kinase required for late nuclear division; Dbf20p [*Saccharomyces cerevisiae*] | PEG | PP | PEG | | | |
| 442 | 74587 | CGPG6774 | 0 | 94 | gi\|17938451\| | ref\|NP_535240.1\|succinate semialdehyde dehydrogenase [*Agrobacterium tumefaciens* str. C58] | PEG | DS | HS | PP | SS | |
| 443 | 72453 | CGPG4735 | 6.00E−67 | 91 | gi\|15218924\| | ref\|NP_174236.1\|auxin-responsive family protein [*Arabidopsis thaliana*] pir\|\|A86417 probable auxin-induced protein, 45653-45228 | CK | PP | SP | SS | | |
| 444 | 72967 | CGPG5742 | 0 | 99 | gi\|6321525\| | ref\|NP_011602.1\|Cytosolic catalase T, has a role in protection from oxidative damage by hydrogen peroxide; Ctt1p [*Saccharomyces cerevisiae*] | CS | CK | HS | LL | PP | SS |
| 445 | 72961 | CGPG5591 | 0 | 95 | gi\|15228498\| | ref\|NP_86975.1\|UTP--glucose-1-phosphate uridylyltransferase, putative/ UDP-glucose pyrophosphorylase, putative/UGPase, putative [*Arabidopsis thaliana*] | PEG | SS | HS | PP | | |
| 446 | 73070 | CGPG5627 | 0 | 90 | gi\|15225044\| | ref\|NP_181451.1\|protein kinase family protein [*Arabidopsis thaliana*] | PEG | PP | SS | | | |
| 447 | 73475 | CGPG6385 | 0 | 100 | gi\|39934021\| | ref\|NP_946297.1\|glyceraldehyde-3-phosphate dehydrogenase(GAPDH) [*Rhodopseudomonas palustris* CGA009] | PEG | PP | SS | | | |
| 448 | 72916 | CGPG1814 | 0 | 97 | gi\|15228871\| | ref\|NP_188303.1\|protein phosphatase 2C, putative/ PP2C, putative [*Arabidopsis thaliana*] | PP | SS | | | | |
| 449 | 72969 | CGPG5789 | 0 | 94 | gi\|6321886\| | ref\|NP_011962.1\|Low-affinity glucose transporter of the major facilitator superfamily, expression is induced by Hxk2p in the presence of glucose and repressed by Rgt1p when glucose is limiting; Hxt1p [*Saccharomyces cerevisiae*] | PP | SP | SS | | | |
| 450 | 74449 | CGPG6659 | 0 | 96 | gi\|15890426\| | ref\|NP_356098.1\|AGR_L_6 19p [*Agrobacterium tumefaciens* str. C58] pir\|\|A98170 hypothetical protein AGR_L_619 [imported] - *Agrobacterium* | PP | SS | | | | |
| 451 | 16615 | CGPG2539 | 0 | 98 | gi\|15890896\| | ref\|NP_356568.1\|AGR_L_1 560p [*Agrobacterium* | PP | | | | | |

TABLE 2-continued

| Pep SEQ Id | construct id | gene | e value | % identity | ncbi id | description | traits | | |
|---|---|---|---|---|---|---|---|---|---|
| | | | | | | *tumefaciens* str. C58] ref|NP_534561.1| glucose-1-phosphate adenylyltransferase [*Agrobacterium tumefaciens* str. C58] | | | |
| 452 | 19187 | CGPG3310 | 0 | 91 | gi|18423163| | ref|NP_568731.1|squamosa promoter-binding protein, putative [*Arabidopsis thaliana*] | PP | | |
| 453 | 19648 | CGPG3134 | 1.00E−179 | 96 | gi|18413950| | ref|NP_568102.1|short-chain dehydrogenase/reductase (SDR) family protein [*Arabidopsis thaliana*] | PP | | |
| 454 | 70864 | CGPG3995 | 0 | 64 | gi|15241312| | ref|NP_196916.1|nodulin family protein [*Arabidopsis thaliana*] | DS | PP | SP |
| 455 | 70421 | CGPG2946 | 0 | 88 | gi|30677077| | ref|NP_178317.2|zinc finger (C2H2 type) family protein [*Arabidopsis thaliana*] | PP | | |
| 456 | 70459 | CGPG3758 | 0 | 95 | gi|15233315| | ref|NP_188242.1|F-box family protein [*Arabidopsis thaliana*] dbj|BAB01261.1| unnamed protein product [*Arabidopsis thaliana*] | PP | | |
| 457 | 70465 | CGPG3775 | 1.00E−155 | 90 | gi|15236937| | ref|NP_195254.1|zinc finger (C2H2 type) family protein [*Arabidopsis thaliana*] | PP | SP | |
| 458 | 70683 | CGPG4587 | 3.00E−65 | 64 | gi|18423239| | ref|NP_568751.1|polyadenylate-binding protein, putative/PABP, putative [*Arabidopsis thaliana*] | PP | | |
| 459 | 70725 | CGPG2097 | 0 | 91 | gi|18420505| | ref|NP_568066.1|expressed protein [*Arabidopsis thaliana*] | CS | PP | |
| 460 | 70852 | CGPG1465 | 0 | 93 | gi|15237075| | ref|NP_195290.1|isocitrate dehydrogenase, putative/ NAD+ isocitrate dehydrogenase, putative [*Arabidopsis thaliana*] | PP | SP | |
| 461 | 71112 | CGPG934 | 1.00E−130 | 94 | gi|15218701| | ref|NP_171806.1|expressed protein [*Arabidopsis thaliana*] pir||E86161 F10O3.11 protein - *Arabidopsis thaliana* gb|AAD25802.1| Belongs to the PF|01027 Uncharacterized protein family UPF0005 with 7 transmembrane domains. [*Arabidopsis thaliana*] | CS | PP | |
| 462 | 71127 | CGPG945 | 0 | 97 | gi|15225307| | ref|NP_179604.1|26S protease regulatory complex subunit 4, putative [*Arabidopsis thaliana*] pir||E84585 26S proteasome subunit 4 [imported] - *Arabidopsis thaliana* | PP | | |
| 463 | 71132 | CGPG1561 | 0 | 98 | gi|15232209| | ref|NP_191550.1|expressed protein [*Arabidopsis thaliana*] | PP | | |
| 464 | 71217 | CGPG95 | 0 | 100 | gi|15221476| | ref|NP_172127.1|shaggy-related protein kinase iota/ ASK-iota (ASK9) (GSK1) [*Arabidopsis thaliana*] (EC 2.7.1.—) | PP | | |
| 465 | 71645 | CGPG4688 | 3.00E−69 | 100 | gi|18401105| | ref|NP_566544.1|phospho-transfer family protein [*Arabidopsis thaliana*] | PP | | |
| 466 | 71726 | CGPG3894 | 0 | 93 | gi|15217677| | ref|NP_171725.1|no apical meristem (NAM) family protein [*Arabidopsis thaliana*] | HS | PP | |

TABLE 2-continued

| Pep SEQ Id | construct id | gene | e value | % identity | ncbi id | description | traits | | |
|---|---|---|---|---|---|---|---|---|---|
| 467 | 72432 | CGPG4562 | 1.00E−144 | 92 | gi\|20152540\| | emb\|CAD29662.1\|putative auxin response factor 23 [*Arabidopsis thaliana*] | PP | SP | |
| 468 | 72450 | CGPG4732 | 1.00E−170 | 100 | gi\|15238890\| | ref\|NP_197366.1\|zinc finger (C3HC4-type RING finger) family protein [*Arabidopsis thaliana*] | LL | PP | |
| 469 | 72455 | CGPG4742 | 1.00E−144 | 93 | gi\|15242893\| | ref\|NP_200597.1\|anthranilate synthase beta subunit, putative [*Arabidopsis thaliana*] | PP | PEG | |
| 470 | 72727 | CGPG5522 | 1.00E−118 | 100 | gi\|6324107\| | ref\|NP_014177.1\|functionally related to TFIIB, affects start site selection in vivo; Ssu72p [*Saccharomyces cerevisiae*] | PP | | |
| 471 | 72817 | CGPG4987 | 0 | 96 | gi\|30679158\| | ref\|NP_567238.2\|AAA-type ATPase family protein [*Arabidopsis*] | PP | | |
| 472 | 72992 | CGPG5777 | 0 | 90 | gi\|6324981\| | ref\|NP_015049.1\|S-adenosylMethionine Permease; Sam3p [*Saccharomyces cerevisiae*] | PP | PEG | |
| 473 | 73007 | CGPG5760 | 0 | 93 | gi\|6320865\| | ref\|NP_010944.1\|One of three possible beta-subunits of the Snf1 kinase complex, allows nuclear localization of the Snf1 kinase complex in the presence of a nonfermentable carbon source; contains glycogen-binding domain; Gal83p [*Saccharomyces cerevisiae*] | PP | | |
| 474 | 73073 | CGPG5688 | 0 | 95 | gi\|16331010\| | ref\|NP_441738.1\|fructose 1,6-bisphosphatase [*Synechocystis* sp. PCC 6803] | PP | | |
| 475 | 73506 | CGPG6496 | 0 | 96 | gi\|23062569\| | ref\|ZP_00087347.1\|COG1012: NAD-dependent aldehyde dehydrogenases [*Pseudomonas fluorescens* PfO-1] | PP | | |
| 476 | 74107 | CGPG6590 | 0 | 95 | gi\|15965198\| | ref\|NP_385551.1\|PYRUVATE DEHYDROGENASE ALPHA2 SUBUNIT PROTEIN [*Sinorhizobium meliloti* 1021] | PP | SS | |
| 477 | 74117 | CGPG6575 | 0 | 81 | gi\|37528116\| | ref\|NP_931461.1\|Phenylacet-aldehyde dehydrogenase (PAD) [*Photorhabdus luminescens* subsp. *laumondii* TTO1] | CS | PP | |
| 478 | 74131 | CGPG6592 | 0 | 96 | gi\|16329404\| | ref\|NP_440132.1\|transaldolase [*Synechocystis* sp. PCC 6803) B - | PP | SS | |
| 479 | 74344 | CGPG5929 | 1.00E−111 | 100 | gi\|15236410\| | ref\|NP_193147.1\|COP9 signalosome subunit, putative/CSN subunit, putative (CSN8) [*Arabidopsis thaliana*] | HS | PP | |
| 480 | 14320 | CGPG1229 | 0 | 100 | gi\|18418018\| | ref\|NP_567894.1\|expressed protein [*Arabidopsis thaliana*] | SP | | |
| 481 | 16756 | CGPG2117 | 1.00E−142 | 85 | gi\|18391249\| | ref\|NP_563885.1\|expressed protein [*Arabidopsis thaliana*] | SP | | |
| 482 | 17448 | CGPG2673 | 1.00E−102 | 72 | gi\|15239624\| | ref\|NP_197993.1\|PHD finger family protein [*Arabidopsis thaliana*] gb\|AAM64729.1\| nucleic acid binding protein-like [*Arabidopsis thaliana*] | SP | | |

TABLE 2-continued

| Pep SEQ Id | construct id | gene | annotation e value | annotation % identity | annotation ncbi id | annotation description | traits | |
|---|---|---|---|---|---|---|---|---|
| 483 | 17633 | CGPG2839 | 1.00E−145 | 85 | gi|18395124| | ref|NP_564171.1|basic helix-loop-helix (bHLH) family protein [*Arabidopsis thaliana*] | SP | |
| 484 | 18876 | CGPG3096 | 1.00E−172 | 89 | gi|18394949| | ref|NP_564133.1|transporter-related [*Arabidopsis thaliana*] pir||G86343 hypothetical protein T22I11.10 | SP | |
| 485 | 19120 | CGPG1976 | 0 | 100 | gi|15232345| | ref|NP_188710.1|fertilization-independent endosperm protein (FIE) [*Arabidopsis thaliana*] | SP | |
| 486 | 19221 | CGPG2958 | 1.00E−159 | 78 | gi|30690446| | ref|NP_182182.2|Dof zinc finger protein DAG2/Dof affecting germination 2 (DAG2) [*Arabidopsis thaliana*] | SP | |
| 487 | 70206 | CGPG4116 | 1.00E−139 | 64 | gi|18412918| | ref|NP_565249.1|phospholipid/glycerol acyltransferase family protein [*Arabidopsis* | SP | |
| 488 | 70223 | CGPG53 | 0 | 93 | gi|15240313| | ref|NP_198006.1|hexose transporter, putative [*Arabidopsis thaliana*] | SP | |
| 489 | 70347 | CGPG3147 | 1.00E−121 | 66 | gi|18416267| | ref|NP_567693.1|Dof-type zinc finger domain-containing protein [*Arabidopsis thaliana*] | SP | |
| 490 | 70406 | CGPG1687 | 0 | 93 | gi|18397470| | ref|NP_564354.1|early-responsive to dehydration stress protein (ERD4) [*Arabidopsis thaliana*] | SP | |
| 491 | 70469 | CGPG3791 | 1.00E−171 | 89 | gi|15237581| | ref|NP_198936.1|MADS-box family protein [*Arabidopsis thaliana*]. | SP | HS |
| 492 | 70564 | CGPG1864 | 0 | 89 | gi|15219067| | ref|NP_173589.1|SWIRM domain-containing protein/DNA-binding family protein gb|AAD41423.1| Contains similarity to gb|AF033823 moira protein from *Drosophila melanogaster* and contains a PF|00249 Myb-like DNA-binding domain. | SP | |
| 493 | 70601 | CGPG2917 | 0 | 91 | gi|15235140| | ref|NP_193702.1|zinc finger (C3HC4-type RING finger) family protein [*Arabidopsis thaliana*] pir||T04748 hypothetical protein T16H5.30 - *Arabidopsis thaliana* | SP | PP |
| 494 | 70612 | CGPG3721 | 0 | 96 | gi|18416732| | ref|NP_568256.1|conserved oligomeric Golgi complex component-related/COG complex component-related [*Arabidopsis thaliana*] | SP | |
| 495 | 70720 | CGPG1358 | 0 | 93 | gi|15238483| | ref|NP_198387.1|lectin protein kinase family protein [*Arabidopsis thaliana*] | SP | |
| 496 | 70735 | CGPG2661 | 1.00E−109 | 100 | gi|15231241| | ref|NP_187953.1|transcription initiation factor IID-1 (TFIID-1)/TATA-box factor 1/TATA sequence-binding protein 1 (TBP1) [*Arabidopsis thaliana*] | SP | |
| 497 | 70846 | CGPG377 | 1.00E−151 | 100 | gi|15221223| | ref|NP_177577.1|zinc finger (C3HC4-type RING finger) family protein [*Arabidopsis thaliana*] pir||D96772 probable RING zinc finger protein | SP | |

TABLE 2-continued

| Pep SEQ Id | construct id | gene | annotation e value | annotation % identity | annotation ncbi id | annotation description | traits | | | | |
|---|---|---|---|---|---|---|---|---|---|---|---|
| 498 | 70923 | CGPG4020 | 0 | 87 | gi|8132347| | gb|AAF73257.1|MAP kinase PsMAPK2 [*Pisum sativum*] | SP | | | | |
| 499 | 71149 | CGPG3457 | 0 | 83 | gi|20141566| | sp|P48001|HKL4_ARATHHomeobox protein knotted-1 like 4 (KNAT4) pir||T51795 HOMEOBOX PROTEIN KNOTTED-1 LIKE 4 (KNAT4) - | SP | | | | |
| 500 | 71608 | CGPG4687 | 0 | 100 | gi|15220438| | ref|NP_172008.1|ent-kaurenoic acid hydroxylase (KAO1)/cytochrome P450 88A3, putative (CYP88A3) [*Arabidopsis thaliana*] | SP | | | | |
| 501 | 71739 | CGPG4345 | 7.00E−89 | 80 | gi|18406944| | ref|NP_566061.1|expressed protein [*Arabidopsis thaliana*] | SP | | | | |
| 502 | 72014 | CGPG5230 | 0 | 100 | gi|25410898| | pir||D84423probable WD-40-repeat protein [imported] - *Arabidopsis thaliana* gb|AAD14533.1| putative stress protein [*Arabidopsis thaliana*] | SP | | | | |
| 503 | 72051 | CGPG5241 | 0 | 93 | gi|18401606| | ref|NP_566585.1|cyclic nucleotide-binding transporter 1/CNBT1 (CNGC20) [*Arabidopsis thaliana*] sp|Q9LD37|CG20_ARATH Probable cyclic nucleotide-gated ion channel 20, chloroplast precursor (Cyclic nucleotide-binding transporter 1) | SP | | | | |
| 504 | 74259 | CGPG5343 | 0 | 96 | gi|15222882| | ref|NP_175431.1|branched-chain amino acid aminotransferase 6/ branched-chain amino acid transaminase 6 (BCAT6) [*Arabidopsis thaliana*] s | CS | HS | SS | | |
| 505 | 72463 | CGPG4760 | 8.00E−48 | 100 | gi|15236351| | ref|NP_193115.1|auxin-responsive protein, putative [*Arabidopsis thaliana*] | CS | SS | HS | LN | PP |
| 506 | 72902 | CGPG5597 | 0 | 88 | gi|15240576| | ref|NP_199800.1|chloride channel protein (CLC-c) [*Arabidopsis thaliana*] sp|Q96282|CLCC_ARATH Chloride channel protein CLC-c (AtCLC-c) | SS | CS | DS | | |
| 507 | 74572 | CGPG6640 | 1.00E−109 | 93 | gi|16331001| | ref|NP_441729.1|unknown protein [*Synechocystis* sp. PCC 6803] | CS | PP | SS | | |
| 508 | 73055 | CGPG5768 | 0 | 97 | gi|6321588| | ref|NP_011665.1|Hypothetical ORF; Ygr149wp [*Saccharomyces cerevisiae*] | SS | CS | HS | | |
| 509 | 74103 | CGPG6558 | 0 | 99 | gi|15833050| | ref|NP_311823.1|fructose-bisphosphate aldolase class II [*Escherichia coli* O157:H7] r | HS | PP | SS | | |
| 510 | 72921 | CGPG5781 | 0 | 93 | gi|6322892| | ref|NP_012965.1|general amino acid permease; Gap1p [*Saccharomyces cerevisiae*] | CK | PEG | SS | | |
| 511 | 72968 | CGPG5772 | 0 | 99 | gi|6321546| | ref|NP_011623.1|role in DNA replication during S phase; Clb6p [*Saccharomyces cerevisiae*] | PEG | LL | SS | | |
| 512 | 19703 | CGPG4172 | 0 | 83 | gi|7488676| | pir||T07150G-box binding factor 2A - soybean (fragment) gb|AAB00097.1| G-box binding factor | HS | SS | | | |
| 513 | 19946 | CGPG4097 | 1.00E−46 | 34 | gi|15219099| | ref|NP_175691.1|2-oxoglutarate-dependent | SS | | | | |

TABLE 2-continued

| Pep SEQ Id | construct id | gene | e value | % identity | ncbi id | description | traits | | |
|---|---|---|---|---|---|---|---|---|---|
| | | | | | | dioxygenase, putative (*Arabidopsis thaliana*) | | | |
| 514 | 19980 | CGPG3914 | 2.00E−63 | 49 | gi\|28629811\| | gb\|AAO45179.1\|transcription factor Myb1 [*Malus xiaojinensis*] | CS | SS | |
| 515 | 70435 | CGPG3701 | 1.00E−150 | 91 | gi\|15236597\| | ref\|NP_193499.1\|casein kinase II beta chain, putative [*Arabidopsis thaliana*] | SS | PP | SP |
| 516 | 71114 | CGPG1657 | 0 | 88 | gi\|30680729\| | ref\|NP_849990.1\|K + efflux antiporter, putative (KEA4) [*Arabidopsis thaliana*] | SS | | |
| 517 | 72451 | CGPG4733 | 0 | 94 | gi\|15239622\| | ref\|NP_197992.1\|mitochondrial substrate carrier family protein [*Arabidopsis thaliana*] | SS | | |
| 518 | 72947 | CGPG5607 | 3.00E−62 | 53 | gi\|1483230\| | emb\|CAA67968.1\|MADS4 protein [*Betula pendula*] | SS | | |
| 519 | 73012 | CGPG5786 | 0 | 97 | gi\|6324187\| | ref\|NP_014257.1\|belongs to a ubiquitous family of cytoplasmic membrane proteins that transport only ammonium (NH(4)(+) + NH(3)).; Mep2p [*Saccharomyces cerevisiae*] | SS | | |
| 520 | 73022 | CGPG5622 | 0 | 86 | gi\|15225518\| | ref\|NP_182083.1\|protein kinase family protein [*Arabidopsis thaliana*] | SS | | |
| 521 | 73488 | CGPG6394 | 1.00E−154 | 94 | gi\|16080620\| | ref\|NP_391447.1\|UTP-glucose-1-phosphate uridylyltransferase [*Bacillus subtilis*] | SS | CS | PP |
| 522 | 73901 | CGPG5237 | 0 | 92 | gi\|18400284\| | ref\|NP_565553.1\|extra-large guanine nucleotide binding protein/G-protein (XLG) | SS | | |
| 523 | 73964 | CGPG5804 | 0 | 88 | gi\|6319773\| | ref\|NP_009855.1\|Na+/Pi cotransporter, active in early growth phase; similar to phosphate transporters of *Neurospora crassa*; transcription regulated by inorganic phosphate concentrations and Pho4p; Pho89p [ | SS | | |
| 524 | 74019 | CGPG5706 | 2.00E−92 | 100 | gi\|16079815\| | ref\|NP_390639.1\|adenine phosphoribosyltransferase [*Bacillus subtilis*] | SS | | |
| 525 | 74022 | CGPG5724 | 0 | 97 | gi\|18378991\| | ref\|NP_563659.1\|glycosyl-hydrolase family 3 protein [*Arabidopsis thaliana*] | SS | SP | |
| 526 | 74114 | CGPG6551 | 0 | 99 | gi\|15888903\| | ref\|NP_354584.1\|AGR_C_2 921p [*Agrobacterium tumefaciens* str. C58] pir\|\|H97551 probable aminotransferase aatc | SS | | |
| 527 | 74262 | CGPG5353 | 0 | 100 | gi\|18416245\| | ref\|NP_568226.1\|histidinol-phosphate aminotransferase, putative [*Arabidopsis thaliana*] | SS | PP | |
| 528 | 74292 | CGPG5367 | 0 | 96 | gi\|15239204\| | ref\|NP_201393.1\|U-box domain-containing protein [*Arabidopsis thaliana*] | SS | | |
| 529 | 74302 | CGPG5384 | 1.00E−59 | 82 | gi\|25313155\| | pir\|\|A96787protein F10A5.6 [imported] - *Arabidopsis thaliana* | PP | SS | |
| 530 | 74325 | CGPG5898 | 1.00E−174 | 86 | gi\|15230382\| | ref\|NP_188576.1\|cinnamyl-alcohol dehydrogenase (CAD) [*Arabidopsis thaliana*] | SS | | |
| 531 | 74429 | CGPG6689 | 0 | 96 | gi\|16077873\| | ref\|NP_388687.1\|acetoin dehydrogenase E1 component (TPP- | SS | | |

TABLE 2-continued

| Pep SEQ Id | construct id | gene | e value | % identity | ncbi id | description | traits | | |
|---|---|---|---|---|---|---|---|---|---|
| 532 | 74440 | CGPG6682 | 6.00E−90 | 82 | gi\|15613838\| | ref\|NP_242141.1\|uridine kinase [*Bacillus halodurans* C-125] dependent alpha subunit) [*Bacillus subtilis*] | SS | | |
| 533 | 74462 | CGPG6668 | 5.00E−67 | 99 | gi\|16332127\| | ref\|NP_442855.1\|unknown protein [*Synechocystis* sp. PCC 6803] | HS | SS | |
| 534 | 74465 | CGPG6692 | 1.00E−119 | 99 | gi\|16078642\| | ref\|NP_389461.1\|similar to ribulose-5-phosphate 3-epimerase [*Bacillus subtilis*] | PP | SS | |
| 535 | 74474 | CGPG6669 | 2.00E−85 | 82 | gi\|16331209\| | ref\|NP_441937.1\|unknown protein [*Synechocystis* sp. PCC 6803] | LL | SS | |
| 536 | 74505 | CGPG6783 | 0 | 100 | gi\|16129426\| | ref\|NP_415984.1\|cryptic nitrate reductase 2 beta subunit [*Escherichia coli* K12] | SS | | |
| 537 | 74507 | CGPG6799 | 0 | 82 | gi\|27479656\| | gb\|AAO17183.1\|Orf17 [*Photorhabdus luminescens*] | SP | SS | |
| 538 | 74562 | CGPG6764 | 0 | 95 | gi\|16077501\| | ref\|NP_388315.1\|similar to pyruvate oxidase [*Bacillus subtilis*] | SS | | |

Screens for Identifying Trait Improving Genes

DS-Improvement of Drought Tolerance Identified by a Soil Drought Stress Tolerance Screen:

Drought is a water deficit condition that imposes osmotic stress on plants. Plants are particularly vulnerable to drought during the flowering stage. The drought condition in the screening process disclosed in Example 1B started from the flowering time and was sustained to the end of harvesting. The drought tolerance-imparting DNA defined for this invention are used in recombinant DNA constructs that improve plant survival rate under drought conditions. Exemplary recombinant DNA which has been identified for conferring such drought tolerance is identified as such in Table 2. Such identified recombinant DNA is useful in generating transgenic plants that are tolerant to the drought condition imposed during flowering time and in other stages of the plant life cycle. As demonstrated from the model plant screen, in some embodiments of transgenic plants with trait-improving recombinant DNA grown under such sustained drought condition also have increased total seed weight per plant in addition to the increased survival rate within a transgenic population, providing a higher yield potential as compared to control plants.

PEG-Improvement of Drought Tolerance Identified by PEG Induced Osmotic Stress Tolerance Screen:

Various drought levels can be artificially induced by using various concentrations of polyethylene glycol (PEG) to produce different osmotic potentials (Pilon-Smits et al., (1995) Plant Physiol. 107:125-130). Several physiological characteristics have been reported as being reliable indications for selection of plants possessing drought tolerance. These characteristics include the rate of seed germination and seedling growth. The traits can be assayed relatively easily by measuring the growth rate of seedling in PEG solution. Thus, a PEG-induced osmotic stress tolerance screen is a useful surrogate for drought tolerance screen. Certain embodiments of transgenic plants with trait-improving recombinant DNA identified in the PEG-induced osmotic stress tolerance screen survive drought conditions providing a higher yield potential as compared to control plants.

SS-Improvement of Drought Tolerance Identified by High Salinity Stress Tolerance Screen:

Three different factors are responsible for salt damages: (1) osmotic effects, (2) disturbances in the mineralization process, (3) toxic effects caused by the salt ions, e.g., inactivation of enzymes. While the first factor of salt stress results in the wilting of the plants that is similar to drought effect, the ionic aspect of salt stress is clearly distinct from drought. Exemplary recombinant DNA which has been identified to help plants maintain biomass, root growth and/or plant development in high salinity conditions are identified as such in Table 2. Since osmotic effect is one of the major components of salt stress, which is common to the drought stress, embodiments of trait-improving recombinant DNA identified in a high salinity stress tolerance screen also provide transgenic crops with improved drought tolerance. Embodiments of transgenic plants with trait-improving recombinant DNA identified in a high salinity stress tolerance screen survive drought conditions and/or high salinity conditions providing a higher yield potential as compared to control plants.

HS-Improvement of Drought Tolerance Identified by Heat Stress Tolerance Screen:

Heat and drought stress often occur simultaneously, limiting plant growth. Heat stress can cause the reduction in photosynthesis rate, inhibition of leaf growth and osmotic potential in plants. Thus, genes identified as heat stress tolerance conferring genes may also impart improved drought tolerance to plants. As demonstrated from the model plant screen, embodiments of transgenic plants with trait-improving recombinant DNA identified in a heat stress tolerance screen can survive better heat stress conditions and/or drought conditions providing a higher yield potential as compared to control plants.

CK and CS-Improvement of Tolerance to Cold Stress:

Low temperature may immediately result in mechanical constraints, changes in activities of macromolecules, and reduced osmotic potential. Two screening conditions, i.e., cold shock tolerance screen (CK) and cold germination tolerance screen (CS), were set up to look for transgenic plants that display visual growth advantage at lower temperature. In cold germination tolerance screen, the transgenic Arabidopsis plants were exposed to a constant temperature of 8 degrees C. from planting until day 28 post planting. The trait-improving recombinant DNA identified by such screen are particular useful for the production of transgenic plant that can germinate more robustly in a cold temperature as compared to the wild type plants. In cold shock tolerance screen, the transgenic plants were first grown under the normal growth temperature of 22 degrees C. until day 8 post planting, and subsequently were placed under 8 degrees C. until day 28 post planting. Embodiments of transgenic plants with trait-improving recombinant DNA identified in a cold shock stress tolerance screen and/or a cold germination stress tolerance screen survive cold conditions providing a higher yield potential as compared to control plants.

Improvement of Tolerance to Multiple Stresses:

Different kinds of stresses often lead to identical or similar reaction in the plants. Genes that are activated or inactivated as a reaction to stress can either act directly in a way the genetic product reduces a specific stress, or they can act indirectly by activating other specific stress genes. By manipulating the activity of such regulatory genes, i.e., multiple stress tolerance genes, plants are enabled to react to different kinds of stresses. For examples, DNA for expressing proteins of SEQ ID NO:352 and SEQ ID NO:353 is useful to improve both heat stress tolerance and cold stress tolerance in plants. Plants transformed with DNa for expressing protein of SEQ ID NO:508 resist heat stress, salt stress and cold stress. Thus, the disclosed stress tolerance conferring genes are useful in combinations to generate transgenic plants that resist multiple stress conditions.

PP-Improvement of Early Plant Growth and Development:

It is known in the art that to minimize the impact of disease on crop profitability, it is important to start the season with healthy vigorous plants. This means avoiding seed and seedling diseases, leading to increased nutrient uptake and increased yield potential. Traditionally early planting and applying fertilizer are the methods used for promoting early seedling vigor. In early development stage, plant embryos establish only the basic root-shoot axis, a cotyledon storage organ(s), and stem cell populations, called the root and shoot apical meristems, that continuously generate new organs throughout post-embryonic development. "Early growth and development" encompasses the stages of seed imbibition through the early vegetative phase. Certain DNA is identified as useful to produce transgenic plants that have advantages in one or more processes including, but not limited to, germination, seedling vigor, root growth and root morphology under non-stressed conditions. The transgenic plants starting from a more robust seedling are less susceptible to the fungal and bacterial pathogens that attach germinating seeds and seedling. Furthermore, seedlings with advantage in root growth are more resistant to drought stress due to extensive and deeper root architecture. Therefore, genes conferring the growth advantage in early stages to plants are used to generate transgenic plants that are more resistant to various stress conditions due to improved early plant development. Exemplary recombinant DNA that confers both stress tolerance and growth advantages to plants, is identified as such in Table 2, e.g., DNA encoding a protein of SEQ ID NO:444 can improve the plant early growth and development, and impart heat and cold tolerance to plants. Embodiments of transgenic plants with trait-improving recombinant DNA identified in the early plant development screen grow better under non-stress conditions and/or stress conditions providing a higher yield potential as compared to control plants.

SP-Improvement of Late Plant Growth and Development:

"Late growth and development" encompasses the stages of leaf development, flower production, and seed maturity. Transgenic plants with late growth and development advantages express DNA that is identified as such in Table 2. Such plants exhibit at least one phenotypic characteristics including, but not limited to, increased rosette radius, increased rosette dry weight, seed dry weight, silique dry weight, and silique length. For example, the rosette radius and rosette dry weight are used as the indexes of photosynthesis capacity, and thereby plant source strength and yield potential of a plant. Seed dry weight, silique dry weight and silique length are used as the indexes for plant sink strength, which are considered as the direct determinants of yield. Embodiments of transgenic plants with trait-improving recombinant DNA identified in the late development screen grow better and/or have improved development during leaf development and seed maturation providing a higher yield potential as compared to control plants.

LL-Improvement of Tolerance to Shade Stress Identified in a Low Light Screen:

The effects of light on plant development are especially prominent at the seedling stage. Under normal light conditions with unobstructed direct light, a plant seeding develops according to a characteristic photomorphogenic pattern, in which plants have open and expanded cotyledons and short hypocotyls. Then the plant's energy is devoted to cotyledon and leaf development while longitudinal extension growth is minimized. Under low light condition where light quality and intensity are reduced by shading, obstruction or high population density, a seedling displays a shade-avoidance pattern, in which the seedling displays a reduced cotyledon expansion, and hypocotyls extension is greatly increased. As the result, a plant under low light condition increases significantly its stem length at the expanse of leaf, seed or fruit and storage organ development, thereby adversely affecting of yield. Recombinant DNA that enables plants to have an attenuated shade avoidance response so that the source of plant can be contributed to reproductive growth efficiently provides embodiments of those plants with higher yield as compared to the wild type plants. Embodiments of transgenic plants with trait-improving recombinant DNA identified in a shade stress tolerance screen have attenuated shade response under shade conditions providing a higher yield potential as compared to control plants. The transgenic plants generated by this invention are suitable for a higher density planting, thereby resulting increased yield per unit area.

LN-Improvement of Tolerance to Low Nitrogen Availability Stress

Nitrogen is a key factor in plant growth and crop yield. The metabolism, growth and development of plants are profoundly affected by their nitrogen supply. Restricted nitrogen supply alters shoot to root ratio, root development, activity of enzymes of primary metabolism and the rate of senescence (death) of older leaves. All field crops have a fundamental dependence on inorganic nitrogenous fertilizer. Since fertilizer is rapidly depleted from most soil types, it must be supplied to growing crops two or three times during the growing season. Enhanced nitrogen use efficiency by plants should enable crops cultivated under low nitrogen availability stress condition resulted from low fertilizer input or poor soil quality.

Recombinant DNA that imparts enhanced nitrogen use efficiency in transgenic plants is identified in Table 2. Such plants exhibit one or more desirable traits including, but not limited to, increased seedling weight, increased number of green leaves, increased number of rosette leaves, altered root length and advanced flower bud formation. Such plants can also have altered amino acid or protein compositions, increased yield and/or better seed quality. Embodiments of such transgenic plants are productively cultivated under nitrogen nutrient deficient conditions, i.e., nitrogen-poor soils and low nitrogen fertilizer inputs that cause the growth of wild type plants to cease or to be so diminished as to make the wild type plants practically useless under such conditions. The transgenic plants also are advantageously used to achieve earlier maturing, faster growing, and/or higher yielding crops and/or produce more nutritious foods and animal feedstocks when cultivated using nitrogen non-limiting growth conditions.

Stacked Traits:

This invention also provides transgenic plants with stacked engineered traits, e.g., a crop having an improved phenotype resulting from expression of a trait-improving recombinant DNA, in combination with herbicide and/or pest resistance traits. For example, genes of the current invention can be stacked with other traits of agronomic interest, such as a trait providing herbicide resistance, for example a glyphosate resistance trait, or insect resistance, such as using a gene from *Bacillus thuringiensis* to provide resistance against lepidopteran, coliopteran, homopteran, hemiopteran, and other insects. Herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and gluphosinate herbicides. To illustrate that the production of transgenic plants with herbicide resistance is a capability of those of ordinary skill in the art, reference is made to U.S. 2003-0106096 A1 and 2002-0112260 A1 and U.S. Pat. Nos. 5,034,322; 5,776,760, 6,107,549 and 6,376,754, all of which are incorporated herein by reference. To illustrate that the production of transgenic plants with pest resistance is a capability of those of ordinary skill in the art reference is made to U.S. Pat. Nos. 5,250,515 and 5,880,275 which disclose plants expressing an endotoxin of *Bacillus thuringiensis* bacteria, to U.S. Pat. No. 6,506,599 which discloses control of invertebrates which feed on transgenic plants which express dsRNA for suppressing a target gene in the invertebrate, to U.S. Pat. No. 5,986,175 which discloses the control of viral pests by transgenic plants which express viral replicase, and to U.S. Patent Application Publication 2003/0150017 A1 which discloses control of pests by a transgenic plant which express a dsRNA targeted to suppressing a gene in the pest, all of which are incorporated herein by reference.

Once one recombinant DNA has been identified as conferring an improved trait of interest in transgenic *Arabidopsis* plants, several methods are available for using the sequence of that recombinant trait-imparting DNA and knowledge about the protein it encodes to identify homologs of that sequence from the same plant and different plant species or other organisms, e.g., bacteria and yeast. Thus, in one aspect, this invention provides methods for identifying a homologous gene with a DNA sequence homologous to any of SEQ ID NO:1 through SEQ ID NO:269, or a homologous protein with an amino acid sequence homologous to any of SEQ ID NO:270 through SEQ ID NO:538. In another aspect, this invention provides a consensus amino acid sequence for respective homologs for each of SEQ ID NO:270 through SEQ ID NO:538. In yet another aspect, this invention also includes linking or associating one or more desired traits, or gene function with a homolog sequence disclosed herein.

The trait-improving recombinant DNA and methods of using such trait-improving recombinant DNA for generating transgenic plants with improved traits provided by this invention are not limited to any particular plant species. Indeed, the plants of this invention encompass many species of monocots and dicots and include agriculturally useful plants which are cultivated for purposes of food production or industrial applications, e.g., corn and soybean plants and cotton plants. Recombinant DNA constructs optimized for soybean transformation and recombinant DNA constructs optimized for corn transformation are disclosed in the following examples. Other plants of this invention include canola, wheat, sunflower, sorghum, alfalfa, barley, millet, rice, tobacco, fruit and vegetable crops, and turfgrass.

Thus, embodiments of this invention include the use of both DNA identified herein and homologs in recombinant DNA for transgenic crop plants with improved traits. Transgenic crop plants with improved traits are identified from populations of plants grown from transgenic events by screening to segregate the plants of this invention from plants without the improved traits. Preferred screens for transgenic crop plants identify plants with improved responses to stress conditions, e.g., assays using imposed stress conditions to detect improved responses to drought stress, nitrogen deficiency, cold growing conditions, or alternatively, under naturally present stress conditions, for example under field conditions. Biomass measures are made on greenhouse or field grown plants and include such measurements as plant height, stem diameter, root and shoot dry weights, and, for corn plants, ear length and diameter.

Trait data on morphological changes is collected by visual observation during the process of plant regeneration as well as in regenerated plants transferred to soil. Such trait data includes characteristics such as normal plants, bushy plants, taller plants, thicker stalks, narrow leaves, striped leaves, knotted phenotype, chlorosis, albino, anthocyanin production, or altered tassels, ears or roots. Other enhanced traits are identified by measurements taken under field conditions, such as days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barrenness/prolificacy, green snap, and pest resistance. In addition, trait characteristics of harvested grain are confirmed, including number of kernels per row on the ear, number of rows of kernels on the ear, kernel abortion, kernel weight, kernel size, kernel density and physical grain quality.

To confirm hybrid yield in transgenic corn plants expressing trait-imparting DNA of this invention, it is useful to test hybrid plants over multiple years at multiple locations in a geographical location where corn is conventionally grown, e.g., in Iowa, Illinois and Kansas, under "normal" field conditions as well as under stress conditions, e.g., under drought or population density stress.

Transgenic crop plants are used to provide other aspects of this invention such as transgenic seeds of crop plants.

Seeds of transgenic plants are used to propagate more progeny plants which contain the trait-improving recombinant DNA constructs of this invention. These progeny plants are within the scope of this invention when they contain a trait-improving recombinant DNA construct of this invention, whether or not these plants are selfed or crossed with different varieties of plants.

Screening Methods for Crop Transgenic Plants with Enhanced Agronomic Trait

Due to variability in transformation many transgenic events which survive to fertile transgenic plants that produce seeds and progeny plants do not exhibit an enhanced agronomic trait. Thus, screening is necessary to identify the transgenic events that produce the transgenic plants and seeds of this invention. Transgenic crop plants having enhanced traits are identified from populations of plants transformed as described herein by evaluating the trait in a variety of assays to detect an enhanced agronomic trait. Useful assays include analyses to detect changes in the chemical composition, biomass, physiological properties and morphology of the plant. Changes in chemical compositions such as nutritional composition of grain are detected by analysis of the seed composition and content of protein, free amino acids, oil, free fatty acids, starch or tocopherols. Changes in biomass characteristics are detected in greenhouse or field grown plants and include plant height, stem diameter, root and shoot dry weights; and, for corn plants, ear length and diameter. Changes in physiological properties are identified by evaluating responses to stress conditions, e.g., assays using imposed stress conditions such as water deficit, nitrogen deficiency, cold growing conditions, pathogen or insect attack or light deficiency, or increased plant density. Changes in morphology are measured by visual observation of tendency of a transformed plant with an enhanced agronomic trait to also appear to be a normal plant as compared to changes toward bushy, taller, thicker, narrower leaves, striped leaves, knotted trait, chlorosis, albino, anthocyanin production, or altered tassels, ears or roots. Other screening properties include days to pollen shed, days to silking, leaf extension rate, chlorophyll content, leaf temperature, stand, seedling vigor, internode length, plant height, leaf number, leaf area, tillering, brace roots, stay green, stalk lodging, root lodging, plant health, barrenness/prolificacy, green snap, and pest resistance. In addition, phenotypic characteristics of harvested grain are evaluated, including number of kernels per row on the ear, number of rows of kernels on the ear, kernel abortion, kernel weight, kernel size, kernel density and physical grain quality.

Seeds for transgenic crop plants with enhanced agronomic traits of this invention are corn, soybean and cotton seeds, as well as seeds for canola, wheat, sunflower, sorghum, alfalfa, barley, millet, rice, tobacco, fruit and vegetable crops, and turfgrass.

A. Screening for Nitrogen Use Efficiency

Many transgenic crop plants of this invention exhibit enhanced nitrogen use efficiency as compared to control plants. Higher nitrogen soil applications increase seed protein and starch accumulation, and lead to larger seed weight and larger kernel number per ear. Recent improvements in elite high yielding corn hybrid genotypes include the ability to utilize nitrogen efficiently. DNA causing the enhanced nitrogen use efficiency in crop plants are especially useful, e.g., for improving yield. Enhanced nitrogen use efficiency is assessed by measuring changes in plant growth such as leaf area production, shoot biomass, chlorophyll content in plants grown in nitrogen limiting conditions and/or nitrogen sufficient conditions. It is useful to conduct a first screen in nitrogen limiting conditions and confirm replicate transgenic events in both nitrogen limiting and nitrogen sufficient conditions. Table 3 shows an amount of nutrients in the nutrient solution for nitrogen limiting conditions (low N) and nitrogen sufficient conditions (high N) which are useful for nitrogen use efficiency screening. For example in a greenhouse screen pots of transgenic plants and control plants are treated with 100 ml of nutrient solution three times a week on alternate days starting at 8 and 10 days after planting for high N and low N screening, respectively.

TABLE 3

| Nutrient stock | 2 mM $NH_4NO_3$ Low nitrogen | 20 mM $NH_4NO_3$ High nitrogen |
|---|---|---|
| 1M $NH_4NO_3$ | 2 mL/L | 20 mL/L |
| 1M $KH_2PO_4$ | 0.5 | 0.5 |
| 1M $MgSO_4 \cdot 7H_2O$ | 2 | 2 |
| 1M $CaCl_2$ | 2.5 | 2.5 |
| 1M $K_2SO_4$ | 1 | 1 |

Note:
Adjust pH to 5.6 with HCl or KOH

After 28 days of plant growth for low N screening and 23 days for high N screening, measurements are taken for total shoot fresh mass, leaf chlorophyll, leaf area, leaf fresh mass and leaf dry mass.

B. Screening for Increased Yield

Many transgenic plants of this invention exhibit improved yield as compared to a control plant. Improved yield can result from a variety or other traits such as enhanced seed sink potential, e.g., the number and size of endosperm cells or kernels, and/or enhanced sink strength, e.g., the rate of starch biosynthesis. Sink potential is established very early during kernel development, as endosperm cell number and cell size are determined within the first few days after pollination.

Much of the increase in corn yield of the past several decades has resulted from an increase in planting density. During that period, corn yield has been increasing at a rate of 2.1 bushels/acre/year, but the planting density has increased at a rate of 250 plants/acre/year. A characteristic of modern hybrid corn is the ability of these varieties to be planted at high density. Many studies have shown that a higher than current planting density should result in more biomass production, but current germplasm does not perform well at these higher densities. One approach to increasing yield is to increase harvest index (HI), the proportion of biomass that is allocated to the kernel compared to total biomass, in high density plantings.

Effective yield screening of transgenic corn uses hybrid progeny of the transgenic event over multiple locations with plants grown under optimal production management practices, and maximum pest control. A useful target for improved yield is a 5% to 10% increase in yield as compared to yield produced by plants grown from seed for a control plant. Useful screening in multiple and diverse geographic locations, e.g., up to 16 or more locations, over one or more planting seasons, e.g., at least two planting seasons, is useful to statistically distinguish yield improvement from natural environmental effects. Useful hybrid screening includes planting multiple transgenic plants, positive and negative control plants, and pollinator plants in standard plots, e.g., 2 row plots, 20 feet long by 5 feet wide with 30 inches distance between rows and a 3 foot alley between ranges. Plants from separate transgenic events can be grouped by recombinant DNA constructs with groups randomly placed in the field. A pollinator plot of a high quality corn line is planted for every two plots to allow open pollination when using male sterile transgenic events. A useful planting density is about 30,000 plants/acre.

Surrogate indicators for screening for yield improvement include source capacity (biomass), source output (sucrose and photosynthesis), sink components (kernel size, ear size, starch in the seed), development (light response, height, density tolerance), maturity, early flowering trait and physiological responses to high density planting, e.g., at 45,000 plants per acre.

When screening for yield improvement a useful statistical measurement approach comprises three components, i.e., modeling spatial autocorrelation of the test field separately for each location, adjusting traits of recombinant DNA events for spatial dependence for each location, and conducting an across location analysis.

A first step in modeling spatial autocorrelation is estimating the covariance parameters of the semivariogram. A spherical covariance model is assumed to model the spatial autocorrelation. Because of the size and nature of the trial, it is likely that the spatial autocorrelation may change. Therefore, anisotropy is also assumed along with spherical covariance structure. The following set of equations describes the statistical form of the anisotropic spherical covariance model.

$$C(h;\theta) = vI(h=0) + \sigma^2\left(1 - \frac{3}{2}h + \frac{1}{2}h^3\right)I(h<l),$$

where I(•) is the indicator function, $h=\sqrt{\dot{x}^2+\dot{y}^2}$, and $$\dot{x}=[\cos(\rho\pi/180)(x_1-x_2)-\sin(\rho\pi/180)(y_1-y_2)]/\omega_x$$

$$\dot{y}=[\sin(\rho\pi/180)(x_1-x_2)+\cos(\rho\pi/180)(y_1-y_2)]/\omega_y$$

where $s_1=(x_1, y_1)$ are the spatial coordinates of one location and $s_2=(x_2, y_2)$ are the spatial coordinates of the second location. There are 5 covariance parameters, $\theta=(v, \sigma^2, \rho, \omega_n, \omega_j)$, where v is the nugget effect, $\sigma^2$ is the partial sill, $\rho$ is a rotation in degrees clockwise from north, $\Omega_n$ is a scaling parameter for the minor axis and $\omega_j$ is a scaling parameter for the major axis of an anisotropical ellipse of equal covariance. The five covariance parameters that define the spatial trend will then be estimated by using data from heavily replicated pollinator plots via restricted maximum likelihood approach. In a multi-location field trial, spatial trend are modeled separately for each location.

After obtaining the variance parameters of the model, a variance-covariance structure is generated for the data set to be analyzed. This variance-covariance structure contains spatial information required to adjust yield data for spatial dependence. In this case, a nested model that best represents the treatment and experimental design of the study is used along with the variance-covariance structure to adjust the yield data. During this process the nursery or the seed batch effects can also be modeled and estimated to adjust the yields for any yield parity caused by seed batch differences.

After spatially adjusted data from different locations are generated, all adjusted data is combined and analyzed assuming locations as replications. In this analysis, intra and inter-location variances are combined to estimate the standard error of yield from transgenic plants and control plants. Relative mean comparisons are used to indicate statistically significant yield improvements.

C. Screening for Water Use Efficiency

Many transgenic crop plants of this invention exhibit improved yield resulting from improved water use efficiency and/or drought tolerance.

A greenhouse screen for transgenic corn plants for water use efficiency measures changes in plant growth rate, e.g., at least a 10% improvement, in height and biomass during a vegetative drought treatment, as compared to control plants. The hydration status of the shoot tissues following the drought is also measured. Shoot Initial Height (SIH) is plant height after 3 weeks of growth under optimum conditions. Shoot Wilt Height (SWH) is plant height at the end of a 6 day drought. Time course experiments have shown that at about 3 days of drought, wild type plants basically stop growing and begin to wilt. Thus a transgenic plant with improved water use efficiency will continue to grow (probably to a lesser extent than with water) and thereby end up as a significantly taller plant at the end of a drought experiment. Shoot Wilt Mass (SWM) is the amount of wet and dry matter in the shoot (plant separated from root ball at the soil line) at the end of the drought; SDM is measure after 2 to 3 weeks in a drying chamber. Shoot Turgid mass (STM) is the SWM plus the mass of the water that is transported into plant tissues in 3 days of soaking in 40 degree C. water in the dark. Experiments show that most of the water is pulled up in 24 hours but it takes 2 more days before additional increase becomes insignificant. STM-SWM is indicative of water use efficiency in plants where recovery from stress is more important than stress tolerance per se. Relative water content (RWC) is a measurement of how much (%) of the plant is water at harvest. RWC=(SWM−SDM)/(STM−SDM)*100. Fully watered corn plants are about 98% RWC. Typically, in a wilt screen the plants are about 60% RWC. Plants with higher RWC at the end of a drought are considered to be healthier plants and more fit for post-drought recovery and growth.

Relative Growth Rate (RGR) is calculated for each shoot using the formula RGR=(SWH−SIH)/((SWH+SIH)/2)*100

D. Screening for Growth Under Cold Stress

Many transgenic crop plants of this invention exhibit improved growth under cold stress, e.g., in a cold germination assay, in a cold shock assay, in an early seedling growth assay and in root-shoot biomass assay.

In a cold germination assay transgenic seeds from transgenic plants, e.g., R2 inbred seeds or F1 hybrid seeds, seeds of two types of control plants, e.g., negative segregants from the transgenic event or wild type, non-transgenic seeds of the transformed genotype, are treated with fungicide. A useful fungicide such as Captan fungicide (available from Arvesta Corp as MAESTRO® 80DF Fungicide) is applied at the rate of 0.43 mL Captan per 45 g of corn seeds which are dried to provide fungicide-coated seeds.

In a useful cold screen for transgenic corn seeds ten seeds per transgenic event are placed on filter paper (e.g., Whatman No. 1) in the lid of a Petri dish with 5 ml of water. A closed Petri dish is placed in a growth chamber set at 11 degrees C. for inbred corn seed or 9.5 degrees C. for hybrid corn seed. 2 ml of water is added on day 3 and day 10. Seeds are considered germinated if the emerged radical size is 1 cm. Cold seeds are scored every 2 days from day 10 up to day 30. Tissue samples are collected at random on the last day of the experiment for confirmation of RNA expression. A germination index (GI) is calculated as $$GI=(\Sigma([T+1-n_i]*[P_i-P_{i-1}]))/T$$

where "T" is the number of days for the experiment, "n" is the number of days after start, "i" is number of times germination is counted including the current day, "P" is the percentage of seed germinated during any given rating. Statistical differences are calculated between positive and wild type control.

In a cold shock assay, seeds are planted in potting media and placed in a growth chamber set at 23 degrees C., relative humidity of 65% with 12 hour day and night photoperiod (300 uE/m2-min). Planted seeds are watered for 20 minute every other day by sub-irrigation and flats are rotated every third day. On day 10 after planting the transgenic positive and wild type control plants are positioned in flats in an alternating pattern. Chlorophyll fluorescence of plants is measured on the tenth day during the dark period of growth by using a Walz PAM-2000 portable fluorometer following manufacturer's instructions. After chlorophyll measurements, leaf samples from each event are collected for confirming the expression of recombinant DNA. The plants are then exposed to temperatures of 5 degrees C. for 4 days. On the fourth day chlorophyll fluorescence is measured and plants are restored to a 23 degrees C. environment for recovery over 3 days. During the recovery period the length of the V3 leaf is measured on the first and third days. After two days of recovery V2 leaf damage is determined visually by estimating percent of green V2 leaf. Statistical differences in V3 leaf growth, V2 leaf necrosis and fluorescence during pre-shock and cold shock can be used for estimation of cold shock damage on corn plants.

In an early seedling growth assay three sets of seeds are assayed. The first set is a group of transgenic seeds from transgenic plants; the second set is negative segregants of the transgenic seed; and the third seed set is seed from two cold tolerant and two cold sensitive wild-type controls. All seeds are treated with a fungicide as indicated above. Seeds are grown in germination paper (12 inch×18 inch pieces of Anchor Paper #SD7606), wetted in a solution of 0.5% $KNO_3$ and 0.1% Thyram. For each paper fifteen seeds are placed on the line evenly spaced such that the radicals will grow toward the same edge. The wet paper is rolled up evenly and tight enough to hold the seeds in place. The roll is secured into place with two large paper clips, one at the top and one at the bottom. The rolls are incubated in a growth chamber at 23 degrees C. for three days in a randomized complete block design within an appropriate container. The chamber is set for 65% humidity with no light cycle. For the cold stress treatment the rolls are then incubated in a growth chamber at 12 degrees C. for fourteen days. The chamber is set for 65% humidity with no light cycle. For the warm treatment the rolls are incubated at 23 degrees C. for an additional two days. After the treatment the germination papers are unrolled and the seeds that did not germinate are discarded. The lengths of the radical and coleoptile for each seed are measured. A coleoptile sample is collected from six individual kernels of each entry for confirming the expression of recombinant DNA. Statistical differences in the length of radical and shoot during pre-shock and cold shock are used for an estimation of the effect of the cold treatment on corn plants. The analysis is conducted independently for the warm and cold treatments.

In a root-shoot biomass assay two sets of seeds are used. The first set is transgenic seeds with recombinant DNA, e.g., R2 inbred seeds or F1 hybrid seeds; the second seed set is non-transgenic, wild type negative control made from the same genotypes as the transgenic seeds. All seeds are treated with a fungicide as indicated above. The seeds are planted in potting media in pots arranged in a randomized complete block design with 6 replications. Pots are watered as and when needed by filling water up to the brim of the pot. Plants are grown in a greenhouse to a V6 stage or approximately for 28 days. Greenhouse lights are turned on after emergence of seedlings with 14 hours of light 10 hours of dark. Plants are fertilized twice each week with water-soluble fertilizer containing 200-ppm nitrogen. For measurement of root and shoot dry weight, two pots are separated carefully to remove adhering sand by washing with water. Washed roots are cut at the first node. The roots are placed in a paper bag after squeezing excess water, folded once and stapled. The shoots are then folded up to a convenient size (approximately 15 cm), placed in a paper bag. Bags are placed over a wire shelve to facilitate drying in a ventilated room maintained at 120 degrees F. to a moisture content of about 13% then weighed to determine dried root and shoot biomass.

E. Screen for Enhanced Oil, Starch, or Protein Levels in Plant Seeds

Oil concentrations are determined in kernels by Near Infrared Transmittance (NIT) from inbred and from hybrid lines. Data are also obtained for protein and starch content from this measurement.

Inbred Kernel Oil Screen

The primary transformants are selfed to produce R1 seed which is planted to segregating seed. An untransformed control line is planted every sixth row. All plants are self-pollinated. A molecular assay is conducted to determine zygosity of the transgene in each plant. Ears are harvested at maturity, and well-filled ears are chosen for proximate analysis. Proximate analysis is conducted on up to 5 homozygous ears. If 5 good homozygous ears are not available, then hemizygous ears will be used to obtain 5 good transgene-positive ears. Statistical analysis is conducted to determine whether proximate values for transgenic events are different from controls. Events with an increase in oil with a p-value of less than or equal to 0.1 are termed "putative leads." Kernel composition is confirmed in an inbred confirmation nursery which is conducted with selected events, and is run with a design similar to that of the Gen2 nursery. A "confirmed lead event" demonstrates an increase in oil with a p-value of less than or equal to 0.1 in two nurseries.

Hybrid Kernel Oil Screen

Grain samples from the multilocation hybrid yield trials are collected at the time of harvest and are analyzed by NIT. Controls are negative segregants, untransformed controls, or pollinators. Data from 3 to 12 locations are pooled for the statistical analysis. Putative leads have increased oil with a p-value of less than or equal to 0.1.

The various aspects of the invention are illustrated by means of the following examples which are in no way intended to limit the full breath and scope of claims.

Example 1. Identification of Recombinant DNA that Confers Improved Trait(s) to Plants A. Expression Constructs for *Arabidopsis* Plant Transformation Each gene of interest was amplified from a genomic or cDNA library using primers specific to sequences upstream and downstream of the coding region. Transformation vectors were prepared to constitutively transcribe DNA in either sense orientation (for enhanced protein expression) or anti-sense orientation (for endogenous gene suppression) under the control of an enhanced Cauliflower Mosaic Virus 35S promoter (U.S. Pat. No. 5,359,142) directly or indirectly (Moore, et al., PNAS 95:376-381, 1998; Guyer, et al., Genetics 149: 633-639, 1998; International patent application NO. PCT/EP98/07577). The transformation vectors also contain a bar gene as a selectable marker for resistance to glufosinate herbicide. The transformation of *Arabidopsis* plants was carried out using the vacuum infiltration method known in the art (Bethtold, et al., Methods Mol. Biol. 82:259-66, 1998). Seeds harvested from the plants, named as T1 seeds, were subsequently grown in a glufosinate-containing selective medium to select for plants which were actually transformed and which produced T2 transgenic seed.

B. Soil Drought Tolerance Screen

This example describes a soil drought tolerance screen to identify *Arabidopsis* plants transformed with recombinant DNA that wilt less rapidly and/or produce higher seed yield when grown in soil under drought conditions T2 seeds were sown in flats filled with Metro/Mix® 200 (The Scotts® Company, USA). Humidity domes were added to each flat and flats were assigned locations and placed in climate-controlled growth chambers. Plants were grown under a temperature regime of 22° C. at day and 20° C. at night, with a photoperiod of 16 hours and average light intensity of 170 μmol/m²/s. After the first true leaves appeared, humidity domes were removed. The plants were sprayed with glufosinate herbicide and put back in the growth chamber for 3 additional days. Flats were watered for 1 hour the week following the herbicide treatment. Watering was continued every seven days until the flower bud primordia became apparent, at which time plants were watered for the last time.

To identify drought tolerant plants, plants were evaluated for wilting response and seed yield. Beginning ten days after the last watering, plants were examined daily until 4 plants/ line had wilted. In the next six days, plants were monitored for wilting response. Five drought scores were assigned according to the visual inspection of the phenotypes: 1 for healthy, 2 for dark green, 3 for wilting, 4 severe wilting, and 5 for dead. A score of 3 or higher was considered as wilted.

At the end of this assay, seed yield measured as seed weight per plant under the drought condition was characterized for the transgenic plants and their controls and analyzed as a quantitative response according to example 1M.

Two approaches were used for statistical analysis on the wilting response. First, the risk score was analyzed for wilting phenotype and treated as a qualitative response according to the example 1L. Alternatively, the survival analysis was carried out in which the proportions of wilted and non-wilted transgenic and control plants were compared over each of the six days under scoring and an overall log rank test was performed to compare the two survival curves using S-PLUS statistical software (S-PLUS 6, Guide to statistics, Insightful, Seattle, Wash., USA). Table 4 provides a list of recombinant DNA constructs that improve drought tolerance in transgenic plants.

TABLE 4

| Pep SEQ ID | Construct_id | Gene | Orientation | Wilt Response Risk score | | | Seed Weight/ plant | | | Survival Anaysis of wilt response diff | | |
|---|---|---|---|---|---|---|---|---|---|---|---|---|
| | | | | RS mean | p-value | c | delta | p-value | c | time to wilting | p-value | c |
| 319 | 10139 | CGPG101 | ANTI-SENSE | 0.115 | 0.024 | S | −0.123 | 0.804 | / | −0.01 | 0.469 | / |
| 320 | 11410 | CGPG103 | SENSE | 0.226 | 0.003 | S | −0.366 | 0.926 | / | 0 | 1 | / |
| 321 | 11604 | CGPG48 | ANTI-SENSE | 0.25 | 0.034 | S | 0.257 | 0.01 | S | −0.24 | 0.38 | / |
| 322 | 12368 | CGPG1006 | SENSE | 0.148 | 0.044 | S | 0.359 | 0.02 | S | −0.06 | 0.764 | / |
| 323 | 13502 | CGPG1354 | SENSE | 0.431 | 0 | S | 0.624 | 0 | S | 1.34 | 0.366 | / |
| 324 | 13745 | CGPG1576 | ANTI-SENSE | −0.021 | 0.711 | / | 0.664 | 0 | S | −0.29 | 0.453 | / |
| 325 | 13821 | CGPG1569 | SENSE | 0.135 | 0.025 | S | 0.128 | 0.402 | / | 0.24 | 0.972 | / |
| 326 | 14240 | CGPG1697 | SENSE | 0.377 | 0.002 | S | −1.305 | 0.991 | / | 0 | 1 | / |
| 327 | 14718 | CGPG1082 | SENSE | 0.168 | 0.001 | S | 0.135 | 0.351 | / | 0.25 | 0.208 | / |
| 328 | 17022 | CGPG1774 | SENSE | 0.06 | 0.124 | T | 0.563 | 0.043 | S | 0 | 0.961 | / |
| 329 | 17924 | CGPG2882 | SENSE | −0.093 | 0.914 | / | 0.288 | 0.021 | S | 0.09 | 0.935 | / |
| 330 | 18259 | CGPG3368 | SENSE | 0.07 | 0.28 | / | 0.391 | 0.058 | T | −0.27 | 0.591 | / |
| 331 | 19171 | CGPG2952 | SENSE | 0.227 | 0.005 | S | 0.846 | 0.001 | S | 0.12 | 0.543 | / |
| 332 | 19201 | CGPG2332 | SENSE | 0.124 | 0.027 | S | −0.435 | 0.785 | / | 0.35 | 0.256 | / |
| 333 | 19317 | CGPG3662 | SENSE | 0.338 | 0 | S | −0.071 | 0.61 | / | 0.63 | 0.106 | T |
| 334 | 70417 | CGPG3427 | SENSE | 0.253 | 0.016 | S | −1.424 | 0.984 | / | 0 | 1 | / |
| 315 | 70427 | CGPG3067 | SENSE | −0.033 | 0.818 | / | 1.004 | 0.002 | S | 0.01 | 0.977 | / |
| 335 | 70467 | CGPG3785 | SENSE | 0.127 | 0.023 | S | −0.448 | 0.946 | / | 0.71 | 0.046 | S |
| 336 | 70806 | CGPG712 | SENSE | 0.246 | 0.046 | S | 0.174 | 0.276 | / | 0.14 | 0.07 | T |
| 337 | 70818 | CGPG479 | SENSE | 0.07 | 0.115 | T | 0.558 | 0.009 | S | 0.61 | 0.283 | / |
| 338 | 70820 | CGPG655 | SENSE | 0.172 | 0.048 | S | 0.036 | 0.441 | / | 0.26 | 0.554 | / |
| 339 | 70919 | CGPG4029 | SENSE | 0.167 | 0.009 | S | −0.565 | 0.904 | / | 0.31 | 0.508 | / |
| 340 | 71623 | CGPG4696 | SENSE | 0.158 | 0.047 | S | 0.421 | 0.04 | S | 0 | 1 | / |
| 390 | 71633 | CGPG857 | SENSE | 0.121 | 0.017 | S | −0.823 | 0.967 | / | 0.45 | 0.139 | T |
| 341 | 71662 | CGPG4679 | SENSE | 0.063 | 0.013 | S | −0.037 | 0.631 | / | 0.16 | 0.957 | / |
| 342 | 71693 | CGPG4652 | SENSE | 0.074 | 0.042 | S | 0.246 | 0.06 | T | 0.34 | 0.616 | / |
| 316 | 71811 | CGPG4426 | SENSE | 0.359 | 0.015 | S | −0.729 | 0.903 | / | 0.15 | 0.822 | / |
| 318 | 72081 | CGPG5279 | SENSE | 0.269 | 0.005 | S | −0.372 | 0.987 | / | 0.17 | 0.404 | / |
| 343 | 72384 | CGPG4639 | SENSE | 0.133 | 0.018 | S | 0.62 | 0.002 | S | 0.17 | 0.359 | / |
| 344 | 72439 | CGPG5075 | SENSE | 0.175 | 0.013 | S | −0.035 | 0.604 | / | 0.23 | 0.244 | / |
| 374 | 72456 | CGPG4745 | SENSE | 0.53 | 0.01 | S | −0.737 | 0.979 | / | −0.08 | 0.823 | / |
| 345 | 72619 | CGPG4835 | SENSE | 0.178 | 0.039 | S | 0.219 | 0.072 | T | 0.96 | 0.691 | / |
| 346 | 72624 | CGPG4842 | SENSE | 0.163 | 0.021 | S | 0.356 | 0.051 | T | 0.3 | 0.375 | / |
| 347 | 72715 | CGPG5521 | SENSE | 0.082 | 0.1 | T | 0.767 | 0.002 | S | 0.12 | 0.628 | / |
| 348 | 72754 | CGPG5548 | SENSE | 0.131 | 0.031 | S | −0.365 | 0.974 | / | 0 | 0.923 | / |
| 349 | 72819 | CGPG4989 | SENSE | 0.094 | 0.026 | S | 0.362 | 0.069 | T | 0.03 | 0.83 | / |

TABLE 4-continued

| Pep SEQ ID | Construct_id | Gene | Orientation | Wilt Response Risk score | | | Seed Weight/ plant | | | Survival Analysis of wilt response diff | | |
|---|---|---|---|---|---|---|---|---|---|---|---|---|
| | | | | RS mean | p-value | c | delta | p-value | c | time to wilting | p-value | c |
| 350 | 75516 | CGPG7689 | SENSE | 0.067 | 0.066 | T | 0.965 | 0.001 | S | 0.24 | 0.464 | / |
| 351 | 75701 | CGPG7856 | SENSE | 0.147 | 0.006 | S | 0.986 | 0.015 | S | 0.15 | 0.448 | / |
| 317 | 73463 | CGPG6384 | SENSE | 0.174 | 0.048 | S | −1.359 | 0.959 | / | 0.09 | 0.984 | / |
| 454 | 70354 | CGPG3995 | SENSE | −0.005 | 0.563 | / | 0.444 | 0.002 | S | 10.29 | 0.9 | / |
| 397 | 71840 | CGPG4353 | SENSE | 0.142 | 0.007 | S | −0.212 | 0.859 | / | 9.29 | 0.99 | / |
| 506 | 72902 | CGPG5597 | SENSE | 0.009 | 0.162 | T | 0.034 | 0.2 | T | 5 | 1 | / |
| 437 | 73549 | CGPG6460 | SENSE | 0.119 | 0.037 | S | −0.774 | 0.949 | / | 6.26 | 0.25 | / |
| 302 | 73586 | CGPG6471 | SENSE | 0.003 | 0.451 | / | 0.588 | 0.002 | S | 6.34 | 0.723 | / |
| 442 | 74587 | CGPG6774 | SENSE | 0.262 | 0.001 | S | −0.117 | 0.574 | / | 7.49 | 0.041 | S |
| 388 | 74652 | CGPG6168 | SENSE | 0.475 | 0 | S | −0.766 | 0.92 | / | 7.48 | 0 | S |

S: represents that the transgenic plants showed statistically significant trait improvement as compared to the reference (p < 0.05, p value, of the delta of a quantitative response or of the risk score of a qualitative response, is the probability that the observed difference between the transgenic plants and the reference occur by chance)
T: represents that the transgenic plants showed a trend of trait improvement as compared to the reference with p < 0.2
/: represents the transgenic plants didn't show any alteration or had unfavorable change in traits examined as compared to the reference in the current dataset.

C. Heat Stress Tolerance Screen

Under high temperatures, *Arabidopsis* seedlings become chlorotic and root growth is inhibited. This example sets forth the heat stress tolerance screen to identify *Arabidopsis* plants transformed with the gene of interest that are more resistant to heat stress based on primarily their seedling weight and root growth under high temperature.

T2 seeds were plated on ½×MS salts, 1/% phytagel, with 10 µg/ml BASTA (7 per plate with 2 control seeds; 9 seeds total per plate). Plates were placed at 4° C. for 3 days to stratify seeds. Plates were then incubated at room temperature for 3 hours and then held vertically for 11 additional days at temperature of 34° C. at day and 20° C. at night. Photoperiod was 16 h. Average light intensity was ~140 µmol/m²/s. After 14 days of growth, plants were scored for glufosinate resistance, root length, final growth stage, visual color, and seedling fresh weight. A photograph of the whole plate was taken on day 14.

The seedling weight and root length were analyzed as quantitative responses according to example 1M. The final grow stage at day 14 was scored as success if 50% of the plants had reached 3 rosette leaves and size of leaves are greater than 1 mm (Boyes, et al., (2001) The Plant Cell 13, 1499-1510). The growth stage data was analyzed as a qualitative response according to example 1L. Table 5 provides a list of recombinant DNA constructs that improve heat tolerance in transgenic plants.

TABLE 5

| Pep SEQ ID | Construct_id | Gene | Orientation | Growth stage | | | Root Length | | | Seedling Weight | | |
|---|---|---|---|---|---|---|---|---|---|---|---|---|
| | | | | RS mean | p-value | c | delta | p-value | c | delta | p-value | c |
| 354 | 19542 | CGPG3069 | SENSE | 0.842 | 0.021 | S | 0.296 | 0.023 | S | 1.616 | 0 | S |
| 355 | 19618 | CGPG3574 | SENSE | 1.072 | 0.005 | S | 0.328 | 0.006 | S | 1.569 | 0 | S |
| 356 | 19649 | CGPG3140 | SENSE | 0.72 | 0.042 | S | 0.243 | 0.054 | T | 1.665 | 0 | S |
| 357 | 19745 | CGPG3973 | SENSE | 0.65 | 0.016 | S | 0.19 | 0.021 | S | 1.505 | 0 | S |
| 358 | 19768 | CGPG4096 | SENSE | 1.06 | 0.035 | S | 0.17 | 0.034 | S | 1.171 | 0 | S |
| 436 | 19771 | CGPG4011 | SENSE | 0.822 | 0.023 | S | 0.201 | 0.001 | S | 1.43 | 0 | S |
| 359 | 19772 | CGPG3939 | SENSE | 0.247 | 0.014 | S | 0.151 | 0.014 | S | 1.344 | 0 | S |
| 360 | 19779 | CGPG4113 | SENSE | 0.605 | 0.051 | T | 0.181 | 0.003 | S | 1.436 | 0 | S |
| 361 | 19833 | CGPG4074 | SENSE | 0.965 | 0.026 | S | 0.266 | 0.007 | S | 1.01 | 0 | S |
| 362 | 19862 | CGPG3961 | SENSE | 0.341 | 0.119 | T | 0.132 | 0.007 | S | 1.22 | 0 | S |
| 363 | 19879 | CGPG4009 | SENSE | 0.734 | 0.002 | S | 0.22 | 0.001 | S | 1.499 | 0 | S |
| 364 | 70445 | CGPG3728 | SENSE | 0.413 | 0.062 | T | 0.148 | 0.114 | T | 1.249 | 0 | S |
| 365 | 70738 | CGPG3195 | SENSE | 0.687 | 0.055 | T | 0.205 | 0.041 | S | 1.261 | 0 | S |
| 366 | 71437 | CGPG4043 | SENSE | 0.094 | 0.198 | T | 0.092 | 0.064 | T | 1.301 | 0 | S |
| 367 | 71572 | CGPG4520 | SENSE | 0.938 | 0.052 | T | 0.441 | 0 | S | 1.633 | 0 | S |
| 368 | 71617 | CGPG1227 | SENSE | 0.809 | 0.012 | S | 0.143 | 0.029 | S | 1.05 | 0.003 | S |
| 408 | 72085 | CGPG5228 | SENSE | 1.234 | 0.02 | S | 0.192 | 0.043 | S | 1.162 | 0 | S |
| 369 | 72532 | CGPG4780 | SENSE | 1.028 | 0.022 | S | 0.198 | 0.052 | T | 1.043 | 0.001 | S |
| 409 | 72744 | CGPG5563 | SENSE | 0.17 | 0.146 | T | 0.04 | 0.359 | / | 0.827 | 0.004 | S |
| 370 | 72757 | CGPG5572 | SENSE | 1.82 | 0.004 | S | 0.14 | 0.091 | T | 1.121 | 0 | S |
| 407 | 72771 | CGPG2166 | SENSE | 1.776 | 0.001 | S | 0.36 | 0 | S | 1.428 | 0 | S |
| 444 | 72967 | CGPG5742 | SENSE | 0.273 | 0.063 | T | 0.147 | 0.102 | T | 1.03 | 0 | S |
| 410 | 73039 | CGPG810 | SENSE | −0.048 | 0.774 | / | −0.135 | 0.957 | / | 0.59 | 0.022 | S |
| 411 | 73054 | CGPG5754 | SENSE | 0.055 | 0.312 | / | 0.236 | 0.001 | S | 1.434 | 0 | S |
| 508 | 73055 | CGPG5768 | SENSE | 0.154 | 0.123 | T | 0.269 | 0 | S | 1.524 | 0 | S |
| 371 | 73412 | CGPG6448 | SENSE | 0.187 | 0.118 | T | 0.134 | 0.06 | T | 1.181 | 0 | S |
| 412 | 73501 | CGPG6456 | SENSE | 1.6 | 0.003 | S | 0.081 | 0.136 | T | 1.119 | 0 | S |
| 352 | 73515 | CGPG6473 | SENSE | −0.037 | 0.758 | / | −0.024 | 0.604 | / | 0.694 | 0.008 | S |
| 437 | 73549 | CGPG6460 | SENSE | 2.612 | 0 | S | 0.199 | 0.017 | S | 1.432 | 0 | S |

TABLE 5-continued

| Pep SEQ ID | Construct_id | Gene | Orientation | Growth stage RS mean | p-value | c | Root Length delta | p-value | c | Seedling Weight delta | p-value | c |
|---|---|---|---|---|---|---|---|---|---|---|---|---|
| 372 | 74102 | CGPG6550 | SENSE | 0.34 | 0.035 | S | 0.268 | 0.002 | S | 1.355 | 0 | S |
| 509 | 74103 | CGPG6558 | SENSE | −0.013 | 1 | / | −0.021 | 0.608 | / | 0.86 | 0 | S |
| 353 | 74684 | CGPG6360 | SENSE | 0.44 | 0.018 | S | 0.254 | 0.002 | S | 1.383 | 0 | S |
| 512 | 19703 | CGPG4172 | SENSE | 0.211 | 0.079 | T | 0.059 | 0.301 | / | 1.262 | 0 | S |
| 273 | 70423 | CGPG3165 | SENSE | 1.456 | 0 | S | 0.418 | 0 | S | 1.912 | 0 | S |
| 491 | 70469 | CGPG3791 | SENSE | 0.143 | 0.28 | / | 0.028 | 0.349 | / | 1.001 | 0.001 | S |
| 434 | 70932 | CGPG4089 | SENSE | 0.354 | 0.1 | T | 0.03 | 0.419 | / | 1.254 | 0 | S |
| 419 | 71134 | CGPG817 | SENSE | 0.522 | 0.106 | T | 0.077 | 0.248 | / | 1.225 | 0 | S |
| 466 | 71726 | CGPG3894 | SENSE | 0.196 | 0.225 | / | 0.082 | 0.2 | T | 1.243 | 0 | S |
| 505 | 72463 | CGPG4760 | SENSE | 1.182 | 0.003 | S | 0.202 | 0.026 | / | 1.702 | 0 | S |
| 445 | 72961 | CGPG5591 | SENSE | 1.195 | 0.013 | S | 0.106 | 0.105 | T | 1.084 | 0 | S |
| 306 | 74136 | CGPG6632 | SENSE | 0.886 | 0.012 | S | 0.306 | 0.009 | S | 1.42 | 0 | S |
| 504 | 74259 | CGPG5343 | SENSE | 1.044 | 0.023 | S | 0.081 | 0.187 | T | 1.274 | 0 | S |
| 310 | 74318 | CGPG5826 | SENSE | 0.407 | 0.075 | T | 0.116 | 0.052 | T | 1.118 | 0 | S |
| 479 | 74344 | CGPG5929 | SENSE | 1.256 | 0.018 | S | 0.118 | 0.125 | T | 1.275 | 0 | S |
| 533 | 74462 | CGPG6668 | SENSE | 0.846 | 0.022 | S | 0.26 | 0.011 | S | 1.425 | 0 | S |
| 313 | 74512 | CGPG32 | SENSE | 0.241 | 0.118 | T | 0.146 | 0.044 | S | 1.062 | 0 | S |
| 442 | 74587 | CGPG6774 | SENSE | 0 | / | / | 0.084 | 0.054 | T | 1.046 | 0 | S |

S: represents the transgenic plants showed statistically significant trait improvement as compared to the reference ($p < 0.05$)
T: represents the transgenic plants showed a trend of trait improvement as compared to the reference with $p < 0.2$
/: represents data points not determined or the transgenic plants didn't show any alteration or had unfavorable change in traits examined as compared to the reference in the current dataset D. Salt Stress Tolerance Screen This example sets forth the high salinity stress screen to identify *Arabidopsis* plants transformed with the gene of interest that are tolerant to high levels of salt based on their rate of development, root growth and chlorophyll accumulation under high salt conditions.

T2 seeds were plated on glufosinate selection plates containing 90 mM NaCl and grown under standard light and temperature conditions. All seedlings used in the experiment were grown at a temperature of 22° C. at day and 20° C. at night, a 16-hour photoperiod, an average light intensity of approximately 120 umol/m$^2$. On day 11, plants were measured for primary root length. After 3 more days of growth (day 14), plants were scored for transgenic status, primary root length, growth stage, visual color, and the seedlings were pooled for fresh weight measurement. A photograph of the whole plate was also taken on day 14.

The seedling weight and root length were analyzed as quantitative responses according to example 1M. The final growth stage at day 14 was scored as success if 50% of the plants reached 3 rosette leaves and size of leaves are greater than 1 mm (Boyes, D. C., et al., (2001), The Plant Cell 13, 1499/1510). The growth stage data was analyzed as a qualitative response according to example 1L. Table 6 provides a list of recombinant DNA constructs that improve high salinity tolerance in transgenic plants

TABLE 6

| Pep SEQ ID | Construct id | Gene | Orientation | Growth Stage RS mean | p-value | c | Root Length at day 11 delta | p-value | c | Root Length at day 14 delta | p-value | c | Seedling Weight at day 14 delta | p-vallue | c |
|---|---|---|---|---|---|---|---|---|---|---|---|---|---|---|---|
| 512 | 19703 | CGPG4172 | SENSE | 1.124 | 0.139 | T | 0.198 | 0.021 | S | 0.072 | 0.116 | T | 0.582 | 0.023 | S |
| 513 | 19946 | CGPG4097 | SENSE | 1.201 | 0.072 | T | 0.02 | 0.89 | / | 0.069 | 0.573 | / | 0.443 | 0.266 | / |
| 514 | 19980 | CGPG3914 | SENSE | 0.904 | 0.146 | T | 0.101 | 0.259 | / | 0.144 | 0.058 | T | 0.706 | 0.016 | S |
| 515 | 70435 | CGPG3701 | SENSE | 1.363 | 0.031 | S | −0.118 | 0.228 | / | 0.161 | 0.038 | S | 0.053 | 0.697 | / |
| 516 | 71114 | CGPG1657 | SENSE | 0.138 | 0.399 | / | 0.245 | 0.009 | S | 0.187 | 0.025 | S | 0.472 | 0.069 | T |
| 517 | 72451 | CGPG4733 | SENSE | 2.226 | 0.02 | S | 0.186 | 0.006 | S | 0.069 | 0.23 | / | 0.466 | 0.011 | S |
| 443 | 72453 | CGPG4735 | SENSE | 1.539 | 0.031 | S | 0.232 | 0.002 | S | 0.216 | 0 | S | 0.737 | 0.001 | S |
| 505 | 72463 | CGPG4760 | SENSE | 3.026 | 0.002 | S | 0.119 | 0.269 | / | 0.202 | 0.073 | T | 1.26 | 0 | S |
| 392 | 72519 | CGPG4749 | SENSE | 0.598 | 0.041 | S | 0.126 | 0.055 | T | 0.172 | 0.003 | S | 0.635 | 0.008 | S |
| 506 | 72902 | CGPG5597 | SENSE | 1.418 | 0.039 | S | 0.114 | 0.286 | / | 0.226 | 0.078 | T | 0.426 | 0.091 | T |
| 448 | 72916 | CGPG1814 | SENSE | 0.682 | 0.181 | T | 0.07 | 0.532 | / | 0.201 | 0.046 | S | 0.387 | 0.079 | T |
| 510 | 72921 | CGPG5781 | SENSE | 1.977 | 0.029 | S | 0.163 | 0.176 | T | 0.211 | 0.073 | T | 0.663 | 0.006 | S |
| 518 | 72947 | CGPG5607 | SENSE | 1.505 | 0.028 | S | 0.024 | 0.899 | / | 0.204 | 0.022 | S | 0.466 | 0.216 | / |
| 445 | 72961 | CGPG5591 | SENSE | 1.879 | 0.007 | S | 0.228 | 0.122 | T | 0.229 | 0.003 | S | 0.817 | 0.04 | S |
| 444 | 72967 | CGPG5742 | SENSE | 2.427 | 0.004 | S | 0.386 | 0.009 | S | 0.369 | 0.001 | S | 1.254 | 0 | S |
| 511 | 72968 | CGPG5772 | SENSE | 1.531 | 0.055 | T | 0.302 | 0.06 | T | 0.209 | 0.073 | T | 0.761 | 0.003 | S |
| 449 | 72969 | CGPG5789 | SENSE | 0.67 | 0.078 | T | 0.029 | 0.789 | / | 0.239 | 0.008 | S | 0.603 | 0.013 | S |
| 519 | 73012 | CGPG5786 | SENSE | 2.371 | 0.001 | S | 0.366 | 0 | S | 0.342 | 0 | S | 1.08 | 0 | S |
| 520 | 73022 | CGPG5622 | SENSE | 1.408 | 0.036 | S | 0.22 | 0.056 | T | 0.347 | 0 | S | 0.492 | 0.03 | S |
| 508 | 73055 | CGPG5768 | SENSE | 3.291 | 0.001 | S | 0.369 | 0.087 | T | 0.417 | 0.005 | S | 1.096 | 0.005 | S |
| 446 | 73070 | CGPG5627 | SENSE | 2.755 | 0.005 | S | 0.188 | 0.392 | / | 0.275 | 0.011 | S | 0.685 | 0.025 | S |
| 447 | 73475 | CGPG6385 | SENSE | 1.11 | 0.059 | T | 0.127 | 0.361 | / | 0.216 | 0.001 | S | 0.474 | 0.06 | T |
| 521 | 73488 | CGPG6394 | SENSE | 2.373 | 0.013 | S | 0.314 | 0.006 | S | 0.262 | 0.002 | S | 1.126 | 0.005 | S |
| 522 | 73901 | CGPG5237 | SENSE | 1.141 | 0.078 | T | 0.207 | 0.197 | T | 0.202 | 0.097 | T | 0.639 | 0.03 | S |
| 523 | 73964 | CGPG5804 | SENSE | 1.235 | 0.043 | S | 0.428 | 0.008 | S | 0.317 | 0.022 | S | 0.955 | 0.002 | S |

TABLE 6-continued

| Pep SEQ ID | Construct id | Gene | Orientation | Growth Stage RS mean | p-value | c | Root Length at day 11 delta | p-value | c | Root Length at day 14 delta | p-value | c | Seedling Weight at day 14 delta | p-value | c |
|---|---|---|---|---|---|---|---|---|---|---|---|---|---|---|---|
| 524 | 74019 | CGPG5706 | SENSE | 0.105 | 0.168 | T | 0.074 | 0.649 | / | 0.171 | 0.106 | T | 0.773 | 0.011 | S |
| 525 | 74022 | CGPG5724 | SENSE | 0.033 | 0.327 | / | −0.065 | 0.616 | / | 0.172 | 0.032 | S | 0.484 | 0.068 | T |
| 509 | 74103 | CGPG6558 | SENSE | 1.225 | 0.074 | T | 0.26 | 0.042 | S | 0.267 | 0.004 | S | 0.543 | 0.042 | S |
| 526 | 74114 | CGPG6551 | SENSE | 3.627 | 0 | S | 0.265 | 0.119 | T | 0.26 | 0 | S | 0.561 | 0.063 | T |
| 504 | 74259 | CGPG5343 | SENSE | 2.802 | 0.003 | S | 0.249 | 0.098 | T | 0.256 | 0.037 | S | 0.995 | 0 | S |
| 527 | 74262 | CGPG5353 | SENSE | 0.225 | 0.319 | / | 0.238 | 0.062 | T | 0.247 | 0 | S | 0.629 | 0.006 | S |
| 528 | 74292 | CGPG5367 | SENSE | 0.327 | 0.199 | T | 0.16 | 0.067 | T | 0.105 | 0.166 | T | 0.565 | 0.013 | S |
| 529 | 74302 | CGPG5384 | SENSE | 1.246 | 0.016 | S | 0.296 | 0.004 | S | 0.25 | 0 | S | 0.705 | 0.004 | S |
| 530 | 74325 | CGPG5898 | SENSE | 1.596 | 0.021 | S | −0.035 | 0.76 | / | 0.094 | 0.106 | T | 0.685 | 0.004 | S |
| 531 | 74429 | CGPG6689 | SENSE | 1.796 | 0.008 | S | 0.298 | 0.037 | S | 0.207 | 0.006 | S | 0.496 | 0.029 | S |
| 532 | 74440 | CGPG6682 | SENSE | 0.223 | 0.334 | / | 0.43 | 0.007 | S | 0.272 | 0.01 | S | 0.744 | 0.017 | S |
| 450 | 74449 | CGPG6659 | SENSE | 0.693 | 0.19 | T | 0.204 | 0.104 | T | 0.205 | 0.022 | S | 0.451 | 0.095 | T |
| 533 | 74462 | CGPG6668 | SENSE | 2.14 | 0.028 | S | 0.244 | 0.038 | S | 0.239 | 0.001 | S | 0.64 | 0.013 | S |
| 534 | 74465 | CGPG6692 | SENSE | 1.245 | 0.016 | S | 0.35 | 0.01 | S | 0.215 | 0.001 | S | 0.575 | 0.043 | S |
| 535 | 74474 | CGPG6669 | SENSE | 3.312 | 0.002 | S | 0.233 | 0.083 | T | 0.338 | 0.003 | S | 0.589 | 0.044 | S |
| 536 | 74505 | CGPG6783 | SENSE | 1.731 | 0.043 | S | 0.272 | 0.007 | S | 0.208 | 0.01 | S | 0.493 | 0.009 | S |
| 537 | 74507 | CGPG6799 | SENSE | 2.32 | 0.009 | S | 0.056 | 0.567 | / | 0.227 | 0.035 | S | 0.476 | 0.126 | T |
| 538 | 74562 | CGPG6764 | SENSE | 1.405 | 0.038 | S | −0.052 | 0.776 | / | 0.215 | 0.014 | S | 0.104 | 0.766 | / |
| 507 | 74572 | CGPG6640 | SENSE | 1.425 | 0.025 | S | 0.201 | 0.009 | S | 0.267 | 0.001 | S | 1.184 | 0 | S |
| 270 | 14324 | CGPG1560 | SENSE | 1.708 | 0.017 | S | 0.307 | 0.01 | S | 0.408 | 0 | S | 0.995 | 0.002 | S |
| 358 | 19768 | CGPG4096 | SENSE | 1.496 | 0.061 | T | 0.163 | 0.187 | T | 0.129 | 0.013 | S | 0.66 | 0.002 | S |
| 436 | 19771 | CGPG4011 | SENSE | 1.666 | 0.051 | T | 0.319 | 0.005 | S | 0.201 | 0.028 | S | 0.68 | 0.031 | S |
| 363 | 19879 | CGPG4009 | SENSE | 2.117 | 0.029 | S | 0.16 | 0.139 | T | 0.091 | 0.202 | / | 0.545 | 0.028 | S |
| 347 | 72715 | CGPG5521 | SENSE | 1.078 | 0.002 | S | 0.207 | 0.141 | T | 0.176 | 0.014 | S | 0.519 | 0.015 | S |
| 407 | 72771 | CGPG2166 | SENSE | 0.564 | 0.256 | / | −0.019 | 0.857 | / | 0.206 | 0.013 | S | 0.306 | 0.05 | S |
| 440 | 72903 | CGPG5584 | SENSE | 0.645 | 0.196 | T | −0.031 | 0.569 | / | 0.097 | 0.389 | / | 0.482 | 0.015 | S |
| 411 | 73054 | CGPG5754 | SENSE | 1.52 | 0.035 | S | 0.198 | 0.089 | T | 0.098 | 0.187 | T | 0.696 | 0.004 | S |
| 476 | 74107 | CGPG6590 | SENSE | 0.772 | 0.036 | S | 0.411 | 0 | S | 0.431 | 0.001 | S | 1.579 | 0 | S |
| 478 | 74131 | CGPG6592 | SENSE | 1.747 | 0.044 | S | 0.316 | 0.004 | S | 0.115 | 0.01 | S | 0.663 | 0.001 | S |
| 442 | 74587 | CGPG6774 | SENSE | 1.754 | 0.01 | S | 0.121 | 0.243 | / | 0.194 | 0.001 | S | 0.681 | 0 | S |

S: represents the transgenic plants showed statistically significant trait improvement as compared to the reference (p < 0.05)
T: represents the transgenic plants showed a trend of trait improvement as compared to the reference with p < 0.2
/: represents the transgenic plants didn't show any alteration or had unfavorable change in traits examined as compared to the reference in the current dataset E. Polyethylene Glycol (PEG) Induced Osmotic Stress Tolerance Screen There are numerous factors, which can influence seed germination and subsequent seedling growth, one being the availability of water. Genes, which can directly affect the success rate of germination and early seedling growth, are potentially useful agronomic traits for improving the germination and growth of crop plants under drought stress. In this assay, PEG was used to induce osmotic stress on germinating transgenic lines of Arabidopsis thaliana seeds in order to screen for osmotically resistant seed lines.

T2 seeds were plated on BASTA selection plates containing 3% PEG and grown under standard light and temperature conditions. Seeds were plated on each plate containing 3% PEG, ½×MS salts, 1% phytagel, and 10 µg/ml glufosinate. Plates were placed at 4° C. for 3 days to stratify seeds. On day 11, plants were measured for primary root length. After 3 more days of growth, i.e., at day 14, plants were scored for transgenic status, primary root length, growth stage, visual color, and the seedlings were pooled for fresh weight measurement. A photograph of the whole plate was taken on day 14.

Seedling weight and root length were analyzed as quantitative responses according to example 1M. The final growth stage at day 14 was scored as success or failure based on whether the plants reached 3 rosette leaves and size of leaves are greater than 1 mm. The growth stage data was analyzed as a qualitative response according to example 1L. Table 7 provides a list of recombinant DNA constructs that improve osmotic stress tolerance in transgenic plants.

TABLE 7

| Pep SEQ ID | Gene | Construct_id | Orientation | Growth Stage RS mean | p-value | c | Root Length at day 11 delta | p-value | c | Root Length at day 14 delta | p-value | c | Seedling Weight at day 14 delta | p-value | c |
|---|---|---|---|---|---|---|---|---|---|---|---|---|---|---|---|
| 413 | 19707 | CGPG4179 | SENSE | 2.653 | 0.019 | S | 0.074 | 0.58 | T | −0.031 | 0.81 | / | 0.427 | 0.063 | T |
| 414 | 19951 | CGPG3941 | SENSE | 1.432 | 0.134 | T | 0.017 | 0.864 | T | −0.08 | 0.28 | / | 0.476 | 0.054 | T |
| 415 | 19967 | CGPG4032 | SENSE | 2.691 | 0.014 | S | 0.01 | 0.934 | T | 0.19 | 0.039 | S | 0.537 | 0.056 | T |
| 416 | 70543 | CGPG3815 | SENSE | 1.735 | 0.077 | T | 0.084 | 0.561 | T | 0.323 | 0.007 | S | 0.676 | 0.006 | S |
| 402 | 70681 | CGPG4584 | SENSE | 2.528 | 0.006 | S | −0.065 | 0.682 | / | −0.179 | 0.05 | / | 0.374 | 0.146 | T |
| 417 | 70707 | CGPG1273 | ANTI-SENSE | 1.42 | 0.095 | T | 0.248 | 0.006 | S | 0.3 | 0.002 | S | 0.331 | 0.007 | S |
| 418 | 70719 | CGPG1712 | ANTI-SENSE | 1.43 | 0.106 | T | −0.007 | 0.968 | / | 0.101 | 0.255 | T | 0.155 | 0.349 | T |
| 419 | 71134 | CGPG817 | SENSE | 1.478 | 0.13 | T | 0.119 | 0.15 | T | 0.035 | 0.684 | T | 0.198 | 0.277 | T |
| 420 | 71146 | CGPG2928 | SENSE | 2.624 | 0.016 | S | 0.227 | 0.101 | T | 0.242 | 0.1 | T | 0.278 | 0.296 | T |
| 405 | 71508 | CGPG1541 | SENSE | 3.153 | 0.001 | S | 0.446 | 0.054 | T | 0.384 | 0.048 | S | 0.782 | 0.003 | S |

TABLE 7-continued

| Pep SEQ ID | Gene | Construct_id | Orientation | Growth Stage RS mean | Growth Stage p-value | Growth Stage c | Root Length at day 11 delta | Root Length at day 11 p-value | Root Length at day 11 c | Root Length at day 14 delta | Root Length at day 14 p-value | Root Length at day 14 c | Seedling Weight at day 14 delta | Seedling Weight at day 14 p-value | Seedling Weight at day 14 c |
|---|---|---|---|---|---|---|---|---|---|---|---|---|---|---|---|
| 421 | 71660 | CGPG4690 | SENSE | 2.893 | 0.005 | S | −0.024 | 0.795 | / | 0.225 | 0.074 | T | 0.165 | 0.329 | T |
| 403 | 71663 | CGPG4638 | SENSE | 0.116 | 0.444 | T | −0.061 | 0.536 | / | 0.358 | 0.041 | S | 0.058 | 0.702 | T |
| 439 | 71928 | CGPG1617 | SENSE | 2.076 | 0.041 | S | 0.353 | 0.013 | S | 0.289 | 0.035 | S | 0.531 | 0.035 | S |
| 318 | 72081 | CGPG5279 | SENSE | 1.262 | 0.138 | T | 0.174 | 0.243 | T | 0.2 | 0.197 | T | −0.105 | 0.714 | / |
| 408 | 72085 | CGPG5228 | SENSE | 4 | 0 | S | 0.22 | 0.046 | S | 0.371 | 0.004 | S | 0.929 | 0 | S |
| 422 | 72086 | CGPG5236 | SENSE | 2.589 | 0.022 | S | 0.281 | 0.033 | S | 0.136 | 0.314 | T | 0.32 | 0.043 | S |
| 423 | 72632 | CGPG4852 | SENSE | 1.663 | 0.053 | T | 0.254 | 0.069 | T | 0.094 | 0.548 | T | 0.471 | 0.015 | S |
| 424 | 72716 | CGPG5529 | SENSE | 2.914 | 0.004 | S | 0.146 | 0.058 | T | 0.007 | 0.925 | T | 0.582 | 0.016 | S |
| 425 | 72723 | CGPG1848 | SENSE | 2.138 | 0.066 | T | 0.043 | 0.728 | T | 0.2 | 0.068 | T | −0.326 | 0.225 | / |
| 409 | 72744 | CGPG5563 | SENSE | 1.636 | 0.05 | / | 0.195 | 0.151 | T | 0.059 | 0.751 | T | 0.539 | 0.005 | S |
| 404 | 72769 | CGPG5573 | SENSE | 2.207 | 0.055 | T | 0.086 | 0.464 | T | −0.134 | 0.162 | / | 0.389 | 0.086 | T |
| 407 | 72771 | CGPG2166 | SENSE | 2.569 | 0.021 | S | 0.169 | 0.221 | T | 0.192 | 0.038 | S | 0.56 | 0.018 | S |
| 440 | 72903 | CGPG5584 | SENSE | 2.161 | 0.061 | T | 0.035 | 0.856 | T | 0.245 | 0.162 | T | 0.06 | 0.871 | T |
| 510 | 72921 | CGPG5781 | SENSE | 2.249 | 0.025 | S | 0.034 | 0.788 | T | 0.225 | 0.077 | T | 0.306 | 0.28 | T |
| 391 | 72948 | CGPG5617 | SENSE | 2.267 | 0.054 | T | 0.054 | 0.495 | T | 0.117 | 0.019 | S | 0.289 | 0.077 | T |
| 445 | 72961 | CGPG5591 | SENSE | 1.19 | 0.14 | T | 0.037 | 0.76 | T | 0.136 | 0.339 | T | 0.588 | 0.027 | S |
| 511 | 72968 | CGPG5772 | SENSE | 3.142 | 0.007 | S | 0.178 | 0.072 | T | −0.031 | 0.781 | / | 0.698 | 0.016 | S |
| 426 | 72987 | CGPG1787 | SENSE | 2.055 | 0.078 | T | −0.058 | 0.64 | / | 0.097 | 0.144 | T | 0.325 | 0.054 | T |
| 438 | 72994 | CGPG5803 | SENSE | 2.674 | 0.013 | S | 0.245 | 0.124 | T | 0.07 | 0.657 | T | 0.599 | 0.035 | S |
| 441 | 73017 | CGPG5733 | SENSE | 4 | 0 | S | 0.343 | 0.09 | T | 0.462 | 0.002 | S | 0.996 | 0 | S |
| 410 | 73039 | CGPG810 | SENSE | 4 | 0 | S | 0.319 | 0.019 | S | 0.237 | 0.05 | / | 0.426 | 0.011 | S |
| 411 | 73054 | CGPG5754 | SENSE | 3.048 | 0.002 | S | 0.556 | 0.003 | S | 0.26 | 0.063 | T | 1.12 | 0.002 | S |
| 446 | 73070 | CGPG5627 | SENSE | 3.439 | 0.001 | S | 0.139 | 0.49 | T | 0.19 | 0.135 | T | 0.24 | 0.365 | T |
| 447 | 73475 | CGPG6385 | SENSE | 1.933 | 0.033 | S | 0.04 | 0.476 | T | 0.009 | 0.897 | T | 0.459 | 0.073 | T |
| 412 | 73501 | CGPG6456 | SENSE | 1.29 | 0.121 | T | 0.143 | 0.118 | T | 0.043 | 0.564 | T | 0.433 | 0.013 | S |
| 427 | 74109 | CGPG6606 | SENSE | 3.517 | 0 | S | 0.159 | 0.136 | T | 0.249 | 0.004 | S | 0.333 | 0.025 | S |
| 428 | 74140 | CGPG6569 | SENSE | 2.05 | 0.039 | S | 0.168 | 0.138 | T | 0.196 | 0.086 | T | 0.71 | 0.012 | S |
| 429 | 74191 | CGPG6597 | SENSE | 2.565 | 0.019 | S | 0.336 | 0.092 | T | 0.199 | 0.112 | T | 0.54 | 0.02 | S |
| 406 | 74248 | CGPG5476 | SENSE | 3.158 | 0.007 | S | 0.14 | 0.192 | T | 0.204 | 0.051 | T | 0.377 | 0.037 | S |
| 430 | 74265 | CGPG5356 | SENSE | 2.208 | 0.023 | S | 0.317 | 0.034 | S | 0.419 | 0.006 | S | 0.577 | 0.008 | S |
| 431 | 74369 | CGPG6076 | SENSE | 3.522 | 0 | S | 0.347 | 0.045 | S | 0.272 | 0.107 | T | 0.624 | 0.02 | S |
| 442 | 74587 | CGPG6774 | SENSE | 3.325 | 0.002 | S | 0.073 | 0.468 | T | 0.414 | 0.002 | S | 0.577 | 0.016 | S |
| 405 | 71508 | CGPG1541 | SENSE | 3.153 | 0.001 | S | 0.446 | 0.054 | T | 0.384 | 0.048 | S | 0.782 | 0.003 | S |
| 439 | 71928 | CGPG1617 | SENSE | 2.076 | 0.041 | S | 0.353 | 0.013 | S | 0.289 | 0.035 | S | 0.531 | 0.035 | S |
| 422 | 72086 | CGPG5236 | SENSE | 2.589 | 0.022 | S | 0.281 | 0.033 | S | 0.136 | 0.314 | / | 0.32 | 0.043 | S |
| 469 | 72455 | CGPG4742 | SENSE | 1.367 | 0.15 | T | 0.026 | 0.764 | / | 0.024 | 0.786 | / | 0.255 | 0.04 | S |
| 382 | 72466 | CGPG4767 | SENSE | 0.735 | 0.101 | T | 0.068 | 0.333 | / | 0.249 | 0.006 | S | −0.341 | 0.278 | / |
| 373 | 72633 | CGPG4853 | SENSE | 1.179 | 0.122 | T | 0.227 | 0.009 | S | 0.097 | 0.065 | T | 0.442 | 0.013 | S |
| 370 | 72757 | CGPG5572 | SENSE | 2.272 | 0.017 | S | 0.125 | 0.361 | / | 0.11 | 0.317 | / | 0.425 | 0.047 | S |
| 472 | 72992 | CGPG5777 | SENSE | 2.233 | 0.056 | T | 0.176 | 0.261 | / | 0.116 | 0.34 | / | 0.511 | 0.019 | S |
| 438 | 72994 | CGPG5803 | SENSE | 2.674 | 0.013 | S | 0.245 | 0.124 | T | 0.07 | 0.657 | T | 0.599 | 0.035 | S |
| 441 | 73017 | CGPG5733 | SENSE | 4 | 0 | S | 0.343 | 0.09 | T | 0.462 | 0.002 | S | 0.996 | 0 | S |
| 411 | 73054 | CGPG5754 | SENSE | 3.048 | 0.002 | S | 0.556 | 0.003 | S | 0.26 | 0.063 | T | 1.12 | 0.002 | S |
| 300 | 73507 | CGPG6504 | SENSE | 0.343 | 0.334 | / | 0.347 | 0.007 | S | 0.261 | 0.032 | S | 0.3 | 0.122 | T |
| 352 | 73515 | CGPG6473 | SENSE | 3.336 | 0.002 | S | 0.279 | 0.009 | S | 0.241 | 0.003 | S | 0.328 | 0.05 | S |
| 428 | 74140 | CGPG6569 | SENSE | 2.05 | 0.039 | S | 0.168 | 0.138 | T | 0.196 | 0.086 | T | 0.71 | 0.012 | S |
| 430 | 74265 | CGPG5356 | SENSE | 2.208 | 0.023 | S | 0.317 | 0.034 | S | 0.419 | 0.006 | S | 0.577 | 0.008 | S |
| 431 | 74369 | CGPG6076 | SENSE | 3.522 | 0 | S | 0.347 | 0.045 | S | 0.272 | 0.107 | T | 0.624 | 0.02 | S |
| 422 | 74587 | CGPG6774 | SENSE | 3.325 | 0.002 | S | 0.073 | 0.468 | / | 0.414 | 0.002 | S | 0.577 | 0.016 | S |

S: represents the transgenic plants showed statistically significant trait improvement as compared to the reference (p < 0.05)
T: represents the transgenic plants showed a trend of trait improvement compared to the reference with p < 0.2
/: represents the transgenic plants didn't show any alteration or had unfavorable change in traits examined as compared to the reference in the current dataset F. Cold Shock Tolerance Screen This example set forth a screen to identify *Arabidopsis* plants transformed with the genes of interest that are more tolerant to cold stress subjected during day 8 to day 28 after seed planting. During these crucial early stages, seedling growth and leaf area increase were measured to assess tolerance when *Arabidopsis* seedlings were exposed to low temperatures. Using this screen, genetic alterations can be found that enable plants to germinate and grow better than wild type plants under sudden exposure to low temperatures.

Eleven seedlings from T2 seeds of each transgenic line plus one control line were plated together on a plate containing ½x Gamborg Salts with 0.8 Phytagel™, 1% Phyta-gel, and 0.3% Sucrose. Plates were then oriented horizontally and stratified for three days at 4° C. At day three, plates were removed from stratification and exposed to standard conditions (16 hr photoperiod, 22° C. at day and 20° C. at night) until day 8. At day eight, plates were removed from standard conditions and exposed to cold shock conditions (24 hr photoperiod, 8° C. at both day and night) until the final day of the assay, i.e., day 28. Rosette areas were measured at day 8 and day 28, which were analyzed as quantitative responses according to example 1M. Table 8 provides a list of recombinant nucleotides that improve cold shock stress tolerance in plants.

TABLE 8

| Pep SEQ ID | Construct_id | Gene | Orientation | rosette area at day 8 delta | p-value | c | rosette area at day 28 delta | p-value | c | difference in rosette area between day 28 and day 8 delta | p-value | c |
|---|---|---|---|---|---|---|---|---|---|---|---|---|
| 270 | 14324 | CGPG1560 | SENSE | 0.054 | 0.429 | / | 0.258 | 0.017 | S | −0.071 | 0.631 | / |
| 271 | 17484 | CGPG2630 | SENSE | −0.189 | 0.759 | / | 0.544 | 0.025 | S | 0.275 | 0.121 | T |
| 272 | 19109 | CGPG1381 | ANTI-SENSE | −0.016 | 0.523 | / | 0.541 | 0.008 | S | 0.818 | 0.014 | S |
| 273 | 70423 | CGPG3165 | SENSE | 0.316 | 0.012 | S | 0.521 | 0.022 | S | 0.89 | 0.018 | S |
| 274 | 70424 | CGPG3180 | SENSE | 0.474 | 0.003 | S | 0.695 | 0.003 | S | 0.693 | 0.043 | S |
| 275 | 70480 | CGPG3833 | SENSE | −0.066 | 0.591 | / | 0.175 | 0.159 | T | 0.474 | 0.059 | T |
| 276 | 70509 | CGPG2420 | SENSE | 0.023 | 0.438 | / | 0.117 | 0.216 | / | 0.609 | 0.032 | S |
| 277 | 70647 | CGPG4334 | SENSE | −0.508 | 0.894 | / | 0.604 | 0.049 | S | 0.895 | 0.047 | S |
| 278 | 70675 | CGPG4519 | SENSE | 0.2 | 0.2 | / | 0.303 | 0.153 | T | 0.507 | 0.034 | S |
| 279 | 70829 | CGPG518 | SENSE | −0.319 | 0.823 | / | 0.804 | 0.002 | S | 1.082 | 0.002 | S |
| 280 | 70849 | CGPG596 | SENSE | −0.039 | 0.564 | / | 0.698 | 0.001 | S | 0.707 | 0.001 | S |
| 281 | 71627 | CGPG1270 | SENSE | −0.146 | 0.748 | / | 0.349 | 0.05 | T | 0.3 | 0.12 | T |
| 282 | 71934 | CGPG2294 | SENSE | −0.068 | 0.796 | / | 0.757 | 0 | S | 0.922 | 0 | S |
| 283 | 72615 | CGPG4829 | SENSE | 0.477 | 0.007 | S | 0.834 | 0 | S | 0.979 | 0.001 | S |
| 286 | 73559 | CGPG6535 | SENSE | 0.143 | 0.093 | T | −0.265 | 0.878 | / | −0.344 | 0.821 | / |
| 287 | 74251 | CGPG5489 | SENSE | 0.377 | 0.021 | S | 0.439 | 0.045 | S | 0.45 | 0.07 | T |
| 389 | 70437 | CGPG3706 | SENSE | −0.273 | 0.916 | / | 0.147 | 0.165 | T | 0.682 | 0.034 | S |
| 402 | 70681 | CGPG4584 | SENSE | 0.352 | 0.155 | T | 0.252 | 0.261 | / | 0.269 | 0.328 | / |
| 403 | 71663 | CGPG4638 | SENSE | 0.358 | 0.013 | S | 0.032 | 0.423 | / | −0.031 | 0.585 | / |
| 404 | 72769 | CGPG5573 | SENSE | 0.381 | 0.049 | S | 0.881 | 0.006 | S | 1.102 | 0.005 | S |
| 407 | 72771 | CGPG2166 | SENSE | 0.993 | 0 | S | 1.381 | 0.003 | S | 1.536 | 0.003 | S |
| 432 | 70217 | CGPG6 | SENSE | 0.275 | 0.067 | T | 0.126 | 0.289 | / | 0.362 | 0.215 | / |
| 433 | 72711 | CGPG1846 | SENSE | 0.774 | 0.001 | S | 0.579 | 0.004 | S | 0.429 | 0.038 | S |
| 438 | 72994 | CGPG5803 | SENSE | 0.116 | 0.381 | / | 0.708 | 0.068 | T | 0.744 | 0.069 | T |
| 510 | 72921 | CGPG5781 | SENSE | 0.265 | 0.057 | T | 0.31 | 0.162 | T | 0.367 | 0.11 | T |
| 414 | 19951 | CGPG3941 | SENSE | 0.729 | 0.006 | S | 0.473 | 0.017 | s | 0.846 | 0.006 | S |
| 273 | 70423 | CGPG3165 | SENSE | 0.316 | 0.012 | S | 0.521 | 0.022 | S | 0.89 | 0.018 | S |
| 416 | 70543 | CGPG3815 | SENSE | 1.584 | 0 | S | 0.86 | 0 | S | 0.82 | 0.002 | S |
| 368 | 71617 | CGPG1227 | SENSE | 0.204 | 0.136 | T | 0.408 | 0.025 | S | 0.458 | 0.057 | T |
| 439 | 71928 | CGPG1617 | SENSE | 0.104 | 0.265 | / | 0.786 | 0 | S | 0.836 | 0.001 | S |
| 382 | 72466 | CGPG4767 | SENSE | 0.497 | 0.017 | S | 0.565 | 0.017 | S | 0.963 | 0.002 | S |
| 383 | 72524 | CGPG4770 | SENSE | 0.438 | 0.02 | S | 0.377 | 0.025 | S | 0.385 | 0.043 | S |
| 409 | 72744 | CGPG5563 | SENSE | 0.52 | 0.058 | T | 0.859 | 0.026 | S | 0.454 | 0.189 | T |
| 444 | 72967 | CGPG5742 | SENSE | 0.955 | 0 | S | 0.629 | 0.009 | S | 0.403 | 0.189 | T |
| 435 | 73518 | CGPG6497 | SENSE | 0.114 | 0.278 | / | 0.319 | 0.01 | S | 0.195 | 0.114 | T |
| 306 | 74136 | CGPG6632 | SENSE | 0.606 | 0.007 | S | 0.523 | 0.036 | S | 0.598 | 0.025 | S |
| 398 | 74240 | CGPG5454 | SENSE | −0.099 | 0.644 | / | 1.277 | 0.003 | S | 1.498 | 0.006 | S |
| 431 | 74369 | CGPG6076 | SENSE | 0.623 | 0.002 | S | 0.62 | 0.04 | S | 0.737 | 0.096 | T |

S: represents the transgenic plants showed statistically significant trait improvement as compared to the reference (p < 0.05)
T: represents the transgenic plants showed a trend of trait improvement compared to the reference with p < 0.2
/: represents the transgenic plants didn't show any alteration or had unfavorable change in traits examined as compared to the reference in the current dataset.

G. Cold Germination Tolerance Screen

This example sets forth a screen to identify *Arabidopsis* plants transformed with the genes of interests are resistant to cold stress based on their rate of development, root growth and chlorophyll accumulation under low temperature conditions.

T2 seeds were plated and all seedlings used in the experiment were grown at 8° C. Seeds were first surface disinfested using chlorine gas and then seeded on assay plates containing an aqueous solution of ½× Gamborg's B/5 Basal Salt Mixture (Sigma/Aldrich Corp., St. Louis, Mo., USA G/5788), 1% Phytagel™ (Sigma-Aldrich, P-8169), and 10 ug/ml glufosinate with the final pH adjusted to 5.8 using KOH. Test plates were held vertically for 28 days at a constant temperature of 8° C., a photoperiod of 16 hr, and average light intensity of approximately 100 umol/m²/s. At 28 days post planting, root length was measured, growth stage was observed, the visual color was assessed, and a whole plate photograph was taken.

The root length at day 28 was analyzed as a quantitative response according to example 1M. The growth stage at day 7 was analyzed as a qualitative response according to example 1L. Table 9 provides a list of recombinant DNA constructs that improve cold stress tolerance in transgenic plants.

TABLE 9

| Pep SEQ ID | Construct_id | Gene | Orientation | Growth stage at day 28 RS mean | p-value | c | Root Length at day 28 delta | p-value | c |
|---|---|---|---|---|---|---|---|---|---|
| 288 | 19631 | CGPG3627 | SENSE | 2.229 | 0.052 | T | 0.094 | 0.252 | / |
| 289 | 70121 | CGPG2380 | SENSE | 2.732 | 0.042 | S | 0.126 | 0.238 | / |
| 290 | 70654 | CGPG4352 | SENSE | 2.474 | 0.026 | S | 0.263 | 0.019 | S |

TABLE 9-continued

| Pep SEQ ID | Construct_id | Gene | Orientation | Growth stage at day 28 RS mean | p-value | c | Root Length at day 28 delta | p-value | c |
|---|---|---|---|---|---|---|---|---|---|
| 291 | 70696 | CGPG4590 | SENSE | 3.092 | 0.01 | S | 0.086 | 0.145 | T |
| 292 | 70713 | CGPG1462 | ANTI-SENSE | 4 | 0 | S | 0.268 | 0.014 | S |
| 293 | 70740 | CGPG3700 | SENSE | 2.485 | 0.024 | S | 0.244 | 0.012 | S |
| 294 | 71321 | CGPG4418 | SENSE | 1.837 | 0.126 | T | 0.014 | 0.474 | / |
| 295 | 71835 | CGPG4634 | SENSE | 3.349 | 0.002 | S | 0.353 | 0.036 | S |
| 296 | 72934 | CGPG5798 | SENSE | 2.222 | 0.023 | S | 0.243 | 0.101 | T |
| 297 | 72945 | CGPG5787 | SENSE | 3.478 | 0.001 | S | 0.236 | 0.011 | S |
| 298 | 72980 | CGPG5773 | SENSE | 3.265 | 0.003 | S | 0.239 | 0.006 | S |
| 299 | 73504 | CGPG6480 | SENSE | 4 | 0 | S | 0.521 | 0 | S |
| 300 | 73507 | CGPG6504 | SENSE | 4 | 0 | S | 0.404 | 0.001 | S |
| 301 | 73573 | CGPG6462 | SENSE | 4 | 0 | S | 0.268 | 0.004 | S |
| 302 | 73586 | CGPG6471 | SENSE | 4 | 0 | S | 0.314 | 0.064 | T |
| 303 | 73770 | CGPG5435 | SENSE | 3.091 | 0.01 | S | 0.303 | 0.085 | T |
| 304 | 74105 | CGPG6574 | SENSE | 3.329 | 0.002 | S | 0.109 | 0.116 | T |
| 305 | 74111 | CGPG6622 | SENSE | 2.226 | 0.021 | S | 0.445 | 0.006 | S |
| 306 | 74136 | CGPG6632 | SENSE | 3.192 | 0.005 | S | 0.328 | 0.002 | S |
| 307 | 74139 | CGPG6561 | SENSE | 4 | 0 | S | 0.254 | 0.092 | T |
| 308 | 74267 | CGPG5364 | SENSE | 3.054 | 0.002 | S | 0.3 | 0 | S |
| 309 | 74291 | CGPG5363 | SENSE | 4 | 0 | S | 0.142 | 0.142 | T |
| 310 | 74318 | CGPG5826 | SENSE | 4 | 0 | S | 0.272 | 0.008 | S |
| 311 | 74319 | CGPG5831 | SENSE | 3.207 | 0.005 | S | 0.201 | 0.002 | S |
| 312 | 74324 | CGPG5885 | SENSE | 3.144 | 0.007 | S | 0.232 | 0.017 | S |
| 313 | 74512 | CGPG32 | SENSE | 4 | 0 | S | 0.332 | 0.011 | S |
| 314 | 74583 | CGPG6649 | SENSE | 3.249 | 0.004 | S | 0.28 | 0.001 | S |
| 315 | 70427 | CGPG3067 | SENSE | 1.567 | 0.108 | T | 0.222 | 0.044 | S |
| 352 | 73515 | CGPG6473 | SENSE | 4 | 0 | S | 0.324 | 0.003 | S |
| 353 | 74684 | CGPG6360 | SENSE | 2.927 | 0.004 | S | 0.426 | 0.003 | S |
| 373 | 72633 | CGPG4853 | SENSE | 2.121 | 0.027 | S | 0.289 | 0.048 | S |
| 405 | 71508 | CGPG1541 | SENSE | 1.99 | 0.039 | S | 0.263 | 0.033 | S |
| 406 | 74248 | CGPG5476 | SENSE | 2.385 | 0.011 | S | 0.217 | 0.017 | S |
| 434 | 70932 | CGPG4089 | SENSE | 3.268 | 0.003 | S | 0.146 | 0.067 | T |
| 435 | 73518 | CGPG6497 | SENSE | 3.373 | 0.002 | S | 0.352 | 0.032 | S |
| 439 | 71928 | CGPG1617 | SENSE | 3.062 | 0.011 | S | 0.18 | 0.002 | S |
| 504 | 74259 | CGPG5343 | SENSE | 3.511 | 0 | S | 0.308 | 0.024 | S |
| 505 | 72463 | CGPG4760 | SENSE | 2.736 | 0.01 | S | 0.032 | 0.386 | / |
| 506 | 72902 | CGPG5597 | SENSE | 3.105 | 0.009 | S | 0.278 | 0.037 | S |
| 507 | 74572 | CGPG6640 | SENSE | 4 | 0 | S | 0.125 | 0.155 | T |
| 508 | 73055 | CGPG5768 | SENSE | 3.173 | 0.006 | S | 0.407 | 0.004 | S |
| 413 | 19707 | CGPG4179 | SENSE | 1.829 | 0.061 | T | 0.169 | 0.018 | S |
| 360 | 19779 | CGPG4113 | SENSE | 4 | 0 | S | 0.213 | 0.017 | S |
| 361 | 19833 | CGPG4074 | SENSE | / | / | / | 0.292 | 0.022 | S |
| 363 | 19879 | CGPG4009 | SENSE | 4 | 0 | S | 0.34 | 0.001 | S |
| 514 | 19980 | CGPG3914 | SENSE | 0.798 | 0.122 | T | 0.278 | 0.011 | S |
| 273 | 70423 | CGPG3165 | SENSE | 2.906 | 0.004 | S | 0.105 | 0.114 | T |
| 459 | 70725 | CGPG2097 | ANTI-SENSE | 1.949 | 0.044 | S | 0.122 | 0.148 | T |
| 461 | 71112 | CGPG934 | SENSE | 2.579 | 0.018 | S | 0.185 | 0.17 | T |
| 444 | 72967 | CGPG5742 | SENSE | 4 | 0 | S | 0.287 | 0.007 | S |
| 438 | 72994 | CGPG5803 | SENSE | 1.072 | 0.098 | T | 0.161 | 0.04 | S |
| 521 | 73488 | CGPG6394 | SENSE | 4 | 0 | S | 0.211 | 0.012 | S |
| 477 | 74117 | CGPG6575 | SENSE | 2.567 | 0.02 | S | 0.123 | 0.04 | S |

S: represents the transgenic plants showed statistically significant trait improvement as compared to the reference (p < 0.05)
T: represents the transgenic plants showed a trend of trait improvement as compared to the reference with p < 0.2
/: represents data points not determined or the transgenic plants didn't show any alteration or had unfavorable change in traits examined compared to the reference in the current dataset H. Shade Tolerance Screen Plants undergo a characteristic morphological response in shade that includes the elongation of the petiole, a change in the leaf angle, and a reduction in chlorophyll content. While these changes may confer a competitive advantage to individuals, in a monoculture the shade avoidance response is thought to reduce the overall biomass of the population. Thus, genetic alterations that prevent the shade avoidance response are associated with higher yields. Genes that favor growth under low light conditions may also promote yield, as inadequate light levels frequently limit yield. This protocol describes a screen to look for *Arabidopsis* plants that show an attenuated shade avoidance response and/or grow better than control plants under low light intensity. Of particular interest, we were looking for plants that didn't extend their petiole length, had an increase in seedling weight relative to the reference and had leaves that were more close to parallel with the plate surface.

T2 seeds were plated on glufosinate selection plates with ½ MS medium. Seeds were sown on ½×MS salts, 1% Phytagel, 10 ug/ml BASTA. Plants were grown on vertical plates at a temperature of 22° C. at day, 20° C. at night and under low light (approximately 30 uE/m$^2$/s, far/red ratio (655/665/725/735) ~0.35 using PLAQ lights with GAM color filter #680). Twenty-three days after seedlings were sown, measurements were recorded including seedling status, number of rosette leaves, status of flower bud, petiole leaf angle, petiole length, and pooled fresh weights. A digital image of the whole plate was taken on the measurement day. Seedling weight and petiole length were analyzed as quantitative responses according to example 1M. The number of rosette leaves, flowering bud formation and leaf angel were analyzed as qualitative responses according to example 1L.

Table 10 provides a list of recombinant DNA constructs that improve shade tolerance in plants

TABLE 10

| Pep SEQ ID | Construct_id | Orientation | flowerbud formation at day 23 RS mean | p-value | c | Leaf Angle at day 23 RS mean | p-value | c | Petiole length at day 23 RS mean | p-value | c | Number of rosette leaves at day 23 RS mean | p-value | c | seedling weight at day 23 delta | p-value | c |
|---|---|---|---|---|---|---|---|---|---|---|---|---|---|---|---|---|---|
| 376 | 70426 | SENSE | 0.719 | 0.09 | T | 0.163 | 0.244 | / | −0.206 | 0.185 | T | −0.225 | 0.984 | / | 0.484 | 0.003 | S |
| 377 | 70772 | SENSE | −0.501 | 0.858 | / | −0.066 | 0.724 | / | −0.692 | 0.004 | S | −0.626 | 0.983 | / | −0.693 | 0.023 | / |
| 378 | 71137 | SENSE | 0.26 | 0.384 | / | 0.11 | 0.168 | T | −0.869 | 0.029 | S | 1.064 | 0.073 | T | −0.453 | 0.288 | / |
| 379 | 71529 | SENSE | 0.89 | 0.108 | T | −0.014 | 1 | / | −0.44 | 0.006 | S | 1.817 | 0.024 | S | −0.022 | 0.914 | / |
| 380 | 71601 | SENSE | 1.79 | 0.066 | T | 0.195 | 0.172 | T | −0.057 | 0.59 | / | −0.483 | 0.961 | / | 0.264 | 0.308 | / |
| 381 | 72362 | SENSE | 1.763 | 0.072 | T | 0.218 | 0.262 | / | −0.109 | 0.242 | / | 0.003 | 0.484 | / | 0.311 | 0.119 | T |
| 374 | 72456 | SENSE | 0.563 | 0.313 | / | 0.751 | 0.186 | T | −0.848 | 0.001 | S | −0.624 | 0.999 | / | −0.85 | 0.025 | / |
| 382 | 72466 | SENSE | −1.382 | 1 | / | −0.092 | 0.645 | / | −0.894 | 0 | S | 1.212 | 0.122 | T | −0.879 | 0.027 | / |
| 383 | 72524 | SENSE | −0.153 | 1 | / | 0.152 | 0.09 | T | −0.952 | 0.002 | S | −0.57 | 1 | / | −1.269 | 0.01 | / |
| 373 | 72633 | SENSE | 3.513 | 0 | S | −0.431 | 0.977 | / | −0.426 | 0.001 | S | −0.735 | 0.994 | / | 0.269 | 0.129 | T |
| 375 | 72963 | SENSE | −0.911 | 0.988 | / | 0.236 | 0.396 | / | −0.753 | 0.003 | S | −0.083 | 0.665 | / | −0.485 | 0.015 | / |
| 384 | 73085 | SENSE | −0.073 | 0.756 | / | 1.212 | 0.122 | T | 0.175 | 0.097 | / | 4 | 0 | S | 0.51 | 0.027 | S |
| 385 | 74241 | SENSE | −0.195 | 0.935 | / | −0.098 | 0.64 | / | −1.077 | 0.01 | S | −0.821 | 0.999 | / | −1.024 | 0.002 | / |
| 386 | 74247 | SENSE | 0.43 | 0.16 | T | 0.203 | 0.095 | T | −0.22 | 0.197 | T | 1.166 | 0.07 | T | 0.483 | 0.018 | S |
| 387 | 74284 | SENSE | 0.062 | 0.22 | / | 2.077 | 0.038 | S | −0.014 | 0.943 | / | 2.348 | 0.04 | S | 0.03 | 0.938 | / |
| 388 | 74652 | SENSE | 0.015 | 0.442 | / | 0.093 | 0.455 | / | −0.073 | 0.621 | / | 0.967 | 0.184 | T | 0.173 | 0.569 | / |
| 363 | 19879 | SENSE | 0.585 | / | / | 0 | / | / | 0.152 | / | / | 0 | / | / | 0.708 | / | / |
| 293 | 70740 | SENSE | 0.44 | 0.137 | T | 0.609 | 0.103 | T | 0.161 | 0.186 | / | / | / | / | 0.45 | 0.001 | S |
| 316 | 71811 | SENSE | −0.025 | 0.637 | / | 0.725 | 0.113 | T | −0.205 | 0.01 | S | / | / | / | −0.517 | 0.037 | / |
| 397 | 71840 | SENSE | 1.498 | 0.12 | T | 0.712 | 0.178 | T | −0.379 | 0.001 | S | −0.188 | 0.765 | / | −0.95 | 0.124 | / |
| 468 | 72450 | SENSE | 0.068 | 0.349 | / | −0.042 | 1 | / | 0.166 | 0.016 | / | 1.62 | 0.049 | S | 0.501 | 0.038 | S |
| 370 | 72757 | SENSE | 3.595 | 0 | S | 0.872 | 0.079 | T | 0.064 | 0.138 | / | −0.767 | 0.997 | / | 0.546 | 0.001 | S |
| 444 | 72967 | SENSE | 1.829 | 0.063 | T | 1.123 | 0.065 | T | 0.133 | 0.196 | / | −0.18 | 0.794 | / | 0.509 | 0.008 | S |
| 511 | 72968 | SENSE | 0.185 | 0.005 | S | 0.48 | 0.179 | T | 0.22 | 0.162 | / | 1.698 | 0.085 | T | 0.382 | 0.031 | S |
| 300 | 73507 | SENSE | 0.248 | 0.086 | T | 0.307 | 0.287 | / | −0.304 | 0.031 | S | / | / | / | 0.05 | 0.86 | / |
| 307 | 74139 | SENSE | −0.011 | 0.556 | / | −0.071 | 1 | / | −0.124 | 0.068 | T | −0.511 | 1 | / | −0.413 | 0.124 | / |
| 535 | 74474 | SENSE | 0.755 | 0.154 | T | −0.145 | 0.857 | / | 0.142 | 0.396 | / | / | / | / | 0.765 | 0.005 | S |
| 400 | 74610 | SENSE | 0.572 | 0.222 | / | 0.177 | 0.22 | / | −0.18 | 0.071 | T | / | / | / | −0.341 | 0.173 | / |

S: represents the transgenic plants showed statistically significant trait improvement as compared to the reference (p < 0.05)
T: represents the transgenic plants showed a trend of trait improvement as compared to the reference with p < 0.2
/: represents data points not determined or the transgenic plants didn't show any alteration or had unfavorable change in traits examined compared to the reference in the current dataset.

I. Early Plant Growth and Development Screen

This example sets forth a plate based phenotypic analysis platform for the rapid detection of phenotypes that are evident during the first two weeks of growth. In this screen, we were looking for genes that confer advantages in the processes of germination, seedling vigor, root growth and root morphology under non-stressed growth conditions to plants. The transgenic plants with advantages in seedling growth and development were determined by the seedling weight and root length at day 14 after seed planting.

T2 seeds were plated on glufosinate selection plates and grown under standard conditions (~100 □E/m²/s, 16 h photoperiod, 22° C. at day, 20° C. at night). Seeds were stratified for 3 days at 4° C. Seedlings were grown vertically (at a temperature of 22° C. at day 20° C. at night). Observations were taken on day 10 and day 14. Both seedling weight and root length at day 14 were analyzed as quantitative responses according to example 1M.

Table 11 provides a list recombinant DNA constructs that improve early plant growth and development.

TABLE 11

| Pep SEQ ID | Construct_id | gene | Orientation | Root Length delta | p-value | c | Seedling Weight delta | p-value | c |
|---|---|---|---|---|---|---|---|---|---|
| 432 | 70217 | CGPG6 | SENSE | 0.038 | 0.469 | / | 0.375 | 0.047 | S |
| 433 | 72711 | CGPG1846 | SENSE | 0.132 | 0.021 | S | 0.601 | 0.001 | S |
| 434 | 70932 | CGPG4089 | SENSE | 0.328 | 0.005 | S | 0.473 | 0.017 | S |

TABLE 11-continued

| Pep SEQ ID | Construct_id | gene | Orientation | Root Length delta | Root Length p-value | Root Length c | Seedling Weight delta | Seedling Weight p-value | Seedling Weight c |
|---|---|---|---|---|---|---|---|---|---|
| 435 | 73518 | CGPG6497 | SENSE | 0.287 | 0 | S | 0.634 | 0.036 | S |
| 436 | 19771 | CGPG4011 | SENSE | 0.218 | 0.076 | T | 0.581 | 0.018 | S |
| 437 | 73549 | CGPG6460 | SENSE | 0.139 | 0.003 | S | 0.349 | 0.03 | S |
| 438 | 72994 | CGPG5803 | SENSE | 0.44 | 0.004 | S | 0.791 | 0.001 | S |
| 439 | 71928 | CGPG1617 | SENSE | 0.073 | 0.427 | / | 0.494 | 0.005 | S |
| 440 | 72903 | CGPG5584 | SENSE | 0.298 | 0.002 | S | 0.399 | 0.044 | S |
| 441 | 73017 | CGPG5733 | SENSE | 0.284 | 0.004 | S | 0.199 | 0.488 | / |
| 442 | 74587 | CGPG6774 | SENSE | 0.111 | 0.075 | T | 0.538 | 0.006 | S |
| 443 | 72453 | CGPG4735 | SENSE | 0.215 | 0.005 | S | 0.416 | 0.069 | T |
| 444 | 72967 | CGPG5742 | SENSE | 0.103 | 0.212 | / | 0.568 | 0.008 | S |
| 445 | 72961 | CGPG5591 | SENSE | 0.177 | 0.046 | S | 0.548 | 0.006 | S |
| 446 | 73070 | CGPG5627 | SENSE | 0.221 | 0.007 | S | 0.652 | 0.005 | S |
| 447 | 73475 | CGPG6385 | SENSE | 0.084 | 0.014 | S | 0.336 | 0.014 | S |
| 448 | 72916 | CGPG1814 | SENSE | 0.182 | 0.067 | T | 0.353 | 0.012 | S |
| 449 | 72969 | CGPG5789 | SENSE | 0.133 | 0.245 | / | 0.45 | 0.069 | T |
| 450 | 74449 | CGPG6659 | SENSE | 0.314 | 0.002 | S | 0.579 | 0.027 | S |
| 451 | 16615 | CGPG2539 | SENSE | 0.223 | 0.023 | S | 0.571 | 0.009 | S |
| 452 | 19187 | CGPG3310 | SENSE | 0.264 | 0.001 | S | 0.51 | 0.08 | T |
| 453 | 19648 | CGPG3134 | SENSE | 0.218 | 0.013 | S | 0.27 | 0.106 | T |
| 454 | 70354 | CGPG3995 | SENSE | 0.152 | 0.046 | S | 0.406 | 0.029 | S |
| 455 | 70421 | CGPG2942 | SENSE | 0.179 | 0.225 | / | 0.581 | 0.013 | S |
| 456 | 70459 | CGPG3758 | SENSE | 0.187 | 0.036 | S | −0.034 | 0.884 | / |
| 457 | 70465 | CGPG3775 | SENSE | −0.009 | 0.899 | / | 0.188 | 0.196 | T |
| 458 | 70683 | CGPG4587 | SENSE | 0.133 | 0.088 | T | 0.402 | 0.014 | S |
| 459 | 70725 | CGPG2097 | ANTI-SENSE | 0.326 | 0.001 | S | 0.116 | 0.548 | / |
| 460 | 70852 | CGPG1465 | SENSE | 0.237 | 0 | S | 0.297 | 0.127 | T |
| 461 | 71112 | CGPG934 | SENSE | 0.199 | 0.013 | S | 0.316 | 0.034 | S |
| 462 | 71127 | CGPG945 | SENSE | 0.097 | 0.02 | S | 0.4 | 0.054 | T |
| 463 | 71132 | CGPG1561 | SENSE | 0.195 | 0.02 | S | 0.08 | 0.524 | / |
| 464 | 71217 | CGPG95 | SENSE | 0.234 | 0 | S | 0.566 | 0.036 | S |
| 465 | 71645 | CGPG4688 | SENSE | 0.475 | 0.003 | S | 0.361 | 0.133 | T |
| 466 | 71726 | CGPG3894 | SENSE | 0.223 | 0.056 | T | 0.458 | 0.033 | S |
| 467 | 72432 | CGPG4562 | SENSE | 0.209 | 0 | S | 0.581 | 0.041 | S |
| 468 | 72450 | CGPG4732 | SENSE | 0.335 | 0 | S | 0.79 | 0 | S |
| 469 | 72455 | CGPG4742 | SENSE | 0.278 | 0.019 | S | 0.482 | 0.051 | T |
| 470 | 72727 | CGPG5522 | SENSE | 0.123 | 0.002 | S | 0.315 | 0.004 | S |
| 471 | 72817 | CGPG4987 | SENSE | 0.254 | 0.023 | S | 0.485 | 0 | S |
| 472 | 72992 | CGPG5777 | SENSE | 0.219 | 0.023 | S | 0.664 | 0.015 | S |
| 473 | 73007 | CGPG5760 | SENSE | 0.139 | 0.093 | T | 0.462 | 0.008 | S |
| 474 | 73073 | CGPG5688 | SENSE | 0.164 | 0.022 | S | 0.285 | 0.247 | / |
| 475 | 73506 | CGPG6496 | SENSE | 0.512 | 0 | S | 0.986 | 0 | S |
| 476 | 74107 | CGPG6590 | SENSE | 0.282 | 0.002 | S | 0.538 | 0.057 | T |
| 477 | 74117 | CGPG6575 | SENSE | 0.211 | 0.002 | S | 0.449 | 0.005 | S |
| 478 | 74131 | CGPG6592 | SENSE | 0.142 | 0.047 | S | 0.586 | 0.003 | S |
| 479 | 74344 | CGPG5929 | SENSE | 0.27 | 0.01 | S | 0.474 | 0.105 | T |
| 323 | 13502 | CGPG1354 | SENSE | 0.57 | 0.002 | S | 0.625 | 0 | S |
| 330 | 18259 | CGPG3368 | SENSE | 0.226 | 0.026 | S | 0.551 | 0.021 | S |
| 361 | 19833 | CGPG4074 | SENSE | 0.259 | 0 | S | 0.472 | 0.016 | S |
| 334 | 70417 | CGPG3427 | SENSE | 0.187 | 0.056 | T | 0.113 | 0.65 | / |
| 273 | 70423 | CGPG3165 | SENSE | 0.03 | 0.747 | / | 0.185 | 0.007 | S |
| 515 | 70435 | CGPG3701 | SENSE | 0.131 | 0.051 | T | 0.394 | 0.014 | S |
| 493 | 70601 | CGPG2917 | SENSE | 0.177 | 0 | S | 0.365 | 0.063 | T |
| 291 | 70696 | CGPG4590 | SENSE | 0.079 | 0.205 | / | 0.331 | 0.024 | S |
| 365 | 70738 | CGPG3195 | SENSE | 0.012 | 0.864 | / | 0.472 | 0.003 | S |
| 293 | 70740 | CGPG3700 | SENSE | 0.103 | 0.082 | T | 0.387 | 0.021 | S |
| 419 | 71134 | CGPG817 | SENSE | 0.063 | 0.548 | / | 0.279 | 0.066 | T |
| 422 | 72086 | CGPG5236 | SENSE | 0.083 | 0.234 | / | 0.398 | 0.05 | S |
| 505 | 72463 | CGPG4760 | SENSE | −0.131 | 0.416 | / | 0.422 | 0.003 | S |
| 285 | 73014 | CGPG5692 | SENSE | 0.11 | 0.391 | / | 0.373 | 0.096 | T |
| 521 | 73488 | CGPG6394 | SENSE | 0.018 | 0.793 | / | 0.398 | 0.1 | T |
| 299 | 73504 | CGPG6480 | SENSE | −0.152 | 0.479 | / | 0.538 | 0.012 | S |
| 300 | 73507 | CGPG6504 | SENSE | 0.15 | 0.002 | S | 0.053 | 0.854 | / |
| 301 | 73573 | CGPG6462 | SENSE | 0.112 | 0.07 | T | 0.375 | 0.006 | S |
| 302 | 73586 | CGPG6471 | SENSE | 0.309 | 0 | S | 0.611 | 0 | S |
| 303 | 73770 | CGPG5435 | SENSE | 0.21 | 0.059 | T | 0.281 | 0.484 | / |
| 509 | 74103 | CGPG6558 | SENSE | 0.374 | 0 | S | 0.561 | 0.024 | S |
| 428 | 74140 | CGPG6569 | SENSE | 0.16 | 0.017 | S | 0.376 | 0.066 | T |
| 527 | 74262 | CGPG5353 | SENSE | 0.203 | 0.012 | S | 0.375 | 0.045 | S |
| 430 | 74265 | CGPG5356 | SENSE | 0.107 | 0.259 | T | 0.432 | 0.067 | T |
| 529 | 74302 | CGPG5384 | SENSE | 0.115 | 0.101 | T | 0.269 | 0.056 | T |
| 431 | 74369 | CGPG6076 | SENSE | 0.138 | 0.03 | S | 0.195 | 0.21 | / |
| 534 | 74465 | CGPG6692 | SENSE | 0.2 | 0.02 | S | 0.688 | 0.042 | S |

TABLE 11-continued

| Pep SEQ ID | Construct_id | gene | Orientation | Root Length delta | p-value | c | Seedling Weight delta | p-value | c |
|---|---|---|---|---|---|---|---|---|---|
| 507 | 74572 | CGPG6640 | SENSE | 0.162 | 0.023 | S | 0.617 | 0 | S |
| 314 | 74583 | CGPG6649 | SENSE | 0.144 | 0.023 | S | 0.403 | 0.008 | S |

S: represents the transgenic plants showed statistically significant trait improvement as compared to the reference (p < 0.05)
T: represents the transgenic plants showed a trend of trait improvement as compared to the reference with p < 0.2
/: represents the transgenic plants didn't show any alteration or had unfavorable change in traits examined as compared to the reference in the current dataset J. Late Plant Growth and Development Screen This example sets forth a soil based phenotypic platform to identify genes that confer advantages in the processes of leaf development, flowering production and seed maturity to plants. *Arabidopsis* plants were grown on a commercial potting mixture (Metro Mix 360, Scotts Co., Marysville, Ohio) consisting of 30-40% medium grade horticultural vermiculite, 35-55% sphagnum peat moss, 10-20% processed bark ash, 1-15% pine bark and a starter nutrient charge. Soil was supplemented with Osmocote time-release fertilizer at a rate of 30 mg/ft$^3$. T2 seeds were imbibed in 1% agarose solution for 3 days at 4° C. and then sown at a density of ~5 per 2½" pot. Thirty-two pots were ordered in a 4 by 8 grid in standard greenhouse flat. Plants were grown in environmentally controlled rooms under a 16 h day length with an average light intensity of ~200 μmoles/m$^2$/s. Day and night temperature set points were 22° C. and 20° C., respectively. Humidity was maintained at 65%. Plants were watered by sub-irrigation every two days on average until mid-flowering, at which point the plants were watered daily until flowering was complete.

Application of the herbicide glufosinate was performed to select T2 individuals containing the target transgene. A single application of glufosinate was applied when the first true leaves were visible. Each pot was thinned to leave a single glufosinate-resistant seedling ~3 days after the selection was applied.

The rosette radius was measured at day 25. The silique length was measured at day 40. The plant parts were harvested at day 49 for dry weight measurements if flowering production was stopped. Otherwise, the dry weights of rosette and silique were carried out at day 53. The seeds were harvested at day 58. All measurements were analyzed as quantitative responses according to example 1M.

Table 12 provides a list of recombinant DNA constructs that improve late plant growth and development.

TABLE 12

| Pep SEQ ID | Construct_id | Orientation | Rosette Dry Weight delta | p-value | c | Rosette Radius delta | p-value | c | Seed Dry Weight delta | p-value | c | Silique Dry Weight delta | p-value | c | Slilique Length delta | p-value | c |
|---|---|---|---|---|---|---|---|---|---|---|---|---|---|---|---|---|---|
| 480 | 14320 | SENSE | −0.145 | 0.94 | / | 0.137 | 0.038 | S | −0.702 | 1 | / | 0.477 | 0.002 | S | 0.016 | 0.276 | / |
| 481 | 16756 | SENSE | 0.485 | 0.016 | S | 0.223 | 0.025 | S | 0.148 | 0.042 | S | 0.481 | 0.002 | S | 0.147 | 0.013 | S |
| 482 | 17448 | SENSE | −0.288 | 0.991 | / | −0.054 | 0.829 | / | 0.376 | 0.008 | S | 0.185 | 0.034 | S | −0.064 | 0.981 | / |
| 483 | 17633 | SENSE | 0.018 | 0.359 | / | 0.13 | 0.106 | T | 0.416 | 0.055 | T | 0.399 | 0.044 | S | 0.116 | 0.08 | T |
| 484 | 18876 | SENSE | 0.257 | 0.016 | S | 0.026 | 0.448 | / | −0.213 | 0.786 | / | 0.386 | 0 | S | −0.015 | 0.705 | / |
| 485 | 19120 | ANTI-SENSE | −0.252 | 0.936 | / | 0.022 | 0.006 | S | −1.042 | 0.95 | / | 0.165 | 0.076 | T | 0.046 | 0.021 | S |
| 486 | 19221 | SENSE | −0.316 | 0.986 | / | 0.153 | 0.097 | T | −0.35 | 0.903 | / | 0.394 | 0.068 | T | 0.183 | 0.028 | S |
| 487 | 70206 | SENSE | 0.125 | 0 | S | 0.074 | 0.18 | T | 0.712 | 0.022 | S | 0.12 | 0.026 | S | 0.019 | 0.403 | / |
| 488 | 70223 | SENSE | 0.197 | 0.026 | S | 0.23 | 0.018 | S | −0.781 | 0.998 | / | 0.134 | 0.039 | S | −0.205 | 0.915 | / |
| 489 | 70347 | SENSE | 0.156 | 0.038 | S | −0.082 | 0.868 | / | −0.153 | 0.752 | / | 0.405 | 0.006 | S | 0.056 | 0.068 | T |
| 490 | 70406 | SENSE | −0.275 | 0.948 | / | −0.245 | 0.992 | / | 0.759 | 0.025 | S | −0.282 | 0.949 | / | −0.121 | 0.939 | / |
| 491 | 70469 | SENSE | 0.032 | 0.392 | / | 0.348 | 0.004 | S | −0.733 | 0.996 | / | 0.325 | 0.059 | T | −0.141 | 0.922 | / |
| 492 | 70564 | SENSE | 0.17 | 0.037 | S | 0.051 | 0.234 | / | 0.772 | 0 | S | −0.381 | 0.977 | / | −0.015 | 0.655 | / |
| 493 | 70601 | SENSE | 0.231 | 0.086 | T | 0.247 | 0.004 | S | −0.257 | 0.959 | / | 0.323 | 0.024 | S | 0.082 | 0.03 | S |
| 494 | 70612 | SENSE | 0.053 | 0.112 | T | 0.082 | 0.096 | T | 1.049 | 0.011 | S | −0.212 | 0.992 | / | 0.07 | 0.004 | S |
| 495 | 70720 | ANTI-SENSE | −0.16 | 0.898 | / | 0.028 | 0.384 | / | 1.312 | 0.009 | S | 0.219 | 0.121 | T | 0.128 | 0.018 | S |
| 496 | 70735 | SENSE | −0.058 | 0.672 | / | 0.156 | 0.087 | T | 0.421 | 0.036 | S | 0.532 | 0.003 | S | 0.033 | 0.038 | S |
| 497 | 70846 | SENSE | 0.086 | 0.255 | / | 0.134 | 0.063 | T | −0.33 | 0.918 | / | 0.142 | 0.151 | T | 0.011 | 0.439 | / |
| 498 | 70923 | SENSE | 0.484 | 0.011 | S | 0.108 | 0.081 | T | −0.4 | 0.844 | / | 0.091 | 0.198 | T | 0.099 | 0.001 | S |
| 499 | 71149 | SENSE | −1.085 | 0.993 | / | −0.043 | 0.681 | / | 0.346 | 0.017 | S | 0.136 | 0.133 | T | 0.066 | 0.077 | T |
| 500 | 71608 | SENSE | −0.849 | 0.907 | / | −0.132 | 0.976 | / | 0.816 | 0.006 | S | 0.279 | 0.004 | S | 0.038 | 0.238 | / |
| 501 | 71739 | SENSE | −0.275 | 0.937 | / | −0.107 | 0.955 | / | 0.334 | 0 | S | −0.075 | 0.815 | / | −0.119 | 0.874 | / |
| 502 | 72014 | SENSE | −0.038 | 0.94 | / | 0.07 | 0.278 | / | 0.732 | 0.06 | T | −0.026 | 0.584 | / | −0.013 | 0.596 | / |
| 503 | 72051 | SENSE | 0.026 | 0.28 | / | 0.311 | 0.003 | S | 0.222 | 0.236 | / | 0.453 | 0.009 | S | 0.052 | 0.168 | T |
| 432 | 70217 | SENSE | −0.202 | 0.893 | / | 0.203 | 0.024 | S | −0.079 | 0.743 | / | 0.27 | 0.07 | T | −0.063 | 0.856 | / |
| 454 | 70354 | SENSE | 0.134 | 0.147 | T | −0.119 | 0.684 | / | 0.48 | 0.02 | S | −0.119 | 0.736 | / | 0.014 | 0.3 | / |
| 334 | 70417 | SENSE | −0.35 | 0.988 | / | −0.041 | 0.637 | / | 0.69 | 0.012 | S | −0.136 | 0.978 | / | 0.004 | 0.411 | / |
| 515 | 70435 | SENSE | 0.664 | 0.014 | S | 0.146 | 0.036 | S | 0.138 | 0.097 | T | 0.33 | 0.038 | S | 0.039 | 0.16 | T |
| 457 | 70465 | SENSE | −0.106 | 0.79 | / | / | / | / | 0.883 | 0.001 | S | −0.27 | 0.945 | / | −0.097 | 0.818 | / |
| 460 | 70852 | SENSE | 0.178 | 0.031 | S | 0.145 | 0.034 | S | −0.525 | 0.904 | / | −0.315 | 0.861 | / | −0.059 | 0.774 | / |
| 405 | 71508 | SENSE | 0.195 | 0.162 | T | 0.251 | 0.017 | S | −0.515 | 0.929 | / | −0.322 | 0.997 | / | −0.196 | 0.982 | / |
| 295 | 71835 | SENSE | 0.139 | 0.055 | T | 0.163 | 0.049 | S | 0.538 | 0.019 | S | 0.27 | 0.068 | T | 0 | 0.496 | / |
| 467 | 72432 | SENSE | 0.146 | 0.021 | S | 0.139 | 0.02 | S | 0.325 | 0.012 | S | 0.074 | 0.149 | T | −0.106 | 0.879 | / |
| 443 | 72453 | SENSE | 0.204 | 0.037 | S | 0.116 | 0.046 | S | −2.198 | 0.995 | / | 0.016 | 0.448 | / | −0.013 | 0.534 | / |

TABLE 12-continued

| Pep SEQ ID | Construct_id | Orientation | Rosette Dry Weight | | | Rosette Radius | | | Seed Dry Weight | | | Silique Dry Weight | | | Silique Length | | |
|---|---|---|---|---|---|---|---|---|---|---|---|---|---|---|---|---|---|
| | | | delta | p-value | c | delta | p-value | c | delta | p-value | c | delta | p-value | c | delta | p-value | c |
| 433 | 72711 | SENSE | 0.292 | 0.058 | T | 0.143 | 0.024 | S | −0.114 | 0.76 | / | −0.04 | 0.667 | / | −0.093 | 0.946 | / |
| 449 | 72969 | SENSE | 0.046 | 0.072 | T | −0.158 | 0.887 | / | 0.39 | 0.031 | S | 0.477 | 0.001 | S | 0.095 | 0.054 | T |
| 426 | 72987 | SENSE | 0.385 | 0.006 | S | / | / | / | 0.098 | 0.104 | T | 0.153 | 0.016 | S | 0.057 | 0.061 | T |
| 525 | 74022 | SENSE | 0.11 | 0.226 | / | −0.069 | 0.844 | / | 0.71 | 0.009 | S | −0.05 | 0.613 | / | −0.004 | 0.544 | / |
| 287 | 74251 | SENSE | −0.56 | 0.961 | / | −0.184 | 0.916 | / | 0.611 | 0.001 | S | 0.174 | 0.229 | / | −0.137 | 0.923 | / |
| 537 | 74507 | SENSE | 0.255 | 0.017 | S | 0.178 | 0.03 | S | 0.318 | 0.032 | S | 0.188 | 0.011 | S | 0.013 | 0.078 | T |
| 313 | 74512 | SENSE | −0.247 | 0.953 | / | 0.107 | 0.015 | S | −0.073 | 0.86 | / | 0.113 | 0.034 | S | 0.05 | 0.175 | T |

S: represents the transgenic plants showed statistically significant trait improvement as compared to the reference ($p < 0.05$)
T: represents data points not determined or the transgenic plants showed a trend of trait improvement compared to the reference with $p < 0.2$
/: represents the transgenic plants didn't show any alteration or had unfavorable change in traits examined as compared to the reference in the current dataset

K. Limited Nitrogen Tolerance Screen

Under low nitrogen conditions, *Arabidopsis* seedlings become chlorotic and have less biomass. This example sets forth the limited nitrogen tolerance screen to identify *Arabidopsis* plants transformed with the gene of interest that are altered in their ability to accumulate biomass and/or retain chlorophyll under low nitrogen condition.

T2 seeds were plated on glufosinate selection plates containing 0.5×N-Free Hoagland's T 0.1 mM $NH_4NO_3$ T 0.1% sucrose T 1% phytagel media and grown under standard light and temperature conditions. At 12 days of growth, plants were scored for seedling status (i.e., viable or non-viable) and root length. After 21 days of growth, plants were scored for visual color, seedling weight, number of green leaves, number of rosette leaves, root length and formation of flowering buds. A photograph of each plant was also taken at this time point.

The seedling weight and root length were analyzed as quantitative responses according to example 1M. The number green leaves, the number of rosette leaves and the flowerbud formation were analyzed as qualitative responses according to example 1L.

Table 13 provides a list of recombinant DNA constructs that improve low nitrogen availability tolerance in plants.

TABLE 13

| Pep SEQ ID | Construct_id | Orientation | Flowerbud formation | | | Number of green leaves | | | Root Length | | | Number of rosette leaves | | | Seedling Weight | | |
|---|---|---|---|---|---|---|---|---|---|---|---|---|---|---|---|---|---|
| | | | RS mean | p-value | c | RS mean | p-value | c | delta | p-value | c | RS mean | p-value | c | delta | p-value | c |
| 375 | 72963 | SENSE | 1.1 | 0.004 | S | 0.293 | 0.021 | S | −0.446 | 0.002 | S | −0.246 | 0.786 | / | 0.137 | 0.001 | S |
| 389 | 70437 | SENSE | −0.28 | 0.982 | / | −0.08 | 0.769 | / | 0.259 | 0.006 | S | 0.5 | 0.005 | S | 0.133 | 0.003 | S |
| 390 | 71633 | SENSE | 0.26 | 0.26 | / | 0.254 | 0.114 | T | −0.1 | 0.539 | / | 0.647 | 0.06 | T | 0.106 | 0.023 | S |
| 391 | 72948 | SENSE | 0.587 | 0.06 | T | 0.539 | 0.029 | S | −0.237 | 0.003 | S | 0.479 | 0.1 | T | 0.078 | 0.121 | T |
| 392 | 72519 | SENSE | 0.749 | 0.033 | S | 0.209 | 0.104 | T | −0.09 | 0.274 | / | 0.276 | 0.264 | / | 0.116 | 0.006 | S |
| 393 | 10475 | SENSE | 1.256 | 0.026 | S | 0.588 | 0.005 | S | −0.378 | 0.002 | S | 0.081 | 0.319 | / | 0.018 | 0.75 | / |
| 394 | 11120 | ANTI-SENSE | 0.795 | 0.033 | S | 0.608 | 0.015 | S | −0.45 | 0.001 | S | 0.287 | 0.106 | T | −0.041 | 0.387 | / |
| 395 | 19736 | SENSE | −0.24 | 0.907 | / | 0.355 | 0.033 | S | 0.014 | 0.864 | / | 0.64 | 0.006 | S | −0.075 | 0.005 | / |
| 396 | 71606 | SENSE | 0.605 | 0.088 | T | 0.176 | 0.11 | T | −0.033 | 0.708 | / | 1.239 | 0.005 | S | 0.133 | 0.002 | S |
| 397 | 71840 | SENSE | 0.408 | 0.235 | / | 0.879 | 0.006 | S | −0.137 | 0.248 | / | 0.524 | 0.032 | S | 0.066 | 0.198 | T |
| 398 | 74240 | SENSE | −0.06 | 0.602 | / | 0.13 | 0.076 | T | −0.107 | 0.306 | / | 0.714 | 0.034 | S | 0.108 | 0.002 | S |
| 399 | 74331 | SENSE | −0.44 | 1 | / | 0.054 | 0.203 | / | 0.132 | 0.055 | T | 1.045 | 0.021 | S | 0.134 | 0.003 | S |
| 400 | 74610 | SENSE | −0.59 | 1 | / | −0.08 | 0.922 | / | 0.289 | 0 | S | 1.241 | 0.017 | S | 0.137 | 0.001 | S |
| 401 | 75527 | SENSE | 0.242 | 0.228 | / | 0.376 | 0.028 | S | −0.183 | 0.045 | / | 0.352 | 0.083 | T | −0.005 | 0.8 | / |
| 316 | 71811 | SENSE | −0.45 | 0.91 | / | / | / | / | −0.112 | 0.202 | / | 0.438 | 0.014 | S | −0.054 | 0.161 | / |
| 505 | 72463 | SENSE | −0.16 | 0.976 | / | / | / | / | 0.112 | 0.109 | T | 0.366 | 0.024 | S | 0.13 | 0.006 | S |
| 351 | 75701 | SENSE | 0.736 | 0.048 | S | 0.07 | 0.861 | / | −0.4 | 0.018 | S | / | / | / | −0.109 | 0.193 | / |

S: represents the transgenic plants showed statistically significant trait improvement as compared to the reference ($p < 0.05$)
T: represents the transgenic plants showed a trend of trait improvement compared than the reference with $p < 0.2$
/: represents data points not determined or the transgenic plants didn't show any alteration or had unfavorable change in traits examined as compared to the reference in the current dataset

L. Statistic Analysis for Qualitative Responses

Table 14 provides a list of responses that were analyzed as qualitative responses

TABLE 14

| response | Screen | categories (success vs. failure) |
|---|---|---|
| wilting response Risk Score | Soil drought tolerance screen | non-wilted vs. wilted |
| growth stage at day 14 | heat stress tolerance screen | 50% of plants reach stage1.03 vs. not |
| growth stage at day 14 | salt stress tolerance screen | 50% of plants reach stage1.03 vs. not |

TABLE 14-continued

| response | Screen | categories (success vs. failure) |
|---|---|---|
| growth stage at day 14 | PEG induced osmotic stress tolerance screen | 50% of plants reach stage1.03 vs. not |
| growth stage at day 7 | cold germination tolerance screen | 50% of plants reach stage 0.5 vs. not |
| number of rosette leaves at day 23 | Shade tolerance screen | 5 leaves appeared vs. not |
| flower bud formation at day 23 | Shade tolerance screen | flower buds appear vs. not |
| leaf angle at day 23 | Shade tolerance screen | >60 degree vs. <60 degree |
| number of green leaves at day 21 | limited nitrogen tolerance screen | 6 or 7 leaves appeared vs. not |
| number of rosette leaves at day 21 | limited nitrogen tolerance screen | 6 or 7 leaves appeared vs. not |
| Flower bud formation at day 21 | limited nitrogen tolerance screen | flower buds appear vs. not |

Plants were grouped into transgenic and reference groups and were scored as success or failure according to criteria in Table 14. First, the risk (R) was calculated, which is the proportion of plants that were scored as of failure plants within the group. Then the relative risk (RR) was calculated as the ratio of R (transgenic) to R (reference). Risk score (RS) was calculated as $-\log_2^{RR}$. Subsequently the risk scores from multiple events for each transgene of interest were evaluated for statistical significance by t-test using S-PLUS statistical software (S-PLUS 6, Guide to statistics, Insightful, Seattle, Wash., USA). RS with a value greater than 0 indicates that the transgenic plants perform better than the reference. RS with a value less than 0 indicates that the transgenic plants perform worse than the reference. The RS with a value equal to 0 indicates that the performance of the transgenic plants and the reference don't show any difference.

M. Statistic Analysis for Quantitative Responses

Table 15 provides a list of responses that were analyzed as quantitative responses.

TABLE 15

| response | screen |
|---|---|
| seed yield | Soil drought stress tolerance screen |
| seedling weight at day 14 | heat stress tolerance screen |
| root length at day 14 | heat stress tolerance screen |
| seedling weight at day 14 | salt stress tolerance screen |
| root length at day 14 | salt stress tolerance screen |
| root length at day 11 | salt stress tolerance screen |
| seedling weight at day 14 | PEG induced osmotic stress tolerance screen |
| root length at day 11 | PEG induced osmotic stress tolerance screen |
| root length at day 14 | PEG induced osmotic stress tolerance screen |
| rosette area at day 8 | cold shock tolerance screen |
| rosette area at day28 | cold shock tolerance screen |
| difference in rosette area from day 8 to day 28 | cold shock tolerance screen |
| root length at day 28 | cold germination tolerance screen |
| seedling weight at day 23 | Shade tolerance screen |
| petiole length at day 23 | Shade tolerance screen |
| root length at day 14 | Early plant growth and development screen |
| Seedling weight at day14 | Early plant growth and development screen |
| Rosette dry weight at day 53 | Late plant growth and development screen |
| rosette radius at day 25 | Late plant growth and development screen |
| seed dry weight at day 58 | Late plant growth and development screen |
| silique dry weight at day 53 | Late plant growth and development screen |
| silique length at day 40 | Late plant growth and development screen |
| Seedling weight at day 21 | Limited nitrogen tolerance screen |
| Root length at day 21 | Limited nitrogen tolerance screen |

The measurements (M) of each plant were transformed by $\log_2$ calculation. The Delta was calculated as log 2M(transgenic)-log 2M(reference). Subsequently the mean delta from multiple events of the transgene of interest was evaluated for statistical significance by t-test using S-PLUS statistical software (S-PLUS 6, Guide to statistics, Insightful, Seattle, Wash., USA). The Delta with a value greater than 0 indicates that the transgenic plants perform better than the reference. The Delta with a value less than 0 indicates that the transgenic plants perform worse than the reference. The Delta with a value equal to 0 indicates that the performance of the transgenic plants and the reference don't show any difference.

Example 2 Identification of Homologs

A BLAST searchable "All Protein Database" was constructed of known protein sequences using a proprietary sequence database and the National Center for Biotechnology Information (NCBI) non-redundant amino acid database (nr.aa). For each organism from which a DNA sequence provided herein was obtained, an "Organism Protein Database" was constructed of known protein sequences of the organism; the Organism Protein Database is a subset of the All Protein Database based on the NCBI taxonomy ID for the organism.

The All Protein Database was queried using amino acid sequence of cognate protein for gene DNA used in trait-improving recombinant DNA, i.e., sequences of SEQ ID NO: 240 through SEQ ID NO: 478 using "blastp" with E-value cutoff of 1e-8. Up to 1000 top hits were kept, and separated by organism names. For each organism other than that of the query sequence, a list was kept for hits from the query organism itself with a more significant E-value than the best hit of the organism. The list contains likely duplicated genes, and is referred to as the Core List. Another list was kept for all the hits from each organism, sorted by E-value, and referred to as the Hit List.

The Organism Protein Database was queried using amino acid sequences of SEQ ID NO: 270 through SEQ ID NO: 538 using "blastp" with E-value cutoff of 1e-4. Up to 1000 top hits were kept. A BLAST searchable database was constructed based on these hits, and is referred to as "SubDB". SubDB was queried with each sequence in the Hit List using "blastp" with E-value cutoff of 1e-8. The hit with the best E-value was compared with the Core List from the corresponding organism. The hit is deemed a likely ortholog if it belongs to the Core List, otherwise it is deemed not a likely ortholog and there is no further search of sequences in the Hit List for the same organism. Likely orthologs from a large number of distinct organisms were identified and are reported by amino acid sequences of SEQ ID NO: 539 to SEQ ID NO: 22568. The relationship of the homologs to the identified trait-improving genes on an amino acid sequence basis is found in Table 16 where the amino acid sequence of a protein encoded by a trait-improving DNA, e.g., SEQ ID NO:270, is followed by the amino acid sequences of protein encoded by homologous genes, e.g., SEQ ID NO:19844, 4248, 2761, 15944, etc. The source organism of each homolog is reported in the Sequence Listing.

TABLE 16

Sequence IDs for homolog proteins
Seq ID NO: homolog Seq ID NOs

| | | | | | | | | | | | |
|---|---|---|---|---|---|---|---|---|---|---|---|
| 270: | 19844 | 4248 | 2761 | 15944 | 11776 | 16144 | 10470 | 9742 | 6776 | 1010 | 2285 | 16333 |
| | 9154 | 20620 | 16454 | 20025 | 8388 | 10646 | 1208 | 6001 | 1706 | 2448 | 14768 | 10226 |
| | 12626 | 19846 | 9302 | 17295 | 17794 | 6354 | 5098 | 1789 | 6430 | 17749 | 821 | 10109 |
| | 7542 | 17855 | 15562 | 17462 | | | | | | | | |
| 271: | 1715 | 5418 | 7208 | 19338 | 7440 | 711 | 8113 | 17151 | 17592 | 18879 | 4807 | 8671 |
| | 9936 | 11315 | 10681 | 3177 | 10519 | 6830 | 13563 | 12162 | 15155 | 1860 | 18072 | 20945 |
| | 6715 | 15032 | 5192 | 10928 | | | | | | | | |
| 272: | 0 | | | | | | | | | | | |
| 273: | 13771 | 8553 | 4219 | 10043 | 10800 | 8345 | 17501 | 13569 | 954 | 17197 | 6188 | 3760 |
| | 13267 | 16169 | 8132 | 2667 | 11216 | 15637 | 4652 | 2270 | 10309 | 5708 | 18374 | 9446 |
| | 12844 | 7790 | 7569 | 4786 | 9725 | 14187 | 12859 | 16948 | 18626 | 13741 | 5525 | 7877 |
| | 4550 | 15544 | 9706 | 7616 | 14358 | 15163 | 13182 | 14560 | 16722 | 1129 | 1472 | 4261 |
| | 10693 | 20144 | 6437 | 21413 | 17893 | 17984 | 17116 | 9925 | 19953 | 20648 | 983 | 2837 |
| | 5663 | 2943 | 10465 | 1841 | 12497 | 6435 | 14763 | 13495 | 12676 | 7513 | 8363 | 16389 |
| | 8162 | 7945 | 14956 | 15029 | 12433 | 22241 | 16071 | 13003 | 16940 | 18847 | 12354 | 7732 |
| | 14013 | 5735 | 11505 | 8833 | 17658 | 16048 | 17609 | 575 | 6641 | 6331 | 3738 | 10842 |
| | 18927 | 21518 | 20097 | 14117 | 5309 | 13744 | 15880 | 19484 | 9648 | 22509 | 1221 | 15515 |
| | 6785 | 852 | 6466 | 17423 | 14164 | 658 | 8704 | 16710 | 19375 | 3306 | 14050 | 16883 |
| | 16322 | 1722 | 15481 | 13636 | 10680 | 6347 | 3552 | 8885 | 21794 | 17703 | 22557 | 14777 |
| | 21189 | 13711 | 3601 | 3968 | 3692 | 4003 | 20044 | 12943 | 19749 | 1865 | 6355 | 14902 |
| | 6137 | 22370 | 19468 | 10410 | 21460 | 10451 | 17175 | 20965 | 12916 | 1206 | 6796 | 11329 |
| | 9139 | 11008 | 10569 | 9058 | 7988 | 19743 | 20088 | 14111 | 8231 | 4522 | 18497 | 11952 |
| | 2866 | 15466 | 3609 | 2403 | 16796 | 13539 | 14806 | 5364 | 12620 | 20699 | 12940 | 15426 |
| | 4409 | 12452 | 5296 | 9156 | 629 | 12665 | 20947 | 3649 | 7530 | | | |
| 274: | 16167 | 5178 | 2412 | 10455 | 20036 | 11246 | 19666 | 6400 | 5573 | 22539 | 8547 | 21845 |
| | 2413 | 20290 | 4036 | 19351 | 5886 | 6071 | 17184 | 9738 | | | | |
| 275: | 14665 | 16694 | 12678 | 14928 | 21489 | 7918 | 1571 | 3959 | 2490 | 2517 | 14615 | 3788 |
| | 10022 | 16096 | 21248 | 13293 | 8541 | 13446 | 6120 | 4360 | 3812 | 15574 | 18938 | 19203 |
| | 2284 | 2215 | 10054 | 14052 | 9653 | 10183 | 17752 | 20776 | 4240 | 22343 | 8270 | 9192 |
| | 17217 | 7374 | 12141 | 20657 | 7674 | 6445 | 2522 | | | | | |
| 276: | 12496 | 3460 | 13599 | 7043 | 9150 | 1664 | | | | | | |
| 277: | 16949 | 9640 | 8150 | 2014 | 12188 | 5779 | 17876 | 14612 | 18293 | 11053 | 15958 | 15263 |
| | 18370 | 20984 | 13094 | 18734 | 7380 | 10318 | 21641 | 12737 | 13028 | 20561 | 7087 | 10686 |
| | 9894 | 7528 | 12573 | 16043 | 14846 | 20513 | 2802 | 8897 | 14716 | 10257 | 16407 | 2727 |
| | 6151 | 1484 | 6831 | 16916 | 10146 | 17756 | 13193 | 7670 | 15946 | 7750 | 9397 | 20046 |
| | 12547 | 5399 | 18644 | 11883 | 12531 | 12530 | 17188 | 2130 | 3805 | 17493 | 16821 | 10181 |
| | 3639 | 3934 | 1419 | 780 | | | | | | | | |
| 278: | 16531 | 9228 | 5799 | 19821 | 10980 | 17656 | 3449 | 19982 | 13335 | 20959 | 11238 | 13084 |
| | 10281 | 17610 | 19623 | 17614 | 9736 | 21375 | 19978 | 5859 | 4943 | 12390 | 18806 | 1349 |
| | 8759 | 21741 | 20400 | 13707 | 9170 | 15899 | 11361 | 4333 | 10631 | 12909 | 2136 | 12776 |
| | 20323 | 7676 | 5847 | 9065 | 19902 | 4545 | 6768 | 546 | 9246 | 14134 | 4442 | 20731 |
| | 9931 | 6700 | 8677 | 19305 | 4828 | 3655 | 17550 | 7579 | 21629 | 9044 | 19475 | 637 |
| | 4209 | 3519 | 3873 | 15884 | 12247 | 10177 | 1407 | 10312 | 15957 | 16955 | 17469 | 20241 |
| | 7267 | 21862 | 16864 | 22192 | 19599 | 6365 | 12324 | 10985 | 6424 | 6449 | 14564 | 3115 |
| | 14885 | 10603 | 911 | 18609 | 3359 | 7059 | 2851 | 5801 | 9613 | 8391 | 18695 | 7987 |
| | 14964 | 1081 | 15171 | 1312 | 14747 | 3060 | 13390 | 22115 | 5060 | 16536 | 19729 | 13468 |
| | 11109 | 21989 | 2230 | 9462 | 9096 | 18775 | 10721 | 11999 | 8340 | 16607 | 22199 | 8687 |
| | 3652 | 8147 | 22073 | 4090 | 3491 | 20506 | 7835 | 10890 | 6781 | 7839 | 14478 | 16371 |
| | 579 | 6442 | 9721 | 5423 | 2566 | 7876 | 17580 | 2023 | 13164 | 9424 | 14096 | 8115 |
| | 15304 | 14818 | 7282 | 6422 | 4841 | 10106 | 1075 | 12995 | 9297 | 21280 | 2309 | 895 |
| | 12373 | 5366 | 22159 | 4499 | 737 | 11369 | 4308 | 13974 | 2794 | 12771 | 16584 | 9250 |
| | 6930 | 8792 | 10185 | 17718 | 13148 | 5054 | 22383 | 9674 | 9868 | 21546 | 15881 | 20000 |
| | 19029 | 4938 | 14024 | 15026 | 15535 | 16386 | 15402 | 21036 | 12653 | 9490 | 4170 | 11551 |
| | 3711 | 4179 | 18619 | 16370 | 14161 | 11294 | 9094 | 2689 | 21881 | | | |
| 279: | 13577 | 10344 | 17371 | 5840 | 13904 | 12689 | 11795 | 21912 | 17226 | 14519 | 8854 | 14229 |
| | 7998 | 8326 | 1400 | 16163 | 11785 | 10117 | 21511 | 21043 | 18205 | 2933 | 2043 | 22181 |
| | 21628 | 20090 | 18018 | 20578 | 19081 | 11011 | 4768 | 2834 | 4635 | 13475 | 6306 | 13119 |
| | 1671 | 21348 | 16926 | 20801 | 6361 | 4269 | 4366 | 15615 | 941 | 7046 | 3166 | 16526 |
| | 6250 | 4790 | 825 | 16541 | 14270 | 3574 | 8127 | 18015 | 13147 | 17950 | 15243 | 6671 |
| | 20662 | 3487 | 11787 | 6762 | 5488 | 7117 | 9417 | 15702 | 4859 | 20527 | 19240 | 17200 |
| | 7115 | 19523 | 12823 | 9115 | 11770 | 20530 | 4791 | 20334 | 11019 | 20645 | 14383 | 1914 |
| | 8945 | 15358 | 9347 | 2496 | 3098 | 11604 | 16441 | 19352 | 18451 | 12451 | 8877 | 15655 |
| | 791 | 12609 | 12588 | 19785 | 18328 | 8143 | 22185 | 1488 | 10212 | 14002 | 16826 | 11779 |
| | 1890 | 3879 | 20130 | 21633 | 20930 | 17222 | 2691 | 18852 | 7120 | 7853 | 644 | 21495 |
| | 14630 | 21041 | 5676 | 8447 | 16750 | 10436 | 4523 | 2686 | 8237 | 2948 | 13559 | 19008 |
| | 3686 | 18465 | 3895 | 7416 | 10170 | 18867 | 14574 | 1159 | | | | |
| 280: | 16310 | 3796 | 10205 | 19486 | 13581 | 11022 | 21960 | 15598 | 12604 | 9662 | 20210 | 21764 |
| | 8626 | 17323 | 11666 | 21316 | 6121 | 7438 | 982 | 2135 | 17499 | 12340 | 20711 | 6553 |
| | 10296 | 17874 | 914 | 17716 | 3723 | | | | | | | |
| 281: | 20551 | 21096 | 13717 | 4006 | 19762 | 10017 | 14425 | 17785 | 6291 | 3855 | 15232 | 11917 |
| | 21856 | 18564 | 19010 | 3910 | 13621 | 19087 | 670 | 10539 | 851 | 5698 | 9112 | 12694 |
| | 14218 | 11947 | 18104 | 21227 | 22348 | 14178 | 1862 | 9829 | 9325 | 14533 | 13149 | 8679 |
| | 17127 | 6507 | 10375 | 2782 | 3357 | 594 | 7548 | 9316 | 5728 | 7981 | 8022 | 13688 |
| | 1294 | 13817 | 21893 | 10781 | 5263 | 11292 | 5492 | 9542 | 8000 | 16102 | 6328 | 11687 |
| | 13695 | 15807 | 4068 | 3478 | 6486 | 13660 | 22165 | 17881 | 19166 | 3613 | 7013 | 6393 |
| | 15983 | 17688 | 5124 | 4243 | 19684 | 17008 | 12366 | 7161 | 20062 | 12194 | 15870 | 14385 |
| | 9124 | 9865 | 6211 | 628 | 6448 | 700 | 8869 | 17941 | 10697 | 21134 | 5586 | 4469 |

TABLE 16-continued

Sequence IDs for homolog proteins
Seq ID NO: homolog Seq ID NOs

|  |  |  |  |  |  |  |  |  |  |  |  |  |
|---|---|---|---|---|---|---|---|---|---|---|---|---|
|  | 21167 | 855 | 20538 | 9251 | 1036 | 10678 | 1977 | 17337 | 4575 | 19974 | 3520 | 10195 |
|  | 14572 | 3870 | 21293 | 19011 | 12921 | 20120 | 11647 | 15054 | 13976 | 21163 | 20362 | 12988 |
|  | 15636 | 2345 | 4740 | 3205 | 17504 | 1953 | 15208 | 16834 | 7654 | 15907 | 8961 |  |
| 282: | 19261 | 3860 | 7076 | 12616 | 1790 | 4886 | 9735 | 12611 | 20478 | 4501 | 18874 | 7032 |
|  | 18024 | 7225 | 4544 | 11443 | 2127 | 19283 | 7367 | 1338 | 4482 | 15213 | 20554 | 3826 |
|  | 14978 | 21769 | 11755 | 4250 | 15506 | 20020 | 6593 | 1286 | 20750 | 18985 | 16069 | 4571 |
|  | 22536 | 3773 | 11152 | 9745 | 13196 | 2190 | 8120 | 7914 | 16863 | 11987 | 16172 | 15399 |
|  | 14422 | 12490 | 8076 | 17180 | 19067 | 14493 | 13105 | 16459 | 18285 | 15863 | 14085 | 18130 |
|  | 11566 | 17352 | 20003 | 2995 | 5386 | 8757 | 19103 | 15685 | 20563 | 18739 | 20815 | 19454 |
|  | 7820 | 20771 | 7972 |  |  |  |  |  |  |  |  |  |
| 283: | 0 |  |  |  |  |  |  |  |  |  |  |  |
| 284: | 10750 | 5276 | 3894 | 3486 | 12240 | 18158 | 12170 | 15393 | 9765 | 11266 | 5031 | 2792 |
|  | 9334 | 20684 | 1144 | 13799 | 10858 | 16622 | 20849 | 22001 | 6897 | 17710 | 15401 | 18589 |
|  | 9550 | 1757 | 10249 | 21993 | 2001 | 19689 | 15058 | 4297 | 19990 | 643 | 11414 | 18208 |
|  | 19995 |  |  |  |  |  |  |  |  |  |  |  |
| 285: | 17916 | 15231 | 15741 | 15829 | 4645 | 21977 | 10291 | 1806 | 21573 | 474 | 6018 | 2663 |
|  | 8036 | 9618 | 16693 | 3960 | 15864 | 14578 | 17125 | 15924 | 21826 | 13440 | 17249 | 8650 |
|  | 20159 | 1986 | 15742 | 19706 | 22092 | 8766 | 6813 | 17830 | 10853 | 21281 | 13394 | 5285 |
|  | 8139 | 21004 | 14220 | 17563 | 2086 | 2488 | 1597 | 4698 | 13233 | 4654 | 1250 | 15737 |
|  | 2907 | 1469 | 9957 | 13288 | 6516 | 22526 | 16496 | 14873 | 10471 | 18290 | 3086 | 11953 |
|  | 18592 | 3185 | 9418 | 17135 | 8081 | 9593 | 19180 | 4673 | 7979 | 16544 | 13933 | 1300 |
|  | 16782 | 15551 | 8460 | 15960 | 3405 | 13997 | 1566 | 21046 | 8636 | 17134 | 6512 | 6596 |
|  | 13346 | 15639 | 14396 | 9252 | 12093 | 21591 | 15042 | 6953 | 18637 | 16784 | 22523 | 6262 |
|  | 16933 | 22440 | 4612 | 19863 | 6076 | 4133 | 19601 | 3344 | 12192 | 16828 | 17089 | 19303 |
|  | 6118 | 15088 | 14986 | 21070 | 771 | 3291 | 2153 | 21234 | 18173 | 11970 | 21215 | 10644 |
|  | 20638 | 4377 | 21183 | 9519 | 13810 | 10948 | 17764 | 15793 | 21029 | 16613 | 18091 | 6526 |
|  | 5846 | 22213 | 22003 | 20765 | 3801 | 21866 | 21771 | 14860 | 861 | 6743 | 5007 | 5529 |
|  | 14267 | 14880 | 21391 | 10210 | 5693 | 5970 | 3793 | 15855 | 1007 | 13001 | 6878 | 9875 |
|  | 16912 | 19329 | 13614 | 10333 | 13714 | 6903 | 21112 | 8204 | 1133 | 21262 | 16852 | 15703 |
|  | 21338 | 6248 | 21547 | 15242 | 13567 | 16788 | 11020 | 18655 | 10528 | 19496 | 17440 | 22414 |
|  | 17480 | 8142 | 7760 | 20388 | 2829 | 16249 | 12914 | 2569 | 14595 | 7096 | 6689 | 12534 |
|  | 6105 | 16041 | 9242 | 9145 | 1552 | 10313 | 1379 | 9596 | 11771 | 5820 | 593 | 15445 |
|  | 3268 | 14744 | 18410 | 6984 | 10872 | 10053 | 9713 | 8837 | 1383 | 4305 | 10421 | 2944 |
|  | 20363 | 19120 | 7463 | 16753 | 20969 | 18430 | 12905 | 10227 | 11066 | 6057 | 13677 | 18640 |
|  | 4083 | 1527 | 19285 | 5385 | 17557 | 20851 | 15693 | 17304 | 1683 | 14391 | 15965 | 19854 |
|  | 8425 | 14916 |  |  |  |  |  |  |  |  |  |  |
| 286: | 16099 | 8075 | 8242 | 420 | 13036 | 10217 | 18174 | 507 | 11062 | 15313 | 16399 | 14594 |
|  | 3820 | 5216 | 5717 | 10394 | 20464 | 15374 | 15526 | 18461 | 17556 | 14810 | 4502 | 12391 |
|  | 11462 | 14924 | 1652 | 18690 | 9504 | 13188 | 8137 | 3327 | 12056 | 2537 | 4030 | 1064 |
|  | 15390 | 6367 | 19001 | 8581 | 6859 | 7602 | 14778 | 7681 | 18172 | 18107 | 12112 | 7417 |
|  | 13896 | 2465 | 12130 | 19906 | 4949 | 17359 | 16220 | 13607 | 526 | 20229 | 16469 | 10705 |
|  | 15889 | 16978 | 8246 | 16554 | 18467 | 9002 | 9780 | 17882 | 21655 | 20242 | 21051 | 3977 |
|  | 19627 | 9063 | 10810 | 15051 | 5705 | 9204 | 11991 | 9915 | 15840 | 16148 | 14589 | 6171 |
|  | 6614 | 20389 | 6007 | 6226 | 5373 | 19830 | 9030 | 14898 | 11912 | 16971 | 18279 | 19602 |
|  | 13078 | 18533 | 1840 | 4491 | 7812 | 8977 | 13027 | 6371 | 15170 | 21310 | 6443 | 9755 |
|  | 12535 | 2819 | 14876 | 3052 | 12267 | 8377 | 3804 | 7983 | 22450 | 22167 | 22369 | 21674 |
|  | 891 | 13549 | 7113 | 14532 | 11064 | 9354 | 7858 | 8394 | 2489 | 17243 | 2044 | 9345 |
|  | 6836 | 2341 | 19148 | 17763 | 13516 | 14240 | 9032 | 15489 | 8304 | 7822 | 17083 | 9993 |
|  | 8188 | 5481 | 11010 | 1093 | 7789 | 21699 | 21306 | 11113 | 8956 | 18128 | 7880 | 3416 |
|  | 2857 | 17664 | 21589 | 11961 | 19154 | 11542 | 4812 | 7486 | 21609 | 5307 | 21506 | 3533 |
|  | 6663 | 4677 | 18511 | 4730 | 696 | 9569 | 17797 | 18687 | 7097 | 20259 | 15252 | 13221 |
|  | 3425 | 3261 | 450 | 6778 | 14692 | 22502 | 14915 | 21157 | 20371 | 3563 | 12591 | 16308 |
|  | 7626 | 4212 | 19798 | 16130 | 21296 | 2832 | 830 | 14553 | 14135 | 6434 | 18295 | 17956 |
|  | 20230 | 476 | 10392 | 12043 | 3289 | 20779 | 1281 | 17745 | 21065 | 5487 | 3754 | 8587 |
|  | 2882 | 12578 | 11548 | 12705 | 15830 | 16586 | 7955 | 15449 | 988 | 20859 | 1768 | 11129 |
|  | 6547 | 22518 | 5552 | 9854 | 11376 | 6669 | 5359 | 9132 | 10964 | 22087 | 1879 | 17298 |
|  | 13137 | 3333 | 20301 | 13752 | 19370 | 2425 | 6946 | 19538 | 14273 | 8003 | 15340 | 6427 |
|  | 17165 | 15603 | 12419 | 10809 | 13658 | 14064 | 4221 | 7387 | 3386 | 13284 | 20981 | 2316 |
|  | 3116 | 8418 | 3578 | 6508 | 18217 | 992 | 22249 | 14855 | 13442 | 3471 | 19949 | 5277 |
|  | 19885 | 2816 | 10917 | 21954 | 9436 | 18538 | 18659 | 12816 | 12308 | 20364 | 15943 | 2649 |
|  | 2515 | 14701 | 9329 | 8193 | 17579 | 22076 | 8890 | 21073 | 8376 | 15177 | 10882 | 859 |
|  | 5990 | 9814 | 16053 | 12078 | 3144 | 5209 | 13848 | 22428 | 19076 | 9604 | 5454 | 3141 |
|  | 17056 | 14918 | 953 | 4088 | 6615 | 15729 | 11270 | 5837 | 14568 | 12544 | 17630 | 2371 |
|  | 4694 | 12396 | 15369 | 16597 | 3697 | 10741 | 13396 | 21621 | 16662 | 8841 | 11120 | 14081 |
|  | 13456 | 21472 | 7487 | 12898 | 12787 | 7866 | 11748 | 8692 | 9484 | 2336 | 15204 | 6565 |
|  | 14320 | 2978 | 9294 | 7482 | 9493 | 1277 | 4576 | 15513 | 21001 | 3242 | 4952 | 7813 |
|  | 7306 | 12296 | 12021 | 6645 | 21060 | 9286 | 22489 | 6264 | 13745 | 16653 | 19069 | 7780 |
|  | 15219 | 16969 | 9271 | 18873 | 14762 | 10802 | 10479 | 16663 | 3678 | 16713 | 7751 | 13703 |
|  | 3630 | 4691 | 9472 | 10709 | 8542 | 7060 | 6112 | 22457 | 21974 | 20476 | 7333 | 6482 |
|  | 14526 | 7151 | 2644 | 835 | 10655 | 12264 | 17372 | 788 | 15452 | 14361 | 11678 | 2754 |
|  | 15289 | 14415 | 9468 | 1673 | 2117 | 17672 | 3643 | 6809 | 9280 | 22095 | 18903 | 3706 |
|  | 15256 | 18593 | 5764 | 11115 | 12583 | 11568 | 622 | 13613 | 2331 | 5136 | 8073 | 15998 |
|  | 5630 | 10889 | 9673 | 9014 | 7950 | 6748 | 9771 | 11716 | 18929 | 14842 | 6789 | 1773 |
|  | 981 | 18575 | 19878 | 21485 | 14269 | 9584 | 12794 | 21399 | 20485 | 9218 | 18691 | 3350 |
|  | 18263 | 4846 | 544 | 19667 | 9933 | 4140 | 1318 | 20418 | 11128 | 20105 | 16734 | 2376 |
|  | 15699 | 7061 | 4232 | 15357 | 14036 | 5339 | 7107 | 19030 | 7165 | 21370 | 12103 | 4848 |
|  | 13211 | 22530 | 15360 | 12863 | 9975 | 6398 | 14067 | 16683 | 21170 | 1924 | 890 | 8155 |

TABLE 16-continued

Sequence IDs for homolog proteins
Seq ID NO: homolog Seq ID NOs

|  | | | | | | | | | | | |
|---|---|---|---|---|---|---|---|---|---|---|---|
|  | 15866 | 10131 | 7187 | 4332 | 1235 | 20330 | 12927 | 7088 | 5099 | 2302 | 12424 | 8303 |
|  | 17466 | 14322 | 11383 | 2282 | 14043 | 15956 | 1818 | 3414 | 12982 | 18548 | 15665 | 10961 |
|  | 21084 | 10824 | 18440 | 16819 | 3730 | 13940 | 18821 | 14864 | 19607 | 7969 | 6546 | 16771 |
|  | 5441 | 8459 | 18266 | 5000 | 15749 | 13014 | 14274 | 8444 | 4707 | 13097 | 15930 | 6281 |
|  | 18662 | 7992 | 9661 | 19875 | 11156 | 3619 | 14086 | 20948 | 16946 | 3456 | 6143 | 6097 |
|  | 786 | 6709 | 13766 | 5954 | 9650 | 17926 | 9083 | 20839 | 17473 | 5462 | 22351 | 12788 |
|  | 5453 | 13277 | 11817 | 9672 | 8255 | 6463 | 15113 | 9053 | 15528 | 1319 | 926 | 17317 |
|  | 6368 | 7704 | 18694 | 3644 | 12154 | 3794 | 21257 | 21638 | 18386 | 18111 | 21498 | 10731 |
|  | 13776 | 5539 | 14530 | 20282 | 7762 | 9529 | 17675 | 15191 | 12380 | 14865 | 15825 | 2818 |
|  | 16442 | 10262 | 10965 | 15558 | 5973 | 22476 | 19408 | 5773 | 5016 | 20819 | 18982 | 19997 |
|  | 4572 | 640 | 19168 | 17905 | 2970 | 2132 | 20312 | 4655 | 16568 | 21093 | 13882 | 5730 |
|  | 7976 | 7079 | 13035 | 3505 | 2800 | 12522 | 8939 | 11219 | 2155 | 15905 | 3206 | 2017 |
|  | 15587 | 6277 | 1297 | 1423 | 9549 | 6119 | 18728 | 12545 | 2037 | 11704 | 9571 | 21379 |
|  | 13089 | 11197 | 13107 | 22367 | 2420 | 17943 | 7599 | 5997 | 1801 | 21374 | 16528 | 8722 |
|  | 16672 | | | | | | | | | | | |
| 287: | 8532 | 19537 | 5344 | 9149 | 21995 | 6924 | 15909 | 4097 | 11901 | 8844 | 7649 | 2133 |
|  | 2202 | 5103 | 10204 | 19005 | 11338 | 19082 | 14317 | | | | | |
| 288: | 19787 | 18784 | 5642 | 15617 | 18773 | 2850 | 21740 | 19753 | 18774 | 8659 | 17768 | 4774 | 15786 |
|  | 13450 | 5349 | 3435 | 11594 | 3337 | 19500 | 18011 | 5026 | 20455 | 17036 | 22287 | 17395 |
|  | 9621 | 6514 | 1386 | 11394 | 7035 | 21823 | 15347 | 11387 | 15362 | 4210 | 5017 | 10279 |
|  | 19441 | 22361 | 7943 | 7642 | 8141 | 16188 | 15181 | 3603 | 7428 | 2749 | 21346 | 17018 |
|  | 10086 | | | | | | | | | | | |
| 289: | 652 | 22063 | 8339 | 21393 | 2555 | 8373 | 21778 | 11080 | 15895 | 10755 | 10659 | 16023 |
|  | 19651 | 17328 | 17996 | 10829 | | | | | | | | |
| 290: | 7684 | 9445 | 17343 | 1187 | 6793 | 10461 | 6245 | 10467 | 20367 | 12284 | | |
| 291: | 19558 | 4465 | 12410 | 21267 | 12416 | | | | | | | |
| 292: | 13619 | 7334 | 20532 | 21542 | 12253 | 16189 | 8764 | 2507 | 21921 | 6586 | 19095 | 9485 |
|  | 5381 | 5599 | 12372 | 14529 | 13331 | 15295 | 19004 | 1397 | 21520 | 14556 | 20510 | 22236 |
|  | 2986 | 7080 | 8521 | 6732 | 13272 | 16558 | 4313 | 20499 | 22483 | 14588 | 9523 | 7470 |
|  | 18752 | 12181 | 20429 | 12348 | 695 | 10907 | 14321 | 14033 | 18144 | 3919 | 8802 | 20993 |
|  | 8165 | 3312 | 17714 | 14662 | 16218 | 6883 | 15696 | 5826 | 8318 | 13408 | 11637 | 4264 |
|  | 1882 | 4226 | 19194 | 12589 | 20866 | 1376 | 21972 | 8106 | 9328 | 11225 | 6391 | 8315 |
|  | 20980 | 16513 | 6488 | 21387 | 10825 | 871 | 22553 | 7860 | 20986 | 5123 | 7178 | 8148 |
|  | 19174 | 5633 | 3500 | 7737 | 17944 | 19517 | 19101 | 2424 | 1678 | 1758 | 16439 | 22408 |
|  | 11623 | 7905 | 18353 | 18641 | 17321 | 18471 | 6775 | 8307 | 11843 | 9722 | 15205 | 20080 |
|  | 16600 | 6416 | 10161 | 8449 | 8858 | 14419 | 19903 | 14156 | 15652 | 13343 | 15817 | 3739 |
|  | 12654 | 14241 | 7430 | 8851 | 6919 | 22017 | 6531 | 1962 | 3371 | 18557 | 2125 | 6815 |
|  | 15392 | 19947 | 6480 | 15023 | 1479 | 1138 | 21122 | 20521 | 21201 | 1677 | 17815 | 9610 |
|  | 8319 | 5949 | 7617 | 10353 | 9342 | 4915 | 6495 | 1682 | 14875 | 17940 | 1204 | 13538 |
|  | 16452 | 19603 | 8029 | 2886 | 14466 | 19507 | 12125 | 6822 | 10351 | 4123 | 9222 | 9605 |
|  | 18244 | 18276 | 17153 | 17212 | 12619 | 14496 | 11337 | 8683 | 15935 | 10084 | 14862 | 5228 |
|  | 20909 | 9138 | 702 | 17034 | 5542 | 16281 | 16905 | 2247 | 17007 | 15480 | 13602 | 16745 |
|  | 3223 | 6163 | 1245 | 10228 | 21595 | 18522 | 6698 | 5750 | 8543 | 21981 | 15735 | 3961 |
|  | 16417 | | | | | | | | | | | |
| 293: | 10002 | 18611 | 6406 | 14073 | 5127 | 8351 | 1241 | 12550 | 10077 | 11772 | 10606 | 3231 |
|  | 10112 | 15857 | 13002 | 6686 | 8210 | 8327 | 4270 | 16125 | 8696 | 5110 | 12311 | 7006 |
|  | 19199 | 6994 | 12597 | 5342 | 12722 | 21575 | 5723 | 2670 | 6046 | 12012 | | |
| 294: | 9532 | 10331 | 15934 | 2046 | 6293 | 19503 | 22316 | 15147 | 14129 | 5699 | 7047 | 13130 |
|  | 2151 | 1110 | 20162 | 9143 | 9176 | 4233 | 8431 | 6088 | 7434 | 18942 | 5356 | 18099 |
|  | 10361 | 3212 | 21551 | 20873 | 2419 | 8077 | 3140 | 13009 | 21068 | 6829 | 20236 | 14326 |
|  | 6208 | 847 | 2330 | 15785 | 1052 | 14929 | 4869 | 16757 | 21501 | 19546 | 10070 | 1727 |
|  | 6317 | 8558 | 3880 | 18261 | 6409 | 6931 | 17666 | 21501 | 12516 | 16760 | 16947 | 3896 |
|  | 3358 | 6554 | 14909 | 1974 | 4835 | 20560 | 11275 | 2659 | 12987 | 18209 | 16896 | 15952 |
|  | 20752 | 15130 | 15569 | 7406 | 13923 | 1051 | 11602 | 3912 | 10042 | 4592 | 22204 | 2430 |
|  | 1382 | 18088 | 15862 | 20314 | 9057 | 10845 | 5041 | 7582 | 21742 | 12835 | 17242 | 15658 |
|  | 8522 | 22493 | 7831 | 1594 | 13654 | 7414 | 12151 | 12808 | 14165 | 15368 | 17979 | 10215 |
|  | 8018 | 22247 | 22220 | 7254 | 654 | 20380 | 2845 | 5061 | 7274 | 5018 | 9568 | 9818 |
|  | 1494 | 3725 | 11235 | 6804 | 8938 | 12700 | 17001 | 19302 | 11190 | 4028 | 3173 | |
| 295: | 21192 | | | | | | | | | | | |
| 296: | 10114 | 6052 | 18680 | 17170 | 11936 | 20081 | 9148 | 3938 | 18585 | 12840 | 14672 | 14951 |
|  | 1544 | 20775 | 4870 | 8723 | 3360 | 19138 | 1416 | 1901 | 18744 | 2625 | 951 | 6936 |
|  | 16543 | 3550 | 9203 | 11070 | 9360 | 21434 | 3920 | 1693 | 10869 | 11881 | 12895 | 1003 |
|  | 5405 | 14684 | 21089 | 14531 | 21626 | 20145 | 17875 | 7549 | 2428 | 2613 | 18036 | 1421 |
|  | 18003 | 6973 | 20577 | 12790 | 22102 | 3375 | 13691 | 15302 | 6589 | 15430 | 18154 | 16596 |
|  | 19645 | 21006 | 17187 | 14709 | 19975 | 1854 | 17428 | 11844 | 10033 | 1792 | 934 | 845 |
|  | 5533 | 21419 | 6582 | 2314 | 19307 | 8902 | 8278 | 20861 | 7030 | 10654 | 9636 | 16002 |
|  | 2969 | 15306 | 5928 | 1894 | 592 | 13534 | 4985 | 5623 | 5150 | 2342 | 22174 | 1686 |
|  | 2688 | 10718 | 20383 | 19440 | 19860 | 618 | 22308 | 10355 | 12565 | 8585 | 15993 | 12725 |
|  | 22563 | 5578 | 14369 | 13712 | 9428 | 20205 | 10767 | 1546 | 5387 | 8364 | 18905 | 18948 |
|  | 2545 | 17156 | 20131 | 22338 | 2223 | 7037 | 15860 | 5111 | 16844 | 14702 | 1634 | 13698 |
|  | 16173 | 17860 | 16802 | 21238 | 20479 | 18313 | 18815 | 16556 | 12453 | 18481 | 19778 | 12153 |
|  | 19470 | 20701 | 1477 | 19657 | 2220 | 5033 | 6117 | 12286 | 12326 | 6566 | 16110 | 13469 |
|  | 17077 | 20231 | 4058 | 9834 | 3780 | 19094 | 6308 | 9548 | 1549 | 21687 | 13080 | 7340 |
|  | 18746 | 2266 | 11139 | 2005 | 14735 | 5543 | 4941 | 2921 | 8468 | 19501 | 3139 | 16192 |
|  | 10723 | 6333 | 11355 | 3845 | 11452 | 19385 | 14092 | 1395 | 5545 | 2216 | 10682 | 21311 |
|  | 15661 | 21100 | 2597 | 14697 | 9008 | 17498 | 17514 | 9946 | 20269 | 5669 | 5062 | 15447 |
|  | 2775 | 6975 | 12793 | 12639 | 8185 | 19766 | 8932 | 4278 | 14889 | 4981 | 22471 | 5952 |

TABLE 16-continued

Sequence IDs for homolog proteins
Seq ID NO: homolog Seq ID NOs

|  | | | | | | | | | | | |
|---|---|---|---|---|---|---|---|---|---|---|---|
|  | 6818 | 16336 | 21140 | 14098 | 21953 | 4979 | 13968 | 16410 | 18878 | 9696 | 4978 | 16146 |
|  | 2609 | 22097 | 16986 | 20921 | 22527 | 16920 | 18126 | 16034 | 5362 | 933 | 15779 | 16770 |
|  | 1772 | 9517 | 6866 | 16982 | 19232 | 19937 | | | | | | |
| 297: | 9912 | 18441 | 5938 | 12696 | 19188 | 22233 | 2840 | 10426 | 16052 | 9508 | 12778 | 15536 |
|  | 19286 | 9563 | 19034 | 20209 | 15518 | 6498 | 21608 | 11026 | 14044 | 10165 | 12621 | 12028 |
|  | 16923 | 21297 | 5646 | 16170 | 12477 | 16660 | 1378 | 2624 | 3809 | 12760 | 16057 | 7256 |
|  | 15500 | 18959 | 10317 | 10326 | 5977 | 4830 | 1143 | 1499 | 10983 | 2571 | 15543 | 13839 |
|  | 12370 | 9041 | 1331 | 8508 | 16831 | 13832 | 4303 | 18599 | 21584 | 9787 | 1548 | 8292 |
|  | 1560 | 18466 | 11683 | 17762 | 17468 | 9815 | 4374 | 18826 | 20637 | 18709 | 16467 | 7307 |
|  | 16512 | 904 | 18899 | 17113 | 10700 | 5006 | 22084 | 5463 | 20856 | 18792 | 1535 | 13608 |
|  | 11312 | 8634 | 19381 | 11435 | 870 | 7232 | 5079 | 6299 | 13314 | 10487 | 15382 | 14552 |
|  | 14878 | 20590 | 14820 | 7911 | 8924 | 12070 | 7581 | 2122 | 18063 | 8338 | 12227 | 14479 |
|  | 3229 | 17500 | 9776 | 16213 | 12767 | 17455 | 5438 | 1839 | 9982 | 4649 | | |
| 298: | 18555 | 7838 | 6652 | 1982 | 15254 | 2218 | 6543 | 13709 | 5154 | 14481 | 4355 | 8406 |
|  | 21382 | 21663 | 19102 | | | | | | | | | |
| 299: | 19421 | 10037 | 3803 | 5108 | 3343 | 20336 | 11002 | 8946 | 12661 | 9168 | 15378 | 18020 |
|  | 16075 | 5607 | 19118 | 22336 | 19724 | 8555 | 2295 | 21579 | 1259 | 8494 | 18083 | 960 |
|  | 13560 | 20787 | 22477 | 19264 | 6401 | 8583 | 9620 | 5248 | 701 | 10759 | 22290 | 2593 |
|  | 21024 | 17543 | 1417 | 15845 | 17793 | 18019 | 6222 | 10575 | 1775 | 8903 | 15288 | 2885 |
|  | 7993 | 20494 | 10001 | 13641 | 11853 | 614 | 12502 | 13330 | 17952 | 13069 | 9420 | 1771 |
|  | 17636 | 13434 | 5588 | 2165 | 19494 | 4998 | 1751 | 16904 | 10306 | 3123 | 12413 | 16515 |
|  | 21706 | 9144 | 19364 | 2394 | 2677 | 15207 | 13710 | 9045 | 11258 | 1042 | 11230 | 13140 |
|  | 18738 | 15056 | 11058 | 930 | 22417 | 8107 | 16349 | 7322 | 16450 | 15822 | 16451 | 6646 |
|  | 18926 | 2197 | 302 | 8630 | 17924 | 14996 | 19753 | 4515 | 10245 | 7300 | 6710 | 21723 |
|  | 12990 | 8111 | 14791 | 13977 | 19581 | 12911 | 22090 | 603 | 15053 | 14851 | 21092 | 14284 |
|  | 20327 | 13846 | 9587 | 21947 | 7441 | 12133 | 14923 | 13939 | 6002 | 5590 | 11909 |
|  | 22216 | 4929 | 14884 | 9941 | 9040 | 12896 | 7903 | 21683 | 11508 | 22006 | 11550 | 5658 |
|  | 2777 | 9977 | 15523 | 5791 | 21963 | 16141 | 18240 | 5322 | 2499 | 19702 | 9292 | 20325 |
|  | 5274 | 9028 | 10531 | 1688 | 20146 | 5153 | 7485 | 18445 | 4165 | 5614 | 10277 | 16781 |
|  | 4563 | 3161 | 6533 | 5957 | 7089 | 2687 | 7105 | 21351 | 21515 | 22453 | 19592 | 7173 |
|  | 1968 | 19358 | 11469 | 8780 | 17266 | 7586 | 12142 | 3066 | 7281 | 14577 | 9430 | 3270 |
|  | 13924 | 12341 | 15761 | 12637 | 10962 | 2998 | 19035 | 4877 | 659 | 9821 | 20906 | 12168 |
|  | 1736 | 20717 | 2543 | 16421 | 1821 | 18042 | 14352 | 15050 | 8399 | 19775 | 21325 | 7525 |
|  | 17680 | 18001 | 19979 | 18487 | 6598 | 5555 | 10444 | 21216 | 21128 | 8987 | 1493 | 17533 |
|  | 16118 | 1639 | 12595 | 6855 | 22098 | 18912 | 3290 | 5745 | 6378 | 9285 | 11287 | 14670 |
|  | 11840 | 9243 | 9669 | 14995 | 13742 | 20118 | 9371 | 11429 | 12747 | 19245 | 1590 | 13573 |
|  | 3695 | 20005 | 2712 | 20008 | 9988 | 1732 | 20129 | 19987 | | | | |
| 300: | 16422 | 16652 | 2702 | 1006 | 429 | 10217 | 533 | 507 | 306 | 535 | 478 | 10780 |
|  | 18650 | 18461 | 13998 | 11343 | 7459 | 5240 | 10390 | 15192 | 6367 | 19001 | 17659 | 17306 |
|  | 18166 | 3899 | 19411 | 17674 | 6453 | 14183 | 9624 | 20799 | 11585 | 14626 | 21314 | 12049 |
|  | 7812 | 18212 | 3745 | 13797 | 8320 | 4940 | 22404 | 21496 | 12527 | 18023 | 6674 | 2559 |
|  | 15926 | 17879 | 9075 | 14547 | 21758 | 1689 | 16481 | 15621 | 18121 | 13519 | 12731 | 5774 |
|  | 10662 | 11761 | 10902 | 17148 | 12381 | 2857 | 17664 | 21589 | 11961 | 19154 | 6201 | 21437 |
|  | 11195 | 20933 | 21506 | 3533 | 4677 | 18511 | 4730 | 696 | 9569 | 17797 | 18687 | 7097 |
|  | 20259 | 15252 | 13221 | 450 | 11335 | 20777 | 12713 | 22502 | 14915 | 21157 | 20371 | 3563 |
|  | 12591 | 16308 | 7626 | 4212 | 19798 | 19458 | 5691 | 18292 | 16130 | 21296 | 2832 | 830 |
|  | 14553 | 6434 | 18295 | 17956 | 829 | 12043 | 20779 | 1281 | 17745 | 1768 | 6547 | 16586 |
|  | 7955 | 12705 | 11376 | 15449 | 988 | 20859 | 11129 | 22518 | 5552 | 9854 | 6669 | 5359 |
|  | 9132 | 10964 | 1879 | 22087 | 13137 | 17298 | 3333 | 13752 | 20301 | 19370 | 2425 | 6946 |
|  | 19538 | 14273 | 17165 | 15340 | 6427 | 15603 | 12419 | 10809 | 8003 | 13658 | 14064 | 4221 |
|  | 7387 | 13284 | 20981 | 2316 | 3116 | 8418 | 3578 | 3386 | 6508 | 18217 | 22249 | 992 |
|  | 13442 | 3471 | 14855 | 19949 | 5277 | 19885 | 2816 | 10917 | 9436 | 18538 | 18659 | 12816 |
|  | 12308 | 15943 | 2515 | 20364 | 14701 | 8193 | 17579 | 22076 | 8890 | 2649 | 9329 | 21073 |
|  | 8376 | 15177 | 10882 | 859 | 5990 | 9814 | 16053 | 5209 | 3144 | 13848 | 22428 | 19076 |
|  | 5454 | 17056 | 14918 | 4088 | 11270 | 5837 | 9604 | 22455 | 19840 | 801 | 12234 | 21301 |
|  | 1149 | 953 | 9960 | 1656 | 3755 | 12278 | 22119 | 21098 | 1005 | 10264 | 13037 | 11702 |
|  | 20954 | 5581 | 5063 | 1118 | 6454 | 20632 | 1696 | 19474 | 14911 | 9381 | 4111 | 13374 |
|  | 2932 | 3071 | 18551 | 22362 | 1431 | 12923 | 6509 | 19229 | 14012 | 5372 | 12362 | 17380 |
|  | 20272 | 16391 | 13395 | 5132 | 901 | 9540 | 19228 | 14568 | 17630 | 2371 | 4694 | 12396 |
|  | 15369 | 16597 | 3697 | 10741 | 16309 | 4927 | 13396 | 21621 | 8841 | 16662 | 11120 | 14081 |
|  | 8692 | 9484 | 15204 | 6565 | 14320 | 2978 | 9294 | 7482 | 9493 | 1277 | 4952 | 7813 |
|  | 7306 | 12296 | 12021 | 6645 | 9286 | 22489 | 13745 | 16653 | 19069 | 7780 | 15219 | 16969 |
|  | 14762 | 18330 | 10802 | 10479 | 16663 | 3678 | 16713 | 7751 | 13703 | 3630 | 4691 | 9472 |
|  | 10709 | 8542 | 7060 | 6112 | 22457 | 21974 | 20476 | 7333 | 6482 | 14526 | 7151 | 2644 |
|  | 835 | 10655 | 12264 | 9315 | 2786 | 16253 | 9488 | 5634 | 17372 | 788 | 9280 | 22095 |
|  | 18903 | 3706 | 15256 | 18593 | 5764 | 11115 | 12583 | 11568 | 13613 | 2331 | 5136 | 8073 |
|  | 15998 | 5630 | 11304 | 19137 | 5817 | 5580 | 18341 | 8588 | 12540 | 2454 | 4970 | 17445 |
|  | 2401 | 11869 | 6193 | 21516 | 10889 | 5190 | 13207 | 14665 | 9673 | 9771 | 11716 | 18575 |
|  | 9584 | 12794 | 21399 | 20485 | 9218 | 18691 | 3350 | 18263 | 4846 | 544 | 19667 | 9933 |
|  | 4140 | 1318 | 20418 | 11128 | 20105 | 16734 | 2376 | 15699 | 7061 | 4232 | 15357 | 14036 |
|  | 5339 | 7107 | 19030 | 7165 | 21370 | 12103 | 4848 | 13211 | 22530 | 15360 | 12863 | 9975 |
|  | 6398 | 14067 | 16683 | 21170 | 1924 | 890 | 8155 | 15866 | 10131 | 7187 | 4332 | 1235 |
|  | 20330 | 12927 | 7088 | 5099 | 2302 | 12424 | 8303 | 17466 | 14322 | 11383 | 2282 | 15956 |
|  | 3414 | 12982 | 18548 | 15665 | 10961 | 21084 | 10824 | 18440 | 16819 | 3730 | 13940 | 18821 |
|  | 14864 | 1818 | 19607 | 7969 | 6546 | 16771 | 5441 | 8459 | 18266 | 5000 | 15749 | 13014 |
|  | 14274 | 8444 | 4707 | 13097 | 15930 | 11872 | 2621 | 7158 | 6942 | 18502 | 5408 | 10837 |
|  | 21928 | 13800 | 5188 | 19614 | 16117 | 4719 | 19714 | 1833 | 13499 | 3107 | 21492 | 12503 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 21929 | 7921  | 1429  | 14398 | 22189 | 6439  | 12993 | 12307 | 6650  | 18994 | 747   | 5932  |
|      | 18630 | 6683  | 1921  | 15651 | 5594  | 6958  | 13597 | 19763 | 10097 | 14124 | 14687 | 1094  |
|      | 5780  | 7770  | 7688  | 15110 | 5797  | 7907  | 21169 | 3329  | 12627 | 4065  | 19882 | 22067 |
|      | 19211 | 2061  | 7038  | 8909  | 16914 | 13129 | 19881 | 13235 | 16317 | 1551  | 14888 | 1201  |
|      | 20264 | 7800  | 7526  | 2209  | 5887  | 10798 | 15317 | 10223 | 11351 | 10105 | 10661 | 15014 |
|      | 2908  | 16412 | 22277 | 19851 | 12003 | 19616 | 11003 | 7768  | 6166  | 4620  | 13850 | 16231 |
|      | 7016  | 20541 | 3458  | 1240  | 15787 | 20099 | 9282  | 11480 | 4994  | 6281  | 18662 | 7992  |
|      | 9661  | 19875 | 11156 | 3619  | 14086 | 20948 | 16946 | 3456  | 6143  | 786   | 6709  | 5954  |
|      | 17926 | 20839 | 22351 | 13277 | 15113 | 6368  | 7704  | 18694 | 3644  | 12154 | 3794  | 21257 |
|      | 21638 | 18386 | 18111 | 21498 | 10731 | 13776 | 5539  | 14530 | 20282 | 7762  | 9529  | 17675 |
|      | 15191 | 12380 | 14865 | 15825 | 2818  | 16442 | 5901  | 8220  | 18578 | 13297 | 2495  | 21913 |
|      | 4526  | 16085 | 10965 | 15558 | 18982 | 2984  | 11245 | 17095 | 7536  | 5117  | 2132  | 20312 |
|      | 4655  | 16568 | 21093 | 13882 | 5730  | 7976  | 7079  | 13035 | 6801  | 2800  | 5619  | 10126 |
|      | 12545 | 2037  | 11704 | 9571  | 21379 | 3712  | 7685  | 4483  | 18456 | 22341 | 11197 | 13107 |
|      | 16006 | 21848 | 20337 |       |       |       |       |       |       |       |       |       |
| 301: | 19000 | 5175  | 17102 | 15893 | 7025  | 2120  | 12938 | 12299 | 15442 | 11496 | 10074 | 5733  |
|      | 14018 | 4497  | 12860 | 17771 | 17375 | 8161  | 11868 | 22009 | 7849  | 15996 | 13313 | 6451  |
|      | 9249  | 12173 | 13520 | 22245 | 9579  | 19128 | 12786 | 5812  | 2509  | 15030 | 5404  |       |
|      | 7335  | 18498 | 6363  | 16355 | 19266 | 14084 | 8908  | 19966 | 8863  | 19169 | 539   | 3459  |
|      | 13467 | 15720 | 2898  | 9093  | 9837  | 17258 | 1976  | 20125 | 1460  | 8614  | 10175 | 5871  |
|      | 15351 | 6426  | 7149  | 12032 | 11271 | 8224  | 11194 | 11907 | 4519  | 3493  | 18304 | 22188 |
|      | 18791 | 10516 | 18657 | 11078 | 6908  | 20626 | 14734 | 4564  | 18762 | 9992  | 1434  | 6230  |
|      | 9846  | 4840  | 12934 | 18658 | 3437  | 11327 | 16354 | 4241  | 1568  | 14609 | 10156 | 19085 |
|      | 969   | 13387 | 20299 | 14003 | 18420 | 8635  | 5706  | 21190 | 1432  | 6124  | 1526  | 18029 |
|      | 16093 | 11179 | 1324  | 22474 | 8016  | 22059 | 5181  | 15454 | 1309  | 4573  | 20643 | 18651 |
|      | 6220  | 9683  | 15336 | 12171 | 3835  | 20676 | 15459 | 11187 | 6374  | 19257 | 8887  | 12249 |
|      | 15479 | 8309  | 2813  | 3769  | 17901 | 16142 | 2063  | 6092  | 19535 | 21118 | 1210  | 8401  |
|      | 7375  | 9531  | 10590 | 7738  | 17854 | 1657  | 9700  | 15494 | 7894  | 15287 | 1226  | 6551  |
|      | 13070 | 19534 | 13610 | 1802  | 22458 | 17237 | 8915  | 14991 | 3591  | 9885  | 9545  | 21263 |
|      | 14344 | 19754 | 11799 | 10504 | 11873 | 18078 | 16699 | 19633 | 15816 | 12846 | 4878  | 20466 |
|      | 21081 | 22381 | 17475 | 18403 | 21905 | 22085 | 18453 | 5736  | 17957 | 4021  | 7834  | 14499 |
|      | 2154  | 13058 | 11572 | 3583  | 10692 | 7183  | 16133 | 15670 | 12332 | 1756  | 16507 | 18601 |
|      | 11306 | 18332 | 20634 | 7994  | 12919 | 9064  | 5045  | 14968 | 9551  | 2414  | 1646  | 4753  |
|      | 1805  | 1502  | 18175 | 18991 | 19442 | 17821 | 1888  | 18587 | 10549 | 18855 | 4858  | 7028  |
|      | 14908 | 22205 | 5964  | 4933  | 4340  | 5271  | 927   | 8374  | 3316  | 9426  | 12837 | 20014 |
|      | 16546 | 20576 | 5008  | 9914  | 10822 | 13163 | 7197  | 6338  | 17347 | 21212 | 3445  | 14444 |
|      | 561   | 1401  | 13989 | 15266 | 20426 | 12281 | 7477  | 7453  | 766   | 14757 | 19524 | 4093  |
|      | 17235 | 17808 | 16762 | 10080 | 9217  | 14800 | 9794  | 18834 | 2718  | 6390  | 20406 | 7926  |
|      | 924   | 20355 | 13005 | 19727 | 8981  | 4683  | 7215  | 4131  | 6381  | 3407  | 11741 | 12599 |
|      | 16185 | 18844 | 16344 | 19195 | 11057 | 8355  | 8958  | 11977 | 19693 | 20196 | 6610  | 14503 |
|      | 22133 | 4744  |       |       |       |       |       |       |       |       |       |       |
| 302: | 8946  | 9168  | 14628 | 299   | 6214  | 4182  | 16075 | 11899 | 18083 | 13560 | 20787 | 22477 |
|      | 16789 | 19264 | 6401  | 9620  | 5248  | 701   | 22290 | 21024 | 4074  | 1417  | 17543 | 11432 |
|      | 17793 | 6222  | 18019 | 21867 | 3019  | 20723 | 20357 | 10575 | 3819  | 6741  | 17742 | 1775  |
|      | 8903  | 15288 | 14774 | 2885  | 20494 | 20292 | 10001 | 11853 | 13330 | 17952 | 16001 | 17214 |
|      | 1751  | 16904 | 10306 | 20788 | 12413 | 1843  | 16515 | 21706 | 2394  | 15207 | 18738 | 15056 |
|      | 9630  | 930   | 15269 | 6646  | 18926 | 4515  | 7300  | 14791 | 6976  | 603   | 21092 | 2483  |
|      | 21947 | 7441  | 14923 | 3660  | 12133 | 22216 | 4929  | 5590  | 11909 | 14884 | 9941  | 6002  |
|      | 9040  | 13939 | 12896 | 7903  | 14465 | 21683 | 11508 | 8978  | 22006 | 5322  | 21963 | 2499  |
|      | 2777  | 18240 | 5791  | 16141 | 9977  | 5658  | 15523 | 9292  | 11550 | 19702 | 1688  | 20325 |
|      | 5274  | 10531 | 9028  | 20146 | 5614  | 7485  | 10844 | 2674  | 18445 | 4072  | 7836  | 5153  |
|      | 4165  | 15169 | 10277 | 16781 | 7814  | 3161  | 5957  | 6533  | 4563  | 7089  | 2687  | 21351 |
|      | 21515 | 22453 | 19592 | 7105  | 7173  | 1968  | 19358 | 10994 | 20056 | 7763  | 9851  | 13457 |
|      | 8780  | 11469 | 7586  | 17266 | 3066  | 12142 | 9430  | 14577 | 13924 | 7281  | 3270  | 19033 |
|      | 15761 | 12341 | 2998  | 12637 | 2543  | 10962 | 19035 | 20906 | 4877  | 659   | 9821  | 12168 |
|      | 20717 | 14352 | 1821  | 18042 | 16421 | 1736  | 15050 | 8399  | 19775 | 17680 | 18001 | 21325 |
|      | 6598  | 18487 | 15537 | 14525 | 21216 | 7525  | 19979 | 5555  | 10444 | 11512 | 21128 | 1493  |
|      | 8987  | 17533 | 22098 | 6855  | 12595 | 18912 | 15079 | 5745  | 6378  | 9285  | 11287 | 14670 |
|      | 11840 | 14995 | 13573 | 3695  | 19886 | 12402 | 20005 | 2712  | 9988  | 1732  | 1437  |       |
| 303: | 11613 | 15600 | 900   | 21525 | 7534  | 8911  | 20350 | 17575 | 7154  | 10397 | 5219  | 15446 |
|      | 9261  | 1171  | 16015 |       |       |       |       |       |       |       |       |       |
| 304: | 14477 | 14507 | 15421 | 17494 | 18062 | 2648  | 7991  | 15716 | 18037 | 11158 | 2783  | 2025  |
|      | 16965 | 22007 | 22121 | 19530 | 11719 | 9318  | 11530 | 17738 | 1299  | 21214 | 12334 | 21809 |
|      | 4864  | 10621 | 8796  | 1194  | 4280  | 19732 | 18120 | 15953 | 3266  | 19426 | 6571  |       |
|      | 6888  | 17781 | 1697  | 10045 | 1251  | 7276  | 7126  | 12814 | 4960  | 7248  | 3598  | 17583 |
|      | 17847 | 7140  | 8316  | 18820 | 21056 | 7036  | 15143 | 13926 | 18581 | 5501  | 1142  | 3253  |
|      | 7339  | 4338  | 10287 | 9635  | 11127 | 20511 | 19012 | 13060 | 4347  | 12691 | 12055 | 20545 |
|      | 21425 | 3704  | 15743 | 19675 | 16542 | 16559 | 21229 | 11524 | 9274  | 11075 | 8804  | 17224 |
|      | 3133  | 3607  | 10123 | 13418 | 2973  | 11620 | 15872 | 11732 | 19109 | 740   | 1359  | 17419 |
|      | 6843  | 1680  | 16067 | 3406  | 4022  | 6395  | 9511  | 2595  | 20688 | 4623  | 22346 | 2369  |
|      | 17333 | 5395  | 11866 | 17305 | 10611 | 7631  | 15733 | 18432 | 1959  | 6814  | 6323  | 13183 |
|      | 9078  | 3032  | 21942 | 3286  | 13158 | 20759 | 22152 | 18157 | 1337  | 3062  | 16447 | 2772  |
|      | 10847 | 14538 | 4797  | 21087 | 7452  | 19143 | 16659 | 16530 | 16620 | 11651 | 17070 | 1585  |
|      | 22147 | 10166 | 6601  | 22431 | 15463 | 10652 | 13842 | 11862 | 1897  | 19136 | 9220  | 17946 |
|      | 12697 | 22065 | 3138  | 16162 | 17146 | 7667  | 19062 | 9071  | 11793 | 11610 | 7968  | 7594  |
|      | 7221  | 10376 | 5672  | 11711 | 3151  | 4084  | 14756 | 8726  | 18769 | 3480  | 10028 | 2838  |
|      | 20595 | 20275 | 1292  | 17594 | 12254 | 4853  | 20642 | 8186  | 16379 | 11759 | 11502 | 8591  |

TABLE 16-continued

Sequence IDs for homolog proteins
Seq ID NO: homolog Seq ID NOs

| | | | | | | | | | | | |
|---|---|---|---|---|---|---|---|---|---|---|---|
| | 4288 | 11992 | 15333 | 9201 | 14724 | 3846 | 15765 | 5294 | 9934 | 3608 | 4038 | 2297 |
| | 1916 | 7144 | 15894 | 19202 | 4614 | 3319 | 11943 | 21007 | 5703 | 7304 | 9147 | 4298 |
| | 11434 | 11341 | 10440 | 4734 | 13768 | 7039 | 7695 | 14607 | 13737 | 10493 | 13662 | 16005 |
| | 5151 | 2008 | 20772 | 4271 | 19954 | 15488 | 16991 | 11303 | 17894 | 5027 | 7608 | 5609 |
| | 16228 | 18306 | 2556 | 13676 | 8198 | 5829 | 17178 | 6626 | 16081 | 16487 | 20616 | 939 |
| | 20854 | 11693 | 16083 | 22378 | 12968 | 16437 | 7624 | 6039 | 10274 | 13230 | 16495 | 10978 |
| | 13806 | 5631 | 6912 | 22114 | 2955 | 21137 | 8847 | 12918 | 16985 | 22400 | 13954 | 16430 |
| | 1905 | 19874 | 9524 | 6234 | 15225 | 4942 | 7297 | 20802 | 5035 | 10180 | 21875 | 20321 |
| | 12454 | 9019 | 4029 | 11248 | 16017 | 3758 | 13953 | 2462 | 4887 | 8042 | 7962 | 11126 |
| | 15081 | 22027 | 16352 | 2791 | 1889 | 15457 | 8559 | 17058 | 7622 | 4393 | 1128 | 8437 |
| | 21033 | 5138 | 12634 | 1952 | 5842 | 21247 | 15955 | 3808 | 10420 | 14719 | 17939 | 4794 |
| | 21353 | 19950 | 18656 | 13160 | 3900 | 11932 | 16466 | 13358 | 19797 | 5206 | 2289 | 9733 |
| | 10875 | 12426 | 15784 | 10942 | 12064 | 7723 | 14341 | 5120 | 18048 | 8171 | 11041 | 17196 |
| | 16314 | 20434 | 21075 | 20432 | 4222 | 8716 | 4904 | 18464 | 630 | 8403 | 6184 | 18819 |
| | 17228 | 16302 | 10762 | 9202 | 16022 | 17350 | 15237 | 12703 | 11159 | 17792 | 4597 | 7291 |
| | 15512 | 1072 | 6812 | 15612 | 4183 | 5466 | 17341 | 9980 | 4892 | 1108 | 1406 | 22046 |
| | 1630 | 11923 | 17859 | 5617 | 18198 | 5043 | 6967 | 20318 | 22123 | 1264 | 12469 | 12218 |
| | 10452 | 13091 | 8047 | 6109 | 14712 | 428 | 22157 | 7745 | 16695 | 22271 | 6934 | 7635 |
| | 18516 | 6231 | 1574 | | | | | | | | | |
| 305: | 8099 | 12755 | 17111 | 978 | 1006 | 1542 | 15083 | 18937 | 12887 | 2035 | 10217 | 535 |
| | 533 | 507 | 306 | 478 | 8894 | 18461 | 12108 | 1501 | 12486 | 21909 | 7034 | 7130 |
| | 11072 | 14307 | 10425 | 15925 | 19332 | 1367 | 13146 | 7730 | 1937 | 9628 | 18825 | 609 |
| | 18335 | 21615 | 4370 | 7330 | 8575 | 15629 | 12213 | 5331 | 3191 | 19367 | 4875 | 5240 |
| | 11492 | 21592 | 7018 | 6367 | 19001 | 20564 | 13807 | 16754 | 21328 | 19708 | 4343 | 9940 |
| | 1066 | 2399 | 12207 | 1629 | 18478 | 7812 | 13667 | 3746 | 5720 | 16976 | 18312 | 3470 |
| | 5618 | 19921 | 17739 | 4546 | 14856 | 18520 | 3007 | 531 | 7912 | 8917 | 11529 | 6283 |
| | 8622 | 8288 | 17072 | 4299 | 7840 | 5830 | 6060 | 19606 | 3409 | 7000 | 8429 | 19346 |
| | 2857 | 17664 | 21589 | 11961 | 19154 | 18239 | 18127 | 11549 | 16493 | 21437 | 11195 | 20933 |
| | 21506 | 1079 | 9281 | 838 | 3533 | 4677 | 18511 | 4730 | 696 | 9569 | 17797 | 18687 |
| | 7097 | 20259 | 15252 | 13221 | 450 | 11335 | 20777 | 12713 | 22502 | 14915 | 21157 | 20371 |
| | 12591 | 3563 | 16308 | 7626 | 4212 | 19798 | 19458 | 5691 | 18292 | 16130 | 2832 | 21296 |
| | 830 | 14553 | 6434 | 18295 | 17956 | 829 | 476 | 12043 | 20779 | 1281 | 17745 | 7955 |
| | 9854 | 988 | 20859 | 6669 | 5359 | 9132 | 16586 | 12705 | 15449 | 1768 | 11129 | 6547 |
| | 22518 | 5552 | 11376 | 10964 | 1879 | 22087 | 13137 | 17298 | 19370 | 3333 | 13752 | 20301 |
| | 2425 | 6946 | 19538 | 14273 | 15340 | 6427 | 17165 | 15603 | 12419 | 8003 | 10809 | 13658 |
| | 14064 | 4221 | 7387 | 13284 | 20981 | 2316 | 3116 | 8418 | 3386 | 6508 | 19949 | 18217 |
| | 3578 | 22249 | 992 | 18538 | 13442 | 3471 | 14855 | 5277 | 19885 | 2816 | 10917 | 9436 |
| | 18659 | 12816 | 12308 | 15943 | 2515 | 20364 | 14701 | 8193 | 17579 | 22076 | 8890 | 2649 |
| | 9329 | 21073 | 8376 | 15177 | 10882 | 859 | 5990 | 9814 | 16053 | 5454 | 5209 | 3144 |
| | 9604 | 13848 | 22428 | 19076 | 17056 | 14918 | 4088 | 9960 | 11270 | 5837 | 22455 | 19840 |
| | 12234 | 21301 | 1149 | 801 | 953 | 1656 | 20632 | 3755 | 12278 | 22119 | 21098 | 1005 |
| | 10264 | 13037 | 11702 | 20954 | 5581 | 5063 | 1118 | 14568 | 17630 | 2371 | 4694 | 12396 |
| | 15369 | 16597 | 3697 | 10741 | 16309 | 4927 | 13396 | 21621 | 8841 | 16662 | 11120 | 14081 |
| | 8692 | 9484 | 15514 | 10745 | 15204 | 6565 | 14320 | 2978 | 9294 | 7482 | 9493 | 1277 |
| | 4952 | 7813 | 7306 | 12296 | 12021 | 6645 | 9286 | 22489 | 13745 | 16653 | 19069 | 7780 |
| | 15219 | 16969 | 14762 | 18330 | 10280 | 10802 | 10479 | 16663 | 3678 | 7751 | 16713 | 13703 |
| | 3630 | 4691 | 9472 | 10709 | 8542 | 7060 | 6112 | 22457 | 21974 | 5278 | 4682 | 10694 |
| | 19198 | 20476 | 7333 | 6482 | 14526 | 7151 | 2644 | 10655 | 12264 | 835 | 9315 | 2786 |
| | 16253 | 9488 | 5634 | 17372 | 788 | 15256 | 22095 | 18903 | 3706 | 9280 | 18593 | 5764 |
| | 12583 | 11568 | 13613 | 2331 | 5136 | 8073 | 5630 | 11115 | 11304 | 15998 | 19137 | 5817 |
| | 5580 | 18341 | 2454 | 8588 | 12540 | 4970 | 17445 | 11869 | 7142 | 4488 | 19396 |
| | 10889 | 5190 | 13207 | 16465 | 9673 | 9771 | 11716 | 16290 | 14313 | 9218 | 15665 | 15699 |
| | 5441 | 20485 | 18548 | 18575 | 18821 | 3350 | 18263 | 20418 | 11128 | 16734 | 19030 | 21370 |
| | 13211 | 22530 | 15360 | 6398 | 14067 | 21170 | 15866 | 10131 | 4332 | 1235 | 12927 | 7088 |
| | 5099 | 2302 | 12424 | 9584 | 8303 | 11383 | 2282 | 8459 | 3414 | 15749 | 18691 | 12982 |
| | 12794 | 10961 | 10824 | 18440 | 16819 | 9975 | 21399 | 8444 | 4707 | 13097 | 15930 | 11872 |
| | 2621 | 7158 | 14864 | 6942 | 19607 | 7969 | 6546 | 5408 | 18266 | 10837 | 21928 | 13800 |
| | 21492 | 5339 | 20330 | 1833 | 4846 | 544 | 19667 | 9933 | 4140 | 1318 | 20105 | 2376 |
| | 7061 | 4232 | 15357 | 14036 | 7107 | 7165 | 12103 | 4848 | 12863 | 16683 | 1924 | 3730 |
| | 890 | 8155 | 7187 | 17466 | 14322 | 14398 | 22189 | 15956 | 21084 | 16117 | 13940 | 1818 |
| | 19714 | 16771 | 6683 | 1921 | 5000 | 13014 | 14274 | 18502 | 6650 | 13499 | 19763 | 10097 |
| | 5188 | 19614 | 4719 | 3107 | 5780 | 12503 | 21929 | 7921 | 1429 | 5797 | 6439 | 12993 |
| | 12307 | 15651 | 18994 | 747 | 5932 | 18630 | 7907 | 5594 | 6958 | 3329 | 4065 | 19882 |
| | 13597 | 14124 | 14687 | 7770 | 1094 | 7688 | 15110 | 21169 | 4526 | 22067 | 19211 | 16914 |
| | 2061 | 1201 | 19616 | 7038 | 8909 | 13129 | 19881 | 16317 | 1551 | 13235 | 14888 | 20264 |
| | 7800 | 7526 | 2209 | 11351 | 5887 | 10798 | 10105 | 15317 | 10223 | 10661 | 15014 | 2908 |
| | 16412 | 15519 | 22277 | 19851 | 12003 | 6166 | 7768 | 11003 | 20541 | 3458 | 1240 | 15787 |
| | 20099 | 9282 | 11480 | 4994 | 6281 | 18662 | 3619 | 7992 | 9661 | 19875 | 14086 | 11156 |
| | 20948 | 16946 | 3456 | 6143 | 786 | 6709 | 5954 | 17926 | 20839 | 22351 | 13277 | 13192 |
| | 15113 | 6368 | 18694 | 3644 | 12154 | 3794 | 21257 | 21638 | 7704 | 21498 | 14865 | 18386 |
| | 18111 | 10731 | 13776 | 5539 | 14530 | 20282 | 7762 | 9529 | 17675 | 15191 | 12380 | 16442 |
| | 15825 | 2818 | 8220 | 5901 | 18578 | 13297 | 2495 | 4526 | 16085 | 10965 | 15558 |
| | 21784 | 775 | 7504 | 10887 | 3135 | 11204 | 15835 | 17679 | 3002 | 18189 | 7516 | 6483 |
| | 9518 | 14034 | 11913 | 9964 | 2126 | 10118 | 3160 | 10150 | 10347 | 14405 | 15486 | 7545 |
| | 12799 | 13960 | 1340 | 3431 | 18982 | 2984 | 15366 | 2275 | 6738 | 11245 | 5295 | 2132 |
| | 20312 | 4655 | 16568 | 21093 | 13882 | 5730 | 7976 | 7079 | 13035 | 18086 | 2800 | 4062 |
| | 8280 | 13990 | 6955 | 16633 | 12655 | 12545 | 2037 | 11704 | 9571 | 21379 | 3712 | 7685 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 4483 | 22341 | 18456 | 11197 | 13107 | 16006 | 9320 | 19090 | | | |
| 306: | 14420 | 1006 | 429 | 10217 | 10190 | 2439 | 478 | 314 | 18461 | 5240 | 6367 | 19001 |
| | 3122 | 4403 | 526 | 11601 | 7812 | 6192 | 17664 | 2857 | 21589 | 11961 | 19154 | 21437 |
| | 11195 | 20933 | 21506 | 3533 | 4677 | 18511 | 4730 | 696 | 9569 | 17797 | 18687 | 7097 |
| | 20259 | 15252 | 13221 | 450 | 11335 | 20777 | 12713 | 22502 | 14915 | 21157 | 20371 | 3563 |
| | 12591 | 16308 | 7626 | 4212 | 19798 | 19458 | 5691 | 18292 | 5019 | 17572 | 15704 | 16130 |
| | 21296 | 2832 | 830 | 14553 | 6434 | 18295 | 17956 | 829 | 476 | 12043 | 20779 | 1281 |
| | 17745 | 16586 | 7955 | 12705 | 15449 | 988 | 20859 | 1768 | 11129 | 6547 | 22518 | 5552 |
| | 9854 | 11376 | 6669 | 5359 | 9132 | 10964 | 1879 | 14844 | 22087 | 13137 | 17298 | 3333 |
| | 13752 | 20301 | 19370 | 2425 | 6946 | 19538 | 14273 | 15340 | 6427 | 17165 | 15603 | 12419 |
| | 18044 | 10809 | 8003 | 13658 | 14064 | 4221 | 7387 | 13284 | 20981 | 19949 | 2316 | 3116 |
| | 8418 | 3386 | 6508 | 18217 | 3578 | 22249 | 992 | 14855 | 13442 | 3471 | 5277 | 19885 |
| | 8739 | 2816 | 10917 | 15943 | 9436 | 18538 | 1973 | 18659 | 12816 | 12308 | 2515 | 20364 |
| | 14701 | 8193 | 17579 | 22076 | 8890 | 2649 | 9329 | 21073 | 8376 | 15177 | 10882 | 859 |
| | 5990 | 9814 | 16053 | 5209 | 3144 | 13848 | 22428 | 19076 | 14918 | 5454 | 17056 | 4088 |
| | 11270 | 5837 | 9604 | 953 | 22455 | 19840 | 12234 | 1149 | 801 | 21301 | 9960 | 1656 |
| | 3755 | 12278 | 22119 | 21098 | 1005 | 10264 | 13037 | 11702 | 20954 | 5581 | 5063 | 1118 |
| | 6454 | 20632 | 1696 | 19474 | 14911 | 9381 | 22362 | 4111 | 13374 | 2932 | 3071 | 18551 |
| | 1431 | 12923 | 6509 | 19229 | 14012 | 5372 | 12362 | 17380 | 20272 | 16391 | 901 | 13395 |
| | 5132 | 9540 | 19228 | 6169 | 11589 | 13306 | 3179 | 14568 | 17630 | 2371 | 4694 | 12396 |
| | 15369 | 11784 | 16597 | 3697 | 10741 | 16309 | 4927 | 13396 | 21621 | 16662 | 8841 | 11120 |
| | 14081 | 8692 | 9484 | 15204 | 6565 | 14320 | 2978 | 9294 | 7482 | 9493 | 1277 | 4952 |
| | 7813 | 7306 | 12296 | 12021 | 6645 | 9286 | 22489 | 13745 | 16653 | 19069 | 7780 | 15219 |
| | 16969 | 14762 | 18330 | 10280 | 10802 | 10479 | 16663 | 3678 | 16713 | 7751 | 13703 | 3630 |
| | 4691 | 9472 | 10709 | 8542 | 7060 | 6112 | 22457 | 21974 | 20476 | 7333 | 6482 | 14526 |
| | 7151 | 2644 | 835 | 10655 | 12264 | 9315 | 2786 | 16253 | 9488 | 5634 | 17372 | 788 |
| | 18247 | 9280 | 22095 | 18903 | 3706 | 15256 | 18593 | 5764 | 11115 | 12583 | 11568 | 13613 |
| | 2331 | 5136 | 8073 | 15998 | 5630 | 11304 | 19137 | 5817 | 5580 | 18341 | 8588 | 12540 |
| | 2454 | 3016 | 4970 | 17445 | 2401 | 11869 | 6193 | 21516 | 2447 | 10889 | 5190 | 13207 |
| | 16465 | 9673 | 9771 | 11716 | 13123 | 18575 | 9584 | 12794 | 21399 | 20485 | 9218 | 18691 |
| | 3350 | 18263 | 4846 | 544 | 19667 | 9933 | 4140 | 1318 | 20418 | 11128 | 20105 | 16734 |
| | 2376 | 15699 | 7061 | 4232 | 15357 | 14036 | 5339 | 7107 | 19030 | 7165 | 21370 | 12103 |
| | 4848 | 13211 | 22530 | 15360 | 12863 | 9975 | 6398 | 14067 | 16683 | 21170 | 1924 | 890 |
| | 8155 | 15866 | 10131 | 7187 | 4332 | 1235 | 20330 | 12927 | 7088 | 5099 | 2302 | 12424 |
| | 8303 | 17466 | 14322 | 11383 | 2282 | 14274 | 15956 | 3414 | 12982 | 18548 | 15665 | 10961 |
| | 21084 | 10824 | 18440 | 16819 | 3730 | 13940 | 18821 | 14864 | 1818 | 19607 | 7969 | 6546 |
| | 16771 | 5441 | 8459 | 18266 | 5000 | 15749 | 13014 | 8444 | 4707 | 13097 | 15930 | 11872 |
| | 2621 | 7158 | 6942 | 18502 | 5408 | 10837 | 21928 | 13800 | 5188 | 19614 | 16117 | 4719 |
| | 1833 | 13499 | 3107 | 21492 | 12503 | 21929 | 7921 | 1429 | 14398 | 22189 | 6439 | 12993 |
| | 12307 | 19714 | 6650 | 18994 | 747 | 5932 | 18630 | 6683 | 1921 | 15651 | 19882 | 5594 |
| | 6958 | 13597 | 19763 | 10097 | 14124 | 14687 | 1094 | 5780 | 7770 | 7688 | 15110 | 5797 |
| | 7907 | 21169 | 3329 | 4065 | 12627 | 22067 | 19211 | 2061 | 13235 | 7038 | 8909 | 16914 |
| | 13129 | 16317 | 19881 | 1551 | 14888 | 1201 | 20264 | 7800 | 7526 | 2209 | 5887 | 10798 |
| | 15317 | 10223 | 11351 | 10105 | 10661 | 15014 | 2908 | 16412 | 12003 | 22277 | 19851 | 19616 |
| | 11003 | 7768 | 6166 | 13850 | 4620 | 16231 | 7016 | 2717 | 20886 | 14522 | 5254 | 15519 |
| | 20541 | 3458 | 1240 | 15787 | 20099 | 9282 | 11480 | 4994 | 6281 | 18662 | 7992 | 9661 |
| | 19875 | 11154 | 3619 | 14086 | 20948 | 16946 | 3456 | 786 | 6709 | 5954 | 17926 | |
| | 20839 | 22351 | 4726 | 13277 | 15113 | 6368 | 7704 | 18694 | 3644 | 12154 | 3794 | 21257 |
| | 21638 | 18386 | 18111 | 21498 | 10731 | 13776 | 5539 | 14530 | 20282 | 7762 | 9529 | 17675 |
| | 15191 | 12380 | 14865 | 15825 | 2818 | 16442 | 5901 | 8220 | 18578 | 13297 | 2495 | 21913 |
| | 4526 | 16085 | 10965 | 15558 | 18982 | 2984 | 11245 | 11137 | 12977 | 2132 | 20312 | 4655 |
| | 16568 | 21093 | 13882 | 5730 | 7976 | 7079 | 13035 | 2800 | 7101 | 509 | 307 | 305 |
| | 12545 | 2037 | 11704 | 9571 | 21379 | 3712 | 7685 | 4483 | 18456 | 22341 | 11197 | 13107 |
| | 14927 | 16006 | 532 | 428 | 372 | | | | | | | |
| 307: | 3349 | 11861 | 16061 | 5336 | 12949 | 18887 | 6597 | 3983 | 22099 | 2324 | 447 | 4512 |
| | 11806 | 9383 | 17441 | 7957 | 16578 | 12877 | 12285 | 6745 | 8158 | 22143 | 14055 | 16201 |
| | 1754 | 1561 | 18005 | 11717 | 9710 | 6672 | 1451 | 10276 | 2243 | 21572 | 5576 | 13128 |
| | 10885 | 6027 | 17037 | 15496 | 10454 | 6068 | 15308 | 2899 | 11018 | 14627 | 20697 | 3974 |
| | 7859 | 15270 | 15938 | 5811 | 2698 | 16879 | 8859 | 21272 | 14729 | 18033 | 840 | 5497 |
| | 13669 | 21714 | 19513 | 5502 | 16413 | 15747 | 1844 | 4651 | 13831 | 22094 | 8195 | 21288 |
| | 3065 | 16776 | 4822 | 18118 | 19091 | 5553 | 14834 | 21349 | 12572 | 16815 | 8955 | 13075 |
| | 12733 | 4648 | 22049 | 5403 | 1029 | 1877 | 22486 | 14277 | 19152 | 1410 | 21143 | 7372 |
| | 21858 | 17690 | 6467 | 9703 | 12831 | 4606 | 4506 | 19173 | 2942 | 1265 | 17141 | 18407 |
| | 8705 | 18889 | 4746 | 3811 | 9106 | 17506 | 7669 | 11911 | 20449 | 10409 | 22212 | 9181 |
| | 21792 | 22305 | 9003 | 8407 | 9234 | 9976 | 16656 | 2745 | 18946 | 4081 | 1944 | 12668 |
| | 7458 | 13728 | 15650 | 11471 | 11697 | 10966 | 5324 | 9173 | 19342 | 21172 | 9379 | 17192 |
| | 21538 | 8949 | 22434 | 3555 | 19594 | 13734 | 9786 | 21821 | 21772 | 21456 | 21196 | 9187 |
| | 10524 | 11998 | 20944 | 6938 | 7779 | 8979 | 13537 | 5360 | 18851 | 21252 | 15297 | 11734 |
| | 1781 | 17886 | 3931 | 16508 | 9825 | 5806 | 12904 | 4987 | 1438 | 8935 | 16959 | 16382 |
| | 1164 | 22141 | 2007 | 17210 | 14488 | 6399 | 14781 | 6373 | 22109 | 599 | 9398 | 9473 |
| | 5195 | 4504 | 5963 | 14256 | 6939 | 6345 | 1162 | 18406 | 17784 | 1442 | 4331 | 6935 |
| | 5879 | 18326 | 2240 | 20428 | 19414 | 11272 | 14731 | 3444 | 1809 | 21833 | 14869 | 12121 |
| | 5793 | 8845 | 20490 | 14861 | 12563 | 4528 | 17811 | 1567 | 9570 | 733 | 11892 | 13985 |
| | 11612 | 1512 | 1070 | 2951 | 19948 | 9341 | 9353 | 1718 | 16198 | 8546 | 15048 | 9919 |
| | 20674 | 3909 | 10843 | 16432 | 10218 | 15654 | 4043 | 14847 | 6714 | 8707 | 9886 | 20997 |
| | 22088 | 13038 | 8037 | 9178 | 5352 | 3851 | 6484 | 16180 | 20444 | 13259 | 20733 | 21480 |
| | 17651 | 22149 | 13792 | 13689 | 6933 | 21822 | 7825 | 13935 | 22010 | 15175 | 7093 | 21104 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 21571 | 14166 | 13059 | 1320  | 19388 | 12387 | 18647 | 10615 | 2572  | 16738 | 17277 | 10671 |
|      | 13485 | 4638  | 2352  | 7397  | 5048  | 13275 | 7941  | 11316 | 9127  | 6631  | 17029 | 14783 |
|      | 5081  | 2879  | 3446  | 12504 | 11878 | 2839  | 3228  | 19752 | 1088  | 1402  | 6179  | 16798 |
|      | 22525 | 16859 | 10813 | 2895  | 20050 | 10689 | 9920  | 13359 | 6382  | 16804 | 22048 | 15372 |
|      | 17024 | 19135 | 2131  | 20708 | 19186 | 7679  | 13583 | 7611  | 8668  | 2471  | 18443 | 8080  |
|      | 14254 | 18267 | 2356  | 17724 | 10645 | 21850 | 7740  | 18043 | 7128  | 21146 | 15408 | 8078  |
|      | 2828  | 15730 | 8513  | 18968 | 650   | 14046 | 3085  | 13243 | 11222 | 15011 | 1105  | 3976  |
|      | 1507  | 15891 | 10269 | 17937 | 6229  | 13505 | 13897 | 17262 | 1497  | 9774  | 5505  | 5939  |
|      | 7480  | 3041  | 12199 | 18054 | 15132 | 17133 | 9987  | 21835 | 578   | 22529 | 20727 | 13110 |
|      | 17553 | 15284 | 5186  | 15066 | 12304 | 21091 | 9863  | 4969  | 14128 | 13927 | 2253  | 22173 |
|      | 20557 | 7177  | 21588 | 7134  | 20606 | 17839 | 15095 | 21594 | 19310 | 4399  | 21404 | 1167  |
|      | 2570  | 8102  | 16155 | 14831 | 9194  | 9119  | 2558  | 21715 | 11856 | 11165 | 7573  | 10855 |
|      | 15158 | 22322 | 8996  | 12383 | 18252 | 20458 | 20237 | 9891  | 4099  | 16104 | 8881  | 12231 |
|      | 2561  | 647   | 22387 | 19765 | 4615  | 21305 | 15139 | 4964  | 20891 | 11812 | 22155 | 16216 |
|      | 18833 | 21797 | 7671  | 15097 | 11028 | 2172  | 17562 | 12574 | 2664  | 9816  | 12353 | 2954  |
|      | 21428 | 12735 | 2392  | 5226  | 8680  | 17177 | 18591 | 20343 | 15667 | 21341 | 11930 | 10157 |
|      | 19825 | 5210  | 7091  | 22444 | 3844  | 717   | 18902 | 14808 | 11659 | 8670  | 1785  | 8233  |
|      | 21693 | 8835  | 7167  | 12659 | 3869  | 22226 | 15589 | 5280  | 13405 | 13156 | 10456 | 10253 |
|      | 16881 | 14660 | 15728 | 6461  | 7132  | 8140  | 20493 | 14049 | 12322 | 15683 | 846   | 12989 |
|      | 4867  | 5866  | 20584 | 15020 | 1964  | 20885 | 21697 | 12785 | 2196  | 12335 | 15689 | 9927  |
|      | 763   | 1531  | 20138 | 11358 | 1132  | 19079 | 14162 | 5361  | 7543  | 18763 | 17112 | 21617 |
|      | 7915  | 20412 | 1643  | 20533 | 8020  | 9158  | 2930  | 19107 | 21064 | 3201  | 11077 | 14726 |
|      | 20135 | 9411  | 15348 | 9402  | 12669 | 15995 | 8168  | 7755  | 3112  | 12219 | 551   | 21933 |
|      | 8916  | 13876 | 14513 | 6877  | 8597  | 18116 | 8268  | 9085  | 9769  | 11890 | 21961 | 11709 |
|      | 10758 | 12800 | 8640  | 1212  | 10509 | 21023 | 11267 | 21751 | 1557  | 18735 | 18051 | 21254 |
|      | 15200 | 5771  | 17912 | 3381  | 18702 | 19564 | 12819 | 17593 | 8712  | 8128  | 1909  | 6496  |
|      | 14338 | 16091 | 948   | 17565 | 16614 | 18595 | 11540 | 18075 | 9306  | 5464  | 18421 | 10608 |
|      | 12167 | 17453 | 9268  | 11122 | 12880 | 13525 | 21522 | 5843  | 7885  | 10162 | 18002 | 13496 |
|      | 9474  | 11489 | 14139 | 5078  | 13260 | 10989 | 5480  | 3428  | 22424 | 15138 | 4252  | 2826  |
|      | 5882  | 20175 | 15811 | 16116 | 7879  | 12274 | 19326 | 5318  | 8325  | 1069  | 22306 | 6156  |
|      | 14294 | 21302 | 22394 | 4521  | 10893 | 5702  | 4766  | 568   | 15271 | 1077  | 17778 | 9726  |
|      | 14452 | 21497 | 5648  | 10532 | 15330 | 3647  | 8350  | 19227 | 17520 | 19834 | 16427 | 12852 |
|      | 9016  | 11208 | 9994  | 5906  | 20197 | 1115  | 15244 | 22452 | 15164 | 4258  | 6471  | 14545 |
|      | 6910  | 6417  | 21796 | 17471 | 17991 | 14998 | 15383 | 3215  | 10382 | 2580  | 8289  | 8452  |
|      | 12605 | 11475 | 6041  | 3868  | 2991  | 13102 | 15010 | 21365 | 21059 | 6894  | 21208 | 11757 |
| 308: | 13659 | 8503  | 5417  | 2636  | 18255 | 14258 | 18186 | 14480 | 2997  | 12520 | 20393 | 16958 |
|      | 14070 | 11296 | 3421  | 20754 | 17033 | 17928 |       |       |       |       |       |       |
| 309: | 22368 | 4230  | 16648 | 2237  | 2516  | 16152 | 10415 | 5473  | 14703 | 19022 | 18480 | 3997  |
|      | 17101 | 4156  | 10514 | 13955 | 12976 | 4059  |       |       |       |       |       |       |
| 310: | 4051  | 3527  | 13345 | 2678  | 8550  | 12739 | 5968  | 11252 | 1249  | 13757 | 11908 | 13883 |
|      | 642   | 18741 | 863   | 15128 | 20888 | 14323 | 4672  | 8571  | 16644 | 10920 | 8004  | 22023 |
|      | 10377 | 10056 | 4837  | 19713 | 7234  | 1632  | 16113 | 13478 | 12526 | 19784 | 19698 | 2701  |
|      | 14658 | 15220 | 8365  | 18917 | 19359 | 21121 | 8529  | 17053 | 2009  | 2989  | 6906  | 5789  |
|      | 4862  | 8968  | 21524 | 13803 | 21337 | 5536  | 3377  | 936   | 20910 | 2445  | 21144 | 20276 |
|      | 15766 | 10716 | 15947 | 17616 | 7904  | 2437  | 12791 | 8028  | 5119  | 21686 | 20353 | 6765  |
|      | 13032 | 12566 | 2929  | 19589 | 6025  | 12404 | 5688  | 7908  | 7436  | 18460 | 14549 | 1975  |
|      | 9403  | 18910 | 15871 | 5414  | 21648 | 22373 | 15001 | 8960  | 8512  | 14839 | 13626 | 2150  |
|      | 18521 | 4687  | 4104  | 15162 | 19653 |       |       |       |       |       |       |       |
| 311: | 7246  | 7633  | 13566 | 4922  | 7189  | 6648  | 3075  | 2678  | 8937  | 18998 | 20791 | 2442  |
|      | 4593  | 2102  | 13757 | 8484  | 11908 | 21901 | 9697  | 3719  | 21432 | 10971 | 8004  | 22023 |
|      | 10056 | 4837  | 6659  | 9021  | 8001  | 9591  | 4169  | 18319 | 12526 | 20405 | 19739 | 12836 |
|      | 12342 | 14209 | 15108 | 19698 | 21200 | 14093 | 4820  | 21147 | 16711 | 686   | 18917 | 21915 |
|      | 21121 | 8529  | 17053 | 2009  | 2989  | 6906  | 12853 | 7577  | 6127  | 14095 | 21524 | 6916  |
|      | 13803 | 7336  | 19598 | 11276 | 21713 | 14811 | 21337 | 20910 | 936   | 2445  | 11616 | 15947 |
|      | 17616 | 8331  | 11034 | 19471 | 5916  | 17862 | 12115 | 14492 | 18721 | 8414  | 19179 | 5371  |
|      | 9277  | 5119  | 17025 | 20374 | 3996  | 5057  | 1399  | 16384 | 9470  | 18719 | 18399 | 3401  |
|      | 8557  | 2158  | 3928  | 19925 | 15780 | 1172  | 19003 | 4754  | 6752  | 7557  | 21304 | 14324 |
|      | 15694 | 2929  | 15268 | 11094 | 19589 | 8713  | 6025  | 14222 | 14987 | 11178 | 3467  | 7373  |
|      | 1975  | 9403  | 2856  | 8286  | 16534 | 8056  | 9369  | 2719  | 15871 | 5414  | 22373 | 21648 |
|      | 1955  | 5457  | 18895 | 17041 | 22161 | 13812 | 8512  | 14839 | 13626 | 18521 | 21678 | 2002  |
|      | 4687  | 18560 | 4104  | 7854  | 18098 | 13647 | 15831 | 11038 | 19653 | 8205  |       |       |
| 312: | 12932 | 12556 | 10612 | 8324  | 20661 | 21261 | 10886 | 21109 | 3162  | 13645 | 12519 | 14154 |
|      | 4627  | 9952  | 7890  | 12288 | 13254 | 22516 | 21541 | 11332 | 12510 | 6556  | 17293 | 7951  |
|      | 6797  | 12554 | 2010  |       |       |       |       |       |       |       |       |       |
| 313: | 15796 | 4326  | 10345 | 13029 | 13317 | 20973 | 19570 | 14613 | 13103 | 3759  | 11764 | 3247  |
|      | 11747 | 9513  | 3029  | 20696 | 20193 | 9454  | 5495  | 18809 | 16012 | 8066  | 7668  | 15744 |
|      | 1836  | 6499  | 12779 | 2481  | 14822 |       |       |       |       |       |       |       |
| 314: | 7479  | 533   | 507   | 535   | 306   | 12575 | 15642 | 18461 | 5073  | 9804  | 18997 | 8666  |
|      | 3659  | 6320  | 6367  | 19001 | 6157  | 11916 | 2258  | 21356 | 9857  | 2163  | 2584  | 3331  |
|      | 20086 | 6423  | 4662  | 3838  | 14933 | 8860  | 19820 | 15915 | 7403  | 4850  | 4714  | 9730  |
|      | 12137 | 14919 | 12016 | 19643 | 3913  | 17315 | 7812  | 21939 | 13951 | 1478  | 7199  | 10536 |
|      | 9491  | 3917  | 15376 | 4608  | 20333 | 7216  | 21640 | 4725  | 16880 | 19870 | 10959 | 4725  |
|      | 15069 | 5944  | 17598 | 6786  | 14232 | 4110  | 10546 | 16887 | 4811  | 15616 | 10586 | 10067 |
|      | 11756 | 20433 | 13391 | 16270 | 10468 | 7655  | 21719 | 5755  | 2857  | 17664 | 21589 | 11961 |
|      | 18800 | 19154 | 879   | 12644 | 16878 | 2030  | 4833  | 5428  | 3533  | 8904  | 4677  | 18511 |
|      | 4730  | 696   | 9569  | 17797 | 18687 | 7097  | 20259 | 15252 | 13221 | 450   | 22502 | 14915 |
|      | 21157 | 20371 | 3563  | 12591 | 16308 | 7626  | 4212  | 19798 | 19458 | 5691  | 18292 | 16130 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 21296 | 2832  | 830   | 14553 | 6434  | 18295 | 476   | 12043 | 20779 | 1281  | 17745 | 16586 |
|      | 7955  | 12705 | 15449 | 988   | 20859 | 1768  | 11129 | 6547  | 22518 | 5552  | 9854  | 11376 |
|      | 6669  | 5359  | 9132  | 10964 | 1879  | 22087 | 13137 | 17298 | 3333  | 13752 | 20301 | 19370 |
|      | 2425  | 6946  | 19538 | 14273 | 15340 | 6427  | 17165 | 15603 | 12419 | 10809 | 8003  | 13658 |
|      | 14064 | 4221  | 7387  | 13284 | 20981 | 2316  | 8421  | 3386  | 6508  | 18217 | 3578  |       |
|      | 22249 | 992   | 13442 | 3471  | 14855 | 19949 | 5277  | 19885 | 2816  | 10917 | 9436  | 18538 |
|      | 18659 | 12816 | 12308 | 15943 | 2515  | 20364 | 14701 | 8193  | 17579 | 22076 | 8890  | 2649  |
|      | 9329  | 21073 | 8376  | 15177 | 10882 | 859   | 5990  | 9814  | 16053 | 5209  | 3144  | 13848 |
|      | 22428 | 19076 | 14568 | 4694  | 12396 | 15369 | 16597 | 3697  | 10741 | 13396 | 21621 | 8841  |
|      | 16662 | 11120 | 14081 | 15204 | 6565  | 14320 | 2978  | 9294  | 7482  | 9493  | 1277  | 7813  |
|      | 7306  | 12296 | 12021 | 6645  | 9286  | 22489 | 13745 | 16653 | 19069 | 7780  | 15219 | 16969 |
|      | 14762 | 10802 | 10479 | 16663 | 3678  | 16713 | 7751  | 13703 | 3630  | 4691  | 9472  | 10709 |
|      | 8542  | 7060  | 6112  | 22457 | 21974 | 20476 | 7333  | 6482  | 14526 | 7151  | 2644  | 835   |
|      | 10655 | 12264 | 788   | 9673  | 9771  | 11716 | 18575 | 9584  | 12794 | 21399 | 6281  | 18662 |
|      | 7992  | 9661  | 19875 | 11156 | 3619  | 14086 | 786   | 20948 | 16946 | 3456  | 6143  | 6709  |
|      | 5954  | 17926 | 20839 | 22351 | 13277 | 10965 | 15558 | 8891  | 10152 | 15189 | 13161 | 3256  |
|      | 13226 | 1748  | 21271 | 22258 | 10136 | 18982 | 20726 | 10154 | 17115 | 12652 | 1426  | 12623 |
|      | 4475  | 16706 | 17850 | 21904 | 545   | 2132  | 20312 | 4655  | 16568 | 21093 | 13882 | 5730  |
|      | 7976  | 7079  | 13035 | 7273  | 14619 | 2800  | 12728 | 15228 | 19263 | 10088 | 305   | 16894 |
|      | 6203  | 22106 | 19049 | 10427 | 11733 | 8133  | 372   | 12866 | 13782 |       |       |       |
| 315: | 3342  | 12667 | 2100  | 12617 | 1136  | 6158  | 17567 | 4891  | 9212  | 13652 | 2310  | 14039 |
|      | 8257  | 4890  | 20474 | 16825 | 8834  | 4127  | 1369  | 14688 | 17548 |       |       |       |
| 316: | 10331 | 15934 | 2046  | 6293  | 19503 | 17105 | 13130 | 7604  | 20972 | 611   | 2151  | 19670 |
|      | 1110  | 20162 | 9143  | 9176  | 19023 | 19084 | 18099 | 5356  | 15439 | 3212  | 10361 | 21551 |
|      | 20873 | 18300 | 6915  | 11130 | 19131 | 17963 | 7910  | 4920  | 4372  | 18216 | 8334  | 5551  |
|      | 11009 | 21068 | 13009 | 6829  | 20236 | 2330  | 15785 | 1052  | 14929 | 4869  | 4064  | 14251 |
|      | 6409  | 4771  | 21722 | 3477  | 22283 | 4071  | 13419 | 2771  | 12516 | 2855  | 6554  | 5053  |
|      | 15301 | 13629 | 22091 | 9959  | 8014  | 18394 | 7184  | 5437  | 10014 | 15912 | 7764  | 9611  |
|      | 13654 | 12151 | 12808 | 1755  | 10215 | 21979 | 12492 | 8018  | 7254  | 20380 | 2845  | 654   |
|      | 5061  | 7274  | 9568  | 5018  | 11235 | 6804  | 8938  | 12700 | 17001 |       |       |       |
| 317: | 7147  | 17102 | 22335 | 21107 | 13529 | 17232 | 12299 | 15442 | 10074 | 12860 | 8161  | 6451  |
|      | 9249  | 12173 | 13520 | 2381  | 7179  | 2397  | 4681  | 8032  | 10026 | 17837 | 1679  | 750   |
|      | 13467 | 22304 | 9093  | 12920 | 8746  | 12849 | 8975  | 8614  | 11049 | 15351 | 6414  | 11194 |
|      | 18365 | 22000 | 10060 | 950   | 10516 | 16860 | 18657 | 11078 | 20626 | 15349 | 9992  | 11321 |
|      | 16068 | 13071 | 20575 | 10629 | 4241  | 12058 | 21534 | 18040 | 574   | 21837 | 6124  | 1526  |
|      | 12392 | 2919  | 22474 | 21550 | 1309  | 19435 | 13170 | 2632  | 14407 | 19257 | 15479 | 17487 |
|      | 7797  | 19535 | 13125 | 7697  | 9338  | 11284 | 15648 | 2144  | 9885  | 3591  | 21263 | 9545  |
|      | 14344 | 6947  | 19431 | 21279 | 4756  | 13704 | 4125  | 11670 | 6044  | 22381 | 21905 | 15904 |
|      | 14499 | 10692 | 12332 | 1756  | 4806  | 18332 | 7994  | 9064  | 18991 | 17391 | 20098 | 22081 |
|      | 5015  | 11957 | 13991 | 17712 | 22029 | 21507 | 3779  | 6619  | 4824  | 1847  | 11561 | 2927  |
|      | 7497  | 1618  | 16567 | 1625  | 1011  | 14504 | 1983  | 2353  | 13906 | 16938 | 11796 | 2922  |
|      | 13819 | 606   | 3676  | 2458  | 20599 | 20531 | 13948 | 7520  | 12498 | 13705 | 8646  | 9042  |
|      | 9750  | 14969 | 563   | 1092  | 8562  | 6341  | 3562  | 11565 | 15599 | 16895 | 12974 | 1939  |
|      | 16577 | 1711  | 21985 | 5754  | 19800 | 15748 | 4371  | 12415 | 2463  | 4827  | 5656  | 6520  |
|      | 14881 | 1513  | 19711 | 6790  | 20528 | 13821 | 9526  | 8611  | 6058  | 17821 | 1888  | 18587 |
|      | 4858  | 18855 | 7028  | 14908 | 22205 | 5964  | 4340  | 5271  | 17773 | 927   | 8374  | 3316  |
|      | 2666  | 20014 | 21527 | 9914  | 10822 | 7197  | 21212 | 13163 | 13989 | 17347 | 15266 | 1401  |
|      | 6338  | 14444 | 3445  | 561   | 9349  | 20565 | 2095  | 7453  | 18711 | 19524 | 4093  | 8735  |
|      | 14800 | 9217  | 16762 | 10080 | 19195 | 11057 | 11977 | 21372 | 20196 | 6610  | 14503 | 22133 |
|      | 19181 |       |       |       |       |       |       |       |       |       |       |       |
| 318: | 4562  | 9606  | 1444  | 14309 | 10107 | 21463 | 18996 | 14333 | 1334  | 13632 | 22339 | 19891 |
|      | 15309 | 3134  | 19973 | 17693 | 15433 | 13252 | 20233 | 7289  | 15373 | 8208  | 21182 | 21283 |
|      | 14523 | 6862  | 8920  | 22389 | 7427  | 19075 | 14622 | 18190 | 16360 | 12132 | 1586  | 14883 |
|      | 3538  | 22299 | 4909  | 6348  | 9295  | 11703 | 6913  | 16728 | 19809 | 21668 | 18897 | 20235 |
|      | 616   | 10625 | 12272 | 10812 | 4295  | 2449  | 11240 | 20715 | 10788 | 12331 |       |       |
| 319: | 11506 | 8025  | 19504 | 17096 | 9236  | 5967  | 13265 | 13150 | 20345 | 2575  | 15093 | 720   |
|      | 9238  | 20846 | 7110  | 18462 | 16689 | 3666  | 13238 | 20249 | 22504 | 5681  | 15821 | 11308 |
|      | 7263  | 2587  | 3204  | 8488  | 1135  | 3170  | 19880 | 7687  | 4736  | 5783  | 20141 | 8454  |
|      | 11622 | 3641  | 10121 | 15474 | 15016 | 3635  | 12476 | 2148  | 6474  | 12754 | 10278 | 4251  |
|      | 2157  | 17396 | 18150 | 5472  | 2435  | 9967  | 3440  | 12802 | 21724 | 16131 | 7711  | 10389 |
|      | 5452  | 18194 | 15428 | 5298  | 16650 | 13697 | 3148  | 15338 | 9355  | 4542  | 7607  | 12624 |
|      | 9835  | 6871  | 1450  | 17202 | 4346  | 18156 | 2256  | 5469  | 11562 | 11593 | 8125  | 13465 |
|      | 21018 | 14122 | 6978  | 1534  | 5284  | 19934 | 13992 | 9438  | 9860  | 16616 | 13159 | 22237 |
|      | 9239  | 12122 | 7442  | 20605 | 16637 | 625   | 10834 | 2546  | 3875  | 5692  | 13941 |       |
| 320: | 5584  | 14500 | 1413  | 1303  | 11425 | 12432 | 20553 | 5678  | 19728 | 1702  | 21840 | 16132 |
|      | 13978 | 8053  | 11638 | 17005 | 7048  | 12602 | 12897 | 18092 | 1532  | 16921 | 11347 | 8929  |
|      | 2022  | 22014 | 21806 | 20100 | 17247 | 5940  | 13718 | 10507 | 20917 | 13044 | 3334  | 11629 |
|      | 3850  | 19276 | 8082  | 15982 | 2091  | 8247  | 2827  | 4647  | 21352 | 16763 | 13875 | 2729  |
|      | 11068 | 14988 | 22366 | 6081  | 6500  | 17279 | 7348  | 9062  | 12873 | 13199 | 7794  | 6832  |
|      | 16726 | 7795  | 12202 | 12467 | 5788  | 10596 | 12756 | 21948 | 11263 | 10951 | 13316 | 8432  |
|      | 13127 | 9984  | 13493 | 8019  | 12038 | 1826  | 14472 | 9125  | 4955  | 19548 | 16684 | 5905  |
|      | 16785 | 3169  | 20313 | 12232 | 10211 | 6536  | 20084 | 4322  | 19294 |       |       |       |
| 321: | 11679 | 7712  | 4765  | 2778  | 10428 | 15613 | 13759 | 8748  | 15529 | 4789  | 4143  | 22492 |
|      | 10520 | 5899  | 5524  | 1150  | 15997 | 6728  | 7250  | 19339 | 3882  | 2486  | 16390 | 13804 |
|      | 4361  | 20834 | 20825 | 586   | 2032  | 2861  | 14363 | 17505 | 15033 | 6284  | 9806  | 19295 |
|      | 8378  | 20979 | 6962  | 22356 | 6126  | 18081 | 16902 | 16016 | 11797 | 14905 | 12294 | 1932  |
|      | 4974  | 560   | 4872  | 19916 | 7886  | 18272 | 11004 | 21567 | 6122  | 3929  | 10292 | 20964 |

TABLE 16-continued

Sequence IDs for homolog proteins
Seq ID NO: homolog Seq ID NOs

| | | | | | | | | | | | |
|---|---|---|---|---|---|---|---|---|---|---|---|
| | 14636 | 4316 | 16294 | 16670 | 6202 | 3283 | 3979 | 708 | 10683 | 3722 | 9024 | 10315 |
| | 7707 | 21597 | 12187 | 21031 | 11517 | 17433 | 1323 | 3512 | 20375 | 12464 | 21941 | 10366 |
| | 13212 | 15089 | 3993 | 3918 | 17676 | 18119 | 2709 | 17107 | 15788 | | | |
| 322: | 10548 | 4897 | 5425 | 7818 | 3878 | 10642 | 3310 | 16365 | 9020 | 12789 | 17219 | 2142 |
| | 13865 | 19002 | 946 | 18211 | | | | | | | | |
| 323: | 12932 | 12556 | 10612 | 8471 | 9836 | 7200 | 3244 | 4931 | 6155 | 11441 | 5925 | 9952 |
| | 1283 | 20609 | 2129 | 3224 | 8050 | 2693 | 11630 | 8765 | 8258 | 10271 | 17801 | 10768 |
| | 7008 | 3010 | 16997 | 6501 | 20840 | 3978 | 2010 | | | | | |
| 324: | 10963 | 8235 | 5742 | 21966 | 17140 | | | | | | | |
| 325: | 15756 | 6758 | 15758 | 5287 | 19343 | 4588 | 17303 | 13336 | 21407 | 16436 | 6718 | |
| 326: | 16712 | 1166 | 15865 | 2733 | 17246 | 15303 | 1381 | 13492 | 6572 | 7728 | 13605 | 12382 |
| | 9290 | 21152 | 7868 | 21359 | 6654 | 2544 | | | | | | |
| 327: | 12913 | 16464 | 16273 | 20905 | 3701 | 8623 | 4539 | 11237 | 7785 | 12606 | 12734 | 1726 |
| | 4555 | 7538 | 13748 | 14436 | 18787 | 11199 | 15234 | 14408 | 15929 | 7578 | 1919 | 8057 |
| | 11210 | | | | | | | | | | | |
| 328: | 14125 | 20217 | 16758 | 5776 | 15086 | 18339 | 9344 | 13845 | 5197 | 20795 | 5897 | 9137 |
| | 9973 | 704 | 18058 | 11958 | 7252 | 2114 | 7827 | 5752 | 4689 | 7592 | 15102 | 22013 |
| | 12505 | 15413 | 5397 | 16345 | 11067 | 11445 | 21494 | 14366 | 3450 | 8189 | 13758 | 10214 |
| | 21577 | 10815 | 1385 | 19042 | | | | | | | | |
| 329: | 3497 | 2714 | 8101 | 4216 | 8074 | 1106 | 1600 | | | | | |
| 330: | 11223 | 1913 | 6535 | 17340 | 17586 | 15949 | 10628 | 5279 | 16989 | 13504 | 22441 | 20437 |
| | 16847 | 20368 | 18727 | 20627 | 677 | 8442 | 2847 | 12004 | 5478 | | | |
| 331: | 13633 | 5900 | 8539 | 14672 | 12233 | 964 | 10478 | 20775 | 5875 | 5805 | 1804 | 1598 |
| | 8760 | 4906 | 10137 | 12276 | 20894 | 3902 | 1838 | 1416 | 13999 | 8927 | 20239 | 21067 |
| | 2846 | 1536 | 951 | 9346 | 9547 | 21436 | 4596 | 12781 | 4010 | 11786 | 8601 | 10761 |
| | 6187 | 19637 | 20291 | 12933 | 1404 | 16680 | 16262 | 4172 | 6985 | 11107 | 10370 | 17700 |
| | 13722 | 7971 | 3488 | 17731 | 14386 | 6750 | 13862 | 2765 | 17564 | 11582 | 6358 | 16691 |
| | 21558 | 16323 | 14350 | 16234 | 10634 | 8984 | 7275 | 21757 | 12586 | 15643 | 921 | 10884 |
| | 20529 | 8362 | 4086 | 15778 | 8213 | 645 | 8641 | 14759 | 21903 | 9293 | 2872 | 7350 |
| | 12282 | 7277 | 21911 | 19806 | 10064 | 12113 | 15339 | 20238 | 1645 | 15286 | 17911 | 15808 |
| | 9799 | 12685 | 4914 | 19213 | 10728 | 2852 | 4839 | 20536 | 7995 | 7379 | 15240 | 12971 |
| | 591 | 20690 | 5666 | 5145 | 10145 | 1126 | 13494 | 13052 | 13798 | 22187 | 6567 | 2224 |
| | 22255 | 22276 | 19919 | 8963 | 4880 | 11857 | 15344 | 20168 | 20601 | 21712 | 7009 | 15363 |
| | 10724 | 8126 | 7044 | 2098 | 12067 | 13898 | 7690 | 17967 | 22554 | | | |
| 332: | 4051 | 7246 | 14199 | 4757 | 2211 | 19939 | 7119 | 18627 | 18219 | 10672 | 19725 | 20509 |
| | 7686 | 2989 | 10561 | 7284 | 936 | 20910 | 3464 | 21563 | 5884 | 11537 | 21063 | 1972 |
| | 3103 | 11411 | 17085 | 21614 | 20041 | 6920 | 896 | 19271 | 21101 | 6679 | 18617 | 19003 |
| | 7557 | 2937 | 8512 | | | | | | | | | |
| 333: | 11864 | 18401 | 7916 | 16388 | 781 | 8033 | 2364 | 22015 | 9748 | 2475 | 765 | 14146 |
| | 13993 | 16445 | 7070 | 19406 | 13139 | 11260 | 21048 | 22437 | 16423 | 12388 | 15277 | 9405 |
| | 13452 | 21701 | 15472 | 21519 | 18268 | 18140 | 17189 | 10852 | 15461 | 8741 | 9641 | 20297 |
| | 21384 | 9522 | 16319 | 4702 | 6436 | 9574 | 18726 | 3628 | 16593 | 18634 | 13820 | 16639 |
| | 4189 | 17966 | 3524 | 13210 | 12214 | 13114 | 18483 | 5974 | 15580 | 4570 | 17225 |
| | 19309 | 11814 | 7466 | 15434 | 16431 | 13455 | 9128 | 17770 | 17597 | 11744 | 5668 | 18077 |
| | 20332 | 12252 | 6487 | 5722 | 19526 | 13902 | 14620 | 19013 | 12349 | 14056 | 3612 | 8715 |
| | 15923 | 4913 | 11247 | 1777 | 16114 | 9983 | 8124 | 7153 | 20006 | 10025 | 1074 | 21879 |
| | 4977 | 19631 | 8517 | 5456 | 9877 | 4139 | 21162 | 4367 | 7696 | 9702 | 1769 | 9365 |
| | 5341 | 7159 | 5323 | 19419 | 19967 | 19719 | 15541 | 14191 | 10391 | 612 | 17071 | 22520 |
| | 2596 | 16797 | 826 | 17040 | 18360 | 6069 | 16301 | 22129 | 12523 | 19596 | 3074 | 6712 |
| | 12666 | 21205 | 18284 | 21965 | | | | | | | | |
| 334: | 22427 | 862 | 20385 | 6265 | 12399 | 22070 | 17740 | 7828 | 4067 | 1153 | 11326 | 2935 |
| | 9841 | 19586 | 16621 | 4285 | 4474 | 5816 | 1468 | 12636 | 2870 | 12256 | 15396 | 20978 |
| | 13936 | 20481 | 9196 | 15850 | 17759 | 14083 | 17877 | 11918 | 14099 | 22052 | 4350 | 14967 |
| | 3030 | 4936 | 6573 | 20255 | 16179 | 17938 | 6661 | 14748 | 18841 | 8544 | 17559 | 16186 |
| | 13096 | 10817 | 20956 | 15131 | 16981 | 20307 | 6896 | 9262 | 16287 | 14784 | 4658 | 18310 |
| | 6506 | 1358 | 8689 | 18061 | 6280 | 1214 | 4418 | 13166 | 8421 | 2972 | 19253 | 6332 |
| | 1033 | 16181 | 10378 | 16100 | 12772 | 1621 | 974 | 9705 | 11370 | 21857 | 9111 | 13663 |
| | 6502 | 15769 | 18274 | 20182 | 18579 | 16062 | 18202 | 10290 | 15049 | 10207 | 10284 | 15057 |
| | 16286 | 790 | 10968 | 5513 | 1193 | 17665 | 4712 | 12568 | 13764 | 17032 | 778 | 11095 |
| | 19866 | 6900 | 21331 | 931 | 14040 | 5675 | 18493 | 5449 | 2779 | 10498 | 12780 | 10602 |
| | 10664 | 9704 | 2890 | 2696 | 4265 | 20376 | 6349 | 5782 | 11580 | 15846 | 4001 | 15619 |
| | 21400 | 16911 | 11079 | 4939 | 15709 | 14567 | 17601 | 14494 | 2988 | 2987 | 3279 | 14867 |
| | 3013 | 15708 | | | | | | | | | | |
| 335: | 15578 | 12136 | 19850 | 745 | 14354 | 11893 | 10400 | 16221 | 5102 | 12842 | 19938 | 8836 |
| | 6356 | | | | | | | | | | | |
| 336: | 1655 | 8875 | 17969 | 16217 | 19832 | 4954 | 10256 | 13907 | 2280 | 7705 | 2896 | 5571 |
| | 6016 | 2423 | 14230 | 7769 | 16575 | 6956 | 11570 | 638 | 22347 | 12730 | 3084 | 7136 |
| | 21153 | 979 | 18133 | 14470 | 4762 | 13775 | 13517 | 18643 | 14115 | 20989 | 4195 | 14211 |
| | 17841 | 21732 | 2378 | 6456 | 2604 | 16482 | 9054 | 9876 | 6696 | 20958 | 9729 | 13852 |
| | 22311 | 12997 | 5664 | 17434 | 511 | 11309 | 2192 | 7514 | 21788 | 10558 | 17846 | 13447 |
| | 19287 | 9827 | 17314 | 19480 | 8685 | 19289 | 9913 | 16783 | 7798 | 15355 | 21362 | |
| 337: | 16000 | 2106 | 21931 | 7956 | 15630 | 12717 | 10346 | 15324 | 20316 | 3593 | 13203 | 3167 |
| | 2799 | 12590 | 13815 | 4459 | 3056 | 18383 | 12953 | 14071 | 22160 | 2913 | 15509 | 16846 |
| | 14685 | 8814 | 5931 | 19964 | 20780 | 14871 | 13615 | 6779 | 997 | | | |
| 338: | 20669 | 3012 | 4857 | 6538 | 14648 | 21791 | 21544 | 15892 | 20656 | 17483 | 5020 | 19379 |
| | 16363 | 12470 | 5494 | 9395 | 17737 | 5910 | 3081 | 8480 | 20365 | 7510 | 1412 | 19099 |
| | 8801 | 14807 | 16161 | 2393 | 10298 | 8123 | 1239 | 10701 | 8769 | 20670 | 18966 | 739 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 17909 | 2578  | 9830  | 13785 | 17449 | 6339  | 13378 | 17851 | 10673 | 17975 | 18270 | 18869 |
|      | 20842 | 16312 | 5144  | 8392  | 13794 | 20142 | 22008 | 4642  | 7811  | 9505  | 7022  | 21431 |
|      | 7054  | 13460 | 4715  | 13880 | 15813 | 16187 | 18556 | 12071 | 5168  | 4445  | 8109  | 6238  |
|      | 19089 | 10095 | 2361  | 20340 | 16200 | 16747 | 6028  | 22386 | 10599 | 2796  | 3476  | 14418 |
|      | 7731  | 5135  | 20971 | 13422 | 21726 |       |       |       |       |       |       |       |
| 339: | 2298  | 2436  | 19901 | 14207 | 19971 | 5786  | 15380 | 16523 | 17629 | 1543  | 2607  | 3939  |
|      | 13893 | 13623 | 19506 | 1858  | 2400  | 20267 | 18864 | 3159  | 17867 | 6744  | 4520  | 5184  |
|      | 1289  | 5953  | 16468 | 8962  | 5695  | 6006  | 21230 | 5243  | 4876  | 2057  | 22012 | 13975 |
|      | 18334 |       |       |       |       |       |       |       |       |       |       |       |
| 340: | 5094  | 13921 | 9689  | 10104 | 19369 | 17978 | 21082 | 2690  | 17645 | 3853  | 21213 | 17435 |
|      | 20373 | 10839 | 8089  | 4282  | 11406 | 17050 | 9439  | 11816 | 3709  | 8068  | 13476 | 14133 |
|      | 17945 | 20398 | 2090  | 4164  | 2229  | 4799  | 13949 | 13578 | 8589  | 10573 | 17122 | 18689 |
|      | 4604  | 7491  | 11399 | 9657  | 1351  | 17934 | 21685 | 9266  | 20395 | 18832 | 4616  | 13018 |
|      | 17935 | 782   | 21358 | 4923  | 2048  | 7355  | 19368 | 10540 | 3418  | 15391 | 6352  | 1454  |
|      | 584   | 6023  | 7278  | 13416 | 7550  | 12889 | 8632  | 13053 | 6040  | 1583  | 16498 | 7544  |
|      | 2590  | 9046  | 601   | 4785  | 7174  | 3594  | 18195 | 11021 | 9022  | 8275  | 1685  | 3624  |
| 341: | 13668 | 15794 | 6342  | 14448 | 9278  | 20512 | 8200  | 16696 | 13521 | 1647  | 7170  | 15662 |
|      | 12079 | 14698 | 21329 | 1853  | 5038  | 11976 | 2478  | 11937 | 22112 | 21927 | 3832  | 2707  |
|      | 4810  | 16842 | 15999 | 3541  | 7952  | 9937  | 1893  | 9025  | 19963 | 10155 | 18805 | 2652  |
|      | 3473  | 21709 | 10794 | 17386 | 16395 | 9463  | 14603 | 17255 | 17919 | 4407  | 21734 | 1453  |
|      | 17376 | 5269  | 14505 | 22325 | 7898  | 5201  | 11700 | 7509  | 3737  | 5907  | 11800 | 14887 |
|      | 18221 | 3408  | 1391  | 6603  | 945   | 2741  | 11668 | 22559 | 13979 | 16492 | 19717 | 12052 |
|      | 13678 | 12316 | 20893 | 10627 | 18110 | 9396  | 17457 | 12447 | 17706 | 4188  | 12736 | 10213 |
|      | 5657  | 1361  | 17750 | 2164  | 20757 | 10342 | 5557  | 13427 | 1459  | 5874  | 11035 | 14177 |
|      | 18713 | 8770  | 13138 | 12686 | 12216 | 4228  | 12420 | 12044 | 4116  | 20177 | 7717  | 20582 |
|      | 6544  | 20287 | 13392 | 5213  | 21383 | 20420 | 12277 | 610   | 7242  | 13209 | 21266 | 15605 |
|      | 17695 | 1713  | 6386  | 7399  | 3771  | 15478 | 14510 | 14171 | 22266 | 6037  | 14656 | 20179 |
|      | 7964  | 7223  | 20189 | 1994  | 21418 | 7850  | 8756  | 18014 | 14079 | 726   | 12260 | 21444 |
|      | 10406 | 2633  | 8511  | 11121 | 10904 | 3092  | 2853  | 17906 | 16524 | 8187  | 17998 | 20778 |
|      | 2286  | 20199 | 3729  | 6145  | 21008 | 2565  | 12962 | 1257  | 15354 | 10610 | 7157  | 1796  |
|      | 6315  | 17300 | 22423 | 14435 | 16471 | 16628 | 6594  | 21171 | 9956  | 9842  | 18573 | 17327 |
|      | 8572  | 9431  | 16077 | 13255 | 10967 | 18428 | 7421  | 19940 | 17552 | 22215 | 6311  | 22128 |
|      | 15501 | 21897 | 19865 | 6983  | 7587  | 17139 | 17241 | 18872 | 10791 | 18810 | 8812  | 5978  |
|      | 20019 | 19994 | 6664  | 13673 | 2650  | 8721  | 16038 | 14722 | 18896 | 21111 | 2762  | 17606 |
|      | 10806 | 18027 | 9130  | 18559 | 12287 | 11513 | 6131  | 3172  | 1990  | 4027  | 5292  | 3287  |
|      | 13481 | 11191 | 19301 | 11297 | 10021 | 9171  | 14682 | 17190 | 14540 | 1140  | 8118  |       |
| 342: | 2631  | 10657 | 18699 | 2536  | 6440  | 2600  | 16629 | 20719 | 4729  | 7634  | 14681 | 5022  |
|      | 8936  | 10883 | 18494 | 6327  | 9575  | 8157  | 8096  | 14112 | 2076  | 9896  | 11151 | 16731 |
|      | 2204  | 9035  |       |       |       |       |       |       |       |       |       |       |
| 343: | 2755  | 21932 | 4777  | 6313  | 21861 | 12723 | 19508 | 1200  | 15989 | 16994 | 5687  | 6685  |
|      | 14644 | 15427 | 18561 | 20955 | 5319  | 10512 | 18861 | 4752  | 4558  | 9237  | 14495 | 2731  |
|      | 18748 | 20853 | 21624 | 4158  | 6682  | 15121 | 13328 | 11123 | 17204 | 3588  | 8417  | 12524 |
|      | 14426 | 12139 | 5914  | 22397 | 13082 | 3579  | 4217  | 4229  | 10653 | 20451 | 3376  | 17804 |
|      | 6004  | 10303 | 2139  | 15227 | 11831 | 18631 | 19845 | 12159 | 11935 | 18000 | 18066 | 13477 |
|      | 5998  | 16773 | 6555  | 6113  | 18981 | 769   | 10905 | 22461 | 18369 | 7501  | 12698 | 17209 |
|      | 22284 | 15974 | 3000  | 1328  | 15319 | 13157 | 21846 | 21899 | 1244  | 17408 | 7057  | 674   |
|      | 11714 | 14760 | 3856  | 22403 | 13952 | 5958  | 18866 | 16803 | 5945  | 7999  | 10446 | 17518 |
|      | 21309 | 12969 | 5105  | 10656 | 10777 | 18972 | 14634 | 7566  | 9182  | 10453 | 6623  | 6029  |
|      | 3857  | 1041  | 17997 | 10387 | 10643 | 1035  | 3246  | 9229  | 18431 | 9219  | 13687 | 4600  |
|      | 14823 | 1650  | 1911  | 1506  | 20935 | 12204 | 6588  | 14467 | 12894 | 12964 | 21745 | 4773  |
|      | 4206  | 8608  | 11403 | 21291 | 15104 | 9577  | 22470 | 10395 | 7106  | 18085 | 1045  | 18438 |
|      | 20164 | 5627  | 6989  | 3125  | 20664 | 9899  | 17477 | 20384 | 8914  | 13339 | 21568 | 14346 |
|      | 15753 | 18139 | 2610  | 22040 | 12680 | 1930  | 10147 | 11672 | 21762 | 14042 | 4281  | 8445  |
|      | 18322 | 7765  | 11544 | 8117  | 10562 | 17367 | 2534  | 14153 | 9918  | 7771  | 16968 | 14118 |
|      | 14857 | 20095 | 4419  | 15545 | 5134  | 11331 | 9802  | 4911  | 9938  | 3150  | 22321 | 8071  |
|      | 13544 | 4128  | 7168  | 8967  | 22547 | 3271  | 5965  | 9073  | 16529 | 16953 | 7176  | 17918 |
|      | 1026  | 16418 | 11579 | 13510 | 11163 | 21202 | 11509 | 15037 | 10348 | 12555 | 7467  | 9767  |
|      | 15877 | 20472 | 13410 | 15361 | 12759 | 10511 | 8273  | 5946  | 3774  | 8121  |       |       |
| 344: | 0     |       |       |       |       |       |       |       |       |       |       |       |
| 345: | 11342 | 13022 | 13189 | 13375 | 19355 | 4603  | 9001  | 693   | 10423 | 19460 | 11989 | 3379  |
|      | 20654 | 19018 | 22196 |       |       |       |       |       |       |       |       |       |
| 346: | 4152  | 1714  | 20305 | 10236 | 21335 | 10203 | 4070  | 20587 | 13194 | 15640 | 10242 | 11539 |
|      | 16862 | 1124  | 10029 | 12355 | 19807 | 3466  | 21983 | 17696 | 21768 | 12283 | 20617 | 17748 |
|      | 17513 | 7821  | 7744  | 10704 | 11320 | 3178  | 16909 | 21864 | 9099  | 11919 |       |       |
| 347: | 15403 | 7222  | 17930 | 22425 | 8943  | 8767  | 5431  | 9412  | 9840  | 7098  | 10706 | 20039 |
|      | 19399 | 18679 | 3063  | 13922 | 12891 | 19177 | 14765 | 8888  | 3766  | 15264 | 15112 | 8346  |
|      | 19249 | 9496  | 8467  | 12097 | 7066  | 13354 | 10438 | 19683 | 1867  | 13713 | 11392 | 20463 |
|      | 8419  | 9530  | 13590 | 19828 | 17789 | 3181  | 19673 | 20308 | 20048 |       |       |       |
| 348: | 22289 | 699   | 7239  | 11768 | 21811 | 2946  | 15818 | 18586 | 10674 | 14308 | 3720  | 10934 |
|      | 14107 | 19528 | 13730 | 3925  | 20977 | 22047 | 4398  | 22391 | 16849 | 20631 |       |       |
| 349: | 6607  | 11545 | 4182  | 16789 | 10863 | 11170 | 7754  | 13889 | 17668 | 6741  | 14774 | 8116  |
|      | 16721 | 683   | 13808 | 10075 | 2147  | 13320 | 7970  | 20540 | 8978  | 11576 | 16025 | 12292 |
|      | 10319 | 5002  | 13246 | 7075  | 22235 | 11091 | 9999  | 20403 | 14955 | 7021  | 7400  | 15424 |
|      | 1403  | 1576  | 15201 | 1547  | 21389 | 2191  | 20891 | 18977 | 17393 | 11512 | 10958 | 14007 |
|      | 6534  | 12539 | 20887 | 4792  |       |       |       |       |       |       |       |       |

TABLE 16-continued

Sequence IDs for homolog proteins
Seq ID NO: homolog Seq ID NOs

| | | | | | | | | | | | |
|---|---|---|---|---|---|---|---|---|---|---|---|
| 350: | 21637 | 9766 | 13473 | 10430 | 2373 | 10229 | 22472 | 2533 | 8573 | 9183 | |
| 351: | 21639 | 6558 | 15717 | 6583 | 1489 | 21115 | 14590 | 22491 | 22170 | 13729 | 14708 | 11897 |
| | 9169 | 16003 | 16657 | 18303 | 2503 | 7619 | 9667 | 19462 | | | |
| 352: | 14832 | 4680 | 730 | 8944 | 19323 | 9756 | 8807 | 16549 | 6800 | 8830 | 14997 | 16942 |
| | 1293 | 1086 | 19167 | 624 | 11497 | 15185 | 11336 | 10574 | 6438 | 21022 | 10877 | 3498 |
| | 1533 | 10113 | 8352 | 18565 | 10340 | 12363 | 3314 | 18700 | 8755 | 21000 | 5888 | 14051 |
| | 11660 | 10255 | 20975 | 16898 | 1028 | 4899 | 9807 | 15549 | 1039 | 16373 | 21500 | 3757 |
| | 4390 | 13334 | 5158 | 7861 | 19157 | 5010 | 21692 | 13142 | 13526 | 12155 | 3025 | 15524 |
| | 4634 | 18132 | 20879 | 11836 | 6517 | 5390 | 6944 | 17642 | 10919 | 12777 | 22312 | 12374 |
| | 12089 | 2107 | 8665 | 10063 | 15827 | 10534 | 19377 | 14693 | 4078 | 16983 | 7351 | 21180 |
| 353: | 9803 | 5872 | 20880 | 7736 | 9394 | 19214 | 20066 | 4813 | 3867 | 8129 | 6810 | 8821 |
| | 14360 | 9758 | 10208 | 22542 | 16794 | 8724 | 2461 | 5260 | 11314 | 17374 | 20064 | 22105 |
| | 20232 | 17121 | 17288 | 16874 | 14516 | 1119 | 2781 | 15198 | 20079 | 14792 | 3439 | 22298 |
| | 12105 | 21450 | | | | | | | | | |
| 354: | 6321 | 5225 | 13406 | 4040 | 4448 | 20067 | 13787 | 8883 | 20377 | 876 | 9126 | 21945 |
| | 4701 | 11644 | | | | | | | | | |
| 355: | 8510 | 12886 | 3986 | 1767 | 22183 | 9676 | 17318 | 13827 | 6552 | 22440 | 15136 | 22229 |
| | 15255 | 8556 | | | | | | | | | |
| 356: | 20329 | 7584 | 18151 | 12782 | 19780 | 869 | 1234 | 4543 | 4443 | 6003 | 10879 | 6195 |
| | 14766 | 2261 | 5303 | 18455 | 14900 | 13423 | 4770 | 7064 | 4996 | | |
| 357: | 1090 | 22239 | 4778 | 3892 | 10096 | 3089 | 20675 | 8225 | 3300 | 3785 | 10016 | 16285 |
| 358: | 7246 | 7633 | 13566 | 4922 | 7189 | 8550 | 21432 | 6659 | 8001 | 9021 | 4169 | 9591 |
| | 18319 | 13478 | 12836 | 12342 | 14209 | 15108 | 19698 | 21556 | 16875 | 20650 | 5851 | 17486 |
| | 6249 | 13780 | 15776 | 11726 | 21200 | 14093 | 18917 | 21915 | 21121 | 8529 | 17053 | 2009 |
| | 2989 | 6906 | 7928 | 14192 | 7577 | 6127 | 6916 | 13803 | 19598 | 11276 | 7336 | 21713 |
| | 21337 | 2445 | 11616 | 17616 | 21069 | 3827 | 12208 | 819 | 16095 | 11103 | 17030 | 6075 |
| | 5459 | 17025 | 20374 | 5057 | 1399 | 3996 | 16384 | 3401 | 8557 | 9470 | 18719 | 18399 |
| | 2158 | 3928 | 19925 | 15780 | 1172 | 19003 | 4754 | 6752 | 7557 | 15694 | 2929 | 15268 |
| | 8286 | 16534 | 8056 | 2719 | 1955 | 18895 | 5457 | 17041 | 22161 | 8512 | 21678 | 7854 |
| | 13647 | 18098 | 15831 | 11038 | 15162 | 8205 | | | | | |
| 359: | 11518 | 14223 | 17501 | 6542 | 13569 | 4821 | 16169 | 8132 | 15637 | 2270 | 10309 | 5708 |
| | 18374 | 9446 | 7790 | 12784 | 7569 | 14187 | 5525 | 7188 | 21691 | 15258 | 4550 | 7616 |
| | 5261 | 15163 | 14560 | 20144 | 10693 | 12244 | 21413 | 6135 | 7464 | 11142 | 13491 | 17655 |
| | 15676 | 14174 | 18333 | 13472 | 20648 | 6435 | 14763 | 13495 | 12676 | 18906 | 12036 | 16066 |
| | 21593 | 21667 | 14370 | 16048 | 17609 | 19658 | 5604 | 575 | 21518 | 5309 | 13744 | 15880 |
| | 19484 | 6704 | 658 | 8704 | 16710 | 12907 | 19375 | 3306 | 19468 | 11042 | 3984 | 17175 |
| | 20965 | 1206 | 9155 | 20970 | 6796 | 17057 | 11008 | 18605 | 3353 | 4650 | 9058 | 7988 |
| | 19743 | 8369 | 3654 | 18497 | 11952 | 2866 | 16796 | 8504 | 20034 | 19086 | 4409 | 12452 |
| | 12908 | 7530 | | | | | | | | | |
| 360: | 13327 | 3981 | 5070 | 16490 | 20204 | 5909 | 15321 | 10310 | 12746 | 5760 | 6045 | 1730 |
| | 1018 | 15233 | 13486 | 17387 | 20991 | 5406 | 13208 | 21716 | 9902 | 21763 | 22315 | 6472 |
| | 824 | 1364 | 18250 | 18767 | 12499 | 21700 | 3665 | 8788 | 19915 | 12114 | 17927 | 19363 |
| 361: | 13771 | 10043 | 10800 | 17501 | 13569 | 6854 | 4637 | 16169 | 8132 | 2667 | 15637 | 2270 |
| | 10309 | 18374 | 5708 | 9446 | 9291 | 12844 | 7790 | 12784 | 10720 | 9725 | 13741 | 5525 |
| | 15920 | 7877 | 7188 | 21691 | 15258 | 6705 | 4550 | 14008 | 15544 | 9706 | 7616 | 14358 |
| | 13182 | 14560 | 16722 | 1472 | 4000 | 1388 | 4261 | 10984 | 9823 | 21413 | 4976 | 9514 |
| | 16806 | 9972 | 9224 | 13061 | 15247 | 17984 | 9925 | 19953 | 10247 | 2676 | 11680 | 9751 |
| | 7643 | 12752 | 14983 | 15727 | 20648 | 3200 | 6435 | 14763 | 13495 | 13003 | 16940 | 7214 |
| | 15976 | 5735 | 6270 | 22352 | 12931 | 14053 | 16048 | 17609 | 575 | 18286 | 21834 | 10842 |
| | 18927 | 21518 | 20097 | 5309 | 13744 | 15880 | 19484 | 658 | 8704 | 16710 | 19375 | 3306 |
| | 6347 | 19468 | 10410 | 10451 | 11618 | 20965 | 12916 | 20970 | 11008 | 1237 | 7988 | |
| | 19743 | 20088 | 8231 | 4522 | 18497 | 11952 | 2866 | 15466 | 20970 | 3609 | 2403 | 16796 | 13539 |
| | 14806 | 5364 | 12620 | 20699 | 15426 | 4409 | 12452 | 5296 | 3102 | 20918 | 9156 | 12665 |
| | 629 | 20947 | 3649 | 7530 | | | | | | | |
| 362: | 1670 | 8427 | 4513 | 13628 | 17835 | 1981 | 20663 | 1254 | 19692 | 11385 | 11148 | 18372 |
| | 18636 | 1663 | 18409 | 21940 | 17744 | 17838 | 14190 | 16086 | 18411 | 682 | | |
| 363: | 2344 | 7205 | 10404 | 18090 | 3530 | 22282 | 2138 | 1522 | 5878 | 7220 | 18971 | 21529 |
| | 18900 | 21077 | 6911 | 22318 | 1047 | 9881 | 13404 | 7614 | 13515 | 13092 | 13300 | 20784 |
| | 3818 | 8910 | 19715 | 892 | 11279 | 3262 | | | | | |
| 364: | 7108 | 14914 | 4339 | 11633 | 1095 | 18100 | 17413 | 19557 | 4087 | 5710 | 14536 | 8563 |
| 365: | 16767 | 7229 | 7241 | 19193 | 14780 | 8455 | 1669 | 2113 | 16394 | 13341 | 4965 | 20987 |
| | 21669 | 16094 | 13151 | 2242 | 9452 | 6246 | 4432 | 1828 | 6419 | 11839 | 6713 | 3448 |
| | 5129 | 7881 | 21433 | 18954 | 18710 | 15718 | 12146 | 16149 | 12186 | 2849 | 17256 | 2464 |
| | 11803 | 21181 | 15404 | 0468 | | | | | | | |
| 366: | 6504 | 7524 | 14750 | 15585 | 13755 | 6170 | 12273 | 16565 | 1049 | 12336 | 18307 | 21260 |
| | 18677 | 18863 | 18346 | 15597 | 19755 | 3751 | 19920 | 2278 | 12086 | 1347 | 858 | 13286 |
| | 14325 | 1020 | 15133 | 10620 | 2444 | 3050 | 16139 | 16876 | 1573 | | |
| 367: | 16254 | 15810 | 10496 | | | | | | | | |
| 368: | 4014 | 5426 | 1644 | 4368 | 10252 | 8347 | 14623 | 6336 | 3143 | 17492 | 2883 | 8191 |
| | 13701 | 14972 | 3068 | 11055 | 13245 | 907 | 1811 | 17743 | 3222 | 22379 | 5180 | 8300 |
| | 10258 | 19899 | 11656 | 9989 | | | | | | | |
| 369: | 12917 | 22561 | 8545 | 4583 | 16643 | 6177 | 17097 | 3916 | 4541 | 14252 | 13870 | 6493 |
| | 5606 | 20188 | 10820 | 20279 | 8970 | 21193 | | | | | |
| 370: | 4823 | 10748 | 15527 | 15435 | 796 | 14678 | 9764 | 10076 | 11244 | 9175 | 7609 | 5115 |
| | 21377 | 11924 | 10595 | 20985 | 18928 | 3164 | 9788 | 11682 | 14840 | 9374 | 7368 | 12999 |
| | 6258 | 1876 | 19771 | 13726 | 657 | 7929 | 12344 | 4713 | 4417 | 19488 | 11641 | 3883 |
| | 6787 | 11345 | 16897 | 10763 | 19559 | 1322 | | | | | |

TABLE 16-continued

Sequence IDs for homolog proteins
Seq ID NO: homolog Seq ID NOs

| | | | | | | | | | | | | |
|---|---|---|---|---|---|---|---|---|---|---|---|---|
| 371: | 7873 | 16841 | 5024 | 667 | 14126 | 19489 | 20718 | 20114 | 6307 | 13749 | 4296 | 12328 |
| | 20713 | 14817 | 9449 | 17512 | 12753 | 3363 | 11373 | 19490 | 20600 | 14723 | 1330 | 10565 |
| | 10981 | 22124 | 10789 | 16941 | 4863 | 19070 | 12635 | 18547 | 1307 | 13095 | 22242 | 5955 |
| | 10082 | 21555 | 19391 | 1056 | 17810 | 15497 | 12220 | 6532 | 15511 | 7786 | 2790 | 6035 |
| | 18667 | 7196 | 17474 | 2121 | 6729 | 19563 | 5810 | 3048 | 746 | 3566 | 16497 | 12050 |
| | 8774 | 22138 | 1519 | 13512 | 22303 | 2143 | 10708 | 12991 | 12651 | 3454 | 16182 | 10091 |
| | 18474 | 18979 | 19291 | 18720 | 9390 | 8536 | 17155 | 6630 | 10710 | 15964 | 7870 | 4033 |
| | 10458 | 1637 | 16790 | 15145 | 11065 | 1445 | 18055 | 8688 | 19251 | 19006 | 13222 | 19365 |
| | 2339 | 7595 | 4454 | 13908 | 19220 | 15364 | 18914 | 10062 | 2726 | 22250 | 16571 | 5841 |
| | 19972 | 14541 | 2092 | 17011 | 19981 | 20191 | 13421 | 15044 | 15913 | 3884 | 17551 | 14501 |
| | 21005 | 6049 | 4670 | 18512 | 20116 | 22469 | 12494 | 12091 | 21526 | 21355 | 8895 | 11631 |
| | 16944 | 11810 | 10807 | 21779 | 906 | 756 | 15963 | 10502 | 12400 | 1579 | 15470 | 8436 |
| | 8930 | 2675 | 20539 | 7266 | 19290 | 13829 | 1855 | 2679 | 8784 | 9380 | 16462 | 6530 |
| | 22546 | 22416 | 17960 | 15631 | 1720 | 21887 | 5290 | 18327 | 18553 | 4590 | 7391 | 7917 |
| | 14645 | 15614 | 13247 | 14642 | 12300 | 11299 | 19418 | 1740 | 14311 | 18764 | 7547 | 14528 |
| | 635 | 9762 | 6404 | 17436 | 12422 | 16799 | 6528 | 15127 | 16603 | 13586 | 8483 | 3332 |
| | 2647 | 22390 | 2094 | 17405 | 13174 | 3330 | 5025 | 17812 | 3810 | 19126 | 12711 | 9225 |
| | 18885 | 11043 | 21479 | 7774 | 21789 | 17915 | 1800 | 13049 | 16606 | 13023 | 2103 | 2956 |
| | 11730 | 6062 | 11525 | 15548 | 21598 | 14233 | 4710 | 17481 | 6481 | 20502 | 21631 | 14591 |
| | 703 | 7865 | 21847 | 18542 | 17238 | 15120 | 19632 | 2874 | 12903 | 20473 | 16809 | 19278 |
| | 15968 | 14351 | 21898 | 19284 | 8790 | 7247 | 6870 | 19794 | 764 | 16079 | 17554 | 10015 |
| | 14157 | 5749 | 18287 | 4764 | 3645 | 13045 | 14959 | 2521 | 18913 | 21473 | 9257 | 12508 |
| | 4304 | 1449 | 12138 | 6240 | 11499 | 7386 | 10591 | 20874 | 4447 | 5379 | 5272 | 10120 |
| | 8267 | 6643 | 6108 | 22137 | 17643 | 4910 | 15972 | 4782 | 15186 | 2068 | 5528 | 12337 |
| | 11658 | 13756 | 3142 | 15763 | 12030 | 13236 | 17079 | 5380 | 18622 | 5896 | 4307 | 3158 |
| | 17067 | 12487 | 14339 | 613 | 6726 | 15106 | 15675 | 11379 | 7371 | 5597 | 12017 | 17274 |
| | 14824 | 18417 | 20721 | 11498 | 16295 | 15954 | 12677 | 9580 | 12641 | 17409 | 19499 | 9907 |
| | 10576 | 21600 | 1559 | 1247 | 18152 | 17273 | 13554 | 16429 | 16780 | 20611 | 10103 | 3507 |
| | 20153 | 6861 | 13556 | 3496 | 16183 | 11289 | 3492 | 3006 | 5273 | 3374 | 9357 | 22451 |
| | 22004 | 19394 | 18283 | 11166 | 15318 | 8768 | 18770 | 9309 | 16332 | 16630 | 17527 | 9479 |
| | 8561 | 16576 | 10695 | 18749 | 17951 | 10930 | 9616 | 3752 | 10469 | 2422 | 4538 | 18515 |
| | 20865 | 7082 | 1739 | 12250 | 6190 | 16535 | 9858 | 7630 | 15712 | 2642 | 22497 | 1808 |
| | 8526 | 18181 | 7296 | 21659 | 16761 | 14816 | 21998 | 13413 | 14852 | 10402 | 11131 | 6668 |
| | 16521 | 11910 | 2019 | 5412 | 11257 | 11346 | 4369 | 17646 | 5667 | 12585 | 1224 | 11092 |
| | 5532 | 10200 | 16673 | 17220 | 17006 | 6359 | 17169 | 14019 | 20289 | 17599 | 5659 | 9944 |
| | 9538 | 3683 | 3521 | 19933 | 16463 | 13655 | 5686 | 21698 | 20758 | 784 | 11603 | 2553 |
| | 8439 | 21559 | 7563 | 14314 | 13522 | 15633 | 1741 | 1518 | 15412 | 5891 | 1375 | 2785 |
| | 14686 | 15611 | 21250 | 11653 | 21545 | 17884 | 18298 | 2764 | 3864 | 12813 | 11218 | 5410 |
| | 16378 | 1570 | 7383 | 9592 | 15460 | 16787 | 1050 | 10032 | 6964 | 19685 | 13788 | 11507 |
| | 3504 | 17418 | 3664 | 20387 | 12935 | 8777 | 20035 | 14635 | 11626 | 3618 | 6519 | 743 |
| | 1923 | 12738 | 13872 | 12436 | 5348 | 10557 | 14330 | 1015 | 17903 | 15405 | 4174 | 2069 |
| | 16438 | 1021 | 19206 | 4166 | 13172 | 10851 | 2780 | 1326 | 13679 | 7285 | 11220 | 4129 |
| | 8228 | 10294 | 19721 | 22543 | 1447 | 5468 | 4193 | 6618 | 3849 | 14474 | 3736 | 3595 |
| | 18582 | | | | | | | | | | | |
| 372: | 1006 | 429 | 14179 | 7479 | 10217 | 535 | 533 | 507 | 306 | 478 | 12575 | 314 |
| | 2254 | 5697 | 5950 | 15642 | 18461 | 5073 | 9804 | 18997 | 8666 | 5240 | 3659 | 6320 |
| | 6367 | 19001 | 6157 | 11916 | 21356 | 2258 | 11071 | 9857 | 2163 | 2584 | 3331 | 526 |
| | 15153 | 20086 | 6423 | 4662 | 3838 | 14933 | 8860 | 19820 | 15915 | 7403 | 13646 | 4850 |
| | 4714 | 9730 | 12137 | 14919 | 12016 | 19643 | 3913 | 17315 | 7812 | 21939 | 13951 | 1478 |
| | 7199 | 10536 | 9491 | 3917 | 18676 | 15376 | 4608 | 16936 | 20333 | 1999 | 7216 | 1589 |
| | 17342 | 21640 | 8527 | 5069 | 16880 | 19870 | 10959 | 4725 | 15069 | 13329 | 20496 | 5944 |
| | 17598 | 6786 | 7612 | 14232 | 18318 | 534 | 531 | 286 | 4110 | 10546 | 16887 | 4811 |
| | 15616 | 10586 | 10067 | 4095 | 692 | 11756 | 20433 | 13391 | 9954 | 10468 | 16270 | 7655 |
| | 21719 | 5755 | 4146 | 2857 | 17664 | 21589 | 11961 | 18800 | 19154 | 879 | 12644 | 16878 |
| | 2030 | 4833 | 21437 | 5428 | 11195 | 20933 | 21506 | 13928 | 8904 | 13072 | 4677 | 18511 |
| | 4730 | 696 | 9569 | 17797 | 18687 | 7097 | 20259 | 15252 | 13221 | 450 | 11335 | 20777 |
| | 12713 | 22502 | 14915 | 21157 | 20371 | 3563 | 12591 | 16308 | 7626 | 4212 | 19798 | 19458 |
| | 5691 | 18292 | 16130 | 21296 | 2832 | 830 | 14553 | 6434 | 18295 | 17956 | 829 | 476 |
| | 12043 | 20779 | 1281 | 17745 | 16586 | 7955 | 12705 | 15449 | 988 | 20859 | 1768 | 11129 |
| | 6547 | 22518 | 5552 | 9854 | 11376 | 6669 | 5359 | 9132 | 10964 | 1879 | 22087 | 13137 |
| | 17298 | 3333 | 13752 | 20301 | 19370 | 2425 | 6946 | 19538 | 14273 | 15340 | 6427 | 17165 |
| | 15603 | 12419 | 10809 | 8003 | 13658 | 4221 | 14064 | 22249 | 7387 | 13284 | 20981 | 2316 |
| | 3116 | 8418 | 3386 | 6508 | 18217 | 3578 | 992 | 13442 | 3471 | 14855 | 19949 | 5277 |
| | 19885 | 2816 | 10917 | 9436 | 18538 | 18659 | 12816 | 12308 | 15943 | 2515 | 20364 | 14701 |
| | 8193 | 17579 | 22076 | 8890 | 2649 | 9329 | 21073 | 8376 | 15177 | 10882 | 859 | 16053 |
| | 5990 | 9814 | 14918 | 5209 | 3144 | 13848 | 22428 | 19076 | 5454 | 17056 | 4088 | 11270 |
| | 5837 | 9604 | 22455 | 19840 | 1656 | 12234 | 1149 | 801 | 953 | 9960 | 21301 | 5581 |
| | 3755 | 12278 | 22119 | 21098 | 1005 | 10264 | 13037 | 11702 | 20954 | 5063 | 1118 | 6454 |
| | 20632 | 1696 | 19474 | 14911 | 9381 | 4111 | 13374 | 2932 | 3071 | 18551 | 22362 | 12923 |
| | 1431 | 6509 | 19229 | 14012 | 5372 | 12362 | 17380 | 20272 | 16391 | 9540 | 13395 | 5132 |
| | 901 | 19228 | 14568 | 17630 | 2371 | 4694 | 12396 | 15369 | 16597 | 3697 | 10741 | 16309 |
| | 4927 | 13396 | 21621 | 8841 | 16662 | 14081 | 8692 | 9484 | 15204 | 6565 | 14320 | |
| | 2978 | 9294 | 7482 | 9493 | 1277 | 4952 | 7813 | 7306 | 12296 | 12021 | 6645 | 9286 |
| | 22489 | 13745 | 16653 | 19069 | 7780 | 15219 | 16969 | 14762 | 18330 | 10802 | 10479 | 16663 |
| | 3678 | 16713 | 7751 | 13703 | 3630 | 4691 | 9472 | 10709 | 8542 | 7060 | 6112 | 22457 |
| | 21974 | 20476 | 7333 | 6482 | 14526 | 7151 | 2644 | 835 | 10655 | 12264 | 9315 | 2786 |
| | 16253 | 9488 | 5634 | 17372 | 788 | 9280 | 22095 | 18903 | 3706 | 15256 | 18593 | 5764 |

TABLE 16-continued

Sequence IDs for homolog proteins
Seq ID NO: homolog Seq ID NOs

|  | | | | | | | | | | | |
|---|---|---|---|---|---|---|---|---|---|---|---|
|  | 11115 | 12583 | 11568 | 13613 | 2331 | 5136 | 8073 | 15998 | 5630 | 11304 | 19137 | 5817 |
|  | 5580 | 18341 | 8588 | 12540 | 2454 | 4970 | 17445 | 2401 | 11869 | 6193 | 21516 | 10889 |
|  | 5190 | 13207 | 16465 | 9673 | 9771 | 11716 | 18575 | 9584 | 12794 | 21399 | 20485 | 9218 |
|  | 18691 | 14036 | 3350 | 18263 | 4846 | 544 | 19667 | 9933 | 4140 | 1318 | 20418 | 11128 |
|  | 20105 | 16734 | 2376 | 15699 | 7061 | 4232 | 15357 | 5339 | 7107 | 19030 | 7165 | 21370 |
|  | 12103 | 4848 | 13211 | 22530 | 15360 | 12863 | 9975 | 6398 | 14067 | 16683 | 21170 | 1924 |
|  | 890 | 8155 | 15866 | 10131 | 7187 | 4332 | 1235 | 20330 | 12927 | 7088 | 5099 | 2302 |
|  | 12424 | 8303 | 17466 | 14322 | 11383 | 2282 | 15956 | 3414 | 12982 | 18548 | 15665 | 10961 |
|  | 21084 | 10824 | 18440 | 16819 | 3730 | 13940 | 18821 | 14864 | 1818 | 19607 | 7969 | 6546 |
|  | 16771 | 5441 | 8459 | 18266 | 5000 | 15749 | 13014 | 14274 | 8444 | 4707 | 13097 | 15930 |
|  | 11872 | 2621 | 7158 | 6942 | 18502 | 5408 | 10837 | 21928 | 13800 | 5188 | 19614 | 16117 |
|  | 4719 | 1833 | 13499 | 3107 | 21492 | 12503 | 21929 | 7921 | 1429 | 14398 | 22189 | 6439 |
|  | 12993 | 12307 | 19714 | 6650 | 18994 | 747 | 5932 | 18630 | 6683 | 1921 | 15651 | 5594 |
|  | 6958 | 13597 | 19763 | 10097 | 19882 | 14124 | 14687 | 1094 | 5780 | 7770 | 7688 | 15110 |
|  | 5797 | 7907 | 21169 | 3329 | 12627 | 4065 | 22067 | 19211 | 2061 | 7038 | 8909 | 16914 |
|  | 13129 | 19881 | 16317 | 1551 | 13235 | 14888 | 1201 | 20264 | 7800 | 7526 | 2209 | 5887 |
|  | 10798 | 15317 | 10223 | 11351 | 10105 | 10661 | 15014 | 2908 | 16412 | 22277 | 19851 | 12003 |
|  | 19616 | 11003 | 7768 | 6166 | 4620 | 13850 | 16231 | 7016 | 20541 | 3458 | 1240 | 15787 |
|  | 20099 | 9282 | 11480 | 4994 | 6281 | 18662 | 7992 | 9661 | 19875 | 11156 | 3619 | 14086 |
|  | 20948 | 16946 | 3456 | 6143 | 786 | 6709 | 5954 | 17926 | 20839 | 22351 | 13277 | 15113 |
|  | 6368 | 7704 | 18694 | 3644 | 12154 | 3794 | 21257 | 21638 | 18386 | 18111 | 21498 | 10731 |
|  | 13776 | 5539 | 14530 | 20282 | 7762 | 9529 | 17675 | 15191 | 12380 | 14865 | 15825 | 2818 |
|  | 16442 | 5901 | 8220 | 18578 | 13297 | 2495 | 21913 | 4526 | 16085 | 10965 | 15558 | 8891 |
|  | 13161 | 15189 | 10152 | 3256 | 22258 | 1748 | 21271 | 13226 | 10136 | 22036 | 22190 | 18982 |
|  | 10154 | 20726 | 17115 | 12652 | 2984 | 12623 | 1426 | 4475 | 16706 | 17850 | 21904 | 11245 |
|  | 427 | 304 | 477 | 545 | 2132 | 20312 | 4655 | 16568 | 21093 | 13882 | 5730 | 7976 |
|  | 7079 | 13035 | 14619 | 7273 | 2800 | 12728 | 15228 | 8972 | 19263 | 509 | 305 | 16894 |
|  | 12545 | 2037 | 11704 | 9571 | 21379 | 3712 | 7685 | 4483 | 18456 | 22341 | 11197 | 13107 |
|  | 22106 | 6203 | 19049 | 10427 | 16006 | 11733 | 8133 | 2264 | 12866 | 13782 | | |
| 373: | 21829 | 10688 | 1896 | 2695 | 15238 | 6923 | 13321 | 678 | 19909 | 6620 | 21886 | 4554 |
|  | 4937 | 9312 | 12000 | 1954 | 4679 | 2233 | 18331 | 21411 | | | | |
| 374: | 6020 | 13479 | 5421 | 1087 | 1989 | 14406 | 16303 | 744 | 882 | 12075 | 4026 | 22268 |
|  | 4422 | 9416 | 14897 | 9425 | 12945 | 10738 | 8798 | 854 | 13950 | 9451 | 21908 | 8474 |
|  | 22358 | 10772 | 3605 | 17605 | 21264 | 20769 | 15607 | 2985 | 11015 | 4905 | 7656 | 19436 |
|  | 14257 | 8375 | 8062 | 4389 | 12310 | 14819 | 10371 | 1341 | 10899 | 5014 | 18145 | 16619 |
|  | 22100 | 13463 | 2860 | 1177 | 15365 | 14952 | 17870 | 14006 | 9642 | 5832 | 1504 | 11884 |
|  | 15546 | 4286 | 20157 | 10385 | 20872 | 9791 | 8771 | 2815 | 22262 | 21484 | 5747 | 8299 |
|  | 21256 | 22118 | 17091 | 16759 | 13043 | 22140 | 18776 | 20913 | 940 | 1270 | 18159 | 1798 |
|  | 2743 | 20782 | 13248 | 7678 | 22155 | 12200 | 20855 | 14226 | 12099 | 17769 | 16419 | 12580 |
|  | 3054 | 20908 | 14508 | 1936 | 4781 | 6302 | 8832 | 7652 | 17179 | 5548 | 11581 | 15473 |
|  | 20439 | 4751 | 15772 | 5864 | 2710 | 20430 | 12577 | 14048 | 13591 | 22217 | 16257 | 11511 |
|  | 9747 | 18047 | 5923 | 8265 | 7628 | 7942 | 7892 | 18958 | 3784 | 7603 | 8156 | 22139 |
|  | 12033 | 735 | | | | | | | | | | |
| 375: | 17388 | 7507 | 6853 | 5756 | 19170 | 605 | 19514 | 774 | 18117 | 6385 | 7365 | 5325 |
|  | 15832 | 13388 | 6982 | 805 | 9639 | 15679 | 21883 | | | | | |
| 376: | 6489 | 1778 | 6165 | 13947 | 15105 | 6175 | 12001 | 16671 | 13761 | 6928 | 4769 | 20271 |
|  | 21491 | 10938 | 7900 | 12795 | 10505 | 14143 | 12592 | 21354 | 13777 | 3510 | 5052 | 16591 |
|  | 12548 | 849 | 3088 | 6774 | 12148 | 9161 | 12039 | 2189 | 17027 | 1969 | 2627 | 11841 |
|  | 9768 | 10979 | 13916 | 11981 | 6032 | 1926 | 3963 | 5427 | 18199 | 9453 | 4199 | 2366 |
|  | 9495 | 7328 | | | | | | | | | | |
| 377: | 15533 | 9191 | 10043 | 2753 | 19146 | 7790 | 4261 | 10984 | 17984 | 14174 | 13472 | 11804 |
|  | 22074 | 3317 | 10460 | 14013 | 11181 | 20629 | 17263 | 5966 | 14272 | 21460 | 17175 | 8369 |
|  | 11952 | 21759 | 11479 | 16405 | 2498 | 10527 | | | | | | |
| 378: | 22075 | 3099 | 19424 | 9211 | 2977 | 18514 | 18017 | 15584 | 2234 | 15782 | 4438 | 4584 |
|  | 3716 | 9235 | 16307 | 16304 | 1846 | 2682 | 20821 | 956 | 5704 | 7923 | 18167 | 11822 |
|  | 6140 | 3047 | 10275 | 21133 | 18224 | 5583 | 15900 | 13725 | 19275 | 17302 | 20181 | 18021 |
|  | 3015 | 5962 | 12164 | 9319 | 20992 | 4622 | 8799 | 22151 | 20338 | 14742 | 22201 | 10555 |
|  | 17777 | 10102 | 7163 | 15444 | 9363 | 21307 | 8269 | 10110 | 4429 | 6632 | 20691 | 9638 |
|  | 14736 | 14020 | 10138 | 20244 | 11555 | 5116 | 14225 | 2312 | 21414 | 10821 | 2249 | 22550 |
|  | 13699 | 938 | 20457 | 5430 | 12992 | 13398 | | | | | | |
| 379: | 2406 | 15415 | 587 | 9691 | 5895 | 21357 | 17711 | 19549 | 17251 | 13715 | | |
| 380: | 10085 | 21760 | 4289 | 13995 | 7446 | 9558 | 14863 | 11606 | 20045 | 17971 | 9039 | 18616 |
|  | 9373 | 14535 | 4825 | 12951 | 3787 | 17677 | 5214 | 18052 | 6875 | 18135 | 21630 | 5232 |
|  | 20890 | 1770 | 10991 | 8146 | 11813 | 4697 | 17003 | 7055 | | | | |
| 381: | 21131 | 21645 | 7243 | 20820 | 5674 | 11731 | 6667 | 10151 | 4817 | 4113 | 1832 | 17312 |
|  | 4832 | 4163 | 2924 | 20194 | 9682 | 19740 | 4054 | 16537 | 8531 | 19852 | 9450 | 8277 |
|  | 12513 | 18904 | 5869 | 17443 | 18723 | 22349 | 1228 | 589 | 14210 | 7986 | 10598 | 6036 |
|  | 822 | 5873 | 20860 | 8502 | 1122 | 16499 | 3922 | 18794 | 17929 | 19216 | 19270 | 21895 |
|  | 2758 | 12314 | 2468 | 11214 | 6717 | 21474 | 11827 | 3203 | 6754 | 13557 | 17019 | 1712 |
|  | 19477 | 13019 | 5645 | 10923 | 3817 | 6215 | 7503 | 816 | 4760 | 3589 | 12238 | 12773 |
|  | 10459 | 10744 | 9856 | 10749 | 18103 | 19048 | 3457 | 21457 | 19189 | 16910 | 16867 | 19415 |
|  | 16265 | 3682 | 16610 | 16470 | 16356 | 5777 | 8013 | 18006 | | | | |
| 382: | 19957 | 3226 | 10525 | 8530 | 7982 | 3708 | 16506 | 20265 | 19422 | 17319 | 17973 | 16769 |
|  | 6887 | 12979 | 5654 | 18163 | | | | | | | | |
| 383: | 8694 | 8251 | 3871 | 9924 | 7519 | 16224 | 22555 | 14009 | | | | |
| 384: | 12702 | 17415 | 4664 | 4449 | 4325 | 19760 | 21746 | 3267 | 10368 | 3093 | 11350 | 3531 |
|  | 16380 | 21838 | 19608 | 11587 | 8367 | 20351 | 2902 | 19733 | 18161 | 18210 | 22500 | 20226 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 13555 |  5126 | 18613 | 16364 | 11894 | 11183 |  4057 | 11226 | 17119 |  9098 |  3211 |  2185 |
|      | 20288 | 20489 | 21647 |  4103 | 11973 | 11885 | 10260 | 12393 |  7832 |  4511 | 20170 |  1928 |
|      | 13833 | 21900 | 14890 |  1027 |  7922 |  6811 |  5790 | 14015 | 17065 |  6010 | 13795 |  9245 |
|      |  9566 | 11876 |  8337 | 15174 |  2263 | 19217 |  5530 |  9598 |  9388 |  1659 | 10101 | 17925 |
|      |  9717 | 14228 | 12740 | 14255 | 18590 | 12269 | 14674 | 17257 | 22064 |  8551 |  1059 | 11112 |
|      |  5338 | 15072 | 18204 | 15279 |  6969 | 14944 | 11583 | 18391 | 14690 |  6503 |  2317 |   785 |
|      |  6692 | 22080 | 20243 | 22421 |  4743 | 11968 |  5398 |  1750 | 12965 | 11391 | 12878 |  4721 |
|      |  9384 | 20075 |  5074 |  2118 | 14173 |  6821 |  5012 |  9798 | 11794 |  9811 | 10818 |  7495 |
|      |  4569 | 11830 | 12957 |  2497 |  1617 |  4507 | 10667 | 12465 |  5796 | 18993 | 12481 |  3573 |
|      | 13319 | 20523 | 21343 | 19968 |  8041 | 15867 | 18712 | 11232 | 18921 |  4109 | 16995 |  2484 |
|      | 14332 |  5833 | 21284 |  1405 | 18264 | 14069 | 17528 | 20295 | 17890 | 20822 | 18580 |  1268 |
|      |  2953 | 21324 | 21132 | 13085 | 21661 | 13618 |   878 | 13234 |  5382 | 11592 |  6749 | 16229 |
|      |  5848 |  4012 | 12378 |  1929 | 19687 |  9013 | 10182 |  7228 |  2028 | 14882 | 10560 |  6987 |
|      | 11978 | 10065 | 16975 | 15791 | 15013 |  5286 | 17958 | 17087 |  8422 | 21303 |  2200 |  3761 |
|      |  1089 | 18218 | 15951 | 21747 | 17124 |  2300 |  8857 |  8486 |  8383 | 19233 |  3427 |  1197 |
|      | 12998 |  7171 |  8654 | 10108 | 13462 | 17054 | 18871 | 15851 |  8291 | 18960 |  4494 | 15966 |
|      | 22488 | 18543 |  7773 | 12235 | 12178 | 22041 | 19129 | 20411 |  2027 | 19172 | 15806 |  6469 |
|      |  6370 | 22096 |  4105 | 13426 |  4809 | 19640 |  4659 | 12156 | 13332 |  9311 |   588 | 10476 |
|      | 22560 | 15961 | 14413 | 21548 |  7803 | 12072 | 17825 | 16719 | 17270 | 21888 |  3990 | 11256 |
|      |  4092 | 19664 | 21590 | 20602 | 20735 |  3685 | 16999 | 11453 | 18129 |  8997 |  1186 |  3952 |
|      |  7692 | 11037 | 17899 | 10950 | 13564 | 21682 | 15755 |  6178 | 12242 | 16297 | 14421 | 11436 |
|      |  3560 | 21531 |  1486 | 13983 | 14970 |  9231 |  6305 |  2459 | 19412 | 13256 | 16829 |  9649 |
|      | 11045 |  1317 | 16681 | 21053 | 19661 | 21038 |  7395 |  6841 |  1114 |  9000 | 14705 | 10494 |
|      |  9108 | 17796 | 20404 |  8446 | 10945 | 13307 | 15299 |  1073 | 16289 |  6701 | 11667 | 17949 |
|      | 18645 | 17044 | 20488 | 19663 | 20206 | 14400 |  4114 | 15577 | 20198 | 18423 |  6253 |  6078 |
|      | 16870 | 15568 | 10782 |  8621 | 17031 | 19360 |  1692 | 11227 |  9123 | 16836 |       |       |
| 385: |  2321 |  2906 | 21872 | 10635 | 21078 |  7065 | 15156 |  1425 | 16772 | 13825 | 20591 | 13813 |
|      | 12899 |  1192 | 19892 | 18999 |  8889 | 11465 | 20504 |  3946 | 12048 | 20666 |  9727 | 18484 |
|      |  4435 |  1280 | 12630 | 17995 |  1807 |  1366 | 12411 |  2542 | 17186 | 15294 | 18206 | 15878 |
|      | 13956 | 14389 |  4053 | 13057 | 11138 |  9564 | 13365 | 14654 |  2060 |  6116 |  1599 | 22293 |
|      |  3117 | 16686 | 18549 |   738 |  1017 | 18097 | 20366 | 10906 |  7412 |   972 |  3303 |  9331 |
|      | 22033 | 22401 |  5340 | 18297 |  5439 | 11324 | 19746 | 22005 | 10666 |  2640 | 21017 | 10814 |
|      | 15503 | 15916 |  4700 | 10384 |  8762 | 17479 | 12301 | 18760 | 11416 | 17765 |       |       |
| 386: |  7205 | 16239 | 22108 | 14974 | 15094 | 21071 |  5878 | 17987 | 14219 |  8882 | 17848 |  8491 |
|      | 10730 | 10766 | 11279 |  3262 | 17261 |       |       |       |       |       |       |       |
| 387: | 11850 |  8199 | 14384 | 16243 |   558 | 13030 | 19215 |  3479 | 17782 |  5827 | 19788 |  4416 |
|      |  9270 |  4145 |  3077 |  7366 |  3904 |  3442 |  6662 | 14375 | 15690 | 11650 | 11821 |  1949 |
|      |  1649 |  4587 | 11211 |  6236 | 21165 |  7837 | 18707 | 13824 | 13754 |  3121 |  9516 |  1966 |
|      | 16645 | 15795 | 15859 | 18232 | 16579 | 16020 | 15502 | 22210 | 11865 | 21270 |  5088 |  2239 |
|      |  6314 | 11933 |  1605 | 15281 | 22051 | 13665 |  9116 |  6153 | 21677 |  5334 | 21914 | 20518 |
|      |  6808 |  1927 | 14427 | 10241 |  5400 |  1667 | 20796 | 14866 | 19395 |  5422 |  7965 | 11136 |
|      |  5440 | 20442 | 14551 |  4855 | 21855 |  2066 | 15805 | 15888 |  3582 |  2334 |  3800 |  4016 |
|      |  7072 | 16877 | 16230 | 17326 |  7806 |  2071 |  7990 | 18865 |   641 | 16590 | 21955 | 17280 |
|      | 17308 |  2396 | 13681 |  3877 |  6148 | 11519 |       |       |       |       |       |       |
| 388: |  3596 |  7515 | 17959 |  3549 | 15024 | 13576 | 15991 |  5407 | 13215 |  8370 | 14374 |  9790 |
|      | 11193 | 17162 | 12026 |  4861 |  2328 |  9153 |  3383 |  2598 | 20929 |  5662 |  2982 | 14262 |
|      | 15841 |  5775 | 18375 |       |       |       |       |       |       |       |       |       |
| 389: |  1348 | 15757 | 11966 | 16108 | 15222 | 19104 | 21321 |  4489 | 18184 |  6470 |  8478 | 20190 |
|      | 12628 |   857 |  9167 | 18660 | 16328 | 21136 | 12320 | 10268 |  9965 |  9361 |   754 | 20342 |
|      | 17110 |  8283 | 11192 | 16702 | 18986 | 16654 |  9350 | 12474 |  2031 | 22089 | 14245 | 18814 |
|      |  2961 | 13231 | 21209 | 11352 | 13736 |  3385 |  5559 |  5208 | 19857 | 21576 | 13363 | 21166 |
|      | 21877 | 19184 | 16154 | 13751 |  7235 | 18147 | 10895 |  7829 |  1343 |  5632 | 11790 | 12936 |
|      |  5995 |  4717 | 22228 | 14767 |  9074 | 21907 | 10830 | 11760 |  8348 | 21924 | 13987 |  8023 |
|      | 20096 | 10747 | 11879 |  2097 | 22475 |  2738 |  9421 |  8592 | 11715 | 20682 | 10679 |  9928 |
| 390: | 11664 | 19373 | 14010 | 12174 | 19349 | 11769 |  4498 |  2274 | 21231 |  2630 | 10572 | 10953 |
|      |  8931 | 12005 |  7156 | 11098 | 17092 |  4856 | 20031 |  3585 | 18340 | 15441 | 19792 |  8259 |
|      |  5870 | 21654 | 18857 |  1161 |  9343 | 17931 | 22246 |  9364 |       |       |       |       |
| 391: | 10049 | 13487 | 22261 | 19856 |  3119 |  7342 | 21599 |  5351 | 21514 | 16751 |  9423 |  5727 |
|      |  5042 |  8667 | 12431 |  7989 |  2965 |  4617 |  5682 | 19205 | 18518 | 12013 |  6053 |  9576 |
|      |  5713 | 11119 |  9862 | 16190 |       |       |       |       |       |       |       |       |
| 392: | 18732 | 10751 | 14514 | 17429 | 18757 |  4995 | 12463 | 17063 | 16460 | 10638 | 21916 | 17344 |
|      |  6287 | 10622 |  9084 |  7641 | 13773 | 14486 |  3055 |  1922 |  8058 | 12612 |  3059 |  4605 |
|      | 19053 |  5881 | 16145 | 10408 |  6114 | 13634 | 14741 |   604 | 18842 | 18868 | 21777 | 10350 |
|      | 10325 |  1510 |  2222 |  7494 | 12825 |  2470 | 17446 | 15874 | 22201 | 13588 | 17843 | 20862 |
| 393: | 14137 |  6491 |  1356 | 15653 |  9544 | 17800 |  4657 |  6563 | 18761 | 19273 |  9502 | 12445 |
|      |  4359 | 12437 | 16199 | 18995 |  2176 |  8009 | 10587 |  4063 |  4005 | 20824 | 17620 | 19815 |
|      | 19234 | 17093 | 19511 | 10545 |  5626 |  9305 | 16800 | 12265 |  9897 |  6943 | 20358 | 12184 |
|      |  3707 | 16211 | 21688 | 10582 |  3368 |  2742 |  2365 | 10339 |  3898 |  8612 |  3028 | 11721 |
|      | 15331 |  5828 | 13918 |  3634 | 19884 | 16538 |  1111 |  1554 | 14399 | 14371 |  5104 |  1829 |
|      |  8104 | 17482 | 13063 | 16292 | 21720 |  7729 | 11408 |  5629 | 16271 | 21292 | 11860 |  3424 |
|      |  9033 | 21268 | 21695 | 15296 | 18354 |  4934 | 13381 | 16156 | 13739 | 13034 |  4472 | 20876 |
|      | 17313 | 16924 | 12087 | 18839 | 13963 |  3248 |   944 |  6344 | 11007 |  8619 | 16418 |       |
|      |  9828 |  5268 | 14031 | 21703 |  8516 | 10388 |   866 |  2809 |  7449 | 17438 | 17555 | 16805 |
|      |  1636 | 15432 |  1152 | 10419 | 17275 | 12821 |  6115 | 15623 |  5603 | 15002 | 12960 |       |
| 394: |  3202 | 16855 | 14393 | 16047 | 12109 | 20443 |  2004 | 17625 |  4349 | 19221 | 15436 |  5819 |
|      | 17066 | 19649 | 12670 |  1965 | 14910 | 21969 |  9893 |  3600 | 12536 |  3822 | 12850 |  4180 |
|      |  6132 | 13648 | 21798 | 18884 | 15981 | 21322 | 10336 | 20424 |  7005 | 13279 | 15017 |  2477 |

TABLE 16-continued

Sequence IDs for homolog proteins
Seq ID NO: homolog Seq ID NOs

|  | | | | | | | | | | | | |
|---|---|---|---|---|---|---|---|---|---|---|---|---|
|  | 13011 | 10124 | 4373 | 14416 | 7377 | 13006 | 8088 | 4485 | 10568 | 6181 | 12408 | 4013 |
|  | 2391 | 10416 | 1220 | 14803 | 9678 | 2564 | 13861 | 16954 | 3199 | 4561 | 21312 | 6627 |
|  | 14292 | 4410 | 5823 | 16748 | 12403 | 14414 | 8669 | 12884 | 734 | 17278 | 562 | 6518 |
|  | 1881 | 4518 | 21380 | 6494 | 15852 | 17368 | 13840 | 12084 | 19239 | 3091 | 7517 | 5984 |
|  | 14268 | 4629 | 5191 | 19861 | 16641 | 17406 | 4144 | 18973 | 21415 | 21258 | 6950 | 14555 |
|  | 7041 | 13342 | 18344 | 19371 | 17541 | 1834 | 8664 | 16235 | 11478 | 14116 | 6540 | 10401 |
|  | 15100 | 22060 | 16196 | 11176 | 13397 | 19092 | 19747 | 10990 | 13435 | 9728 | 7131 | 8313 |
|  | 8349 | 9269 | 11964 | 1483 | 16810 | 1500 | 2320 | 14402 | 11184 | 3721 | 1256 | 10000 |
|  | 920 | 14238 | 8919 | 5685 | 20117 | 4235 | 9693 | 6412 | 5084 | 10715 | 7364 | 9817 |
|  | 5924 | 6015 | 15928 | 18253 | 21113 | 17516 | 623 | 7726 | 7224 | 14801 | 7682 | 8966 |
|  | 18692 | 11054 | 14527 | | | | | | | | | |
| 395: | 15084 | 19366 | 8811 | 1190 | 6727 | 4321 | 12649 | 19433 | 12507 | 3995 | 12015 | 20152 |
|  | 21429 | 17657 | 22463 | 5534 | 8079 | 16111 | 6899 | 3734 | 13762 | 19928 | 19272 | 17507 |
|  | 6452 | 12037 | 16857 | 11523 | 12569 | 6792 | 18238 | 5763 | 14939 | 12699 | 21275 | 3930 |
|  | 16987 | 2452 | 2193 | 21219 | 4796 | 14984 | 6885 | 7888 | 6130 | 13135 | 14954 | 1935 |
|  | 2387 | 6161 | 8499 | 19730 | 6609 | 2287 | 21882 | 2634 | 15588 | 11487 | 4376 | 17509 |
|  | 21610 | 2093 | 18802 | 7506 | 11993 | 4406 | 20544 | 8974 | 1016 | 16510 | 12662 | 20736 |
|  | 14836 | 15691 | 17920 | 7734 | 11742 | 21957 | 21727 | 7743 | 12157 | | | |
| 396: | 14699 | 6724 | 12500 | 6101 | | | | | | | | |
| 397: | 4537 | 6708 | 17900 | 6960 | 21012 | 6873 | 21604 | 2141 | 7919 | 10956 | 4205 | 10702 |
|  | 6611 | 13911 | 7162 | 10797 | 21569 | 16752 | 6012 | 6869 | | | | |
| 398: | 16076 | 2321 | 4451 | 19562 | 5982 | 1411 | 2156 | 12558 | 8727 | 16772 | 14543 | 9800 |
|  | 22191 | 22531 | 13050 | 12479 | 8829 | 9890 | 18225 | 2623 | 2538 | 1627 | 16157 | 3656 |
|  | 21344 | 15134 | 15798 | 9715 | 5142 | 2700 | 1902 | 22110 | 11093 | 7017 | 1409 | 20559 |
|  | 10443 | 9498 | 11500 | 15719 | | | | | | | | |
| 399: | 5094 | 13921 | 11673 | 21082 | 2690 | 17779 | 21361 | 3853 | 21213 | 10839 | 20373 | 8089 |
|  | 10464 | 18576 | 8718 | 15705 | 2229 | 4135 | 17410 | 12062 | 1263 | 10684 | 4844 | 14376 |
|  | 13578 | 8589 | 10573 | 17122 | 19674 | 11088 | 5570 | 7753 | 17311 | 3616 | 11735 | 4466 |
|  | 20847 | 13877 | 22288 | 22274 | 8170 | 8179 | 8272 | 5234 | 21652 | 20395 | 3764 | 17831 |
|  | 14489 | 8729 | 13018 | 2082 | 3516 | 719 | 14264 | 7662 | 13451 | 8424 | 15025 | 6352 |
|  | 2590 | 8632 | 13053 | 6040 | 1583 | 16498 | 5182 | 601 | 17476 | 6142 | 7174 | 3594 |
|  | 4785 | 18195 | 11021 | 9022 | 3624 | 8275 | 1685 | | | | | |
| 400: | 20186 | 17002 | 688 | 20774 | 5087 | 2884 | 14965 | 22528 | 18781 | 1690 | 4912 | 5577 |
|  | 11728 | 16448 | 16807 | 10976 | 1638 | 15429 | 8957 | 580 | 4493 | 5637 | 5091 | 16774 |
|  | 7160 | 16922 | 15404 | 15627 | 18041 | 10475 | 11189 | 17861 | 6458 | 12796 | 2292 | 15539 |
|  | 10144 | 3302 | 20470 | 15550 | 17536 | 14443 | 18302 | 11535 | 18222 | 3339 | 19330 | 20436 |
|  | 12330 | 4213 | 11378 | 13719 | 1446 | 18705 | 18359 | 16604 | 7847 | 4055 | 1915 | 4452 |
|  | 7369 | | | | | | | | | | | |
| 401: | 8043 | 17358 | 11675 | 2116 | 16697 | 17985 | 22056 | 14520 | 11577 | 10169 | 8676 | 13033 |
|  | 5205 | 2318 | 6687 | 11694 | 2175 | 13809 | 11141 | 20423 | 6267 | 21105 | 10537 | 11944 |
|  | 20585 | 17725 | 18065 | 11722 | 4293 | 11413 | 1336 | 17250 | 5565 | 20625 | 13141 | 8797 |
|  | 11621 | 2433 | 14925 | 10070 | 20907 | 16241 | 14430 | 8061 | 5447 | 21832 | 6570 | 13938 |
|  | 7924 | 2863 | 13858 | 15223 | 21239 | 17416 | 17782 | | | | | |
| 402: | 12881 | 6207 | 13353 | 11751 | 15876 | 1666 | 22177 | 13826 | 8030 | 20136 | 19068 | 10849 |
|  | 6185 | 15941 | 3633 | 6034 | 14463 | 19984 | 9404 | 13322 | | | | |
| 403: | 6523 | 1729 | 4595 | 16330 | 20515 | 15902 | 19588 | 3043 | 18919 | 11708 | 20497 | 2327 |
|  | 1441 | 669 | 18540 | 19877 | 6224 | 20250 | 22038 | 16853 | 15290 | 17729 | 14201 | 6522 |
|  | 6639 | 958 | 6067 | 9352 | 10585 | 13076 | 22253 | 20296 | 15055 | 16741 | 856 | 13376 |
|  | 4656 | 741 | 7600 | 3292 | 2041 | 12712 | 9536 | 7469 | 18070 | 17534 | 11560 | 1612 |
|  | 12461 | 21026 | 10734 | 16245 | 11563 | 6734 | 14728 | 2065 | 12210 | 7856 | 6660 | 21451 |
|  | 19555 | 3908 | 11196 | 7863 | 3537 | 4208 | 19879 | 1538 | 19512 | 18260 | 12688 | 20261 |
|  | 4516 | 10861 | 13969 | 17758 | 753 | 6479 | 4375 | 12255 | 14160 | 16212 | 16720 | 16343 |
|  | 8787 | 1275 | 20369 | 8862 | 14259 | 6209 | 11213 | 8389 | 15695 | 8160 | 17885 | 1848 |
|  | 22162 | 17147 | 13696 | 14312 | 4009 | 8381 | 15581 | 21090 | 8703 | 15075 | 12930 | 5299 |
|  | 2236 | 11851 | 22418 | 6073 | 6225 | 7353 | 12257 | 3365 | 8254 | 20943 | 7181 | 15879 |
|  | 9322 | 10783 | 967 | 9671 | 5003 | 19304 | 21876 | | | | | |
| 404: | 20121 | 4845 | 16755 | 15934 | 12656 | 20703 | 22316 | 10903 | 1987 | 15141 | 15570 | 565 |
|  | 19322 | 15992 | 21094 | 9068 | 15986 | 19707 | 21551 | 8077 | 3154 | 5118 | 3193 | 22498 |
|  | 2768 | 10551 | 21158 | 3298 | 8643 | 5107 | 10916 | 16268 | 21127 | 14373 | 13081 | 4348 |
|  | 2952 | 5053 | 3842 | 20761 | 1985 | 10588 | 14743 | 18380 | 9448 | 6324 | 8451 | 11229 |
|  | 12521 | 5321 | 13117 | 13654 | 3189 | 9466 | 973 | 16177 | 20685 | 18436 | 6742 | 8800 |
|  | 8329 | 17207 | 10301 | 16839 | 21523 | 20549 | 8368 | 16906 | 21295 | 16634 | 14165 | 16440 |
|  | 18858 | 11979 | 19688 | 11752 | 20704 | 8049 | 5101 | 12140 | 6150 | 18457 | 17776 | 10823 |
|  | 1055 | 10714 | 2685 | 17863 | 16832 | 18771 | 9387 | 18448 | 11154 | 16274 | 12172 | 16594 |
|  | 19936 | 10508 | 11531 | 11286 | 3525 | 16791 | 20273 | 17444 | 20714 | 13542 | 11356 | 22016 |
|  | 9568 | 15624 | 2045 | 8938 | 12700 | 17001 | | | | | | |
| 405: | 15903 | 14278 | 19149 | 8514 | 3419 | 8145 | 3547 | 17612 | 11032 | 20571 | 12663 | |
| 406: | 17617 | 22319 | 7205 | 6865 | 16239 | 9494 | 6282 | 3807 | 1614 | 20370 | 12460 | 4224 |
|  | 10012 | 14713 | 14403 | 11097 | 4784 | 11736 | 5165 | 8086 | 18191 | 18915 | 19519 | 8491 |
|  | 10730 | 11279 | 3262 | | | | | | | | | |
| 407: | 2891 | 3958 | 11588 | 15385 | 3069 | 2735 | 20029 | 11448 | 11546 | | | |
| 408: | 9532 | 10331 | 19503 | 14129 | 5699 | 15147 | 7047 | 5185 | 7604 | 2151 | 19670 | 9143 |
|  | 1141 | 10189 | 18230 | 4233 | 9176 | 19023 | 18942 | 18099 | 5356 | 3212 | 10361 | 20873 |
|  | 12438 | 9248 | 1233 | 17267 | 19131 | 21068 | 13009 | 6829 | 20236 | 14326 | 6208 | 21773 |
|  | 15785 | 1052 | 14929 | 4869 | 4397 | 13900 | 6409 | 3254 | 21501 | 12516 | 1974 | 20560 |
|  | 11275 | 2659 | 5053 | 9051 | 18988 | 22150 | 21521 | 17242 | 12835 | 5328 | 12151 | 12808 |

TABLE 16-continued

Sequence IDs for homolog proteins
Seq ID NO: homolog Seq ID NOs

|      |       |       |       |       |       |       |       |       |       |       |       |
|------|-------|-------|-------|-------|-------|-------|-------|-------|-------|-------|-------|
|      | 14165 | 1755  | 10215 | 22220 | 22247 | 7254  | 20380 | 5061  | 2845  | 654   | 5018  | 7274 |
|      | 9568  | 11235 | 6804  | 8938  | 3173  | 12045 | 19302 | 4028  | 11190 | 14318 |       |      |
| 409: | 17878 | 16387 | 12478 | 9552  | 20335 | 20588 | 14328 | 20566 | 9985  | 11470 | 9847  | 3078 |
|      | 10774 | 13004 | 16036 | 17980 | 12297 | 19736 | 12682 | 20732 | 15994 | 18840 | 14761 | 7615 |
|      | 3382  | 13301 | 14704 | 1253  | 8175  | 1203  | 14879 | 16511 | 18949 | 17910 | 4951  | 12305 |
|      | 12551 | 984   | 5460  | 6545  | 17611 | 15062 | 3611  | 21636 | 4337  | 22142 | 17887 | 5729 |
|      | 13561 | 7326  | 7817  | 4775  | 12683 | 18165 | 11442 |       |       |       |       |      |
| 410: | 19444 | 20278 | 7007  | 15467 | 10031 | 19083 | 20001 | 8653  | 7474  | 9943  | 2052  | 11515 |
|      | 1185  | 15759 | 16848 | 7867  | 18893 | 18562 | 4415  | 7309  | 16700 | 646   | 22398 | 21783 |
|      | 11681 | 20677 | 13180 | 18105 | 19115 | 9525  | 21934 | 4239  | 9535  | 3136  | 7961  | 4042 |
|      | 17090 | 13917 | 13550 | 6807  | 15815 | 5083  | 14397 | 15406 | 5715  | 18413 | 1545  | 1181 |
|      | 18323 | 18109 | 4215  | 21611 | 15464 | 20382 | 18532 | 10295 | 3243  | 557   | 7871  | 21405 |
|      | 21910 | 742   | 17206 | 11102 | 8305  | 8131  | 8342  | 13021 | 21027 | 6288  | 21249 | 8657 |
|      | 3604  | 2514  | 17634 | 15990 | 20228 | 10314 | 8380  | 7680  | 4394  | 11472 | 9447  | 8886 |
|      | 14484 | 732   | 21164 | 5885  | 1582  | 18950 | 4256  | 13943 | 10878 | 4921  | 18817 | 9457 |
|      | 13643 | 5491  | 10600 | 6106  | 7932  | 12303 | 8523  | 7259  | 15802 | 15381 | 10690 | 5244 |
|      | 2547  | 9595  | 13530 | 3278  | 7558  | 787   | 14423 | 1602  | 7317  | 8244  | 875   | 22340 |
|      | 2864  | 14957 | 7393  | 18265 | 8733  | 9103  | 19853 | 11368 | 18367 | 16756 | 15487 | 19985 |
|      | 15688 | 15114 | 9775  | 5561  | 11959 | 3943  | 9409  | 7846  | 14829 | 11027 | 10403 | 18628 |
|      | 18693 | 10737 | 1258  | 16202 | 22195 | 7356  | 22522 | 660   | 14611 | 1131  | 8690  | 1624 |
|      | 19314 | 19584 | 2161  | 13946 | 12833 | 2228  | 22353 | 20610 | 5071  | 22372 | 14247 | 6017 |
|      | 7666  | 12648 | 14029 | 21735 | 14114 | 20694 | 13015 | 18234 | 681   | 10081 | 11147 | 18808 |
|      | 19321 | 6914  | 2616  | 12379 | 10311 | 15491 | 18766 | 3328  | 17588 | 18807 | 17753 | 12618 |
|      | 11319 | 20579 | 10231 | 2975  | 15216 | 2793  | 16097 | 1795  | 18974 | 14473 | 20268 | 21825 |
|      | 19495 | 18545 | 14979 | 5483  | 4788  | 9820  | 13325 | 2386  | 8747  | 14646 | 4173  | 8861 |
|      | 11690 | 17653 | 8169  | 5892  | 19300 | 15684 | 9216  | 665   | 16990 | 4535  | 11520 | 8301 |
|      | 5772  | 10373 | 13686 | 13843 | 9665  | 19610 | 10235 | 17272 | 17334 | 22154 | 18621 | 865  |
|      | 3789  | 1076  | 18122 | 12966 | 12081 | 14558 | 1943  | 10356 | 2299  | 11243 | 18708 | 10234 |
|      | 14621 | 11538 | 20401 | 7508  | 14752 | 11476 | 8779  | 13046 | 15566 | 2029  | 5433  | 2096 |
|      | 1102  | 12085 | 13461 | 16044 | 8180  |       |       |       |       |       |       |      |
| 411: | 9901  | 16263 |       |       |       |       |       |       |       |       |       |      |
| 412: | 2162  | 18233 | 20049 | 12022 | 11201 | 15202 | 8052  | 7238  | 12584 | 4327  | 7460  | 9562 |
|      | 19525 | 21286 | 14793 | 5936  | 10320 | 1414  | 6411  | 4718  | 9260  | 8095  | 16930 | 16698 |
|      | 18606 | 2323  | 7175  | 13143 | 20113 | 14775 | 19888 | 9560  | 2539  | 9038  | 9327  | 18125 |
|      | 11362 | 1014  | 9813  | 17983 | 8842  | 7807  | 2893  | 11880 | 14342 | 9378  | 3540  | 3096 |
|      | 19574 | 14434 | 16029 | 13644 | 4168  | 6269  | 3249  | 12029 | 19054 | 8470  | 14290 | 17635 |
|      | 13553 | 18138 | 15398 | 9069  | 18935 | 2699  | 5624  | 1368  | 7752  | 20623 | 8011  | 16598 |
|      | 2959  | 7392  | 16359 | 2033  | 13502 | 14870 | 6425  | 15173 | 5707  | 18089 | 13368 | 20148 |
|      | 5202  | 12293 | 7625  | 10367 | 22375 | 9160  | 16642 | 1146  | 8644  | 18822 | 6890  | 4761 |
|      | 16943 | 2968  | 15397 | 10530 | 4187  | 21770 | 6917  | 9741  | 21455 | 11557 | 12319 | 13100 |
|      | 16735 | 11024 | 6580  | 16704 | 17268 | 12608 | 10727 | 17252 | 2824  | 12882 | 11405 | 20525 |
|      | 6174  | 16284 | 14249 | 11514 | 4780  | 19770 | 4323  | 7269  | 18976 | 6189  | 4008  | 10736 |
|      | 14087 | 19567 | 22011 | 14971 | 14023 | 17424 | 2305  | 7312  | 3592  | 16956 | 7560  | 1738 |
|      | 12942 | 21285 | 20899 | 11460 | 19580 | 21557 | 17786 | 17161 | 3227  | 5470  | 5918  | 1584 |
|      | 6167  | 21290 | 18980 | 5133  | 22328 | 17322 | 3423  | 15190 | 20764 | 18753 | 17010 | 16011 |
|      | 3336  | 4391  | 7094  | 15896 | 7833  | 16618 | 16299 | 7848  | 21863 | 6217  | 20647 | 1230 |
|      | 22513 | 18373 | 7471  | 12642 | 20594 | 15221 | 18254 | 7661  | 18439 | 4382  | 21156 | 10463 |
|      | 3841  | 9623  | 18957 | 1044  | 10437 | 20165 | 17833 | 1374  | 15273 | 7844  | 19571 | 16820 |
|      | 11643 | 1575  | 1920  | 1695  | 11209 | 7958  | 10668 | 13971 | 5416  | 7100  | 13690 | 4695 |
|      | 12664 | 13185 | 8604  | 18811 | 916   | 3631  | 20925 | 6998  | 12127 | 1325  | 18046 | 17290 |
|      | 2206  | 18785 | 10243 | 13121 | 8060  | 8498  | 7423  | 7638  | 19073 | 2589  | 3866  | 17454 |
|      | 20816 | 16178 | 20033 | 1467  | 16026 | 8181  | 1941  | 8720  | 17669 | 4852  | 1609  | 20526 |
|      | 4534  | 20245 | 18223 | 21627 | 17568 | 18939 | 13054 | 14168 | 5856  | 18898 | 11014 | 19510 |
|      | 9810  | 12845 | 4047  | 20300 | 8236  | 15824 | 1098  | 16088 | 13424 | 14404 | 7164  | 14512 |
|      | 21944 | 14356 | 18936 | 12143 | 10894 | 5086  | 16950 | 18427 | 2265  | 12701 | 10676 | 14700 |
|      | 636   | 7556  | 1255  | 21562 | 20004 | 4018  | 14365 | 7792  | 21836 | 22515 | 4626  | 7954 |
|      | 2981  | 3277  | 20156 | 14224 | 17076 | 11402 | 8579  | 1038  | 19802 | 8390  | 4147  | 20742 |
|      | 19929 | 17647 | 3352  | 12885 | 17628 | 22490 | 3315  | 8629  | 6094  | 6966  | 14651 | 5256 |
|      | 8279  | 11688 | 6703  | 11108 | 1457  | 14601 | 9351  | 8986  | 2075  | 8490  | 2577  | 15644 |
|      | 14025 | 2586  | 2646  | 3999  | 9581  | 14960 | 19190 | 15504 | 18393 | 7405  | 2505  | 7583 |
|      | 10066 | 9356  | 8520  | 21298 | 7640  | 20817 | 21774 | 15316 | 7810  | 6357  | 19520 | 17972 |
|      | 21917 | 15777 | 13859 | 21642 | 3703  | 5853  | 1354  | 21366 | 12726 | 4471  | 1978  | 4480 |
|      | 2810  | 5335  | 21970 | 14779 | 22384 | 3393  | 5141  | 2928  | 5815  | 5890  | 8839  | 5761 |
|      | 19941 | 2036  | 7211  | 760   | 9097  | 1184  | 5514  | 15671 | 4895  | 2808  | 12236 | 11124 |
|      | 11100 | 16580 | 8441  | 6767  | 10567 | 19813 | 7882  | 20630 | 8524  | 3825  | 22209 | 13732 |
|      | 18168 | 5582  | 4896  | 6403  | 15710 | 3400  | 12466 | 7217  | 21299 | 649   | 918   | 4342 |
|      | 3021  | 10027 | 21150 | 13145 | 6798  | 20339 | 2003  | 8395  | 18183 | 5409  | 11431 | 19105 |
|      | 15632 | 1529  | 11293 | 12867 | 2841  | 12448 | 8092  | 20698 | 17823 | 17746 | 9681  | 10359 |
|      | 16092 | 22422 |       |       |       |       |       |       |       |       |       |      |
| 413: | 22034 | 8322  | 12008 | 13273 | 812   | 11765 | 21273 | 20302 | 7255  | 570   | 20174 | 13723 |
|      | 6666  | 22086 | 18541 | 9801  | 12646 | 17511 | 3238  | 4002  | 10019 | 21775 | 19200 | 1284 |
|      | 18777 | 16126 | 10941 | 18730 | 16545 | 2655  | 10677 | 1823  | 3378  | 22507 | 22487 | 2105 |
|      | 21401 | 16277 | 16134 | 17411 | 11463 | 10282 | 1387  | 17316 | 814   | 12211 | 10675 | 5919 |
|      | 2531  | 8234  | 15950 | 13303 | 20240 | 15142 | 6343  | 17332 | 698   | 8256  | 18799 | 16961 |
|      | 7465  | 15483 | 15126 | 11265 | 1248  | 13144 | 4991  | 910   | 12748 | 14534 | 20200 | 1113 |
|      | 9537  | 549   | 10854 | 14460 | 6577  | 14432 | 1556  | 6735  | 19416 | 16300 | 21874 | 14903 |
|      | 5716  | 1511  | 13958 | 10119 | 16522 | 6561  | 5477  | 12441 | 6266  | 14367 | 2568  | 7559 |

TABLE 16-continued

Sequence IDs for homolog proteins
Seq ID NO: homolog Seq ID NOs

| | | | | | | | | | | | | |
|---|---|---|---|---|---|---|---|---|---|---|---|---|
| | 19472 | 19810 | 11611 | 12517 | 13165 | 12364 | 21402 | 12768 | 9589 | 5941 | 15456 | 1565 |
| | 5435 | 14242 | 21793 | 4776 | 7231 | 1961 | 19032 | 1380 | 19110 | 4711 | 18525 | 20467 |
| | 16120 | 1422 | 22131 | 18435 | 17158 | 21488 | 4267 | 21287 | 8136 | 21470 | 13657 | 7855 |
| | 7462 | 20952 | 6100 | 21395 | 1091 | 7935 | 12221 | 4220 | 4275 | 22272 | 11605 | 1109 |
| | 6087 | 13735 | 21333 | 11724 | 18084 | 1628 | 1346 | 8072 | 15856 | 19515 | 2451 | 14016 |
| | 9102 | 7499 | 20103 | 6129 | 8681 | 14265 | 22363 | 10518 | 18395 | 20658 | 15572 | 20900 |
| | 17981 | 16009 | 11950 | 11074 | 707 | 8846 | 9190 | 18652 | 12428 | 10283 | 19835 | 9740 |
| | 19502 | | | | | | | | | | | |
| 414: | 6834 | 6684 | 1593 | 14718 | 639 | 18288 | 5930 | 12385 | 11749 | 15764 | 10482 | 14872 |
| | 20500 | 17253 | 17922 | 10034 | 9808 | 1699 | 3559 | 8697 | 16121 | 8791 | 12687 | 718 |
| | 18476 | 13223 | 1062 | 17385 | 11440 | | | | | | | |
| 415: | 13988 | 14945 | 6635 | 15700 | 20023 | 11536 | 17004 | 12834 | 5317 | 19374 | 10116 | 7960 |
| | 5032 | 17692 | 21336 | 1492 | 19786 | 6860 | 14502 | 20681 | 5259 | 9724 | 20051 | 567 |
| | 3863 | 6677 | 19709 | 7411 | 16573 | | | | | | | |
| 416: | 5198 | 4396 | 18094 | 11888 | 17143 | 5694 | 21019 | 8021 | 21392 | 3175 | 21815 | 18035 |
| | 12729 | 6083 | 4640 | 17336 | 18325 | 1938 | 5227 | 15019 | 16822 | 2110 | 2441 | 1780 |
| | 11073 | 2067 | | | | | | | | | | |
| 417: | 4094 | 4249 | 6447 | 4266 | 21799 | 11386 | 7114 | 19998 | 8507 | 4118 | 4930 | 21755 |
| | 7422 | 470 | 10048 | 18342 | 16272 | | | | | | | |
| 418: | 12195 | 18355 | 21055 | 18016 | 20402 | 12963 | 12102 | 17702 | 3106 | 18678 | 18424 | 22227 |
| | 19413 | 1979 | 17990 | 22510 | 17357 | 1360 | 17490 | 9376 | 2639 | 8398 | 14303 | 1563 |
| | 9512 | 20310 | 20534 | 2405 | 3798 | 12350 | 16708 | 19648 | 22564 | 959 | 8091 | 13262 |
| | 18778 | | | | | | | | | | | |
| 419: | 8007 | 9185 | 12493 | 17152 | 21173 | 10594 | 13523 | 16563 | 10079 | 2431 | 10753 | 19487 |
| | 20147 | 9647 | 14147 | 9929 | 1830 | 1654 | 17021 | 19317 | 3147 | 1112 | 10779 | 8538 |
| | 3237 | 6408 | 13120 | 3049 | 22221 | 899 | 15039 | 8907 | 16324 | 4879 | 3957 | 783 |
| | 19624 | 12762 | 8261 | 15668 | 12832 | 19114 | 10457 | 3297 | 5741 | 17704 | 16175 | 15159 |
| | 6999 | 11766 | 8413 | 11239 | 8954 | 8566 | 11458 | 11367 | 8923 | 11782 | 3384 | 18544 |
| | 8298 | 18012 | 21849 | 14689 | 1883 | 11942 | 728 | 1701 | 15090 | 13910 | 20183 | 12952 |
| | 1872 | 3776 | 5981 | 21830 | 14524 | 4742 | 9043 | 15217 | 19665 | 12092 | 13500 | 7051 |
| | 5615 | 9310 | 10058 | 672 | 11082 | 16588 | 21831 | | | | | |
| 420: | 11518 | 6542 | 21976 | 16169 | 2667 | 11216 | 15637 | 2270 | 12844 | 12784 | 7569 | 16948 |
| | 13741 | 15920 | 7877 | 4550 | 7616 | 14358 | 13182 | 14560 | 4000 | 4261 | 10693 | 20144 |
| | 8084 | 21413 | 5610 | 16074 | 7572 | 9778 | 1745 | 15641 | 21565 | 16376 | 10773 | 18848 |
| | 1071 | 17984 | 9925 | 22043 | 15210 | 10247 | 20648 | 3200 | 983 | 20360 | 6435 | 14763 |
| | 13495 | 12676 | 12528 | 8206 | 20705 | 3157 | 4565 | 9878 | 16048 | 17609 | 21518 | 13885 |
| | 7244 | 5309 | 13744 | 15880 | 19484 | 658 | 8704 | 16710 | 12907 | 7984 | 6137 | 22370 |
| | 19468 | 10410 | 9826 | 17175 | 20965 | 6796 | 9139 | 11329 | 17057 | 3353 | 18605 | 9058 |
| | 8231 | 2866 | 8504 | 16796 | 20034 | 12940 | 6134 | 15426 | 4409 | 917 | 9156 | 12665 |
| | 629 | 12908 | 7530 | | | | | | | | | |
| 421: | 15638 | 19372 | 18500 | 2446 | 1148 | 7739 | 10757 | 13616 | 14797 | 4533 | 4130 | 21278 |
| | 9633 | 2203 | 20379 | 16812 | 11738 | 4453 | 7875 | 17989 | 11775 | 6848 | 21289 | 15564 |
| | 17637 | 18961 | 2109 | 17883 | 5751 | 4470 | 13318 | 19225 | 8496 | 999 | 19409 | 7694 |
| | 4874 | 3523 | 21721 | 18661 | 5643 | 6235 | 15475 | 4993 | 8534 | 2734 | 16838 | 841 |
| | 8087 | 7343 | 11926 | 5112 | 4748 | 2697 | 17805 | 22050 | 13444 | 20480 | 12313 | 19959 |
| | 1236 | 14235 | 21517 | 18071 | 19134 | 12869 | 2268 | 16339 | 6198 | 11473 | 8372 | 13642 |
| | 19849 | 19983 | 19150 | 7473 | 17895 | 14624 | 12838 | 18434 | 8867 | 10445 | 17390 | 4706 |
| | 4050 | 4847 | 16631 | 13356 | 6505 | 18534 | 1687 | 1794 | | | | |
| 422: | 5236 | 21619 | 6397 | 2990 | 20047 | 22291 | 6084 | 2760 | 5267 | 5082 | 12765 | 16136 |
| | 9918 | 13383 | 21449 | 6268 | 20961 | 21232 | 5855 | 7138 | 1995 | 14576 | 1013 | 12134 |
| | 10069 | 15073 | 6212 | 15451 | 8899 | 18412 | 4849 | 4386 | 4988 | 16988 | 4076 | 12237 |
| | 5275 | 16208 | 20027 | 947 | 6757 | 10538 | 21003 | 4705 | 12576 | 20998 | 19553 | 17590 |
| | 14359 | 11013 | 19927 | 6707 | 17088 | 18975 | 18429 | 14985 | 13721 | 17584 | 21718 | 20322 |
| | 1390 | 19701 | 8055 | 6576 | 18610 | 20621 | 22331 | 12128 | 6286 | 7906 | 19843 | 18623 |
| | 20065 | 11146 | 18095 | 21935 | 18101 | 573 | 11564 | 9180 | 14490 | 7031 | 11030 | 15407 |
| | 20068 | 22044 | 7315 | 18849 | 17381 | 20667 | 5814 | 8717 | 2914 | 14041 | 6827 | 11083 |
| | 22344 | 21424 | 1648 | 14123 | 11982 | 18740 | 20583 | 4741 | 19612 | 1957 | 6206 | 19071 |
| | 15555 | 14347 | 15150 | 22534 | 1958 | 16979 | 5465 | 17615 | 13167 | 9714 | 3221 | 17417 |
| | 1787 | 20324 | 4795 | 20150 | 11040 | 19333 | 5877 | 2311 | 2374 | 14089 | 20555 | 1581 |
| | 853 | 11842 | 5451 | 3675 | 12229 | 8405 | | | | | | |
| 423: | 7073 | 8473 | 19204 | 13490 | 15419 | 10302 | 3067 | 4727 | 8682 | 22082 | 19922 | 8178 |
| | 18347 | 11384 | 16646 | 9838 | | | | | | | | |
| 424: | 21999 | 10083 | 17047 | 19988 | 17430 | | 10414 | 4089 | 1514 | 16232 | 9556 | 12818 | 19256 |
| | 18022 | 1716 | 9583 | 12552 | 17581 | 13890 | 9464 | 2246 | 15706 | 18577 | 15783 | 9368 |
| 425: | 8789 | 9460 | 12638 | 14787 | 661 | 13830 | 20570 | 19781 | 2510 | 17126 | 17660 | 1608 |
| | 2111 | 19080 | 6968 | 16599 | 5238 | 20160 | 4150 | 9643 | 16795 | 2152 | 20203 | 17640 |
| | 20673 | 20994 | 13131 | 12812 | 8991 | 987 | 22355 | 19043 | 18108 | 15045 | 14625 | 18638 |
| | 2854 | 600 | 13108 | 14921 | 11424 | 11994 | 19459 | 3294 | 9066 | 11477 | 13026 | 15931 |
| | 6981 | 9953 | 20837 | 1046 | 8701 | 4413 | 3741 | 4408 | | | | |
| 426: | 6366 | 17652 | 5554 | 20635 | 17360 | 4793 | 14236 | 21110 | 8866 | 5732 | 11691 | 19410 |
| 427: | 1006 | 14786 | 20756 | 8495 | 10217 | 5541 | 16973 | 535 | 3260 | 11264 | 12854 | 314 |
| | 18315 | 18461 | 5544 | 18823 | 5240 | 2104 | 12358 | 16966 | 17291 | 6367 | 19001 | 15260 |
| | 3597 | 5549 | 20568 | 10778 | 12440 | 1988 | 13743 | 11485 | 1783 | 18629 | 526 | 17425 |
| | 9565 | 20151 | 9300 | 11185 | 5246 | 15752 | 2084 | 18185 | 2918 | 8400 | 3763 | 3837 |
| | 5746 | 20378 | 7812 | 13638 | 17369 | 4080 | 10663 | 17802 | 2070 | 4989 | 7198 | 21781 |
| | 14194 | 4437 | 8103 | 12106 | 16298 | 13285 | 19237 | 5066 | 19712 | 16970 | 17382 | 14671 |
| | 9686 | 5137 | 13854 | 11867 | 2123 | 3011 | 15148 | 11900 | 22193 | 17908 | 9773 | 16561 |

TABLE 16-continued

Sequence IDs for homolog proteins
Seq ID NO: homolog Seq ID NOs

| | | | | | | | | | | | |
|---|---|---|---|---|---|---|---|---|---|---|---|
| | 14739 | 22164 | 2058 | 837 | 20811 | 16636 | 19327 | 18664 | 13237 | 18684 | 19318 | 3797 |
| | 6139 | 2857 | 17664 | 21589 | 11961 | 19154 | 21437 | 16338 | 11195 | 20933 | 21506 | 3533 |
| | 9255 | 4677 | 18511 | 4730 | 696 | 9569 | 17797 | 18687 | 7097 | 20259 | 4425 | 3003 |
| | 22502 | 14915 | 21157 | 1139 | 2541 | 4460 | 16130 | 21296 | 2832 | 830 | 14553 | 6434 |
| | 18295 | 17956 | 829 | 476 | 12043 | 3677 | 7659 | 5486 | 9761 | 5540 | 8443 | 15590 |
| | 15367 | 14935 | 4602 | 18472 | 9627 | 7490 | 20779 | 1281 | 14568 | 17630 | 2371 | 4694 |
| | 12396 | 15369 | 16597 | 3697 | 10741 | 16309 | 4927 | 13396 | 2277 | 21198 | 5308 | 21621 |
| | 8841 | 16662 | 11120 | 14081 | 7321 | 10424 | 15204 | 6565 | 14320 | 2978 | 9294 | 7482 |
| | 9493 | 1277 | 4952 | 7813 | 7306 | 12296 | 12021 | 6645 | 9286 | 22489 | 15165 | 9809 |
| | 16089 | 15681 | 13745 | 16653 | 19069 | 7780 | 12587 | 19236 | 8110 | 4594 | 14762 | 10802 |
| | 10479 | 16663 | 3678 | 16713 | 7751 | 13703 | 3630 | 4691 | 9472 | 10709 | 8542 | 7060 |
| | 6112 | 22457 | 21974 | 20476 | 7333 | 6482 | 14526 | 7151 | 2644 | 835 | 10655 | 12264 |
| | 9315 | 2786 | 16253 | 9488 | 5634 | 17372 | 10399 | 10547 | 16039 | 14345 | 5365 | 10379 |
| | 14566 | 788 | 5943 | 10889 | 5190 | 13207 | 16465 | 10488 | 17136 | 6257 | 8306 | 2432 |
| | 11948 | 16340 | 15326 | 5415 | 9673 | 15586 | 20108 | 20541 | 3458 | 1240 | 15787 | 20099 |
| | 9282 | 11480 | 4994 | 9189 | 12928 | 10743 | 7111 | 16707 | 19389 | 2889 | 19161 | 9422 |
| | 21510 | 10965 | 22018 | 15558 | 4315 | 21926 | 12010 | 3187 | 21634 | 19556 | 2333 | 13869 |
| | 18982 | 20495 | 2984 | 2763 | 5448 | 20219 | 12749 | 2389 | 7476 | 15067 | 3515 | 5375 |
| | 1465 | 12770 | 18281 | 1243 | 13198 | 9265 | 1763 | 1615 | 5056 | 11143 | 12570 | 11245 |
| | 2293 | 2132 | 20312 | 4655 | 16568 | 21093 | 13882 | 5730 | 7976 | 7079 | 13035 | 16007 |
| | 2800 | 3186 | 7053 | 15790 | 7591 | 22480 | 20744 | 22093 | 6055 | 15875 | 305 | 12545 |
| | 2037 | 11704 | 9571 | 21379 | 3712 | 7685 | 4483 | 18456 | 22341 | 10909 | 11197 | 13107 |
| | 16635 | 16006 | 372 | 18722 | 18324 | | | | | | | |
| 428: | 14507 | 15421 | 14477 | 17494 | 566 | 7991 | 15716 | 19769 | 6346 | 11158 | 2783 | 18037 |
| | 18920 | 14200 | 1991 | 21228 | 2025 | 16965 | 22007 | 22121 | 19530 | 17216 | 16560 | 11719 |
| | 9318 | 17738 | 1299 | 21214 | 12334 | 12769 | 13914 | 10771 | 21809 | 10996 | 18789 | 3482 |
| | 8428 | 15625 | 18025 | 21461 | 4486 | 4864 | 18259 | 1869 | 18894 | 5076 | 10621 | 8796 |
| | 15953 | 1037 | 18120 | 21047 | 8656 | 2967 | 13154 | 6569 | 12338 | 19732 | 3033 | 10633 |
| | 15359 | 15028 | 16103 | 12423 | 19646 | 3561 | 2797 | 6835 | 16222 | 3266 | 19426 | 6571 |
| | 21319 | 4126 | 22537 | 6888 | 17781 | 1697 | 10045 | 1251 | 7003 | 7276 | 19243 | 14694 |
| | 15687 | 11467 | 11444 | 12814 | 7126 | 7580 | 4960 | 7248 | 3598 | 14355 | 7140 | 17847 |
| | 8316 | 17583 | 16488 | 4421 | 19550 | 8999 | 1180 | 18026 | 20573 | 8479 | 18820 | 21056 |
| | 7036 | 15143 | 13926 | 18737 | 18581 | 16569 | 13403 | 1142 | 3253 | 7394 | 4463 | 11832 |
| | 14382 | 7339 | 16547 | 15305 | 10604 | 4338 | 16236 | 16768 | 4138 | 18754 | 442 | 18246 |
| | 10039 | 12847 | 6541 | 21176 | 20831 | 13811 | 12065 | 10287 | 11127 | 9635 | 20511 | 19012 |
| | 13060 | 12724 | 898 | 4347 | 8702 | 12055 | 21425 | 20545 | 19336 | 8006 | 14571 | 5579 |
| | 15743 | 3704 | 19675 | 16542 | 16559 | 21229 | 11524 | 9274 | 11075 | 8804 | 4132 | 17224 |
| | 3133 | 3607 | 12684 | 13418 | 10123 | 13007 | 14891 | 18308 | 10517 | 2973 | 11620 | 15395 |
| | 10374 | 3168 | 3051 | 15872 | 11732 | 9301 | 740 | 19109 | 1359 | 17419 | 10051 | 6843 |
| | 1680 | 5509 | 10865 | 11707 | 16067 | 22296 | 1000 | 3406 | 18908 | 8719 | 9844 | 20469 |
| | 12031 | 11698 | 9632 | 4041 | 4022 | 2595 | 20688 | 6395 | 9511 | 16615 | 4623 | 22346 |
| | 2369 | 17333 | 14975 | 19292 | 12095 | 14281 | 11866 | 5395 | 16733 | 3840 | 17783 | 15322 |
| | 17305 | 10611 | 1428 | 7631 | 15733 | 5563 | 18432 | 3777 | 1959 | 18192 | 1274 | 9859 |
| | 16608 | 6676 | 5894 | 4159 | 21902 | 6323 | 6814 | 7759 | 17670 | 10954 | 17330 | 3090 |
| | 8154 | 15122 | 14026 | 9078 | 475 | 20224 | 15939 | 13183 | 2171 | 20320 | 12959 | 18620 |
| | 6196 | 16678 | 13224 | 21618 | 9870 | 17904 | 435 | 11481 | 4738 | 13205 | 11111 | 6886 |
| | 4385 | 10224 | 21396 | 16032 | 22294 | 3286 | 13158 | 7249 | 8239 | 1725 | 17508 | 13407 |
| | 19123 | 1165 | 2912 | 20759 | 22152 | 18157 | 16447 | 2772 | 12222 | 10847 | 14538 | 17604 |
| | 14596 | 20901 | 4797 | 3679 | 21087 | 19143 | 7452 | 9348 | 17993 | 21440 | 14394 | 16530 |
| | 16659 | 10434 | 15793 | 9088 | 17239 | 4831 | 6340 | 2684 | 689 | 15731 | 9528 | 16620 |
| | 17353 | 14180 | 11651 | 17070 | 2073 | 1585 | 8281 | 12298 | 22147 | 10166 | 22431 | 15463 |
| | 6601 | 8700 | 16540 | 2993 | 4260 | 9664 | 10652 | 15975 | 13842 | 14457 | 15948 | 11412 |
| | 5572 | 7389 | 11862 | 1897 | 19136 | 11526 | 10222 | 1819 | 9220 | 12697 | 22065 | 20558 |
| | 17946 | 2983 | 18633 | 13258 | 13996 | 5429 | 20450 | 10529 | 15553 | 3208 | 12002 | 14696 |
| | 12270 | 16162 | 9071 | 7594 | 17146 | 7667 | 11793 | 2416 | 11610 | 19062 | 19931 | 6868 |
| | 7221 | 5047 | 7968 | 10376 | 5672 | 2355 | 11711 | 4084 | 8726 | 14756 | 9731 | 18769 |
| | 5680 | 10960 | 10209 | 17713 | 4926 | 14217 | 6624 | 9314 | 3151 | 6850 | 4560 | 18134 |
| | 17898 | 12386 | 5636 | 3480 | 10028 | 2838 | 20595 | 1292 | 20275 | 12254 | 17594 | 4853 |
| | 20642 | 8186 | 16379 | 10383 | 4591 | 11759 | 11502 | 8591 | 4288 | 11992 | 17721 | 15333 |
| | 9201 | 12553 | 14724 | 3846 | 22481 | 1723 | 15765 | 17537 | 17720 | 5294 | 9934 | 3608 |
| | 16724 | 3395 | 2370 | 22184 | 6889 | 3455 | 7902 | 13093 | 4038 | 2297 | 7376 | 1916 |
| | 7144 | 16736 | 15894 | 19202 | 4614 | 10304 | 12063 | 3319 | 11943 | 21007 | 5703 | 6099 |
| | 3369 | 4162 | 18750 | 20614 | 3762 | 6621 | 7015 | 7304 | 4298 | 9147 | 11434 | 11341 |
| | 10440 | 4734 | 13768 | 14607 | 7695 | 13737 | 10493 | 7039 | 16005 | 5151 | 2008 | 20772 |
| | 4271 | 19954 | 7608 | 5609 | 5027 | 11303 | 8198 | 15488 | 16991 | 16228 | 17894 | 18306 |
| | 2556 | 6626 | 20616 | 16083 | 12968 | 22378 | 16437 | 7624 | 19737 | 2476 | 20184 | 8948 |
| | 13230 | 16495 | 6039 | 10274 | 10978 | 13806 | 5631 | 6912 | 22114 | 2955 | 21137 | 13954 |
| | 22400 | 1905 | 19874 | 16430 | 12918 | 16985 | 8847 | 4942 | 18505 | 6234 | 9524 | 15225 |
| | 3274 | 6369 | 1408 | 7297 | 20802 | 5035 | 20321 | 12454 | 13377 | 9019 | 4029 | 11248 |
| | 3758 | 16017 | 6780 | 2467 | 8343 | 727 | 18768 | 2737 | 1889 | 15457 | 2791 | 8559 |
| | 7622 | 17058 | 4393 | 1128 | 13953 | 2462 | 12634 | 4887 | 5138 | 7962 | 11126 | 15081 |
| | 22027 | 8042 | 16352 | 21033 | 8437 | 1952 | 10420 | 21247 | 20139 | 11118 | 19561 | 15955 |
| | 3808 | 17939 | 13239 | 4794 | 21353 | 13160 | 11932 | 16466 | 19950 | 18656 | 9789 | 3900 |
| | 11330 | 1626 | 21761 | 16275 | 839 | 16058 | 1199 | 5355 | 10804 | 10251 | 19141 | 19986 |
| | 19797 | 13358 | 5206 | 9701 | 1661 | 11677 | 2289 | 10875 | 9733 | 12426 | 10942 | 7723 |
| | 15784 | 12064 | 14341 | 5120 | 6223 | 5983 | 18048 | 8171 | 11041 | 10670 | 17196 | 16314 |
| | 20434 | 21075 | 20432 | 1709 | 8716 | 4904 | 18464 | 630 | 8403 | 6184 | 18819 | 13412 |

TABLE 16-continued

Sequence IDs for homolog proteins
Seq ID NO: homolog Seq ID NOs

|  | | | | | | | | | | | | |
|---|---|---|---|---|---|---|---|---|---|---|---|---|
| | 17228 | 16302 | 10762 | 4918 | 9392 | 16256 | 4056 | 5523 | 9202 | 16022 | 17350 | 304 |
| | 477 | 437 | 537 | 12703 | 15237 | 17792 | 11159 | 4597 | 7291 | 15512 | 1072 | 6812 |
| | 15476 | 15612 | 4183 | 5466 | 17341 | 12261 | 10729 | 21044 | 4892 | 1108 | 1406 | 1630 |
| | 5617 | 11923 | 17859 | 18198 | 6967 | 1264 | 20318 | 12469 | 22123 | 10452 | 5701 | 13091 |
| | 15516 | 2225 | 1997 | 712 | 14602 | 8047 | 16361 | 6109 | 14712 | 22157 | 7745 | 16695 |
| | 22271 | 11050 | 6934 | 6231 | 7635 | 1574 | 21574 | 18516 | 4245 | | | |
| 429: | 4085 | 2527 | 1065 | 15525 | 14455 | 18955 | 8686 | 14616 | 12315 | 16572 | 15135 | 18501 |
| | 11081 | 5251 | 21737 | 20520 | 691 | 6761 | 19795 | 13031 | 3691 | 6753 | 3599 | 17478 |
| | 19773 | 21114 | 6014 | 3843 | 12406 | 18706 | 4803 | 19871 | 5593 | 19334 | 19269 | 16267 |
| | 7830 | 3347 | 21925 | 18962 | 16676 | 22334 | 12165 | 16013 | 9753 | 7457 | 5446 | 17495 |
| | 20783 | 3532 | 19992 | 4641 | 17715 | 4676 | 10300 | 11655 | 22264 | 21804 | 2482 | 3288 |
| | 11375 | 10949 | 13571 | 5392 | 22506 | 4117 | 12147 | 9177 | 12485 | 12082 | 14102 | 16550 |
| | 8227 | 7887 | 9151 | 10009 | 2194 | 8035 | 3263 | 2456 | 10489 | 4324 | 17182 | 18539 |
| | 10448 | 18491 | 18289 | 3508 | 9164 | 17132 | 9114 | 3276 | 7050 | 5077 | 679 | 14103 |
| | 7303 | 20808 | 18812 | 5767 | 9247 | 20679 | 11242 | 19578 | 10187 | 6168 | 13518 | 22465 |
| | 10647 | 6086 | 8411 | 19641 | 21890 | 15074 | 12875 | 17324 | 6537 | 5971 | 5621 | 4007 |
| | 3671 | 5808 | 7390 | 2901 | 10617 | 17896 | 3947 | 21371 | 18983 | 19065 | 5064 | 8637 |
| | 18056 | 8308 | 7938 | 11745 | 19805 | 2000 | 1635 | 14446 | 18226 | 8264 | 6511 | 6429 |
| | 20857 | 18717 | 10669 | 18388 | 21752 | 2576 | 14131 | 18309 | 6243 | 2219 | 5023 | 15274 |
| | 22359 | 8379 | 1196 | 17230 | 21410 | 4530 | 10035 | 18136 | 20678 | 8008 | 3975 | 22206 |
| | 7027 | 14101 | 9482 | 8164 | 18390 | 11397 | 4582 | 20372 | 17760 | 16433 | 21946 | 13871 |
| | 7967 | 9095 | 17117 | 9950 | 6587 | 14695 | 5445 | 3749 | 17681 | 19020 | 11758 | 8793 |
| | 9612 | 10927 | 2881 | 20172 | 17530 | 3965 | 10328 | 18563 | 5640 | 17022 | 14773 | 3998 |
| | 19518 | 6413 | 13513 | 21860 | 10059 | 4735 | 8090 | 17595 | 22329 | 18064 | 11254 | 4553 |
| | 5196 | 7698 | 6952 | 13389 | 11495 | 4755 | 6529 | 14647 | 755 | 3688 | 17603 | 11692 |
| | 15799 | 7721 | 11607 | 1907 | 5972 | 12763 | 20832 | 5479 | 6622 | 14733 | 843 | 8870 |
| | 17397 | 3483 | 11493 | 19618 | 5858 | 18527 | 4566 | 20709 | 6716 | 19382 | 5368 | 13548 |
| | 7884 | 20519 | 2015 | 18102 | 11949 | 19869 | 7193 | 21204 | 8094 | 22071 | 1179 | 8989 |
| | 687 | 3082 | 1061 | 9091 | 4149 | 3083 | 19222 | 3949 | 20094 | 5822 | 13984 | 6059 |
| | 18698 | 5004 | 9193 | 7842 | 2013 | 15901 | 10055 | 17023 | 9839 | 17902 | 6839 | 14943 |
| | 21717 | 9782 | 8458 | 1749 | 6940 | 4589 | 14640 | 12339 | 16830 | 2964 | 18200 | 9685 |
| | 7385 | 3184 | 18909 | 12110 | 11069 | 17845 | 2560 | 4950 | 3891 | 6893 | 12525 | 5770 |
| | 4468 | 20897 | 13934 | 19823 | 2551 | 11904 | 3681 | 22519 | 2294 | 4619 | 581 | 12706 |
| | 20766 | 3718 | 18030 | 8652 | 13568 | 7092 | 5748 | 13595 | 21125 | 11323 | 6294 | 7245 |
| | 16341 | 18013 | 21906 | 7756 | 20468 | 12807 | 8952 | 4854 | 12892 | 20932 | 17233 | 15059 |
| | 14597 | 10337 | 3390 | 2083 | 16457 | 2550 | 6863 | 18213 | 15149 | 18389 | 13296 | 2910 |
| | 16845 | 800 | 9561 | 7305 | 5114 | 20251 | 14853 | 21958 | 20953 | 13079 | 4928 | 12827 |
| | 18923 | 12922 | 12166 | 4134 | 8385 | 16411 | 6965 | 15063 | 1198 | 16204 | 2303 | 10341 |
| | 9006 | 17038 | 3101 | 4223 | 12243 | 5951 | 19417 | 14082 | 8354 | 18716 | 5876 | 1912 |
| | 10613 | 2494 | 17074 | 6579 | 21936 | 20024 | 9076 | 15771 | 8144 | 18836 | 21381 | 752 |
| | 15962 | 2074 | 7618 | 7564 | 6180 | 14316 | 20422 | 20988 | 5743 | 1333 | 16210 | 5635 |
| | 6971 | 21853 | 13791 | 11654 | 848 | 13920 | 16054 | 21997 | 16890 | 8874 | 3252 | 14854 |
| | 18045 | 15844 | 1948 | 2167 | 19790 | 7872 | 15068 | 14737 | 9874 | 19597 | 19839 | 10412 |
| | 18454 | 3700 | 11597 | 3064 | 19734 | 6549 | 14176 | 16329 | 18535 | 22267 | 1097 | 4574 |
| | 8296 | 12640 | 20748 | 9752 | 18291 | 15724 | 1817 | 20274 | 2199 | 11298 | 12660 | 14557 |
| | 21233 | 19952 | 16014 | 18187 | 20646 | 4479 | 15036 | 19259 | 10006 | 11951 | 14208 | 807 |
| | 17472 | 22405 | 14906 | 11172 | 3156 | 4287 | 8159 | 7673 | 17535 | 1537 | 14931 | 1539 |
| | 22567 | 5737 | 13603 | 19699 | 9407 | 1651 | 6379 | 10581 | 19260 | 3165 | 14667 | 7864 |
| | 9195 | 1596 | 13152 | 16816 | 7742 | 6806 | 1616 | 17544 | 17707 | 20454 | 6937 | 3411 |
| | 18482 | 20603 | 12839 | 21210 | 2018 | 11104 | 7947 | 15160 | 8893 | 5218 | 15123 | 19207 |
| | 2443 | 10521 | 17888 | 19288 | 11689 | 13671 | 1060 | 7139 | 4723 | 16589 | 12750 | 20823 |
| | 21620 | 13574 | 8321 | 3982 | 8782 | 19710 | 7192 | 18007 | 8616 | 10833 | 19376 | 1910 |
| | 15804 | 21373 | 14004 | 10937 | 1232 | 14661 | 15988 | 3876 | 11632 | 4668 | 17814 | 12594 |
| | 19491 | 10832 | 9955 | 715 | 15438 | 10841 | 3640 | 9007 | 971 | 6389 | 21095 | 16446 |
| | 17276 | 14461 | 2963 | 15035 | 11615 | 3420 | 8456 | 9895 | 20407 | 21560 | 16473 | 17496 |
| | 7402 | 5937 | 16861 | 18408 | 18177 | 14755 | 15184 | 9227 | 12946 | 18987 | 11729 | 4477 |
| | 14072 | 12541 | 20612 | 4203 | 11063 | 18943 | 22467 | 12279 | 17726 | 13181 | 1130 | 19124 |
| | 12801 | 22244 | 16404 | 4962 | 17046 | 2469 | 2626 | 10801 | 569 | 7725 | 2704 | 8430 |
| | 18169 | 17621 | 14239 | 22342 | 20154 | 12018 | 6110 | 3490 | 20465 | 12047 | 553 | 5605 |
| | 2628 | 16250 | 2059 | 9087 | 3888 | 731 | 1827 | 21528 | 6858 | 5758 | 9971 | 9055 |
| | 19121 | 12596 | 9582 | 4484 | 11624 | 14798 | 6138 | 15283 | 7826 | 6756 | 11874 | 17055 |
| | 9759 | 17852 | 4798 | 22395 | 20864 | 12972 | 13464 | 710 | 16153 | 11807 | 13928 | 12179 |
| | 4667 | 18624 | 20452 | 2395 | 16837 | 8335 | 12798 | 16367 | 2473 | 10503 | 15101 | 11372 |
| | 17828 | 16195 | 20015 | 2994 | 16716 | 1892 | 19350 | 3636 | 17068 | 17570 | 11645 | 1327 |
| | 7475 | 20149 | 10068 | 20414 | 14198 | 6292 | 22295 | 12872 | 21980 | 3940 | 12542 | 18299 |
| | 9655 | 2119 | 18038 | 8871 | 8658 | 17301 | 11886 | 2039 | 3626 | 2453 | 8245 | 11903 |
| | 20419 | 2748 | 18668 | 6038 | 20076 | 11931 | 18793 | 3924 | 4613 | 6432 | 14061 | 11825 |
| | 10785 | 4319 | 20931 | 20293 | 12868 | 20904 | 13240 | 9080 | 5315 | 18550 | 5568 | 3790 |
| | 19960 | 18123 | 4607 | 21807 | 11927 | 7809 | 10838 | 3410 | 7219 | 3828 | 9117 | 4802 |
| | 17766 | 7596 | 18685 | 14850 | 2868 | 2410 | 17525 | 18227 | 5587 | 748 | 9922 | 6817 |
| | 13414 | 4122 | 14886 | 6795 | 20797 | 1302 | 13981 | 13919 | 12280 | 20227 | 13694 | 3432 |
| | 3581 | 17689 | 19868 | 22144 | 2368 | 4292 | 15152 | 803 | 7632 | 8409 | 12829 | 22148 |
| | 18235 | 17947 | 2085 | 4436 | 22035 | 19521 | 12094 | 1279 | 20990 | 7209 | 22178 | 9906 |
| | 5312 | 962 | 12098 | 7610 | 20672 | 14380 | 1096 | 4197 | 11149 | 11974 | 5660 | 10939 |
| | 21240 | 21535 | 6515 | 17591 | 13604 | 20996 | 6136 | 21870 | 19319 | 4234 | 6030 | 1908 |
| | 3858 | 15291 | 7352 | 15060 | 2897 | 10563 | 1195 | 7862 | 18600 | 13786 | 13041 | 4898 |
| | 2026 | 19040 | 19171 | 16313 | 14963 | 5034 | 1080 | 22252 | 3765 | 15468 | 11773 | 5638 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 12937 | 5393  | 13796 | 9419  | 21859 | 15071 | 8173  | 759   | 8785  | 10233 | 12251 | 10936 |
|      | 13190 | 19896 | 6977  | 14271 | 14981 | 14593 | 7058  | 1904  | 16109 | 1104  | 9497  | 9142  |
|      | 17439 | 2429  | 3251  | 1743  | 15595 | 776   | 11599 | 957   | 18835 | 15453 | 11273 | 11954 |
|      | 11554 | 9554  | 14263 | 13171 | 11110 | 17426 | 11221 | 20644 | 11573 | 20653 | 13888 | 8606  |
|      | 21124 | 21083 | 881   | 7084  | 6656  | 7589  | 1372  | 21363 | 12603 | 1875  | 14364 | 12080 |
|      | 923   | 17921 | 6852  | 4045  | 16278 | 13047 | 5535  | 17042 | 3118  | 9872  | 3494  | 11980 |
|      | 20390 | 19044 | 13195 | 11777 | 10230 | 14014 | 9456  | 5040  | 5358  | 12359 | 10174 | 7896  |
|      | 15061 | 19132 | 17294 | 9949  | 7651  | 19331 | 16609 | 5096  | 11833 | 5926  | 12692 | 793   |
|      | 7709  | 17994 | 10740 | 21923 | 4044  | 18803 | 7948  | 12708 | 4621  | 7049  | 15789 | 3183  |
|      | 19757 | 20773 | 18237 | 13118 | 11870 | 7824  | 12271 | 20914 | 19595 | 2904  | 7799  | 5575  |
|      | 11905 | 17160 | 7767  | 15836 | 1947  | 9981  | 9284  | 16661 | 19158 | 10592 | 7940  | 12764 |
|      | 14604 | 1540  | 8753  | 2822  | 16765 | 15532 | 1631  | 9675  | 17723 | 5039  | 9590  | 12994 |
|      | 21045 |       |       |       |       |       |       |       |       |       |       |       |
| 430: | 10036 | 20702 | 8519  | 2198  | 16727 | 19676 | 5461  | 9855  | 22269 | 16042 | 7071  | 17892 |
|      | 17842 | 9521  | 21420 | 10703 | 799   | 9651  | 7127  | 11809 | 20361 | 1641  | 6056  | 19650 |
|      | 2134  | 9375  | 17502 | 21016 | 902   | 22224 | 8402  | 19626 | 7011  | 22503 | 19144 | 15490 |
|      | 2388  | 16766 | 6922  | 16601 | 9905  |       |       |       |       |       |       |       |
| 431: | 10556 | 12984 | 17708 | 9241  | 19697 | 1495  | 14030 | 9734  | 14027 | 5836  | 7290  | 3964  |
|      | 13438 | 20803 | 17948 | 4643  | 8743  | 19246 | 8822  | 22019 | 15937 | 17296 | 18828 | 14438 |
|      | 21756 | 1588  | 19060 | 15098 | 4646  | 10462 |       |       |       |       |       |       |
| 432: | 9532  | 10331 | 15934 | 2046  | 6293  | 19503 | 15147 | 5699  | 7047  | 14129 | 17105 | 9079  |
|      | 5185  | 13130 | 2151  | 9143  | 1141  | 10189 | 18230 | 19023 | 8431  | 18942 | 18099 | 5356  |
|      | 3212  | 10361 | 22388 | 21551 | 20873 | 5482  | 17963 | 7910  | 21068 | 13009 | 6829  | 14326 |
|      | 20236 | 6208  | 21773 | 15785 | 14929 | 1052  | 4869  | 16502 | 3926  | 4567  | 14892 | 13401 |
|      | 6433  | 9709  | 18261 | 6409  | 22223 | 21368 | 11301 | 6931  | 15940 | 17666 | 21501 | 12516 |
|      | 3358  | 6554  | 1974  | 4835  | 20560 | 11275 | 2659  | 5053  | 16358 | 7498  | 14297 | 15569 |
|      | 19582 | 20331 | 6857  | 8522  | 22493 | 2638  | 19738 | 13482 | 13654 | 7414  | 12151 | 12808 |
|      | 14165 | 1755  | 10215 | 8018  | 22220 | 22247 | 7254  | 20380 | 2845  | 654   | 7274  | 5061  |
|      | 5018  | 9568  | 9818  | 1494  | 3725  | 11235 | 10859 | 8938  | 12700 | 17001 | 19302 | 11190 |
|      | 4028  | 12045 | 3173  | 14318 |       |       |       |       |       |       |       |       |
| 433: | 540   | 20745 | 4392  | 9539  | 7190  | 4968  | 12434 | 2894  | 9916  | 18824 | 15969 | 2549  |
|      | 13484 | 14142 | 5455  | 8922  | 14475 | 9503  | 12306 | 9461  | 18965 | 943   | 1591  | 20055 |
|      | 3802  | 8501  | 6629  | 7934  | 6828  | 21142 |       |       |       |       |       |       |
| 434: | 18584 | 20810 | 16027 | 15628 | 21406 | 7354  | 15327 | 14802 | 20743 | 2149  | 9585  | 6022  |
|      | 1273  | 9506  | 9718  | 22409 | 3023  |       |       |       |       |       |       |       |
| 435: | 20813 | 11290 | 7991  | 15677 | 22007 | 11719 | 11530 | 9318  | 1246  | 18259 | 1869  | 18894 |
|      | 5076  | 8796  | 1194  | 21241 | 4280  | 6152  | 3266  | 19426 | 6888  | 17781 | 10045 | 1251  |
|      | 15687 | 11467 | 7270  | 18820 | 4999  | 20923 | 20417 | 3253  | 11348 | 11482 | 14368 | 12055 |
|      | 19675 | 16542 | 16559 | 11524 | 9274  | 4132  | 12684 | 10517 | 11459 | 11732 | 9301  | 1359  |
|      | 17419 | 6843  | 11707 | 16067 | 9844  | 20469 | 16615 | 1849  | 2369  | 12095 | 14281 | 7631  |
|      | 725   | 21902 | 14026 | 3032  | 7802  | 1337  | 3062  | 21087 | 17626 | 17682 | 15601 | 15731 |
|      | 689   | 16620 | 17353 | 12317 | 12298 | 15292 | 10166 | 14717 | 13048 | 9220  | 15209 | 1054  |
|      | 10376 | 2355  | 11711 | 10028 | 2838  | 4853  | 11759 | 11502 | 9201  | 22481 | 15765 | 5294  |
|      | 9934  | 19837 | 18485 | 1903  | 16398 | 7376  | 3319  | 11943 | 7304  | 11341 | 13768 | 5151  |
|      | 2008  | 20772 | 16083 | 22378 | 12968 | 19737 | 8948  | 3528  | 5985  | 21137 | 7297  | 17939 |
|      | 4794  | 21353 | 18048 | 8171  | 10670 | 8716  | 12196 | 630   | 6184  | 9202  | 16022 | 537   |
|      | 15237 | 12703 | 1072  | 5466  | 12261 | 21044 | 4892  | 1108  | 11923 | 17859 | 5617  | 712   |
|      | 6109  | 7745  | 16695 | 11050 |       |       |       |       |       |       |       |       |
| 436: | 16500 | 8982  | 2601  | 9214  | 5987  | 9273  | 2383  | 3132  | 16871 | 4889  | 1471  |       |
| 437: | 14507 | 14477 | 15421 | 18062 | 17494 | 2654  | 566   | 7991  | 19769 | 6346  | 18037 | 2783  |
|      | 11158 | 1991  | 2025  | 16965 | 22007 | 22121 | 19530 | 17738 | 1299  | 10771 | 4864  | 1869  |
|      | 18259 | 5076  | 18894 | 10621 | 8796  | 1194  | 21241 | 4280  | 16103 | 3266  | 19426 | 6888  |
|      | 1697  | 10045 | 1251  | 7276  | 7003  | 19243 | 7580  | 12814 | 7126  | 16291 | 7248  | 3598  |
|      | 18820 | 18737 | 12671 | 18581 | 16569 | 13403 | 4999  | 20923 | 1142  | 14188 | 5501  | 20417 |
|      | 21625 | 3253  | 10604 | 7339  | 7394  | 4463  | 10287 | 9635  | 898   | 4347  | 12691 |       |
|      | 8702  | 12055 | 20545 | 15743 | 3704  | 10510 | 16542 | 16559 | 21229 | 11524 | 9274  | 11075 |
|      | 8804  | 17224 | 3133  | 3607  | 10123 | 13418 | 15872 | 11732 | 740   | 19109 | 1359  | 17419 |
|      | 10051 | 6843  | 5509  | 1680  | 11707 | 10865 | 22296 | 16067 | 1000  | 18908 | 3406  | 9844  |
|      | 20469 | 8719  | 4041  | 6395  | 20688 | 22346 | 4623  | 17333 | 14975 | 11866 | 3840  | 16733 |
|      | 5395  | 17783 | 17305 | 10611 | 7631  | 1274  | 3777  | 16608 | 21902 | 3032  | 10224 | 13407 |
|      | 20759 | 22152 | 18157 | 1337  | 16447 | 12222 | 2772  | 10847 | 17604 | 4797  | 20901 | 21087 |
|      | 19143 | 7452  | 8263  | 17993 | 16659 | 22147 | 10166 | 2993  | 14457 | 11862 | 9220  | 12697 |
|      | 16162 | 17146 | 7667  | 9071  | 7594  | 19062 | 11610 | 5047  | 11793 | 10376 | 5672  | 2355  |
|      | 3480  | 10028 | 20595 | 20275 | 1292  | 17594 | 12254 | 20642 | 4853  | 8186  | 16379 | 11759 |
|      | 11502 | 8591  | 4288  | 15333 | 9201  | 12553 | 3846  | 15765 | 17537 | 5294  | 9934  | 16724 |
|      | 3395  | 2370  | 4038  | 2297  | 1916  | 7144  | 12063 | 3319  | 11943 | 4162  | 7304  | 4298  |
|      | 9147  | 11434 | 11341 | 10440 | 4734  | 13768 | 5151  | 2008  | 20772 | 4271  | 19954 | 22378 |
|      | 12968 | 22114 | 2955  | 21137 | 20802 | 5035  | 10180 | 17939 | 4794  | 16466 | 19950 | 18656 |
|      | 13358 | 19797 | 9733  | 18048 | 8171  | 11041 | 10670 | 17196 | 16314 | 21075 | 20434 | 20432 |
|      | 4222  | 8716  | 4904  | 18464 | 630   | 8403  | 6184  | 18819 | 5523  | 6647  | 14751 | 16022 |
|      | 17350 | 12703 | 4597  | 17792 | 11159 | 7291  | 15512 | 1072  | 15476 | 6812  | 15612 | 4183  |
|      | 17341 | 12261 | 10729 | 21044 | 9980  | 1108  | 4892  | 1406  | 22046 | 17859 | 11923 | 5617  |
|      | 18198 | 6967  | 5043  | 1264  | 22123 | 20318 | 12469 | 10452 | 12218 | 13091 | 15516 | 5701  |
|      | 8047  | 16361 | 6109  | 14712 | 21918 | 22157 | 7745  | 16695 | 22271 | 11050 | 6934  | 7635  |
|      | 6231  |       |       |       |       |       |       |       |       |       |       |       |
| 438: | 3768  | 9465  | 20939 | 10052 | 11543 | 2583  | 2455  | 10554 | 14401 | 2398  | 18197 | 15151 |
|      | 12975 | 22406 | 10665 | 9509  | 15663 | 5927  | 13360 | 6164  | 16012 | 7099  | 21660 | 8046  |

TABLE 16-continued

Sequence IDs for homolog proteins
Seq ID NO: homolog Seq ID NOs

|   | | | | | | | | | | | |
|---|---|---|---|---|---|---|---|---|---|---|---|
| | 5207 | 4255 | 5194 | 15420 | 1613 | 12275 | 14710 | 16908 | 3629 | 20166 | 7194 | 4457 |
| | 5992 | 7677 | 13929 | 12101 | 15458 | 11274 | 20283 | 7521 | 14721 | | | |
| 439: | 14966 | 4405 | 7118 | 6146 | 8600 | 7777 | 22037 | 13873 | 8489 | 21468 | 8655 | 19547 |
| | 10433 | 17970 | 9362 | 20687 | 16031 | 887 | 7010 | 20077 | 4253 | 21851 | 14561 | 6562 |
| | 15040 | 11590 | 1611 | 13370 | 21623 | 10658 | 13700 | 6147 | 16428 | 6376 | 14491 | 7527 |
| | 12266 | 22380 | 14286 | 8408 | 4247 | 10369 | 7295 | 19540 | 12488 | 11421 | 18418 | 20410 |
| | 4446 | 3422 | 5527 | 5306 | 1906 | 20728 | 7396 | 20941 | 2529 | 6606 | 4873 | 7218 |
| | 19654 | 13098 | 12189 | 18969 | 15325 | 4309 | 13598 | 20706 | 9719 | 8328 | 20122 | 16518 |
| | 4685 | 8609 | 21086 | 1946 | 9979 | 2746 | 15560 | 7370 | 17671 | 15455 | 6005 | 3018 |
| | 4686 | 4101 | 22066 | 4236 | 21839 | 3651 | 4990 | 11914 | 15738 | 6771 | 3325 | 20546 |
| | 14826 | 19572 | 9615 | 13650 | 13899 | 13584 | 8742 | 3543 | 17869 | 19591 | 17545 | 22430 |
| | 2960 | 4200 | 2077 | 8177 | 7719 | 2622 | 6263 | 9849 | 1470 | 5989 | 1311 | 21426 |
| | 17824 | 7804 | 768 | 15927 | 14310 | 9131 | 19750 | 19247 | 21469 | 14334 | 14266 | 14771 |
| | 6820 | 17114 | 15394 | 15812 | 13253 | 2599 | 12929 | 5170 | 19859 | 15229 | 15346 | 19250 |
| | 1984 | 14570 | 11409 | 5996 | 20660 | 21736 | 20018 | 22326 | 19741 | 21896 | 19744 | 14409 |
| | 13692 | 3399 | 3194 | 17618 | 14100 | 18368 | 2518 | 690 | 20346 | 14843 | 6521 | 4745 |
| | 19127 | 22103 | 15018 | 18736 | 20115 | 1684 | 21656 | 3590 | 20651 | 2319 | 16368 | 7672 |
| | 3740 | 21690 | 1173 | 6846 | 5212 | 19894 | 8599 | 13173 | 8940 | 12978 | 16135 | 15091 |
| | 18853 | 20615 | 1491 | 18437 | 15682 | 13879 | 16777 | 19476 | 17619 | 1577 | 7748 | 13631 |
| | 13915 | 10365 | 12457 | 15298 | 8901 | 8625 | 5241 | 7358 | 14305 | 18568 | 18524 | 14410 |
| | 11871 | 21891 | 15823 | 20498 | 6200 | 9264 | 16240 | 19297 | 18458 | 2821 | 14785 | 3126 |
| | 14169 | 5798 | 9737 | 21776 | 19585 | 3198 | 14858 | 22300 | 7338 | 8554 | 11016 | 18990 |
| | 9617 | 18528 | 8024 | 16993 | 22122 | 4137 | 8570 | 22146 | 12226 | 9200 | 11674 | 21612 |
| | 14895 | 9476 | 16664 | 3321 | 16193 | 18447 | 16049 | 5313 | 18953 | 8533 | 11938 | 13683 |
| | 5508 | 2740 | 18932 | 19696 | 7262 | 8603 | 9275 | 18376 | 10691 | 20818 | 7714 | 1458 |
| | 12356 | 7720 | 7819 | 17020 | 17844 | 13115 | 5156 | 10998 | 6550 | 16814 | 12176 | 777 |
| | 14663 | 18952 | 3941 | 6256 | 10163 | 1231 | 14652 | 12351 | 20934 | 5346 | 3674 | 3417 |
| | 3413 | 20689 | 13348 | 3105 | 5424 | 8660 | 8772 | 19183 | 22278 | 21459 | 16873 | 20072 |
| | 17120 | 16743 | 19690 | 4218 | 3991 | 11096 | 10955 | 5602 | 886 | 19026 | 21015 | 19125 |
| | 13706 | 10726 | 19356 | 12958 | 17574 | 18510 | 16516 | 22357 | 8610 | 3240 | 7095 | 3522 |
| | 21988 | 5616 | 7937 | 3174 | 1747 | 3775 | 10024 | 6702 | 4908 | 6372 | 2579 | 18940 |
| | 21345 | 5519 | 15356 | 13540 | 14244 | 5795 | 14821 | 14518 | 20309 | 12120 | 2485 | 17587 |
| | 14150 | 15819 | 9978 | 12910 | 11595 | 16932 | 1960 | 694 | 14412 | 11488 | 18681 | 8778 |
| | 12679 | 17521 | 8810 | 5092 | 21175 | 2974 | 13020 | 10931 | 21585 | 2789 | 4153 | 18786 |
| | 18329 | 1083 | 19178 | 2493 | 21206 | 9256 | 15592 | 13324 | 16856 | 12883 | 15416 | 22022 |
| | 685 | 13962 | 7186 | 2183 | 1824 | 7815 | 9340 | 13838 | 4490 | 22377 | 18686 | 9359 |
| | 16226 | 1355 | 9864 | 4384 | 15337 | 14450 | 4671 | 8942 | 10589 | 3962 | 9323 | 19836 |
| | 12509 | 15215 | 5193 | 8404 | 6144 | 21817 | 7541 | 10871 | 1525 | 21274 | 13622 | 9110 |
| | 8628 | 2177 | 7874 | 14877 | 8824 | 18554 | 3163 | 18907 | 15713 | 2835 | 16426 | 3153 |
| | 20949 | 2770 | 7004 | 14833 | 12848 | 4690 | 18093 | 18783 | 15352 | 8130 | 7593 | 18583 |
| | 3501 | 4178 | 14120 | 14899 | 3694 | 21340 | 1642 | 6921 | 16503 | 11048 | 5058 | 2817 |
| | 9969 | 13347 | 19955 | 11925 | 20475 | 21679 | 16040 | 21148 | 2936 | 11490 | 9879 | 3668 |
| | 15510 | 9259 | 5266 | 11317 | 15129 | 15828 | 17404 | 18074 | 18271 | 12632 | 22568 | 6154 |
| | 19613 | 4529 | 14306 | 9441 | 17517 | 20968 | 2859 | 19635 | 2252 | 15293 | 3989 | 7716 |
| | 16280 | 13326 | 11344 | 11586 | 14234 | 9625 | 5215 | 13361 | 1156 | 16246 | 444 | 20628 |
| | 5316 | 13449 | 3080 | 16715 | 10685 | 19801 | 5171 | 1815 | 3509 | 16084 | 17427 | 995 |
| | 9018 | 10526 | 18574 | 10099 | 13402 | 17849 | 6159 | 17431 | 3824 | 555 | 9659 | 14148 |
| | 9887 | 22551 | 16739 | 20950 | 2267 | 11455 | 5169 | 15137 | 17589 | 4048 | 18400 | 8026 |
| | 1816 | 14675 | 4107 | 22512 | 7319 | 16725 | 20176 | 1188 | 3250 | 10266 | 3394 | 15649 |
| | 6275 | 16233 | 11157 | 7931 | 10836 | 20212 | 6842 | 21580 | 18201 | 18602 | 7675 | 17976 |
| | 14515 | 12856 | 12375 | 20806 | 1835 | 10204 | 928 | 877 | 18843 | 14059 | 6197 | 22517 |
| | 12239 | 14250 | 21061 | 548 | 2492 | 19311 | 18449 | 5757 | 16595 | 21416 | 19162 | 10349 |
| | 18182 | 5204 | 19779 | 22446 | 2313 | 11619 | 20729 | 18442 | 6595 | 12083 | 6350 | |
| 440: | 13290 | 13287 | 12491 | 9089 | 17221 | 9777 | 9141 | 4749 | 6525 | 10696 | 2418 | |
| 441: | 5159 | 5787 | 3587 | 20298 | 1786 | 13310 | 1389 | 10380 | 15437 | 20220 | 15554 | 14498 |
| | 1082 | 9121 | 21871 | 18718 | 1610 | 17142 | 16098 | 20306 | 17432 | 20695 | 8310 | 15692 |
| | 2042 | 20770 | 15746 | 11972 | 20448 | 7362 | 5959 | 17865 | 8865 | 4630 | 3037 | 6655 |
| | 4037 | 16478 | 11125 | 6160 | 10003 | 14982 | 9652 | 7150 | 5560 | 21884 | 7298 | 3602 |
| | 9622 | 20738 | 13828 | 4091 | 21632 | 1885 | 10098 | 5784 | 19579 | 11915 | 1619 | 4973 |
| | 4953 | 15722 | 18588 | 9009 | 3874 | 3245 | 15203 | 22499 | 1147 | 19826 | 15124 | 8880 |
| | 21552 | 2999 | 14657 | 21323 | 6418 | 1393 | 5831 | 1681 | 17953 | 9370 | 9708 | 13283 |
| | 7660 | 9230 | 20542 | 6634 | 21649 | 6803 | 7555 | 12376 | 14548 | 16219 | 9559 | 21885 |
| | 10474 | 5522 | 13930 | 9391 | 12268 | 15620 | 22031 | 14151 | 12757 | 13437 | 1509 | 3933 |
| | 21317 | 8728 | 11995 | 13090 | 16778 | 11699 | 16105 | 1278 | 2276 | 10571 | 834 | |
| | 14094 | 1564 | 4767 | 5915 | 1665 | 19312 | 9166 | 2756 | 14136 | 20976 | 11340 | 16028 |
| | 13738 | 1229 | | | | | | | | | | |
| 442: | 12225 | 16626 | 7991 | 19769 | 20707 | 21228 | 18920 | 15677 | 22007 | 1246 | 1299 | 4864 |
| | 1869 | 18259 | 5076 | 18894 | 8796 | 1194 | 19426 | 3266 | 19426 | 6888 | 17781 | 10045 |
| | 1251 | 11444 | 7126 | 7580 | 7248 | 17460 | 18820 | 16569 | 4999 | 20923 | 5501 | 20417 |
| | 12724 | 12691 | 8702 | 12055 | 8006 | 14571 | 19675 | 16542 | 11524 | 14891 | 11459 | 15395 |
| | 15872 | 9301 | 740 | 19109 | 15861 | 1359 | 17419 | 10051 | 6843 | 5509 | 16067 | 22296 |
| | 18908 | 12031 | 4041 | 3840 | 17305 | 10611 | 1428 | 10769 | 7631 | 21902 | 14896 | 20759 |
| | 22152 | 18157 | 1337 | 10847 | 14596 | 3679 | 21087 | 17626 | 10092 | 3743 | 21220 | 22333 |
| | 4831 | 12317 | 17353 | 2073 | 22147 | 9664 | 11526 | 9220 | 2983 | 5429 | 13258 | 10529 |
| | 12270 | 3138 | 6868 | 10376 | 2355 | 11711 | 9314 | 6624 | 17713 | 17898 | 12386 | 10028 |
| | 20595 | 10383 | 4591 | 11502 | 11759 | 11992 | 15333 | 9201 | 12553 | 15765 | 5294 | 4038 |
| | 7144 | 1916 | 10304 | 3319 | 11943 | 7304 | 9147 | 4298 | 11434 | 11341 | 9677 | 12289 |

TABLE 16-continued

Sequence IDs for homolog proteins
Seq ID NO: homolog Seq ID NOs

|      |       |       |       |       |       |       |       |       |       |       |       |
|------|-------|-------|-------|-------|-------|-------|-------|-------|-------|-------|-------|
|      | 5151  | 20772 | 19954 | 22175 | 19748 | 3020  | 16083 | 19737 | 21137 | 3274  | 6780  | 14060 |
|      | 10848 | 7124  | 17939 | 21761 | 1661  | 9701  | 6223  | 5983  | 18048 | 10670 | 1709  | 8716  |
|      | 12196 | 630   | 8582  | 9202  | 16022 | 17350 | 7291  | 21223 | 15476 | 12261 | 21044 | 1108  |
|      | 4892  | 1406  | 22046 | 11923 | 18198 | 6967  | 22123 | 20318 | 12469 | 10452 | 8047  | 6109  |
|      | 14712 | 7745  | 11374 |       |       |       |       |       |       |       |       |       |
| 443: | 620   | 12442 | 20304 | 1418  | 14021 | 9656  | 19898 | 1753  | 11261 | 6048  | 9339  | 20785 |
|      | 14195 | 2548  | 20087 | 4601  | 12996 | 2180  | 21054 | 8933  | 8763  | 20471 | 14140 | 10491 |
|      | 10186 | 6478  | 12177 | 17437 | 1521  | 8613  | 20482 | 15739 | 2169  | 12190 | 15573 | 15908 |
|      | 1717  | 6770  | 16901 | 15379 | 7349  | 10141 | 17028 | 12150 | 9400  | 11457 | 15837 | 15021 |
|      | 17531 | 12650 | 16974 | 10219 | 14993 |       |       |       |       |       |       |       |
| 444: | 7118  | 14966 | 4405  | 6146  | 8600  | 7777  | 13873 | 22037 | 8489  | 21468 | 8655  | 10433 |
|      | 19547 | 9362  | 20687 | 16031 | 20077 | 4253  | 21851 | 14561 | 6562  | 15040 | 11590 | 1611  |
|      | 13370 | 21623 | 10658 | 6147  | 16428 | 19540 | 10369 | 13700 | 14491 | 7527  | 4247  | 14286 |
|      | 12266 | 12488 | 6376  | 22380 | 18418 | 8408  | 11421 | 7295  | 20410 | 4446  | 3422  | 5527  |
|      | 5306  | 1906  | 20728 | 7396  | 2529  | 20941 | 4873  | 7218  | 19654 | 13098 | 12189 | 18969 |
|      | 15325 | 4309  | 13598 | 20706 | 8328  | 9719  | 20122 | 2746  | 15560 | 1946  | 9979  | 21086 |
|      | 17671 | 6005  | 7370  | 15455 | 3018  | 4101  | 4686  | 22066 | 4236  | 21839 | 3651  | 4990  |
|      | 11914 | 15738 | 3325  | 6771  | 20546 | 14826 | 19572 | 13650 | 9615  | 13899 | 13584 | 3543  |
|      | 17869 | 19591 | 17545 | 22430 | 2960  | 2077  | 4200  | 8177  | 7719  | 2622  | 6263  | 9849  |
|      | 1470  | 5989  | 1311  | 17824 | 21426 | 7804  | 768   | 15927 | 14310 | 9131  | 19750 | 19247 |
|      | 21469 | 14771 | 14334 | 14266 | 15812 | 15394 | 17114 | 6820  | 2599  | 19859 | 12929 | 5170  |
|      | 15229 | 15346 | 19250 | 1984  | 14570 | 11409 | 5996  | 21736 | 20018 | 22326 | 20660 | 19741 |
|      | 21896 | 19744 | 14409 | 13692 | 3194  | 17618 | 3399  | 17236 | 14100 | 18368 | 2518  | 690   |
|      | 20346 | 14843 | 15018 | 1684  | 18736 | 20115 | 21656 | 3590  | 20651 | 1173  | 5212  | 6846  |
|      | 8599  | 19894 | 13173 | 12978 | 8940  | 16135 | 15091 | 18853 | 20615 | 1491  | 15682 | 13879 |
|      | 16777 | 19476 | 17619 | 1577  | 7748  | 13631 | 13915 | 10365 | 15298 | 12457 | 8901  | 8625  |
|      | 14305 | 18568 | 18524 | 14410 | 11871 | 21891 | 6326  | 13311 | 6747  | 13835 | 5310  | 2038  |
|      | 11820 | 1116  | 18682 | 439   | 21539 | 20042 | 6396  | 15465 | 17351 | 4069  | 12600 | 18504 |
|      | 4527  | 20683 | 15823 | 12851 | 18338 | 6200  | 20498 | 9264  | 16240 | 12538 | 14814 | 15115 |
|      | 18458 | 19297 | 9737  | 21776 | 14169 | 5798  | 3126  | 14785 | 19585 | 3198  | 14858 | 22300 |
|      | 21664 | 7338  | 8554  | 18990 | 21738 | 9617  | 20013 | 11016 | 8024  | 16993 | 22122 | 4137  |
|      | 8570  | 22146 | 12226 | 9200  | 11674 | 21612 | 9476  | 3321  | 16049 | 16193 | 18447 | 11938 |
|      | 8533  | 5508  | 13683 | 2740  | 18932 | 19696 | 7262  | 8603  | 10691 | 18376 | 20818 | 7714  |
|      | 1970  | 8639  | 12180 | 20962 | 1458  | 12356 | 17844 | 7720  | 17020 | 7819  | 13115 | 5156  |
|      | 10998 | 6550  | 16814 | 12176 | 14663 | 777   | 18952 | 6256  | 3941  | 3417  | 3413  | 3105  |
|      | 5424  | 8660  | 20689 | 13348 | 8772  | 19183 | 11096 | 16873 | 22278 | 886   | 21459 | 3991  |
|      | 19690 | 4218  | 5602  | 3174  | 1747  | 6702  | 4908  | 10024 | 2579  | 6372  | 18940 | 5795  |
|      | 3775  | 14821 | 5519  | 15356 | 13540 | 14518 | 21345 | 14244 | 20309 | 12120 | 2485  | 9978  |
|      | 17587 | 11595 | 12910 | 15819 | 14150 | 694   | 16932 | 8778  | 1960  | 5092  | 17521 | 2770  |
|      | 2183  | 685   | 22022 | 12883 | 15416 | 13962 | 6144  | 1824  | 7815  | 19836 | 4384  | 4671  |
|      | 16226 | 8942  | 1355  | 9864  | 10589 | 14450 | 7186  | 13838 | 9359  | 9340  | 18686 | 9323  |
|      | 3962  | 4490  | 22377 | 15337 | 15215 | 7874  | 5193  | 8404  | 21817 | 7541  | 12509 | 3501  |
|      | 10871 | 1525  | 9110  | 13622 | 8628  | 14833 | 3163  | 18554 | 15713 | 21274 | 8824  | 16426 |
|      | 20949 | 2177  | 14877 | 7004  | 3153  | 18907 | 12848 | 18783 | 14120 | 4690  | 11925 | 18093 |
|      | 14899 | 15352 | 6921  | 18583 | 19635 | 16503 | 3694  | 21340 | 9969  | 7593  | 11048 | 11344 |
|      | 11586 | 14234 | 13449 | 3080  | 16715 | 19801 | 3509  | 17427 | 16084 | 10099 | 17849 | 13402 |
|      | 6159  | 17431 | 14148 | 3824  | 555   | 9659  | 22551 | 9887  | 2267  | 16739 | 20950 | 11455 |
|      | 5169  | 15137 | 16725 | 1188  | 20176 | 3250  | 10266 | 3394  | 15649 | 6275  | 16233 | 11157 |
|      | 7931  | 10836 | 20212 | 6842  | 17976 | 21580 | 18201 | 7675  | 18602 | 14515 | 12856 | 12375 |
|      | 20806 | 1835  | 928   | 877   | 14059 | 18843 | 6197  | 22517 | 12239 | 14250 | 21061 | 548   |
|      | 2492  | 19311 | 18449 | 5757  | 16595 | 10349 | 18182 | 5204  | 19779 | 22446 | 2313  | 11619 |
|      | 20729 | 18442 | 6595  | 12083 | 6350  |       |       |       |       |       |       |       |
| 445: | 21014 | 8217  | 3568  | 15315 | 16602 | 22197 | 20633 | 10719 | 22273 | 7927  | 12557 | 3214  |
|      | 5391  | 17035 | 16717 | 18176 | 3239  | 21949 | 541   | 17286 | 20722 | 21074 | 17292 | 19789 |
|      | 4688  | 6904  | 4467  | 1219  | 19816 | 19041 | 17181 | 21332 | 18859 | 22211 | 8218  | 2257  |
|      | 6585  | 7606  | 16882 | 11061 | 6736  | 15760 | 18569 | 22238 | 10997 | 3586  | 4444  | 11325 |
|      | 16288 | 5712  | 12397 | 13355 | 14617 | 8607  | 12841 | 4510  | 17747 | 8828  | 10495 | 7078  |
|      | 11921 | 20794 | 5507  | 14664 | 17923 | 2708  | 13572 | 15775 | 2513  | 11167 | 14105 | 3111  |
|      | 11389 | 3370  | 20781 | 7301  | 10605 | 20844 | 14047 | 14130 | 22186 | 16977 | 10134 | 11180 |
|      | 19900 | 10713 | 1464  | 7899  | 2349  | 6473  | 6149  | 17373 | 2862  | 15797 | 14327 | 10299 |
|      | 17623 | 20126 | 6074  | 2179  | 9070  | 18653 | 19230 | 14764 | 18671 | 15774 | 11854 | 9254  |
|      | 7597  | 9029  | 4935  | 1891  | 7776  | 14288 | 7040  | 20201 | 10153 | 16227 | 4268  | 19425 |
|      | 11328 | 17458 | 2842  | 14940 | 6228  | 15942 | 6091  | 22429 | 723   | 13304 | 7975  | 9105  |
|      | 16127 | 19403 | 11783 | 823   | 6252  | 21376 | 13980 | 4302  | 22514 | 6008  | 19617 | 15008 |
|      | 5641  | 9634  | 543   | 14573 | 2873  | 11280 | 18674 | 12111 | 5653  | 8223  | 7146  | 12775 |
|      | 12377 | 16801 | 7816  | 4017  | 16666 | 19793 | 7002  |       |       |       |       |       |
| 446: | 10867 | 18970 | 4967  | 22194 | 5235  | 18316 | 19541 | 18967 | 16679 | 12435 | 17897 | 14632 |
|      | 9836  | 7200  | 3244  | 4931  | 6155  | 724   | 767   | 11956 | 2291  | 15034 | 1158  | 4627  |
|      | 22468 | 2941  | 13822 | 6431  | 20840 | 3978  | 3058  | 2820  | 4352  | 17463 | 13357 | 17354 |
|      | 2351  | 1025  | 3451  | 8214  | 2208  |       |       |       |       |       |       |       |
| 447: | 3349  | 11861 | 16061 | 20185 | 18887 | 5336  | 6597  | 12949 | 13433 | 7265  | 3983  | 19704 |
|      | 21765 | 4512  | 9383  | 17441 | 11806 | 19145 | 7957  | 1660  | 16578 | 8361  | 12877 | 12285 |
|      | 6745  | 14055 | 16201 | 22143 | 8158  | 1754  | 1561  | 9710  | 18005 | 11717 | 18079 | 2243  |
|      | 21572 | 10276 | 6672  | 1451  | 5576  | 13128 | 10885 | 6027  | 6068  | 15496 | 10454 | 833   |
|      | 15308 | 2899  | 11018 | 20697 | 14627 | 3974  | 7859  | 15270 | 16400 | 15938 | 15725 | 15423 |
|      | 5811  | 19619 | 2698  | 19513 | 5502  | 3862  | 14005 | 6242  | 14353 | 16413 | 5739  | 5131  |
|      | 1844  | 15747 | 8386  | 4651  | 22360 | 19139 | 7085  | 13831 | 22094 | 8195  | 21288 | 3065  |

TABLE 16-continued

Sequence IDs for homolog proteins
Seq ID NO: homolog Seq ID NOs

|   | | | | | | | | | | | |
|---|---|---|---|---|---|---|---|---|---|---|---|
|   | 16776 | 4822 | 18118 | 19091 | 5553 | 12572 | 14834 | 21349 | 16815 | 8955 | 13075 | 12733 |
|   | 4648 | 21653 | 22049 | 5403 | 1029 | 1877 | 1485 | 22486 | 14277 | 19152 | 7372 | 4606 |
|   | 21858 | 17690 | 9703 | 12831 | 6467 | 10808 | 13527 | 19173 | 11175 | 11657 | 2942 | 16325 |
|   | 1265 | 17141 | 11133 | 17532 | 18407 | 20507 | 14912 | 8705 | 18889 | 792 | 12024 | 4746 |
|   | 6954 | 5377 | 14106 | 3811 | 9106 | 7669 | 17506 | 18207 | 11911 | 10409 | 20449 | 9181 |
|   | 18488 | 21792 | 22305 | 9003 | 12668 | 7458 | 11471 | 11697 | 19342 | 10966 | 5324 | 17192 |
|   | 9173 | 21172 | 21538 | 9379 | 8949 | 22434 | 3555 | 19594 | 13734 | 5195 | 4504 | 5963 |
|   | 14256 | 6939 | 6345 | 1162 | 18406 | 2357 | 17784 | 1442 | 4331 | 6935 | 5879 | 18326 |
|   | 2240 | 20428 | 19414 | 11272 | 3444 | 14731 | 8631 | 1809 | 21833 | 14869 | 9442 | 3632 |
|   | 12121 | 8845 | 20490 | 19745 | 13155 | 12792 | 12563 | 14861 | 14746 | 14813 | 4528 | 17811 |
|   | 1567 | 2911 | 10316 | 11855 | 21730 | 13905 | 22042 | 3872 | 20386 | 9570 | 6304 | 9122 |
|   | 6011 | 10819 | 2612 | 733 | 11892 | 20852 | 15230 | 16137 | 13985 | 13024 | 11612 | 8752 |
|   | 1512 | 3948 | 22301 | 14196 | 1070 | 2951 | 8433 | 842 | 12944 | 19948 | 22053 | 9341 |
|   | 9353 | 1718 | 16198 | 8546 | 15048 | 9919 | 20674 | 21812 | 3909 | 10843 | 16432 | 15654 |
|   | 4043 | 6714 | 14847 | 8707 | 9886 | 20997 | 22088 | 13038 | 8037 | 9178 | 2878 | 21388 |
|   | 5352 | 3851 | 6484 | 13259 | 20733 | 16180 | 20444 | 5834 | 17651 | 21480 | 13792 | 22149 |
|   | 13049 | 13689 | 6933 | 5650 | 21822 | 22010 | 13935 | 7093 | 15175 | 21104 | 21571 | 13059 |
|   | 14166 | 1320 | 14676 | 19388 | 12387 | 10615 | 2572 | 18647 | 16738 | 21225 | 7210 | 15278 |
|   | 11859 | 4902 | 21097 | 13308 | 18378 | 12809 | 17277 | 1707 | 10671 | 4638 | 13485 | 7397 |
|   | 2352 | 5048 | 7941 | 13275 | 5252 | 11316 | 3053 | 9127 | 6631 | 5081 | 2879 | 17029 |
|   | 14783 | 12504 | 3446 | 5574 | 11878 | 2839 | 3228 | 16798 | 6179 | 1088 | 1402 | 19752 |
|   | 22525 | 21445 | 16859 | 10813 | 2895 | 8708 | 2051 | 20050 | 10689 | 13359 | 6382 | 9920 |
|   | 16804 | 3557 | 13937 | 22048 | 15372 | 19186 | 2356 | 21850 | 10645 | 17724 | 7740 | 18043 |
|   | 18443 | 14254 | 8080 | 7679 | 18267 | 13583 | 7611 | 8668 | 2471 | 7128 | 21146 | 15408 |
|   | 1163 | 8078 | 5556 | 13897 | 17262 | 5961 | 22314 | 15730 | 18968 | 650 | 8513 | 11528 |
|   | 7068 | 3085 | 14046 | 13243 | 11222 | 15011 | 3976 | 15891 | 1507 | 6229 | 10269 | |
|   | 17937 | 9774 | 5505 | 5939 | 7480 | 1497 | 3041 | 15132 | 9987 | 18054 | 12199 | 21835 |
|   | 22529 | 20727 | 7448 | 2979 | 5186 | 13110 | 17553 | 15284 | 15066 | 21091 | 12304 | 13927 |
|   | 2253 | 22173 | 14128 | 9863 | 4969 | 20557 | 7177 | 21588 | 7134 | 20606 | 17839 | 15095 |
|   | 4399 | 2214 | 21594 | 19310 | 3008 | 2570 | 8102 | 16155 | 4099 | 18252 | 20237 | 9891 |
|   | 20458 | 14831 | 9119 | 9194 | 7573 | 11856 | 2558 | 21715 | 10855 | 5766 | 15158 | 3389 |
|   | 1154 | 11165 | 21797 | 3985 | 15097 | 8881 | 12231 | 16104 | 647 | 19765 | 22387 | 4155 |
|   | 2561 | 4615 | 21305 | 15139 | 4964 | 16030 | 20281 | 8285 | 15689 | 12785 | 2196 | 1531 |
|   | 12335 | 20138 | 9927 | 1132 | 4098 | 6925 | 14275 | 10776 | 22136 | 15697 | 16176 | 15977 |
|   | 2664 | 9816 | 17562 | 11028 | 11930 | 10157 | 8670 | 12353 | 12574 | 2954 | 21428 | 12735 |
|   | 2392 | 5226 | 8680 | 17177 | 8835 | 7167 | 15667 | 18591 | 21341 | 2172 | 3869 | 15589 |
|   | 20343 | 19825 | 5210 | 7091 | 22444 | 3844 | 717 | 18902 | 14808 | 11659 | 1785 | 13405 |
|   | 22226 | 8233 | 21693 | 10456 | 13156 | 14660 | 12659 | 6461 | 10253 | 7132 | 5280 | 16881 |
|   | 15728 | 12322 | 846 | 14049 | 12744 | 8140 | 20493 | 15683 | 11033 | 12989 | 5866 | 18113 |
|   | 1964 | 14109 | 15020 | 20584 | 17016 | 18813 | 5845 | 7915 | 21617 | 20412 | 1643 | 20533 |
|   | 8020 | 9158 | 19107 | 2930 | 21064 | 15660 | 21586 | 18572 | 10523 | 4610 | 13545 | 7585 |
|   | 1761 | 2480 | 16383 | 16486 | 1541 | 8462 | 2592 | 3201 | 11077 | 14726 | 20135 | 9411 |
|   | 9402 | 12669 | 15995 | 15348 | 7755 | 8168 | 551 | 8916 | 3112 | 13876 | 21933 | 12219 |
|   | 14513 | 6877 | 8898 | 8597 | 18116 | 8268 | 9085 | 9769 | 11890 | 21961 | 11709 | 10758 |
|   | 12800 | 8640 | 1212 | 10509 | 21023 | 21751 | 11267 | 1557 | 18735 | 18051 | 21254 | 15200 |
|   | 5771 | 17912 | 3381 | 18702 | 19564 | 12819 | 15172 | 17593 | 8712 | 8128 | 1909 | 6496 |
|   | 14338 | 16091 | 948 | 17565 | 16614 | 18595 | 11540 | 18075 | 9306 | 10608 | 12167 | 9268 |
|   | 17453 | 12880 | 21522 | 13525 | 10162 | 5843 | 7885 | 18002 | 13496 | 9474 | 11489 | 13260 |
|   | 14139 | 10989 | 5078 | 5480 | 16165 | 3428 | 2826 | 5882 | 20175 | 15811 | 16116 | 7879 |
|   | 5318 | 8325 | 1069 | 22306 | 21302 | 6156 | 22394 | 14294 | 5702 | 4766 | 568 | 15271 |
|   | 1077 | 16409 | 17778 | 9726 | 14452 | 5648 | 10532 | 3647 | 15330 | 8350 | 18444 | |
|   | 19227 | 19834 | 3890 | 21780 | 12302 | 13191 | 21151 | 13104 | 12185 | 20101 | 10857 | 11960 |
|   | 7382 | 18469 | 4948 | 11036 | 12852 | 11208 | 9994 | 14197 | 5906 | 16060 | 20197 | 3576 |
|   | 1115 | 6471 | 4258 | 14545 | 21796 | 17471 | 17991 | 14998 | 3215 | 307 | 10382 | 6929 |
|   | 2580 | 6731 | 8289 | 9480 | 9118 | 11333 | 12900 | 8452 | 12605 | 11475 | 19577 | 6041 |
|   | 2991 | 13102 | 15010 | 21059 | 21365 | 6894 | 11757 | 21208 | | | | |
| 448: | 17617 | 22319 | 7205 | 5436 | 22282 | 1508 | 1614 | 12460 | 8290 | 21670 | 8595 | 18790 |
|   | 19872 | 21481 | 5282 | 5245 | 2363 | 9283 | 17848 | 10766 | 892 | 11279 | 3262 | |
| 449: | 13633 | 5900 | 8539 | 14672 | 20311 | 964 | 12233 | 10478 | 5805 | 8760 | 4906 | 10137 |
|   | 3902 | 1838 | 13999 | 21067 | 4596 | 12781 | 4010 | 10761 | 8601 | 11786 | 6187 | 19637 |
|   | 20291 | 12933 | 1404 | 16680 | 16262 | 4172 | 11107 | 2757 | 4381 | 11802 | 14386 | 6750 |
|   | 3881 | 20169 | 3124 | 11582 | 4779 | 14837 | 16691 | 21558 | 16323 | 14350 | 7275 | 16234 |
|   | 10634 | 8984 | 12657 | 3036 | 20253 | 12586 | 15643 | 8362 | 20529 | 4086 | 15778 | 15634 |
|   | 10975 | 7311 | 15107 | 8618 | 8213 | 4431 | 2716 | 12985 | 488 | 2869 | 18696 | 12025 |
|   | 7468 | 6477 | 4900 | 14759 | 645 | 8641 | 3783 | 17104 | 16899 | 21903 | 9293 | 2872 |
|   | 7277 | 12282 | 7350 | 15064 | 2602 | 14650 | 13112 | 15517 | 7433 | 889 | 15267 | 21911 |
|   | 19806 | 10064 | 15339 | 1645 | 20835 | 16525 | 12947 | 16705 | 22317 | 19397 | 18277 | 11661 |
|   | 16082 | 8992 | 9337 | 17911 | 12718 | 11845 | 12581 | 12948 | 1001 | 4151 | 15609 | 5506 |
|   | 19445 | 5163 | 11501 | 20741 | 15240 | 10944 | 3217 | 5255 | 11017 | 20435 | 15575 | 13834 |
|   | 12427 | 2375 | 8287 | 6080 | 20581 | 16884 | 20690 | 12613 | 4380 | 15312 | 5145 | 10145 |
|   | 1126 | 13494 | 15530 | 15431 | 22255 | 22276 | 19919 | 8963 | 4880 | 20168 | 20601 | 7009 |
|   | 15363 | 10724 | 8126 | 7044 | 2098 | 13898 | 22554 | 17967 | | | | |
| 450: | 1006 | 429 | 10217 | 535 | 507 | 533 | 306 | 478 | 314 | 12870 | 18461 | 5240 |
|   | 6367 | 19001 | 17394 | 8913 | 526 | 17484 | 7812 | 286 | 534 | 531 | 300 | 21030 |
|   | 2857 | 17664 | 21589 | 11961 | 19154 | 21437 | 11195 | 20933 | 21506 | 3533 | 4677 | 18511 |
|   | 4730 | 696 | 9569 | 17797 | 18687 | 7097 | 20259 | 15252 | 13221 | 22502 | 14915 | 21157 |
|   | 22126 | 18059 | 20371 | 3563 | 12591 | 16308 | 7626 | 4212 | 20262 | 19798 | 19458 | 5691 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 18292 | 11428 | 18877 | 16130 | 21296 | 2832 | 830 | 14553 | 6434 | 18295 | 17956 | 829 |
| | 476 | 12043 | 9077 | 20779 | 1281 | 17745 | 16586 | 7955 | 12705 | 15449 | 988 | 20859 |
| | 1768 | 11129 | 6547 | 22518 | 5552 | 9854 | 11376 | 6669 | 5359 | 9132 | 10964 | 1879 |
| | 22087 | 13137 | 17298 | 3333 | 13752 | 20301 | 19370 | 2425 | 6946 | 19538 | 14273 | 15340 |
| | 6427 | 17165 | 15603 | 12419 | 10809 | 8003 | 13658 | 18296 | 14064 | 4221 | 14568 | 17630 |
| | 2371 | 4694 | 12396 | 15369 | 16597 | 3697 | 10741 | 16309 | 4927 | 13396 | 9785 | 21621 |
| | 8841 | 16662 | 11120 | 14081 | 15204 | 6565 | 14320 | 2978 | 9294 | 7482 | 9493 | 1277 |
| | 4952 | 7813 | 7306 | 12296 | 12021 | 6645 | 9286 | 22489 | 13745 | 16653 | 19069 | 7780 |
| | 15219 | 16969 | 14762 | 18330 | 10802 | 10479 | 16663 | 3678 | 16713 | 7751 | 13703 | 3630 |
| | 4691 | 9472 | 10709 | 8542 | 7060 | 6112 | 22457 | 21974 | 20476 | 7333 | 6482 | 14526 |
| | 7151 | 2644 | 835 | 10655 | 12264 | 9315 | 2786 | 16253 | 9488 | 5634 | 17372 | 16548 |
| | 13727 | 19096 | 10973 | 788 | 10889 | 5190 | 13207 | 16465 | 13178 | 9673 | 5374 | 9771 |
| | 11716 | 10164 | 20541 | 3458 | 1240 | 15787 | 20099 | 9282 | 11480 | 4994 | 4865 | 1120 |
| | 6281 | 18662 | 7992 | 9661 | 19875 | 11156 | 3619 | 14086 | 20948 | 16946 | 3456 | 6143 |
| | 786 | 6709 | 5954 | 17926 | 20839 | 22351 | 13277 | 10965 | 15558 | 18982 | 2984 | 11245 |
| | 2132 | 20312 | 4655 | 16568 | 21093 | 13882 | 5730 | 7976 | 7079 | 13035 | 2800 | 305 |
| | 307 | 509 | 12545 | 2037 | 11704 | 9571 | 21379 | 3712 | 7685 | 4483 | 18456 | 22341 |
| | 3094 | 11197 | 13107 | 16006 | 532 | | | | | | | |
| 451: | 3345 | 751 | 19630 | 15890 | 21334 | 2502 | 16406 | 10364 | 15556 | 10330 | 10995 | 14378 |
| | 13458 | 16021 | 7590 | 20173 | 3502 | 572 | 19897 | 3673 | 12693 | 3848 | 6462 | 21994 |
| | 20804 | 17582 | 4276 | 16244 | 8615 | 17497 | 11060 | 9796 | 2390 | 21178 | 7166 | 2759 |
| | 19905 | 12817 | 14186 | 14243 | 5490 | 6784 | 5792 | 13470 | 1101 | 12561 | 6617 | 11241 |
| | 6402 | 9027 | 20751 | 1813 | 16709 | 11278 | 10008 | 3046 | 7793 | 13443 | 5592 | 8736 |
| | 3403 | 14205 | 19027 | 2511 | 14794 | 10004 | 16347 | 3927 | 13109 | 8732 | 21235 | 10480 |
| | 19155 | 2047 | 21601 | 2804 | 11826 | 19016 | 20937 | 21978 | 13295 | 3255 | 17452 | 6272 |
| | 19822 | 8274 | 14395 | 20792 | 1967 | 4644 | 19536 | 3230 | 8051 | 21408 | 16552 |
| | 17526 | 4434 | 6675 | 10332 | 16527 | 11695 | 11834 | 4106 | 21315 | 20826 | 18978 | 17269 |
| | 22168 | 21255 | 19151 | 14377 | 2774 | 19782 | 12983 | 9784 | 9962 | 16564 | 850 | 18492 |
| | 20740 | 21582 | 7445 | 1779 | 10977 | 17687 | 11634 | 18743 | 18450 | 11001 | 19140 | 11439 |
| | 11743 | 13008 | 6064 | 17602 | 13592 | 13552 | 15418 | 11134 | 16033 | 20106 | 17363 | 12458 |
| | 12874 | 6513 | 15906 | 16223 | 1784 | 874 | 1125 | 9165 | 17183 | 4284 | 8998 | 583 |
| | 17287 | 963 | 5591 | 19466 | 4320 | 9188 | 20258 | 21605 | 17648 | 19691 | 3335 | 6816 |
| | 19609 | 22222 | 3733 | 6330 | 8114 | 19196 | 6605 | 22558 | 3373 | 5980 | 4992 | 10542 |
| | 21937 | 2186 | 4838 | 2923 | 20053 | 20960 | 4335 | 13352 | 2747 | 5898 | 8059 | 18499 |
| | 19914 | 7292 | 2255 | 21251 | 19565 | 10896 | 14138 | 1474 | 1803 | 22420 | 2054 | 18604 |
| | 4980 | 12543 | 19544 | 7953 | 17754 | 18426 | 21889 | 21464 | 7125 | 21785 | 14725 | 10578 |
| | 7357 | 2460 | 2281 | 4747 | 13666 | 6881 | 21446 | 19660 | 14216 | 1004 | 17442 | 21195 |
| | 9433 | 21820 | 7213 | 8549 | 21471 | 8344 | 17607 | 6026 | 13716 | 12371 | 18944 | 19208 |
| | 20867 | 13887 | 15334 | 8749 | 16682 | 14433 | 12986 | 7761 | 12475 | 15833 | 15505 | 8725 |
| | 627 | 20270 | 7644 | 15253 | 15959 | 13593 | 13483 | 12343 | 18196 | 3966 | 1640 | 20730 |
| | 3351 | 10803 | 1315 | 1603 | 19482 | 6421 | 12053 | 1137 | 8850 | 12068 | 12197 | 8734 |
| | 19465 | 2535 | 2409 | 22297 | 7627 | 19726 | 1553 | 13474 | 15450 | 3620 | 5719 | 11963 |
| | 3815 | 19768 | 758 | 13039 | 16269 | 11639 | 7621 | 5670 | 7361 | 8209 | 17309 | 14298 |
| | 22309 | 19799 | 6584 | 3893 | 10041 | 3814 | 2858 | 7122 | 20012 | 8232 | 12230 | 820 |
| | 11268 | 7920 | 3024 | 942 | 16980 | 14141 | 2812 | 19328 | 19907 | 16962 | 16151 | 12559 |
| | 3658 | 994 | 16669 | 2146 | 14691 | 14451 | 2080 | 3146 | 18837 | 7883 | 935 | 4402 |
| | 21465 | 15552 | 7472 | 6823 | 18275 | 16984 | 17026 | 7620 | 5223 | 8813 | 21417 | 1708 |
| | 22055 | 15118 | 13508 | 19764 | 22214 | 16335 | 1874 | 6227 | 19122 | 5567 | 20812 | 16276 |
| | 19961 | 11837 | 11145 | 14544 | 15166 | 9889 | 16056 | 20845 | 14946 | 6840 | 722 | 13349 |
| | 14215 | 14913 | 12175 | 2181 | 19628 | 13753 | 5595 | 13445 | 8711 | | | |
| 452: | 21725 | 4108 | 17790 | 10816 | 10072 | 11215 | 7845 | 21938 | 14000 | 12290 | 9072 | 2188 |
| | 13197 | | | | | | | | | | | |
| 453: | 17069 | 19235 | 13531 | 17697 | 11206 | 10541 | 21126 | 13101 | 21378 | 21802 | 1329 | 11808 |
| | 2880 | 22230 | 1218 | 9626 | 19047 | 3040 | 17741 | 3001 | 15767 | 17052 | 3724 | 7152 |
| | 16952 | 20547 | 5794 | 17379 | 9932 | 18433 | 2347 | 8182 | 3667 | 10010 | 9258 |
| | 4330 | 16872 | 13931 | 10125 | 15345 | 15750 | 14295 | 6095 | 14904 | 11788 | 22535 | 2662 |
| | 5270 | 2833 | 2917 | 19197 | 11031 | 8241 | 18241 | 12357 | 932 | 9546 | 3545 | 5011 |
| | 5922 | 15762 | 21458 | 11169 | 19093 | 2950 | 4496 | 8786 | 17325 | 12345 | 8819 | 14838 |
| | 11101 | 7574 | 21973 | 11052 | 5177 | 10577 | 9162 | 18537 | 19268 | 11571 | 9690 | 8586 |
| | 17826 | 10897 | 21454 | 12803 | 2767 | 20158 | 11415 | 6018 | 16018 | 13857 | 10790 | 8706 |
| | 12567 | 13232 | 21790 | 2221 | 16327 | 22364 | 9930 | 11940 | 14381 | 12027 | 5625 | 20421 |
| | 6213 | 18883 | 15885 | 991 | 14231 | 1117 | 8576 | 18603 | 5865 | 1558 | 1668 | 7347 |
| | 20793 | 5291 | 16647 | 5611 | | | | | | | | |
| 454: | 10637 | 2260 | 13315 | 5883 | 11574 | 14796 | 9991 | 4552 | 7533 | 6653 | 8525 | 1420 |
| | 15386 | 21880 | 6261 | 12607 | 8500 | 22030 | 1956 | | | | | |
| 455: | 7653 | 1606 | 10840 | 3715 | 10418 | 14035 | 4843 | 2101 | 19615 | 10922 | 3554 | 1735 |
| | 3155 | 13503 | 6907 | 7784 | 20054 | 21733 | 1169 | 1452 | 5818 | 22385 | | |
| 456: | 0 | | | | | | | | | | | |
| 457: | 3034 | 22132 | 9120 | 13729 | 6791 | 11897 | 5149 | 22382 | 7782 | 1951 | | |
| 458: | 21696 | 15323 | 6711 | 794 | 10202 | 21441 | 6649 | 17320 | 15012 | 6988 | 16064 | 7702 |
| | 2108 | 7337 | 13972 | 18351 | 2384 | 18596 | 11446 | 5769 | 20712 | 818 | 9873 | 11398 |
| | 20352 | 19777 | 18363 | 16843 | 5030 | 6560 | 11056 | 12761 | 9908 | 4279 | 12906 | 8596 |
| | 16833 | 6392 | 2335 | 20071 | 16868 | 4580 | 21828 | 17448 | 14949 | 21452 | 5673 | 10050 |
| | 5093 | 22411 | 1705 | 11285 | 10329 | 5612 | | | | | | |
| 459: | 655 | 11975 | 8069 | 20491 | 17684 | 1394 | 19340 | 17701 | 5908 | 684 | 14348 | 21852 |
| | 5434 | 14730 | 2715 | 13227 | 21854 | 8282 | 16106 | 10308 | 21982 | 7567 | 4049 | 15967 |
| | 16174 | 14809 | 13372 | 20868 | 798 | 20016 | 19024 | 1342 | 3575 | 14227 | | |

TABLE 16-continued

Sequence IDs for homolog proteins
Seq ID NO: homolog Seq ID NOs

| | | | | | | | | | | | |
|---|---|---|---|---|---|---|---|---|---|---|---|
| 460: | 19142 | 17102 | 15893 | 22335 | 12299 | 15442 | 11496 | 10074 | 5733 | 14018 | 4497 | 12860 |
| | 17771 | 17375 | 8161 | 11868 | 317 | 11262 | 6451 | 9249 | 12173 | 13520 | 2381 | 4681 |
| | 6996 | 6490 | 9579 | 1276 | 5404 | 8032 | 6363 | 10026 | 7316 | 14084 | 8908 | 17837 |
| | 8863 | 19169 | 750 | 18053 | 13467 | 9093 | 12920 | 8746 | 301 | 4625 | 12849 | 8975 |
| | 1460 | 8614 | 20285 | 11049 | 15351 | 15199 | 22494 | 14045 | 10173 | 6414 | 13682 | 21841 |
| | 1623 | 17211 | 18365 | 4519 | 21203 | 2011 | 22000 | 10060 | 950 | 10516 | 18657 | 11078 |
| | 6908 | 20626 | 18762 | 9992 | 11321 | 16068 | 13071 | 20575 | 9335 | 10629 | 4241 | 17420 |
| | 13570 | 10156 | 14609 | 12058 | 7665 | 21534 | 18040 | 5706 | 574 | 11168 | 21837 | 3354 |
| | 20317 | 6124 | 1526 | 12392 | 16093 | 22474 | 21550 | 2099 | 15300 | 14848 | 1309 | 13170 |
| | 19435 | 2632 | 6374 | 14407 | 14649 | 12249 | 8309 | 550 | 7797 | 3769 | 17901 | 16142 |
| | 2063 | 6092 | 19535 | 13070 | 9812 | 1776 | 3443 | 17767 | 15918 | 12414 | 2144 | 9885 |
| | 3591 | 9545 | 21263 | 14344 | 19754 | 19431 | 11670 | 6760 | 19223 | 12846 | 21920 | 21081 |
| | 22381 | 17475 | 18403 | 21905 | 12709 | 15904 | 5736 | 14499 | 13058 | 11572 | 10692 | 7183 |
| | 16133 | 15670 | 12332 | 1756 | 16939 | 22104 | 4806 | 15031 | 18332 | 20634 | 7994 | 12919 |
| | 9064 | 5045 | 14968 | 9551 | 2414 | 1646 | 4753 | 1805 | 18175 | 18991 | 9750 | 1618 |
| | 17712 | 22081 | 22029 | 14969 | 2458 | 1011 | 14504 | 3779 | 21507 | 6619 | 4824 | 5015 |
| | 20098 | 2353 | 13906 | 16938 | 1847 | 13819 | 11957 | 12498 | 17391 | 1983 | 2927 | 13991 |
| | 20531 | 20599 | 1625 | 606 | 8646 | 7497 | 11561 | 11796 | 8562 | 3676 | 16567 | 11565 |
| | 15599 | 13705 | 12415 | 13948 | 1711 | 2922 | 7520 | 21985 | 563 | 3562 | 1939 | 5754 |
| | 19800 | 6341 | 9042 | 15748 | 16577 | 12974 | 4827 | 4371 | 1092 | 14881 | 16895 | 20528 |
| | 1513 | 6790 | 19711 | 13821 | 5656 | 6520 | 2463 | 9526 | 17821 | 1888 | 18587 | 10549 |
| | 18855 | 4858 | 7028 | 14908 | 22205 | 5964 | 4933 | 5271 | 927 | 8374 | 3316 |
| | 20014 | 21527 | 5008 | 9914 | 10822 | 13989 | 15266 | 13163 | 17347 | 7197 | 21212 | 6338 |
| | 1401 | 3445 | 561 | 14444 | 20426 | 12281 | 9349 | 20565 | 7453 | 19524 | 4093 | 17235 |
| | 8735 | 14800 | 9217 | 16762 | 10080 | 19195 | 11057 | 11977 | 8958 | 21372 | 19693 | 20196 |
| | 6610 | 14503 | 22133 | 19181 | | | | | | | | |
| 461: | 21226 | 10722 | 9090 | 9917 | 17608 | 3307 | 17248 | 19659 | 12888 | 16315 | 15869 | 13541 |
| | 11628 | 14989 | 5547 | 13844 | 21236 | 9910 | 11202 | 10862 | 3786 | 7783 | 20043 | 16159 |
| | 21123 | 21149 | 1353 | 5976 | 20875 | 12245 | 2040 | 1496 | 18804 | 8260 | 2945 | 3653 |
| | 21684 | 4427 | 20639 | 22232 | 20700 | 626 | 868 | 17999 | 20858 | 2479 | 14206 | 10988 |
| | 22292 | 12471 | 7299 | 12462 | 21503 | 15092 | 2732 | 4462 | 16160 | 13957 | 17698 | 19014 |
| 462: | 10915 | 15022 | 4450 | 11366 | 20814 | 8548 | 7447 | 2554 | 10246 | 14947 | 16967 | 18188 |
| | 8578 | 3396 | 12439 | 21412 | 21085 | 10559 | 15980 | 13299 | 6199 | 5121 | 3610 | 8985 |
| | 5265 | 4663 | 6420 | 19456 | 9646 | 7090 | 9324 | 14666 | 21020 | 13611 | 3580 | 3309 |
| | 3503 | 10431 | 15493 | 1658 | 4414 | 10484 | 19347 | 18475 | 3196 | 10873 | 7062 | 5347 |
| | 14932 | 697 | 8959 | 9970 | 13746 | 17123 | 19066 | 3791 | 6974 | 21237 | 4075 | 21728 |
| | 13369 | 5804 | 15214 | 3905 | 7104 | 15534 | 15425 | 15645 | 14841 | 13863 | 17523 | 14583 |
| | 13266 | 16008 | 19678 | 809 | 17661 | | | | | | | |
| 463: | 15610 | 19505 | 3188 | 13558 | 22207 | 789 | 18180 | 4508 | 22145 | 6608 | 12144 | 14753 |
| | 3301 | 17632 | 6183 | 18032 | 8172 | 21197 | 9377 | 13065 | 15119 | 10305 | 14673 | 12954 |
| | 12468 | 8469 | | | | | | | | | | |
| 464: | 7246 | 2525 | 8937 | 1249 | 20791 | 2442 | 13757 | 2102 | 8484 | 20391 | 22436 | 8284 |
| | 6769 | 10971 | 8004 | 22023 | 4837 | 6659 | 8039 | 542 | 11456 | 2562 | 13478 | 12526 |
| | 20405 | 19784 | 19698 | 17561 | 14237 | 21200 | 20356 | 7320 | 10248 | 1737 | 18419 | 11847 |
| | 10624 | 18917 | 21915 | 21121 | 18416 | 17053 | 8529 | 2009 | 1335 | 2989 | 17827 | 5789 |
| | 7577 | 14095 | 21524 | 13803 | 19598 | 11276 | 12421 | 21337 | 2916 | 21144 | 20276 | 15766 |
| | 10716 | 15947 | 19883 | 13961 | 9267 | 13637 | 16960 | 18795 | 2343 | 10609 | 15000 |
| | 4509 | 3285 | 1871 | 22443 | 9056 | 14293 | 11451 | 17137 | 11684 | 5432 | 21943 | 5119 |
| | 17025 | 20216 | 6625 | 22445 | 4609 | 21217 | 19722 | 18262 | 17059 | 19393 | 8393 | 18989 |
| | 14155 | 18379 | 19003 | 4754 | 6752 | 7557 | 21304 | 14324 | 2929 | 15268 | 11094 | 6025 |
| | 8713 | 14222 | 2187 | 1975 | 2856 | 8286 | 16534 | 8056 | 9369 | 15871 | 22373 | 5414 |
| | 5457 | 8512 | 14839 | 13626 | 13511 | 18521 | 18560 | 2002 | 4104 | 11038 | 15162 | 19653 |
| | 9129 | | | | | | | | | | | |
| 465: | 6459 | 6394 | 20221 | 2332 | 21782 | 13055 | 10580 | 2279 | 21367 | 19818 | 15567 | 13294 |
| | 11815 | 16237 | 17819 | 16570 | 1622 | 15858 | 19159 | 18654 | 9082 | 10360 | 8884 | |
| 466: | 17835 | 13628 | 20663 | | | | | | | | | |
| 467: | 20037 | 7346 | 1314 | 12511 | 16115 | 17491 | 18854 | 2329 | | | | |
| 468: | 17297 | 12034 | 9186 | 19531 | 5960 | 3320 | 6107 | 989 | 17365 | 1448 | 5740 | 10535 |
| | 13789 | 18153 | 3130 | 2668 | 16090 | 6274 | 11423 | 19113 | 19718 | | | |
| 469: | 8693 | 16592 | 5005 | 19306 | 6604 | 16732 | 9754 | 13116 | 8230 | 21139 | 4079 | 5166 |
| | 18517 | 6465 | 2795 | 16685 | 16688 | 21959 | 6043 | 13767 | 6173 | 22310 | 3259 | 13685 |
| | 20252 | 7455 | 5044 | 3534 | 9389 | 10900 | 11649 | 8773 | 10993 | 11006 | 9330 | 11087 |
| | 5753 | 19387 | 21478 | 15236 | 21689 | 1435 | 21991 | 913 | 7484 | 14285 | 18519 | 20798 |
| | 16122 | 2721 | 770 | 15723 | 20967 | 12158 | 21702 | 18984 | 12751 | 12455 | 5999 | 11116 |
| | 11824 | 9843 | 12418 | 7936 | 7869 | 5363 | 4568 | 3972 | 16205 | 22566 | 18031 | 20763 |
| | 17285 | 18882 | 7781 | 5471 | 19353 | 4312 | 4716 | 18663 | 9603 | 15043 | 11217 | 14246 |
| | 16326 | 9289 | 1155 | 13216 | 13122 | 13400 | 3648 | 8238 | 13201 | 897 | 19164 | 9520 |
| | 12035 | 8212 | 12560 | 22169 | 3281 | 12562 | 11339 | 17667 | 12309 | 8806 | 22280 | 18666 |
| | 22125 | 9307 | 6640 | 20092 | 2145 | 19241 | 15914 | 1213 | 13453 | 5332 | 6133 | 21968 |
| | 9060 | 20524 | 10171 | 20916 | 20091 | 19282 | 10648 | 21566 | 4242 | 19533 | 11739 | 14917 |
| | 21058 | 17627 | 7451 | 13855 | 20246 | 872 | 19965 | 10868 | 11173 | 2843 | 8856 | 6802 |
| | 6353 | 5160 | 6251 | 13175 | 12961 | 12248 | 21646 | 18733 | 1820 | 15077 | 6061 | 2722 |
| | 19163 | 13367 | 10128 | 22117 | 17264 | 16640 | 22485 | 19560 | 8034 | 1100 | 17788 | 13010 |
| | 7758 | 19682 | 1515 | 12783 | 21145 | 7575 | 3152 | 16168 | 2508 | 13380 | 8293 | 1473 |
| | 9684 | 17719 | 8565 | 4032 | 17866 | 18951 | 14592 | 14121 | 19857 | 5090 | 19600 | 22439 |
| | 21996 | 16150 | 952 | 14805 | 7722 | 18382 | 14204 | 12365 | 18343 | 18356 | 17329 | 19831 |
| | 6021 | 4198 | 17799 | 3839 | 721 | 9477 | 11433 | 18772 | 8387 | 1287 | 8906 | 17051 |

TABLE 16-continued

Sequence IDs for homolog proteins
Seq ID NO: homolog Seq ID NOs

|  | | | | | | | | | | | |
|---|---|---|---|---|---|---|---|---|---|---|---|
|  | 17649 | 19824 | 20739 | 20085 | 3542 | 5975 | 20850 | 9850 | 9401 | 8873 | 15065 | 7512 |
|  | 19446 | 6993 | 10543 | 8853 | 18552 | 12124 | 18137 | 16070 | 1895 | 21102 | 9226 | 7191 |
|  | 4365 | 12533 | 4665 | 5929 | 15384 | 20652 | 15768 | 3859 | | | | |
| 470: | 4094 | 4249 | 6447 | 417 | 9699 | 4266 | 21799 | 19998 | 8507 | 4118 | 4930 | 21755 |
|  | 7422 | 16272 | | | | | | | | | | |
| 471: | 5778 | 13042 | 20693 | 6337 | 16080 | 1704 | 20548 | 2346 | 20737 | 5152 | 6633 | 17650 |
|  | 2524 | 19716 | 3465 | 3548 | 16517 | 9459 | 12501 | 10090 | 1759 | 3273 | 12472 | 21412 |
|  | 14456 | 8135 | 18797 | 3137 | 17061 | 3402 | 9770 | 1269 | 2404 | 4759 | 7648 | 8568 |
|  | 8662 | 21076 | 11318 | 18004 | 13312 | 14804 | 6000 | 10393 | 14666 | 21987 | 3309 | 18931 |
|  | 14379 | 6524 | 14185 | 6945 | 8382 | 7629 | 16509 | 1933 | 4728 | 21025 | 17218 | 17638 |
|  | 1752 | 16078 | 3430 | 16885 | 19841 | 13228 | 577 | 3035 | 15647 | 12625 | 14586 | 21237 |
|  | 4075 | 7439 | 13720 | 15834 | 12529 | 21705 | 3905 | 17339 | 10133 | 5868 | 20567 | 18269 |
|  | 22275 | 13814 | 5994 | 10239 | 18618 | 20112 | 19325 | 13266 | 2962 | 2905 | 3571 | |
| 472: | 1296 | 2585 | 13077 | 15698 | 8567 | 10322 | 16480 | 13708 | 15397 | 17974 | 17451 | 15792 |
|  | 19280 | 10142 | 3469 | 11718 | 8642 | 15847 | 3638 | 2801 | 9326 | 3742 | 10221 | 13816 |
|  | 4884 | 3280 | 9923 | 15873 | 20214 | 10492 | 13528 | 8475 | 3713 | 15933 | 21666 | 11740 |
|  | 1633 | 11990 | 9134 | 17965 | 1788 | 6764 | 20492 | 17131 | 19212 | 13533 | 16793 | 11371 |
|  | 8594 | 20347 | 3728 | 17461 | 13823 | 8134 | 22260 | 7419 | 19185 | 22026 | 3272 | 1884 |
|  | 8730 | 8990 | 19977 | 1859 | 10999 | 4586 | 16348 | 19281 | 19991 | 11567 | 1008 | 20028 |
|  | 7658 | 20830 | 19756 | 20878 | 3207 | 20070 | 2980 | 18632 | 2087 | 6612 | 5122 | 7489 |
|  | 19025 | 20408 | 5867 | 8896 | 19056 | 19348 | 18818 | 3699 | 779 | 22456 | 11541 | 15161 |
|  | 11135 | 20058 | 2201 | 6739 | 16612 | 14992 | 19392 | 15341 | 8872 | 4204 | 21922 | 22540 |
|  | 19457 | 14075 | 4186 | 15353 | 17073 | 5661 | 13025 | 14487 | 6849 | 20671 | 6103 | 10343 |
|  | 4142 | 17366 | 14159 | 18164 | 2380 | 8153 | 15839 | 19958 | 6670 | 2506 | 8947 | 15249 |
|  | 9712 | 1377 | 18798 | 8620 | 19625 | 10515 | 9429 | 5493 | 7939 | 18930 | 8714 | 19761 |
|  | 3572 | 20073 | 19642 | 9602 | 11161 | 7180 | 10987 | 2971 | 8438 | 4675 | 8709 | 2938 |
|  | 4636 | 3485 | 9435 | 18162 | 15411 | 20078 | 14563 | 15262 | 14349 | 19829 | 9555 | 8928 |
|  | 16342 | 19361 | 1362 | 12060 | 11259 | 1940 | 18358 | 7454 | 21475 | 16972 | 20517 | 14458 |
|  | 5311 | 4246 | 3026 | 9206 | 21394 | 17932 | 5647 | 18756 | 632 | 3100 | 13204 | 18856 |
|  | 14390 | 13351 | 12707 | 15711 | 10265 | 18751 | 14958 | 5221 | 17138 | 17198 | 808 | 10940 |
|  | 11642 | 19473 | 3009 | 13298 | 15678 | 3551 | 14990 | 9133 | 19864 | 6205 | 1024 | 9670 |
|  | 22172 | 21447 | 19672 | 2996 | 6377 | 6123 | 21676 | 2672 | 19700 | 21984 | 15674 | 9974 |
|  | 14920 | 2725 | 11780 | 7537 | 15508 | 9998 | 18115 | 3670 | 16824 | 20178 | 4972 | 18635 |
|  | 8472 | 13466 | 21265 | 2831 | 8951 | 14511 | 7701 | 18486 | 7554 | 17622 | 11381 | 6309 |
|  | 22198 | 20143 | 15854 | 21658 | 12398 | 12681 | 11609 | 16625 | 12161 | 6162 | 3022 | 5109 |
|  | 7314 | 14439 | 8366 | 13945 | 12198 | 11746 | 13801 | 5301 | 15197 | 3210 | 11365 | 15206 |
|  | 17546 | 19669 | 2720 | 10926 | 1742 | 6963 | 11828 | 6972 | 1267 | 14550 | 8450 | 11591 |
|  | 19644 | 11212 | 14447 | 15125 | 18385 | 14497 | 17159 | 5903 | 832 | 17245 | 7432 | 3663 |
|  | 3061 | 9406 | 7511 | 4860 | 10188 | 13056 | 4196 | 11132 | 3684 | 3623 | 8675 | 8119 |
|  | 10193 | 16296 | 17100 | 11852 | 16004 | 17566 | 10552 | | | | | |
| 473: | 2421 | 20836 | 18507 | 17807 | 18922 | 14668 | 9172 | 2056 | 648 | 16255 | 7978 | 2322 |
|  | 11200 | | | | | | | | | | | |
| 474: | 17916 | 15231 | 15741 | 4645 | 21977 | 15829 | 10291 | 21573 | 1806 | 2663 | 8036 | 9618 |
|  | 16693 | 3960 | 15864 | 14578 | 17125 | 15924 | 21826 | 13440 | 17249 | 8650 | 20159 | 15742 |
|  | 1986 | 19706 | 22092 | 8766 | 6813 | 17830 | 10853 | 21281 | 13394 | 5285 | 8139 | 21004 |
|  | 14220 | 17563 | 2086 | 2488 | 1597 | 4698 | 13233 | 4654 | 1250 | 15737 | 2907 | 1469 |
|  | 9957 | 13288 | 6516 | 22526 | 16496 | 14873 | 10471 | 18290 | 3086 | 11953 | 18592 | 3185 |
|  | 9418 | 17135 | 8081 | 9593 | 19180 | 4673 | 7979 | 1300 | 13933 | 16544 | 16782 | 15551 |
|  | 8460 | 15960 | 13997 | 3405 | 1566 | 21046 | 8636 | 17134 | 6596 | 6512 | 13346 | 15639 |
|  | 21591 | 15042 | 12093 | 14396 | 9252 | 18637 | 22523 | 6953 | 16784 | 6262 | 16933 | 22448 |
|  | 4612 | 19863 | 6076 | 19303 | 12192 | 16828 | 17089 | 4133 | 19601 | 6118 | 3344 | 15088 |
|  | 14986 | 21070 | 2153 | 771 | 3291 | 10644 | 20638 | 4377 | 21183 | 9519 | 21234 | 11970 |
|  | 21215 | 18173 | 18301 | 17764 | 13810 | 10948 | 3781 | 21029 | 11162 | 16613 | 18091 | 22003 |
|  | 3801 | 21866 | 22213 | 6526 | 5846 | 20765 | 21771 | 14860 | 5007 | 861 | 6743 | 5529 |
|  | 14267 | 14880 | 21391 | 10210 | 5693 | 5970 | 3793 | 15855 | 1007 | 13001 | 6878 | 9875 |
|  | 16912 | 19329 | 13614 | 10333 | 13714 | 8204 | 21112 | 6903 | 1133 | 21262 | 21547 | 15703 |
|  | 21338 | 6248 | 15242 | 13567 | 16788 | 11020 | 18655 | 19496 | 10528 | 22414 | 8142 | 17440 |
|  | 20388 | 7760 | 17480 | 18357 | 14595 | 12914 | 2829 | 16249 | 2569 | 7096 | 6689 | 12534 |
|  | 6105 | 16041 | 9145 | 9242 | 1552 | 1379 | 10313 | 9596 | 10872 | 11771 | 3268 | 15445 |
|  | 593 | 5820 | 18410 | 6984 | 14744 | 9713 | 10053 | 1383 | 8837 | 676 | 4305 | 10421 |
|  | 2944 | 20363 | 19120 | 7463 | 16753 | 20969 | 18430 | 10227 | 12905 | 11066 | 6057 | 13677 |
|  | 18640 | 4083 | 1527 | 285 | 19285 | 5385 | 17557 | 20851 | 15693 | 17304 | 1683 | 14391 |
|  | 15965 | 19854 | 8425 | 14916 | | | | | | | | |
| 475: | 17494 | 14507 | 18062 | 7991 | 15677 | 2025 | 16965 | 15154 | 22007 | 1299 | 4864 | 1869 |
|  | 18259 | 5076 | 18894 | 10621 | 1194 | 21241 | 4280 | 3561 | 13154 | 8656 | 12338 | 18120 |
|  | 3266 | 19426 | 6888 | 17781 | 1697 | 1251 | 15687 | 7276 | 7126 | 4960 | 7248 | 3598 |
|  | 8316 | 21056 | 7036 | 15143 | 13926 | 18581 | 16569 | 4999 | 20923 | 5501 | 4338 | 10604 |
|  | 10287 | 9635 | 11127 | 8702 | 12055 | 20545 | 19675 | 16542 | 11075 | 17224 | 15872 | 11732 |
|  | 6843 | 1680 | 5509 | 10865 | 16067 | 3406 | 18908 | 8719 | 4022 | 6395 | 4623 | 22346 |
|  | 12095 | 17333 | 5395 | 17305 | 10611 | 7631 | 18432 | 21902 | 7759 | 3032 | 10224 | 17508 |
|  | 1337 | 3062 | 10847 | 4797 | 20901 | 3679 | 21087 | 9348 | 17993 | 3743 | 10092 | 14394 |
|  | 9088 | 16620 | 9528 | 17353 | 12317 | 17070 | 22147 | 22431 | 10652 | 9220 | 12697 | 20558 |
|  | 11610 | 11793 | 17146 | 2355 | 4084 | 3480 | 10028 | 2838 | 20595 | 20642 | 8186 | 16379 |
|  | 10383 | 4591 | 4288 | 8591 | 15333 | 9201 | 15765 | 5294 | 3608 | 4038 | 2297 | 7144 |
|  | 1916 | 16736 | 3319 | 11341 | 10440 | 4734 | 20772 | 4271 | 19954 | 7624 | 2955 | 17939 |
|  | 21353 | 11932 | 19797 | 2289 | 9733 | 10875 | 12426 | 18048 | 20434 | 18464 | 630 | 8403 |
|  | 6184 | 18819 | 5523 | 17228 | 16302 | 10762 | 9202 | 16022 | 17350 | 11159 | 4597 | 17792 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 15612 | 4183  | 5466  | 17341 | 10729 | 21044 | 9980  | 4892  | 1108  | 1406  | 18198 | 1264  |
|      | 712   | 13091 | 8047  | 14712 | 22157 | 7745  | 6934  | 7635  |       |       |       |       |
| 476: | 3284  | 22524 | 15910 | 13589 | 1006  | 11575 | 20349 | 10911 | 18523 | 22545 | 13067 | 2372  |
|      | 10217 | 9609  | 535   | 306   | 507   | 533   | 5233  | 478   | 4966  | 9015  | 21390 | 314   |
|      | 1764  | 12941 | 18461 | 9866  | 21665 | 7323  | 5049  | 9997  | 7294  | 5240  | 7571  | 6367  |
|      | 19001 | 13429 | 2814  | 21443 | 20459 | 1880  | 1396  | 3615  | 13867 | 7787  | 22538 | 13411 |
|      | 13344 | 8482  | 1205  | 18398 | 13083 | 12473 | 14941 | 17485 | 1550  | 757   | 11281 | 11029 |
|      | 21967 | 827   | 1873  | 21174 | 14091 | 5281  | 885   | 7332  | 8229  | 10933 | 12672 | 21103 |
|      | 4400  | 1012  | 15883 | 7812  | 7121  | 22179 | 16424 | 1339  | 1866  | 3474  | 11617 | 19918 |
|      | 16996 | 14296 | 1352  | 17699 | 9135  | 12367 | 19265 | 15111 | 3388  | 20896 | 20167 | 6697  |
|      | 6564  | 10047 | 19989 | 9358  | 22350 | 21749 | 15375 | 4618  | 531   | 16283 | 300   | 534   |
|      | 286   | 6575  | 7081  | 11468 | 2641  | 13543 | 15224 | 3097  | 15540 | 19380 | 19031 | 14287 |
|      | 6260  | 5051  | 12104 | 13901 | 11086 | 12459 | 12824 | 919   | 13271 | 15196 | 6303  | 4194  |
|      | 14638 | 1182  | 15803 | 1842  | 19299 | 7287  | 2857  | 17664 | 21589 | 11961 | 19154 | 12506 |
|      | 21814 | 4986  | 5343  | 21106 | 6334  | 21437 | 20936 | 11195 | 21506 | 2582  | 22069 | 5476  |
|      | 3533  | 7949  | 19583 | 22113 | 4677  | 18511 | 4730  | 696   | 9569  | 17797 | 18687 | 7097  |
|      | 20259 | 15252 | 13221 | 13305 | 450   | 22502 | 14915 | 21157 | 19855 | 11089 | 1744  | 10324 |
|      | 19917 | 6730  | 2195  | 20371 | 3563  | 12591 | 16308 | 7626  | 4212  | 19798 | 19458 | 5691  |
|      | 18292 | 8005  | 20912 | 21422 | 6721  | 10358 | 13601 | 6637  | 1272  | 17775 | 16130 | 21296 |
|      | 2832  | 830   | 14553 | 6434  | 18295 | 17956 | 829   | 12043 | 2457  | 5731  | 4395  | 10908 |
|      | 3209  | 13959 | 12384 | 5220  | 21843 | 19341 | 16539 | 19751 | 20779 | 1281  | 13763 | 17745 |
|      | 16586 | 7955  | 12705 | 15449 | 988   | 20859 | 1768  | 11129 | 6547  | 22518 | 5552  | 9854  |
|      | 11376 | 6669  | 5359  | 9132  | 10964 | 14922 | 1879  | 22087 | 13137 | 17298 | 3333  | 13752 |
|      | 20301 | 19370 | 2425  | 14659 | 6946  | 19538 | 14273 | 15340 | 6427  | 17165 | 15603 | 7257  |
|      | 12419 | 10809 | 8003  | 13658 | 14064 | 4221  | 7387  | 13284 | 20981 | 2316  | 3116  | 8418  |
|      | 3386  | 6508  | 18217 | 3578  | 22249 | 992   | 13442 | 3471  | 14855 | 19949 | 5277  | 19885 |
|      | 2816  | 10917 | 9436  | 18538 | 18659 | 12816 | 12308 | 15943 | 2515  | 20364 | 14701 | 8193  |
|      | 17579 | 22076 | 8890  | 2649  | 9329  | 21073 | 8376  | 15177 | 10882 | 859   | 5990  | 9814  |
|      | 16053 | 5209  | 7718  | 3144  | 13848 | 22428 | 19076 | 5454  | 17056 | 14918 | 4088  | 11270 |
|      | 5837  | 9604  | 22455 | 19840 | 12234 | 1149  | 801   | 953   | 9960  | 21301 | 1656  | 3755  |
|      | 12278 | 22119 | 13793 | 21098 | 1005  | 10264 | 13037 | 11702 | 20954 | 5581  | 5063  | 1118  |
|      | 6454  | 20632 | 1696  | 6301  | 9792  | 5396  | 19474 | 14911 | 20315 | 9381  | 4111  | 11600 |
|      | 7691  | 13374 | 2932  | 3071  | 18551 | 22362 | 1431  | 8710  | 12923 | 6509  | 19229 | 14012 |
|      | 5372  | 12362 | 17380 | 14108 | 20272 | 16391 | 19694 | 13395 | 5132  | 901   | 14568 | 17630 |
|      | 2371  | 4694  | 12396 | 15369 | 13051 | 16597 | 3697  | 10741 | 16309 | 4927  | 13396 | 21621 |
|      | 8841  | 16662 | 11120 | 14081 | 21259 | 19449 | 8692  | 9484  | 15204 | 6565  | 18317 | 14304 |
|      | 2769  | 14320 | 2978  | 9294  | 7482  | 9493  | 1277  | 4952  | 7813  | 7306  | 12296 | 21386 |
|      | 12021 | 6645  | 16505 | 9286  | 22489 | 3622  | 13745 | 16653 | 19069 | 7780  | 15219 | 16969 |
|      | 14762 | 10802 | 10479 | 16663 | 3678  | 16713 | 7751  | 13703 | 3630  | 4691  | 9472  | 10709 |
|      | 8542  | 7060  | 6112  | 22457 | 21974 | 20476 | 7333  | 6482  | 14526 | 7151  | 2644  | 835   |
|      | 10655 | 12264 | 9315  | 2786  | 16253 | 9488  | 5634  | 17372 | 3836  | 18362 | 11559 | 7637  |
|      | 4946  | 18143 | 12059 | 6995  | 17942 | 3772  | 3625  | 788   | 20809 | 16318 | 18862 | 7143  |
|      | 13134 | 9280  | 22095 | 18903 | 3706  | 15256 | 18593 | 5764  | 11115 | 12583 | 11568 | 13613 |
|      | 2331  | 5136  | 8073  | 15998 | 5630  | 11304 | 19137 | 5817  | 5580  | 18341 | 8588  | 12540 |
|      | 2454  | 4970  | 17445 | 2401  | 11869 | 6193  | 2434  | 3951  | 10889 | 5190  | 13207 | 16465 |
|      | 5825  | 17346 | 3323  | 13177 | 5354  | 2210  | 9333  | 13864 | 21502 | 19147 | 15973 | 9673  |
|      | 11863 | 9771  | 9608  | 11716 | 16811 | 18575 | 9584  | 12794 | 21399 | 20485 | 9218  | 18691 |
|      | 3350  | 18263 | 4846  | 544   | 19667 | 9933  | 4140  | 1318  | 20418 | 11128 | 20105 | 16734 |
|      | 2376  | 15699 | 7061  | 4232  | 15357 | 14036 | 5339  | 7107  | 19030 | 7165  | 21370 | 12103 |
|      | 4848  | 13211 | 22530 | 15360 | 12863 | 9975  | 6398  | 14067 | 16683 | 21170 | 1924  | 890   |
|      | 8155  | 15866 | 10131 | 7187  | 4332  | 1235  | 20330 | 12927 | 7088  | 5099  | 2302  | 12424 |
|      | 8303  | 17466 | 14322 | 11383 | 2282  | 15956 | 3414  | 12982 | 18548 | 15665 | 10961 | 21084 |
|      | 10824 | 18440 | 16819 | 3730  | 13940 | 18821 | 14864 | 1818  | 19607 | 7969  | 6546  | 16771 |
|      | 5441  | 8459  | 18266 | 5000  | 15749 | 13014 | 14274 | 8444  | 4707  | 13097 | 15930 | 11872 |
|      | 2621  | 7158  | 6942  | 18502 | 5408  | 10837 | 21928 | 13800 | 5188  | 19614 | 16117 | 4719  |
|      | 1833  | 13499 | 3107  | 21492 | 12503 | 21929 | 7921  | 1429  | 14398 | 22189 | 6439  | 12993 |
|      | 12307 | 19714 | 6650  | 21398 | 18994 | 747   | 5932  | 18630 | 6683  | 1921  | 15651 | 5594  |
|      | 6958  | 13597 | 19763 | 10097 | 14124 | 14687 | 1094  | 5780  | 7770  | 7688  | 15110 | 5797  |
|      | 7907  | 21169 | 3329  | 12627 | 4065  | 19882 | 22067 | 19211 | 2061  | 7038  | 8909  | 16914 |
|      | 13129 | 19881 | 16317 | 1551  | 13235 | 14888 | 1201  | 20264 | 7800  | 7526  | 2209  | 7384  |
|      | 5887  | 10798 | 15317 | 10223 | 11351 | 10105 | 10661 | 15014 | 2908  | 16412 | 22277 | 19851 |
|      | 12003 | 19616 | 11003 | 7768  | 6166  | 4620  | 8674  | 20541 | 3458  | 1240  | 15787 | 20099 |
|      | 9282  | 11480 | 4994  | 19545 | 802   | 17144 | 13420 | 13439 | 14301 | 1357  | 14011 | 7026  |
|      | 1145  | 6281  | 5258  | 6013  | 2805  | 18662 | 7992  | 9661  | 19875 | 11156 | 3619  | 14086 |
|      | 20948 | 16946 | 3456  | 6143  | 786   | 6709  | 5954  | 17926 | 20839 | 22351 | 21072 | 13277 |
|      | 15307 | 11701 | 15113 | 22057 | 6368  | 7704  | 18694 | 3644  | 12154 | 3794  | 21257 | 21638 |
|      | 18386 | 18111 | 21498 | 10731 | 13776 | 5539  | 14530 | 20282 | 7762  | 9529  | 17675 | 15191 |
|      | 12380 | 14865 | 15825 | 2818  | 5956  | 16442 | 6255  | 5901  | 8220  | 6918  | 18578 | 17465 |
|      | 13297 | 2495  | 21913 | 4526  | 16085 | 10965 | 15558 | 22565 | 22251 | 810   | 14127 | 7570  |
|      | 2692  | 13168 | 10912 | 15666 | 20574 | 4894  | 2526  | 10115 | 18982 | 19796 | 4020  | 2984  |
|      | 11522 | 11245 | 21570 | 8695  | 427   | 16749 | 17392 | 7325  | 10184 | 2132  | 20312 | 4655  |
|      | 16568 | 21093 | 13882 | 5730  | 7976  | 7079  | 13035 | 2800  | 16658 | 18348 | 16408 | 4157  |
|      | 5264  | 8112  | 509   | 307   | 305   | 12545 | 2037  | 11704 | 9571  | 21379 | 3712  | 7685  |
|      | 4483  | 18456 | 22341 | 3397  | 11197 | 13107 | 675   | 16006 | 532   | 20604 | 18536 |       |
| 477: | 14477 | 7991  | 15716 | 18037 | 2783  | 11158 | 22007 | 11719 | 9318  | 11530 | 1246  | 21214 |
|      | 10621 | 8796  | 4280  | 19646 | 1037  | 3266  | 19426 | 6571  | 6888  | 17781 | 1697  | 10045 |
|      | 1251  | 14694 | 7276  | 7126  | 12814 | 14355 | 17583 | 1180  | 17847 | 8316  | 20573 | 7140  |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 18820 | 7036 | 21056 | 15143 | 13926 | 18581 | 4999 | 20923 | 5501 | 1142 | 3253 | 7339 |
| | 4338 | 16547 | 15305 | 10287 | 11127 | 20511 | 19012 | 13060 | 4347 | 12691 | 12055 | 3704 |
| | 15743 | 19675 | 16542 | 21229 | 11524 | 9274 | 11075 | 8804 | 17224 | 3133 | 3607 | 10123 |
| | 11459 | 11620 | 2973 | 15872 | 11732 | 19109 | 740 | 1359 | 17419 | 10051 | 6843 | 1680 |
| | 16067 | 3406 | 4041 | 4022 | 9511 | 2595 | 4623 | 2369 | 19292 | 17333 | 5395 | 17305 |
| | 10611 | 1428 | 7631 | 15733 | 18432 | 1959 | 21902 | 6814 | 13183 | 20320 | 12959 | 3032 |
| | 4738 | 13205 | 22294 | 3286 | 19123 | 13158 | 20759 | 22152 | 18157 | 16447 | 10847 | 14538 |
| | 4797 | 21087 | 7452 | 19143 | 16659 | 16620 | 11651 | 17070 | 10166 | 6601 | 15463 | 22431 |
| | 10652 | 13842 | 11862 | 19136 | 1897 | 9220 | 12697 | 22065 | 20558 | 17946 | 13996 | 16162 |
| | 7667 | 10376 | 2355 | 4084 | 14756 | 8726 | 10960 | 18769 | 3480 | 2838 | 20595 | 20275 |
| | 1292 | 4853 | 20642 | 11502 | 11759 | 11992 | 9201 | 12553 | 14724 | 15765 | 17537 | 5294 |
| | 9934 | 3608 | 15894 | 19202 | 4614 | 3319 | 11943 | 7304 | 4298 | 9147 | 11434 | 11341 |
| | 10440 | 4734 | 13768 | 7695 | 7039 | 10493 | 13737 | 14607 | 16005 | 5151 | 2008 | 20772 |
| | 4271 | 19954 | 4883 | 11303 | 15488 | 5027 | 17894 | 16991 | 7608 | 5609 | 16228 | 8198 |
| | 18306 | 2556 | 6626 | 5829 | 13676 | 20616 | 12968 | 22378 | 16437 | 7624 | 20184 | 6039 |
| | 10274 | 13230 | 16495 | 10978 | 13806 | 5631 | 6912 | 2955 | 21137 | 12918 | 16985 | 16430 |
| | 8847 | 22400 | 13954 | 1905 | 19874 | 18505 | 9524 | 7297 | 20802 | 5035 | 20321 | 12454 |
| | 9019 | 13953 | 2462 | 4887 | 16352 | 1889 | 17058 | 8559 | 7962 | 11126 | 15081 | |
| | 22027 | 2791 | 7622 | 8042 | 4393 | 8437 | 1128 | 12634 | 21033 | 21247 | 5138 | 1952 |
| | 10420 | 4794 | 21353 | 11932 | 13160 | 19797 | 13358 | 2289 | 10875 | 9733 | 12426 | 14341 |
| | 7723 | 5120 | 12064 | 10942 | 15784 | 8171 | 17196 | 20434 | 21075 | 20432 | 4222 | 8716 |
| | 18464 | 12196 | 630 | 8403 | 8582 | 6184 | 18819 | 9392 | 16256 | 4056 | 17228 | 16302 |
| | 10762 | 13412 | 17350 | 12703 | 17792 | 4597 | 11159 | 7291 | 1072 | 4183 | 5466 | 17341 |
| | 4892 | 1108 | 22046 | 1630 | 17859 | 11923 | 5617 | 18198 | 20318 | 1264 | 22123 | 2225 |
| | 1997 | 13091 | 5701 | 8047 | 6109 | 22157 | 7745 | 16695 | 6934 | 1574 | 18516 | |
| 478: | 19887 | 10135 | 21002 | 14580 | 12123 | 15919 | 12579 | 5844 | 2744 | 4525 | 1601 | 15195 |
| | 13066 | 547 | 20326 | 18377 | 314 | 8202 | 4733 | 7841 | 16690 | 17977 | 2012 | 6367 |
| | 10918 | 3637 | 18964 | 16866 | 17780 | 7398 | 19262 | 8152 | 16337 | 16385 | 15522 | 10127 |
| | 11277 | 18934 | 3901 | 22130 | 7812 | 16808 | 7324 | 19680 | 2408 | 19428 | 11882 | 19522 |
| | 16434 | 9215 | 10784 | 19210 | 9199 | 9487 | 12925 | 15096 | 6578 | 16140 | 12862 | 976 |
| | 11288 | 12658 | 20505 | 12973 | 11420 | 19873 | 8358 | 17414 | 300 | 8602 | 17310 | 6259 |
| | 15328 | 15736 | 16123 | 1022 | 4666 | 6077 | 8815 | 10323 | 18236 | 1980 | 4532 | 17009 |
| | 7605 | 19668 | 1127 | 2857 | 17664 | 21589 | 11961 | 19154 | 6093 | 3017 | 11359 | 3533 |
| | 21439 | 16651 | 4677 | 18511 | 4730 | 696 | 9569 | 17797 | 18687 | 7097 | 20259 | 450 |
| | 9399 | 14915 | 21157 | 20002 | 20371 | 3563 | 12591 | 16308 | 15626 | 7639 | 2807 | 13480 |
| | 8017 | 8740 | 16746 | 716 | 21161 | 1662 | 7626 | 4212 | 19798 | 19458 | 5691 | 18292 |
| | 16130 | 21296 | 2832 | 830 | 14553 | 6434 | 18295 | 22345 | 20848 | 19451 | 4148 | 6755 |
| | 20779 | 1281 | 17745 | 16586 | 7955 | 12705 | 15449 | 988 | 20859 | 1768 | 11129 | 6547 |
| | 22518 | 5552 | 9854 | 11376 | 6669 | 5359 | 9132 | 10964 | 1879 | 22087 | 13137 | 17298 |
| | 3333 | 13752 | 20301 | 19370 | 2425 | 6946 | 14568 | 4694 | 21621 | 8841 | 16662 | 11120 |
| | 14081 | 7280 | 15204 | 6565 | 1345 | 14320 | 2978 | 9294 | 7482 | 9493 | 1277 | 7813 |
| | 7306 | 12296 | 12021 | 6645 | 9286 | 22489 | 13745 | 16653 | 19069 | 7780 | 16663 | 20476 |
| | 7333 | 6482 | 14526 | 7151 | 14429 | 6992 | 788 | 4653 | 2925 | 17755 | 9673 | 7253 |
| | 9771 | 3362 | 11716 | 21088 | 4458 | 18575 | 9584 | 12794 | 21399 | 14605 | 15265 | 10699 |
| | 6281 | 18662 | 7992 | 9661 | 19875 | 11156 | 3619 | 14086 | 20948 | 16946 | 3456 | 6143 |
| | 16455 | 786 | 6709 | 5954 | 17926 | 20839 | 22351 | 19605 | 13277 | 16667 | 9507 | 1392 |
| | 9772 | 15558 | 21992 | 22438 | 5600 | 18371 | 10363 | 11144 | 11875 | 3318 | 21951 | |
| | 4300 | 19052 | 16019 | 10566 | 17447 | 7523 | 21878 | 18982 | 5589 | 4804 | 15183 | 17109 |
| | 19009 | 17084 | 20892 | 22180 | 11635 | 13124 | 4102 | 12865 | 2079 | 3506 | 509 | 6351 |
| | 4815 | 532 | 372 | 6844 | 9299 | 5904 | 14428 | | | | | |
| 479: | 21743 | 1760 | 3495 | 6194 | 14521 | 17761 | 15144 | 21403 | 16214 | 6891 | 10614 | 7713 |
| | 1057 | 3816 | 17150 | 12489 | 10225 | 5157 | 8783 | | | | | |
| 480: | 21754 | 6794 | 12450 | 9614 | 4412 | 5824 | 9276 | 21813 | 1463 | 11059 | 4808 | 13206 |
| | 9578 | 13428 | 3072 | 15596 | 4328 | 3690 | 8876 | 7086 | 15462 | 6444 | 12263 | 8993 |
| | 5420 | 6407 | 12246 | 1242 | 4404 | 4259 | 22020 | 4611 | 9408 | 14680 | 3680 | 10238 |
| | 9797 | 6568 | 8934 | 7500 | | | | | | | | |
| 481: | 17081 | 17400 | 17733 | 17377 | 12323 | 9631 | 5203 | 18639 | 16889 | 16035 | 17467 | 19493 |
| | 3726 | 14585 | 14637 | | | | | | | | | |
| 482: | 6638 | 7562 | 10477 | 1852 | 4661 | 1068 | 13778 | 18473 | 9233 | 12209 | 5474 | 831 |
| | 3220 | 16416 | 19485 | 21657 | 17736 | 2773 | 6559 | 19274 | 11791 | 2362 | 1290 | |
| 483: | 15521 | 9926 | 9372 | 3535 | 14815 | 17378 | 15342 | 16992 | 22270 | 6694 | 8651 | 10442 |
| | 9501 | 20248 | 14291 | 19051 | 3324 | 8926 | 19254 | 5893 | 16393 | 10149 | 19420 | 11920 |
| | 8831 | 8248 | 4517 | 12007 | 9386 | 15721 | 21801 | 17774 | 10932 | 11965 | 11946 | |
| 484: | 3750 | 6233 | 2713 | 11380 | 12023 | 5512 | 8397 | 9963 | 4401 | 17914 | 21042 | 20938 |
| | 15212 | 2563 | 21028 | 4455 | 18141 | 21707 | 15335 | 2976 | 12163 | | | |
| 485: | 12915 | 8353 | 10649 | 15559 | 21532 | 1766 | 2706 | 8964 | 20052 | 20655 | 17361 | 14417 |
| | 5510 | 14469 | 5001 | 8855 | 14600 | 20649 | 14614 | 15591 | 20286 | 2606 | 9471 | 1305 |
| | 12051 | 13261 | 12077 | 17015 | 15608 | 2231 | 9209 | 13625 | 14471 | 16566 | 18336 | 20911 |
| | 10270 | 15117 | 22496 | 11939 | 2250 | 12212 | 10593 | 15979 | 5988 | | | |
| 486: | 21080 | 8598 | 20902 | 564 | 3747 | 14584 | 4202 | 15248 | 1415 | 21487 | 2776 | 8440 |
| | 6441 | 6856 | 4639 | 13249 | 14411 | 6300 | 7237 | 7568 | 8497 | 20720 | 5330 | 2288 |
| | 3218 | 10413 | 16585 | 19827 | 2466 | 13415 | 19277 | 19479 | 4274 | 5139 | 8341 | 13715 |
| 487: | 6455 | 20477 | 1176 | 8864 | 15945 | 3915 | 15571 | 16266 | 6450 | 1211 | 18350 | 6737 |
| | 21409 | 1653 | 14641 | 22433 | 16158 | 5655 | 11725 | | | | | |
| 488: | 13633 | 11464 | 17818 | 4487 | 22079 | 19811 | 14672 | 20311 | 5875 | 1804 | 5805 | 8760 |
| | 3617 | 12276 | 17631 | 6644 | 1838 | 1416 | 13999 | 2846 | 1536 | 21067 | 951 | 9346 |
| | 9547 | 21436 | 4596 | 13884 | 12781 | 4010 | 10761 | 12933 | 16680 | 14715 | 12582 | 16262 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 4172 | 17700 | 6985 | 11107 | 17731 | 21246 | 3488 | 4816 | 11798 | 4381 | 9680 | 2173 |
| | 8661 | 11802 | 13722 | 4211 | 7971 | 6750 | 14655 | 2765 | 2588 | 17564 | 9533 | 14335 |
| | 13862 | 22447 | 12417 | 16557 | 9483 | 20169 | 6497 | 2050 | 3881 | 20747 | 3124 | 21130 |
| | 11454 | 11582 | 14837 | 2614 | 4779 | 6358 | 16323 | 14350 | 7275 | 16234 | 10634 | 8984 |
| | 18673 | 3036 | 12657 | 921 | 5211 | 10884 | 8362 | 20529 | 8627 | 7103 | 8149 | 15778 |
| | 6773 | 11819 | 1672 | 12073 | 7102 | 20447 | 2872 | 7433 | 19593 | 19806 | 21911 | 5516 |
| | 15286 | 11661 | 8992 | 14562 | 3219 | 17911 | 15808 | 5506 | 20741 | 21530 | 15240 | 20344 |
| | 18214 | 15575 | 12427 | 3217 | 20435 | 7796 | 2375 | 11017 | 10944 | 13834 | 12971 | 20581 |
| | 6080 | 16884 | 1900 | 7505 | 3937 | 11188 | 811 | 9207 | 2830 | 20690 | 12613 | 5666 |
| | 4380 | 15312 | 18349 | 17639 | 10145 | 13494 | 664 | 6567 | 13052 | 6979 | 13432 | 17364 |
| | 2224 | 22187 | 6961 | 13798 | 7944 | 4112 | 9995 | 15431 | 15530 | 10764 | 1676 | 8678 |
| | 7407 | 22255 | 22276 | 8963 | 4880 | 11857 | 15344 | 7420 | 20168 | 20601 | 21712 | 7009 |
| | 15363 | 8126 | 3045 | 7044 | 2098 | 12067 | 13898 | 7690 | | | | |
| 489: | 21080 | 8598 | 20111 | 19932 | 20211 | 6441 | 6856 | 13249 | 4639 | 14411 | 6300 | 15103 |
| | 8497 | 20720 | 5330 | 2288 | 19827 | 16585 | 13715 | | | | | |
| 490: | 18170 | 1316 | 6082 | 19848 | 9272 | 9871 | 15911 | 5917 | 19405 | 7429 | 21327 | 20596 |
| | 8045 | 10178 | 4720 | 16346 | 7401 | 11417 | 5176 | 9427 | 22532 | 19611 | 6616 | 10826 |
| | 2235 | 7529 | 22399 | 668 | 22163 | 10888 | 10947 | 17345 | 20889 | 1019 | 13964 | 12858 |
| | 12745 | 21803 | 19731 | 15370 | 19455 | | | | | | | |
| 491: | 14629 | | | | | | | | | | | |
| 492: | 9026 | 18203 | 9034 | 17176 | 19316 | 18425 | 10191 | 3057 | 4291 | 19993 | 19117 | 633 |
| | 19344 | 14181 | 6581 | 17129 | 12690 | 10130 | 10179 | 8823 | 14022 | 7424 | 4363 | |
| 493: | 11676 | 10500 | 20010 | 22061 | 13770 | 5046 | 17871 | 10828 | 15052 | 1942 | 11251 | 10057 |
| | 14213 | | | | | | | | | | | |
| 494: | 2867 | 20983 | 17787 | 12926 | 13702 | 2680 | 4336 | 1898 | 7033 | 4692 | 1931 | 11547 |
| | 4004 | 17355 | 7966 | 21453 | 6141 | 17522 | 20009 | 20155 | 3861 | 20641 | 13805 | 9004 |
| | 5518 | 9100 | 6706 | 6460 | 9101 | 19945 | 14203 | 18615 | 8818 | 2078 | 21644 | 13350 |
| | 9869 | 8593 | | | | | | | | | | |
| 495: | 10049 | 5921 | 9432 | 4046 | 3753 | 21873 | 9833 | 14362 | 8333 | 13672 | 19390 | 1216 |
| | 3131 | 18992 | 9486 | 11253 | | | | | | | | |
| 496: | 3127 | 1607 | 15003 | 2751 | 9086 | 18256 | 7201 | 3526 | 20063 | 8184 | 14575 | 14132 |
| | 3886 | 15754 | 11997 | 10334 | 8002 | 19176 | 6325 | 12719 | 15443 | 14454 | 10921 | 14581 |
| | 14745 | 9990 | 9911 | 1762 | 10972 | 16402 | 1520 | 16638 | 1856 | 10874 | 3967 | 20026 |
| | 4426 | 20686 | 9163 | 20462 | 20942 | 17529 | 11988 | 17803 | 8476 | 6783 | 21168 | 19191 |
| | 2426 | 12096 | 15664 | 7561 | 11891 | 12826 | 17289 | 3387 | 19858 | 12743 | 9853 | 19481 |
| | 615 | 8569 | 14610 | 1310 | 14283 | 3903 | 16792 | 22556 | 12950 | 6759 | 5113 | 5803 |
| | 20040 | 13866 | 7531 | 12876 | 9534 | 7024 | 13251 | 663 | 2377 | 20537 | 22479 | 20413 |
| | 17045 | 11984 | 22225 | 3341 | 1812 | 7226 | 19298 | 20768 | 6766 | 10544 | 12090 | 22407 |
| | 18361 | 8222 | 5162 | 22240 | 11887 | 8295 | 15781 | 14468 | 2137 | 9880 | 12861 | 16260 |
| | 21244 | 21191 | 22495 | | | | | | | | | |
| 497: | 4536 | 12720 | 13909 | 16764 | 14068 | 5500 | 2174 | 17809 | 20213 | | | |
| 498: | 7246 | 13566 | 4922 | 7189 | 11908 | 21432 | 19713 | 9021 | 8001 | 4169 | 9591 | 18319 |
| | 12836 | 14209 | 15108 | 20572 | 4881 | 2021 | 2629 | 13362 | 21200 | 14093 | 18917 | 5199 |
| | 21121 | 8529 | 17053 | 2009 | 2989 | 6906 | 19492 | 5789 | 6127 | 7577 | 22482 | 6916 |
| | 4185 | 8063 | 10716 | 15947 | 17616 | 22376 | 714 | 9711 | 8995 | 19804 | 16484 | 10432 |
| | 16415 | 18397 | 17120 | 5711 | 20348 | 11410 | 22426 | 5459 | 17025 | 20374 | 5057 | 3996 |
| | 1399 | 16384 | 8557 | 3401 | 18399 | 9470 | 18719 | 2158 | 3928 | 19925 | 15780 | 1172 |
| | 19003 | 4754 | 6752 | 7557 | 15694 | 2929 | 15268 | 8286 | 16534 | 8056 | 2719 | 1955 |
| | 18895 | 5457 | 22161 | 17041 | 8512 | 21678 | 7854 | 18098 | 13647 | 15831 | 11038 | 15162 |
| | 8205 | | | | | | | | | | | |
| 499: | 14500 | 1413 | 1282 | 1702 | 21840 | 19911 | 17917 | 16929 | 17820 | 4161 | 16375 | 12532 |
| | 18092 | 1532 | 5902 | 19438 | 13718 | 6024 | 19735 | 13044 | 2787 | 19276 | 8082 | 9213 |
| | 13875 | 2729 | 19946 | 19636 | 13441 | 11906 | 5009 | 21052 | 8166 | 12467 | 5788 | 10596 |
| | 21948 | 8953 | 11461 | 18890 | 14782 | 22256 | 22200 | 7502 | 22419 | 22028 | 9688 | 19279 |
| | 20234 | 20394 | 3662 | 13624 | 5037 | 17822 | 19294 | | | | | |
| 500: | 17384 | 19962 | 11922 | 12514 | 975 | 11652 | 22218 | 7145 | 9489 | 16374 | 595 | 10439 |
| | 11174 | 6276 | 2673 | 2273 | 5345 | 20790 | 14336 | 21369 | 16362 | 13555 | 12890 | 20920 |
| | 16827 | 21155 | 6409 | 16703 | 4160 | 18249 | 5053 | 1371 | 16010 | 3265 | 21504 | 10158 |
| | 7203 | 22449 | 12631 | 15261 | 19335 | 9198 | 7318 | 16504 | 7195 | 4503 | 21207 | 10641 |
| | 8201 | 15388 | 10167 | 17571 | 2611 | 3434 | 12571 | 13501 | 9308 | 8098 | 13986 | 4294 |
| | 6690 | 17338 | 11438 | 16124 | 14788 | 9510 | 20668 | 22077 | 11494 | 16723 | 5320 | 3714 |
| | 18672 | 19620 | 11228 | 1183 | 17223 | 1503 | 20710 | 7345 | 17503 | 10327 | 18402 | 18415 |
| | 3756 | 1040 | 19384 | 13970 | 1810 | 20021 | 12766 | 10244 | 7980 | 16489 | 3481 | 1266 |
| | 2213 | 5652 | 5230 | 6678 | 19037 | 22307 | 5389 | 18546 | 3014 | 22259 | | |
| 501: | 16649 | 18243 | 16414 | 4207 | 20589 | 9444 | 16449 | | | | | |
| 502: | 22464 | 13448 | 15971 | 16611 | 16582 | 2337 | 16931 | 10640 | 13818 | 19924 | 15868 | 13017 |
| | 5333 | 7271 | 18106 | 6613 | 20999 | 5327 | 19529 | 19566 | 15187 | 19703 | 13925 | 6927 |
| | 17013 | 11388 | 20074 | 15701 | 3553 | 10267 | 14357 | | | | | |
| 503: | 10199 | 16886 | 2241 | 18245 | 1886 | 9716 | 7985 | 8744 | 20562 | 11084 | 13088 | 19819 |
| | 22302 | 17049 | 990 | 2306 | 15235 | 2417 | 1433 | 2115 | 19923 | 19064 | 1002 | 16264 |
| | 8492 | 2272 | 709 | 13399 | 12601 | 4956 | 19182 | 6191 | 7426 | 9434 | 14994 | 11105 |
| | 6247 | 10698 | 8645 | | | | | | | | | |
| 504: | 8253 | 556 | 21865 | 11532 | 13731 | 17389 | 13431 | 10078 | 1271 | 12610 | 10733 | 21490 |
| | 10485 | 18060 | 14669 | 11177 | 20124 | 7109 | 12716 | 1462 | 14936 | 5986 | 8097 | 5080 |
| | 6289 | 3372 | 19867 | 2939 | 10924 | 773 | 11608 | 16138 | 4495 | 6375 | 3829 | 10354 |
| | 13565 | 9492 | 7772 | 17813 | 19072 | 19386 | 6691 | 804 | 12615 | 3475 | 9031 | 16143 |
| | 1291 | 12201 | 12820 | 1857 | 14937 | 19224 | 20789 | 10619 | 4585 | 1580 | 8663 | 12262 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 20460 | 1321 | 17853 | 6723 | 5237 | 11503 | 749 | 5651 | 8384 | 14280 | 17145 | 5419 |
| | 15332 | 13013 | 5297 | 12732 | 19655 | 7901 | 7020 | 16059 | 19539 | 4387 | 1475 | 21505 |
| | 2671 | 5714 | 1191 | 2608 | 21672 | 3296 | 15495 | 21919 | 1209 | 12295 | 15820 | 14193 |
| | 14631 | 6254 | 7207 | 20109 | 13220 | 15146 | | | | | | |
| 505: | 15140 | 1261 | 13853 | 2474 | 14749 | 2848 | 6699 | 13353 | 5174 | 10742 | 4290 | 12981 |
| | 5167 | 19956 | 3782 | 14080 | 3433 | | | | | | | |
| 506: | 4704 | 7409 | 3027 | 1782 | 17403 | 2728 | 12116 | 22243 | 18039 | 19464 | 20608 | 21816 |
| | 20161 | 9586 | 9832 | 1168 | 20257 | 8215 | 2055 | 2915 | 21159 | 8994 | 19097 | 4800 |
| | 10831 | 3258 | 3511 | 5759 | 8010 | 5683 | 18509 | 3517 | 13649 | 8892 | 8848 | 13892 |
| | 15978 | 11205 | 19106 | 17806 | 10914 | 8163 | 22263 | 5036 | 9958 | 17199 | 17195 | 12100 |
| | 14343 | 7851 | 2637 | 16675 | 11823 | | | | | | | |
| 507: | 1698 | 1006 | 429 | 10217 | 7363 | 6232 | 18461 | 5240 | 6367 | 19001 | 18925 | 7778 |
| | 526 | 3438 | 7812 | 20057 | 286 | 2857 | 17664 | 21589 | 11961 | 19154 | 21437 | 11195 |
| | 20933 | 21506 | 3533 | 4677 | 18511 | 4730 | 696 | 9569 | 17797 | 18687 | 7097 | 20259 |
| | 15252 | 13221 | 450 | 11335 | 20777 | 12713 | 22502 | 14915 | 21157 | 20371 | 3563 | 12591 |
| | 16308 | 7626 | 4212 | 19798 | 19458 | 5691 | 18292 | 17864 | 4456 | 16130 | 21296 | 2832 |
| | 830 | 14553 | 6434 | 18295 | 17956 | 829 | 476 | 12043 | 20779 | 1281 | 17745 | 16586 |
| | 7955 | 12705 | 15449 | 988 | 20859 | 1768 | 11129 | 6547 | 22518 | 5552 | 9854 | 11376 |
| | 6669 | 5359 | 9132 | 10964 | 1879 | 22087 | 13137 | 884 | 17298 | 3333 | 13752 | 20301 |
| | 19370 | 2425 | 6946 | 19538 | 14273 | 15340 | 6427 | 17165 | 15603 | 12419 | 10809 | 8003 |
| | 13658 | 14064 | 4221 | 7387 | 13284 | 20981 | 2316 | 3116 | 8418 | 3386 | 6508 | 18217 |
| | 3578 | 22249 | 992 | 13442 | 3471 | 14855 | 19949 | 5277 | 19885 | 2816 | 10917 | 9436 |
| | 18538 | 18659 | 12816 | 12308 | 15943 | 2515 | 20364 | 14701 | 8193 | 17579 | 22076 | 8890 |
| | 2649 | 9329 | 21073 | 8376 | 15177 | 10882 | 859 | 5990 | 9814 | 16053 | 5209 | 3144 |
| | 13848 | 22428 | 19076 | 5454 | 17056 | 14918 | 4088 | 11270 | 5837 | 9604 | 22455 | 19840 |
| | 12234 | 1149 | 801 | 953 | 9960 | 21301 | 1656 | 3755 | 12278 | 22119 | 21098 | 1005 |
| | 10264 | 13037 | 11702 | 20954 | 5581 | 5063 | 1118 | 6454 | 20632 | 1696 | 19474 | 14911 |
| | 9381 | 4111 | 13374 | 2932 | 3071 | 18551 | 22362 | 1431 | 12923 | 6509 | 19229 | 14012 |
| | 5372 | 12362 | 17380 | 20272 | 16391 | 13395 | 5132 | 901 | 9540 | 19228 | 14568 | 17630 |
| | 2371 | 4694 | 12396 | 15369 | 16597 | 3697 | 10741 | 16309 | 4927 | 13396 | 21621 | 8841 |
| | 16662 | 11120 | 14081 | 21135 | 8692 | 9484 | 15204 | 6565 | 14320 | 2978 | 9294 | 7482 |
| | 9493 | 1277 | 4952 | 7813 | 7306 | 12296 | 12021 | 6645 | 9286 | 22489 | 13745 | 16653 |
| | 19069 | 7780 | 15219 | 16969 | 14762 | 18330 | 10802 | 10479 | 16663 | 3678 | 16713 | 7751 |
| | 13703 | 3630 | 4691 | 9472 | 10709 | 8542 | 7060 | 6112 | 22457 | 21974 | 20476 | 7333 |
| | 6482 | 14526 | 7151 | 2644 | 835 | 10655 | 12264 | 9315 | 2786 | 16253 | 9488 | 5634 |
| | 17372 | 788 | 11307 | 11198 | 9280 | 22095 | 18903 | 3706 | 15256 | 18593 | 5764 | 11115 |
| | 12583 | 11568 | 13613 | 2331 | 5136 | 8073 | 15998 | 5630 | 11304 | 19137 | 5817 | 5580 |
| | 14145 | 18341 | 8588 | 12540 | 2454 | 4970 | 17445 | 2401 | 11869 | 6193 | 21516 | 10889 |
| | 5190 | 13207 | 16465 | 9673 | 9771 | 11716 | 22279 | 18575 | 9584 | 12794 | 21399 | 20485 |
| | 9218 | 18691 | 3350 | 18263 | 4846 | 544 | 19667 | 9933 | 4140 | 1318 | 20418 | 11128 |
| | 20105 | 16734 | 2376 | 15699 | 7061 | 4232 | 15357 | 14036 | 5339 | 7107 | 19030 | 7165 |
| | 21370 | 12103 | 4848 | 13211 | 22530 | 15360 | 12863 | 9975 | 6398 | 14067 | 16683 | 21170 |
| | 1924 | 890 | 8155 | 15866 | 10131 | 7187 | 4332 | 1235 | 20330 | 12927 | 7088 | 5099 |
| | 2302 | 12424 | 8303 | 17466 | 14322 | 11383 | 2282 | 15956 | 3414 | 12982 | 18548 | 15665 |
| | 10961 | 21084 | 10824 | 18440 | 16819 | 3730 | 13940 | 18821 | 14864 | 1818 | 19607 | 7969 |
| | 6546 | 16771 | 5441 | 8459 | 18266 | 5000 | 15749 | 13014 | 14274 | 8444 | 4707 | 13097 |
| | 15930 | 11872 | 2621 | 7158 | 6942 | 18502 | 5408 | 18037 | 21928 | 13800 | 5188 | 19614 |
| | 16117 | 4719 | 1833 | 13499 | 3107 | 21492 | 12503 | 21929 | 7921 | 1429 | 14398 | 22189 |
| | 6439 | 12993 | 12307 | 19714 | 6650 | 18994 | 747 | 5932 | 18630 | 6683 | 1921 | 15651 |
| | 5594 | 6958 | 13597 | 19763 | 10097 | 14124 | 14687 | 1094 | 5780 | 7770 | 7688 | 15110 |
| | 5797 | 7907 | 21169 | 3329 | 4065 | 19882 | 12627 | 22067 | 19211 | 2061 | 7038 | 8909 |
| | 16914 | 13129 | 19881 | 16317 | 1551 | 13235 | 14888 | 1201 | 20264 | 7800 | 7526 | 2209 |
| | 5887 | 10798 | 15317 | 10223 | 11351 | 10105 | 10661 | 15014 | 2908 | 16412 | 22277 | 19851 |
| | 12003 | 19616 | 11003 | 7768 | 6166 | 4620 | 13850 | 16231 | 7016 | 2717 | 20541 | 3458 |
| | 1240 | 15787 | 20099 | 9282 | 11480 | 4994 | 6281 | 18662 | 7992 | 9661 | 19875 | 11156 |
| | 3619 | 14086 | 20948 | 16946 | 3456 | 6143 | 786 | 6709 | 5954 | 17926 | 20839 | 22351 |
| | 13277 | 21057 | 15113 | 6368 | 7704 | 18694 | 3644 | 12154 | 3794 | 21257 | 21638 | 18386 |
| | 18111 | 21498 | 10731 | 13776 | 5539 | 14530 | 20282 | 7762 | 9529 | 17675 | 15191 | 12380 |
| | 14865 | 15825 | 2818 | 16442 | 5901 | 8220 | 18578 | 13297 | 2495 | 21913 | 4526 | 16085 |
| | 10965 | 15558 | 18982 | 2984 | 11245 | 20659 | 477 | 304 | 427 | 12456 | 2132 | 20312 |
| | 4655 | 16568 | 21093 | 13882 | 5730 | 7976 | 7079 | 13035 | 2800 | 19890 | 12545 | 2037 |
| | 11704 | 9571 | 21379 | 3712 | 7685 | 4483 | 18456 | 22341 | 11197 | 13107 | 12449 | 16006 |
| | 532 | | | | | | | | | | | |
| 508: | 19543 | 4932 | 20425 | 19108 | 19812 | 10140 | 21350 | 7766 | 14738 | 13289 | 13966 | 559 |
| | 10501 | 18670 | 21326 | 12614 | 16425 | 9945 | 1996 | 21651 | 12806 | 13430 | 17362 | 21330 |
| 509: | 5942 | 14707 | 1006 | 429 | 20069 | 10217 | 6051 | 533 | 535 | 478 | 10352 | 18305 |
| | 21211 | 21561 | 20755 | 17549 | 15547 | 13386 | 8817 | 2523 | 18461 | 15773 | 19497 | 5240 |
| | 22508 | 3614 | 6367 | 19001 | 3539 | 12446 | 15801 | 15469 | 13944 | 13012 | 20409 | 13620 |
| | 15377 | 4732 | 4983 | 11962 | 10129 | 873 | 20622 | 7812 | 18242 | 8809 | 14606 | 18228 |
| | 2931 | 3322 | 9023 | 6902 | 3558 | 3304 | 13684 | 21120 | 3950 | 12291 | 4958 | 21675 |
| | 7657 | 4473 | 17017 | 4318 | 22410 | 19999 | 2415 | 22330 | 534 | 6329 | 4819 | 10093 |
| | 8054 | 966 | 16945 | 14639 | 6901 | 14032 | 21397 | 2354 | 2669 | 10194 | 5075 | 2367 |
| | 11025 | 6751 | 20059 | 21308 | 14038 | 2857 | 17664 | 21589 | 11961 | 19154 | 2340 | 7408 |
| | 6244 | 17569 | 13074 | 21437 | 14633 | 11195 | 20933 | 21506 | 4167 | 3533 | 18759 | 4677 |
| | 18511 | 4730 | 696 | 9569 | 17797 | 18687 | 7097 | 20259 | 15252 | 13221 | 450 | 10725 |
| | 22502 | 14915 | 21157 | 18816 | 20371 | 3563 | 12591 | 16308 | 7626 | 4212 | 19798 | 19458 |
| | 5691 | 18292 | 16130 | 21296 | 2832 | 830 | 14553 | 6434 | 18295 | 17956 | 829 | 476 |

TABLE 16-continued

Sequence IDs for homolog proteins
Seq ID NO: homolog Seq ID NOs

|      |       |       |       |       |       |       |       |       |       |       |       |       |
|------|-------|-------|-------|-------|-------|-------|-------|-------|-------|-------|-------|-------|
|      | 12043 | 2658  | 7437  | 19427 | 14568 | 17630 | 2371  | 4694  | 12396 | 15369 | 16597 | 3697  |
|      | 10741 | 16309 | 4927  | 13396 | 21621 | 8841  | 16662 | 11120 | 14081 | 8692  | 9484  | 15204 |
|      | 6565  | 14320 | 2978  | 9294  | 7482  | 9493  | 1277  | 4952  | 7813  | 7306  | 12296 | 12021 |
|      | 6645  | 9286  | 22489 | 13745 | 16653 | 19069 | 7780  | 15219 | 16969 | 14762 | 18330 | 10802 |
|      | 10479 | 16663 | 3678  | 16713 | 7751  | 13703 | 3630  | 4691  | 9472  | 10709 | 8542  | 7060  |
|      | 6112  | 22457 | 21974 | 20476 | 7333  | 6482  | 14526 | 7151  | 2644  | 835   | 10655 | 12264 |
|      | 9315  | 2786  | 16253 | 9488  | 5634  | 17372 | 21009 | 788   | 5630  | 10889 | 5190  | 13207 |
|      | 16465 | 3748  | 4100  | 8138  | 14088 | 9673  | 20541 | 3458  | 1240  | 15787 | 20099 | 9282  |
|      | 11480 | 4994  | 5496  | 4783  | 20946 | 10965 | 15558 | 12797 | 4801  | 18251 | 14926 | 14677 |
|      | 6310  | 18248 | 15246 | 7925  | 15740 | 18982 | 2984  | 5765  | 4060  | 11245 | 20786 | 4379  |
|      | 2132  | 20312 | 4655  | 16568 | 21093 | 13882 | 5730  | 7976  | 7079  | 13035 | 2360  | 2800  |
|      | 16617 | 17577 | 19315 | 17164 | 15726 | 12545 | 2037  | 11704 | 9571  | 21379 | 3712  | 7685  |
|      | 4483  | 18456 | 22341 | 11197 | 13107 | 2227  | 16006 | 17470 | 10632 | 372   | 16331 | 4975  |
|      | 18567 | 13264 |       |       |       |       |       |       |       |       |       |       |
| 510: | 2585  | 13077 | 1296  | 15698 | 1085  | 3129  | 8567  | 7012  | 16480 | 1063  | 15389 | 13708 |
|      | 17974 | 17451 | 15792 | 19280 | 10142 | 3469  | 4227  | 11718 | 15847 | 3638  | 2801  | 9326  |
|      | 10221 | 3742  | 13816 | 3280  | 4884  | 9923  | 11360 | 17722 | 15873 | 1490  | 20214 | 10492 |
|      | 13528 | 3713  | 8475  | 15933 | 21666 | 11740 | 9134  | 1633  | 11990 | 17965 | 20492 | 19212 |
|      | 13533 | 17131 | 16793 | 11371 | 3728  | 8594  | 17461 | 20347 | 8134  | 13823 | 22260 | 9279  |
|      | 7419  | 22025 | 5521  | 19185 | 8730  | 10999 | 4586  | 16348 | 19281 | 11567 | 19991 | 17098 |
|      | 20028 | 1067  | 6210  | 7658  | 19756 | 20830 | 10712 | 16037 | 2865  | 20878 | 3207  | 18632 |
|      | 20070 | 2980  | 6612  | 2087  | 5122  | 7489  | 19025 | 20408 | 5867  | 9692  | 13244 | 17130 |
|      | 19056 | 19348 | 18818 | 779   | 3699  | 15218 | 22456 | 11541 | 11135 | 2201  | 20058 | 15161 |
|      | 16612 | 6739  | 10651 | 14992 | 19392 | 15341 | 4204  | 21922 | 22540 | 19457 | 14075 | 17880 |
|      | 4186  | 15353 | 17073 | 5661  | 13025 | 14487 | 20671 | 6849  | 10343 | 6103  | 4142  | 17366 |
|      | 14159 | 2380  | 18164 | 13366 | 8153  | 19958 | 15839 | 6670  | 8947  | 2506  | 15249 | 9712  |
|      | 22234 | 1377  | 18798 | 8620  | 19625 | 10515 | 15887 | 9429  | 5493  | 7939  | 18930 | 19761 |
|      | 8714  | 3572  | 20073 | 19642 | 9602  | 11161 | 19552 | 7180  | 10987 | 2971  | 8438  | 4675  |
|      | 2938  | 8709  | 9900  | 4636  | 9435  | 3485  | 18162 | 15411 | 20078 | 15262 | 14563 | 3415  |
|      | 19829 | 9555  | 8928  | 16342 | 19361 | 1362  | 1940  | 12060 | 11259 | 18358 | 21475 | 7454  |
|      | 16972 | 20517 | 14458 | 5311  | 9206  | 3026  | 4246  | 21394 | 11663 | 5647  | 21680 | 18756 |
|      | 632   | 3100  | 18856 | 13204 | 14390 | 13351 | 12707 | 15711 | 10265 | 5221  | 14958 | 18751 |
|      | 17138 | 17198 | 2504  | 8197  | 10940 | 11642 | 7410  | 19473 | 13298 | 3551  | 3009  | 15678 |
|      | 14990 | 9133  | 18124 | 6205  | 1024  | 9670  | 14097 | 21447 | 2996  | 6377  | 19672 | 22172 |
|      | 21975 | 4551  | 21676 | 6123  | 2672  | 21984 | 2725  | 19700 | 14920 | 15674 | 7537  | 9974  |
|      | 11780 | 5242  | 13895 | 9998  | 3670  | 18115 | 16824 | 20178 | 18010 | 7493  | 13466 | 21265 |
|      | 8951  | 14511 | 18486 | 7701  | 6098  | 7554  | 17622 | 11381 | 6309  | 22198 | 19059 | 21658 |
|      | 15854 | 16625 | 12681 | 12161 | 11609 | 12398 | 6162  | 3022  | 5109  | 7314  | 14439 | 8366  |
|      | 13945 | 12198 | 11746 | 19463 | 8918  | 13801 | 5301  | 15197 | 3210  | 11365 | 15206 | 19669 |
|      | 17546 | 2720  | 10926 | 1742  | 6963  | 11828 | 6972  | 8450  | 14550 | 1267  | 11591 | 19644 |
|      | 11212 | 14447 | 15125 | 21242 | 13309 | 14497 | 17159 | 832   | 17245 | 5903  | 7432  | 18321 |
|      | 3663  | 3061  | 4860  | 9406  | 7511  | 10188 | 13056 | 4196  | 11132 | 3684  | 3623  | 8675  |
|      | 14569 | 21430 | 19252 | 10739 | 16443 | 8119  | 10193 | 17100 | 16296 | 16004 | 11852 | 17566 |
|      | 10552 |       |       |       |       |       |       |       |       |       |       |       |
| 511: | 1655  | 3326  | 8875  | 4957  | 8311  | 19832 | 4954  | 10256 | 13907 | 20915 | 2896  | 5571  |
|      | 12394 | 6016  | 4944  | 12546 | 7522  | 2423  | 2681  | 8552  | 10982 | 7116  | 5314  | 12119 |
|      | 21099 | 18607 | 12329 | 4674  | 13459 | 21805 | 3969  | 20266 | 14769 | 22203 | 3114  | 336   |
|      | 12480 | 7283  | 9746  | 8207  | 7204  | 14337 | 11300 | 20397 | 20746 | 1530  | 5147  | 14828 |
|      | 21034 | 3906  | 2359  | 21177 | 8537  | 10139 | 16166 | 2594  | 13784 | 16485 | 20871 | 14720 |
|      | 1825  | 16147 | 17234 | 8065  | 17167 | 16501 | 11902 | 18924 | 5861  | 14539 | 14230 | 2788  |
|      | 2072  | 18571 | 2501  | 4192  | 13524 | 4842  | 3095  | 7769  | 10089 | 16575 | 6956  | 16293 |
|      | 11570 | 10846 | 19759 | 20187 | 21448 | 19904 | 10891 | 15038 | 1868  | 12675 | 6957  | 653   |
|      | 16915 | 12203 | 12409 | 8067  | 4947  | 19061 | 2619  | 13364 | 4888  | 5566  | 10650 | 17254 |
|      | 18049 | 16316 | 7313  | 11076 | 14440 | 1765  | 10770 | 13783 | 5839  | 16261 | 12061 | 9852  |
|      | 10237 | 10732 | 19814 | 4893  | 6882  | 6805  | 4262  | 4557  | 3971  | 638   | 11527 | 13153 |
|      | 22347 | 12730 | 10796 | 3084  | 18028 | 9061  | 7136  | 21153 | 925   | 8750  | 18082 | 12774 |
|      | 8584  | 13536 | 12518 | 6788  | 979   | 8900  | 18133 | 5696  | 15970 | 16063 | 14470 | 16701 |
|      | 5862  | 12183 | 3705  | 6658  | 16350 | 9557  | 8971  | 3717  | 1724  | 22354 | 16718 | 3854  |
|      | 3536  | 4599  | 16869 | 11895 | 16555 | 16258 | 4214  | 20552 | 21819 | 7135  | 16259 | 15280 |
|      | 4762  | 13775 | 4531  | 3367  | 13517 | 21549 | 8105  | 18643 | 4066  | 13282 | 14115 | 5130  |
|      | 10429 | 5920  | 4306  | 3192  | 5443  | 21499 | 6557  | 11929 | 20598 | 20903 | 4176  | 9050  |
|      | 15849 | 2723  | 15314 | 5993  | 12041 | 21869 | 14163 | 7930  | 9081  | 20569 | 9795  | 20396 |
|      | 11150 | 12443 | 4358  | 9475  | 10811 | 2552  | 11877 | 17685 | 21729 | 20974 | 12598 | 14790 |
|      | 20989 | 15004 | 17240 | 6237  | 17208 | 21930 | 8580  | 11818 | 5442  | 17259 | 20256 | 16046 |
|      | 5065  | 2308  | 2128  | 12182 | 17118 | 2251  | 7155  | 2892  | 13229 | 9845  | 20431 | 4311  |
|      | 16583 | 21037 | 18490 | 9763  | 6826  | 11713 | 15211 | 21554 | 16813 | 7056  | 18009 | 3039  |
|      | 19296 | 6673  | 11484 | 17841 | 21732 | 6456  | 2378  | 9054  | 19996 | 15355 | 21362 | 7381  |
| 512: | 11789 | 20550 | 12924 | 14464 | 4011  | 19063 | 17858 | 14825 | 17933 | 18215 | 18506 | 8574  |
|      | 11311 | 14714 | 10870 | 5173  | 18503 | 12871 | 11792 | 6319  | 5991  | 16072 | 5679  | 7664  |
|      | 7997  | 7724  | 13724 | 15843 | 5179  | 21486 | 13257 | 20843 | 5253  | 15239 | 8745  | 4317  |
|      | 11829 | 5762  | 17201 |       |       |       |       |       |       |       |       |       |
| 513: | 5799  | 17656 | 10980 | 3449  | 13335 | 20959 | 11238 | 9736  | 21154 | 8759  | 1349  | 18282 |
|      | 16665 | 17907 | 1107  | 9170  | 6492  | 20516 | 7727  | 5847  | 9065  | 19902 | 9931  | 8677  |
|      | 21320 | 19055 | 9044  | 19475 | 21629 | 4209  | 3873  | 10407 | 3831  | 21694 | 7261  | 11569 |
|      | 1480  | 1407  | 5128  | 14542 | 607   | 2784  | 18463 | 12009 | 8535  | 4917  | 22501 | 18918 |
|      | 12152 | 19362 | 6874  | 3988  | 10827 | 20140 | 18080 | 14167 | 1710  | 4124  | 3650  | 20877 |
|      | 6031  | 11044 | 12822 | 11665 | 16321 | 4669  | 19156 | 10011 | 15957 | 10312 | 16955 | 17469 |

TABLE 16-continued

Sequence IDs for homolog proteins
Seq ID NO: homolog Seq ID NOs

|   | | | | | | | | | | | |
|---|---|---|---|---|---|---|---|---|---|---|---|
|   | 9415 | 12205 | 21650 | 12324 | 10985 | 4763 | 17086 | 19498 | 18609 | 9205 | 19889 | 13760 |
|   | 11234 | 3128 | 3060 | 17868 | 7045 | 10721 | 18775 | 8340 | 16607 | 22199 | 8687 | 3652 |
|   | 8147 | 19720 | 4090 | 22058 | 13973 | 15250 | 5813 | 3005 | 6442 | 5423 | 4181 | 11396 |
|   | 20254 | 11686 | 18648 | 22257 | 3514 | 5054 | 17718 | 19944 | 22383 | 13148 | 10185 | 9304 |
|   | 9674 | 13580 | 20000 | 5106 | 14024 | 15026 | 15535 | 16386 | 22442 | 21036 | 12653 | 8647 |
|   | 894 | 4170 | 18619 | 16370 | 14161 | 13064 | 13337 | 2689 | | | | |
| 514: | 19430 | 2217 | 13653 | 7909 | 3447 | 18614 | 2248 | 3672 | 3914 | 9037 | 2661 | 14057 |
| 515: | 21829 | 10688 | 1896 | 2695 | 15238 | 6923 | 13321 | 678 | 19909 | 21886 | 6620 | 4554 |
|   | 4937 | 9312 | 1954 | 4679 | 2233 | 18331 | 21411 | | | | | |
| 516: | 12014 | 16420 | 2750 | 15538 | 18414 | 1466 | 5013 | 18876 | 17795 | 12046 | 9951 | 6600 |
|   | 5934 | 11750 | 5835 | 2034 | 4693 | 13740 | 10307 | 909 | 4231 | 1436 | 13779 | 16112 |
|   | 13219 | 4984 | 13214 | 18231 | 18179 | 2811 | 4814 | 18531 | 554 | 6050 | 18257 | 2903 |
|   | 3484 | 19943 | 17271 | 7129 | 1721 | 20263 | 20319 | 16055 | 20881 | 9942 | 13994 | 18838 |
|   | 11636 | 7029 | 16119 | 5257 | 1043 | 19478 | 20619 | 13417 | 11422 | 10160 | 20613 | 5029 |
|   | 8196 | 19429 | 9805 | 1861 | 17540 | 5288 | 14683 | 10272 | 7443 | 2656 | 16627 | 2315 |
|   | 772 | 9104 | 9410 | 4096 | 4548 | 9824 | 8485 | 17962 | 16475 | 22107 | 21011 | 15087 |
|   | 8840 | 15594 | 20392 | 9440 | 6125 | 9757 | 11164 | 17673 | 20924 | 4254 | 8176 | 16401 |
|   | 14437 | 18646 | 12057 | 12830 | 10159 | 17174 | 8040 | | | | | |
| 517: | 13062 | 19774 | 2825 | 8829 | 8332 | 18558 | 21964 | 19050 | 1627 | 16157 | 11534 | 19742 |
|   | 19647 | 13280 | 1517 | 9695 | 19320 | 10835 | 10293 | 13202 | 9174 | 14643 | 15719 | |
| 518: | 3195 | 21607 | 10760 | 14223 | 22323 | 21616 | 11305 | 21976 | 16169 | 8132 | 2667 | 11216 |
|   | 15637 | 4652 | 2270 | 8808 | 10309 | 18374 | 9291 | 7790 | 12784 | 7569 | 1295 | 5525 |
|   | 20767 | 17464 | 15920 | 7877 | 6705 | 4550 | 14008 | 15544 | 7616 | 1791 | 14358 | 15686 |
|   | 13182 | 14560 | 16722 | 8357 | 1472 | 4000 | 4261 | 10693 | 20144 | 4624 | 13338 | 17893 |
|   | 7464 | 11142 | 13491 | 15676 | 17655 | 17116 | 17984 | 9925 | 18333 | 10247 | 16818 | 4579 |
|   | 2385 | 20648 | 983 | 3200 | 6435 | 14763 | 13495 | 12036 | 16066 | 6740 | 14948 | 2307 |
|   | 14063 | 6851 | 10240 | 1728 | 16533 | 12629 | 10196 | 17078 | 16048 | 17609 | 11181 | 20629 |
|   | 575 | 18286 | 21518 | 5309 | 13744 | 15880 | 19484 | 16840 | 4959 | 15622 | 1288 | 18892 |
|   | 15176 | 815 | 7329 | 1175 | 20218 | 8827 | 7588 | 658 | 8704 | 16710 | 12907 | 17705 |
|   | 21364 | 16998 | 4945 | 15440 | 14372 | 12879 | 20119 | 17194 | 19468 | 10410 | 10451 | 11618 |
|   | 12006 | 12191 | 17175 | 20965 | 12916 | 6796 | 9139 | 17057 | 11008 | 18605 | 3353 | 4650 |
|   | 12741 | 1237 | 7988 | 20088 | 8231 | 4522 | 18497 | 11952 | 2866 | 15466 | 10449 | 5850 |
|   | 8504 | 22473 | 14806 | 5364 | 12620 | 20699 | 20034 | 4409 | 917 | 9156 | 629 | 12665 |
|   | 12908 | 7530 | | | | | | | | | | |
| 519: | 11427 | 19017 | 6602 | 1864 | 10522 | 13385 | 3923 | 15070 | 3821 | 6415 | 1572 | 5050 |
|   | 15882 | 10935 | 5721 | 20535 | 12645 | 22402 | 8448 | 1350 | 7112 | 8649 | 5148 | 21245 |
|   | 11236 | 6476 | 14907 | 12714 | 20807 | 15311 | 9469 | 4739 | 13575 | 9732 | 8564 | 14799 |
|   | 12721 | 13373 | 4868 | 12893 | 19038 | 13333 | 8973 | 17817 | 15414 | 18146 | 11390 | 22248 |
|   | 13609 | 10100 | 15109 | 10007 | 5125 | 12633 | 6880 | 5388 | 20060 | 21032 | 8509 | 17168 |
|   | 19622 | 20280 | 21442 | 12066 | 17299 | 20123 | 12902 | 2062 | 656 | 6457 | 19453 | 20032 |
|   | 10850 | 8420 | 3813 | 21339 | 19516 | 16171 | 21635 | 2450 | 21079 | 19226 | 22202 | 17856 |
|   | 19847 | 1215 | 16964 | 11846 | 9253 | 18683 | 16927 | 3145 | 2877 | 4684 | 8416 | 4696 |
|   | 4925 | 14172 | 18178 | 10122 | 20134 | 11437 | 19509 | 20038 | 17265 | 10957 | 11114 | 11985 |
|   | 13382 | 4424 | 21277 | 6642 | 11395 | 19354 | 3216 | 17000 | 10584 | 4383 | 608 | 11099 |
|   | 3606 | 4061 | 6926 | 11774 | 3799 | 5172 | 3696 | 17840 | 9961 | 17641 | 22548 | 13507 |
|   | 6182 | 1731 | 2207 | 5353 | 5367 | 13860 | 8912 | 20922 | 11967 | 3241 | 16963 | 17734 |
|   | 10073 | 13903 | 22521 | 12149 | 4120 | 617 | 13506 | 13612 | 8031 | 6763 | 7546 | 6218 |
|   | 16311 | 10707 | 1223 | 21269 | 9414 | 8360 | 4885 | 3852 | 955 | 17284 | 19833 | 11354 |
|   | 2803 | 14827 | 1301 | 19175 | 10717 | 10910 | 12224 | 11516 | 13340 | 5262 | 5684 | 2178 |
|   | 13200 | 5913 | 9157 | 7959 | 17542 | 20440 | 18229 | 4805 | 8038 | 13587 | 16238 | 15602 |
|   | 18860 | 3544 | 7650 | 12674 | 17624 | 7074 | 576 | 17060 | 7413 | 22374 | 15047 | 21681 |
|   | 651 | 17560 | 6085 | 12160 | 12805 | 10775 | 4709 | 11401 | 6838 | 18364 | 17014 | 10752 |
|   | 17012 | 8980 | 17510 | 10711 | 8219 | 16107 | 16692 | 19401 | 17191 | 18405 | 15984 | 5384 |
|   | 19201 | 4362 | 883 | 6527 | 6410 | 867 | 12321 | 17889 | 17964 | 11941 | 14152 | 6591 |
|   | 4578 | 7461 | 4633 | 14845 | 14113 | 9478 | 16306 | 10792 | 5394 | 8423 | 16472 | 5538 |
|   | 5726 | 15272 | 22541 | 13274 | 19969 | 1344 | 17982 | 3299 | 6241 | 17488 | 6970 | 16632 |
|   | 2724 | 14874 | 2212 | 22392 | 12804 | 12135 | 15618 | 11858 | 552 | 17686 | 5585 | 19912 |
|   | 21050 | 1222 | 14554 | 13068 | 15732 | 8905 | 5854 | | | | | |
| 520: | 12932 | 18316 | 8070 | 15251 | 8216 | 15182 | 21583 | 18345 | 17227 | 19404 | 5489 | 17421 |
|   | 19679 | 6636 | 1134 | 14441 | 20247 | 13276 | 19767 | 5072 | | | | |
| 521: | 14618 | 7172 | 4577 | 10111 | 4971 | 9921 | 11310 | 2304 | 19058 | 4919 | 2407 | 21318 |
|   | 6019 | 13841 | 12405 | 6079 | 22166 | 21222 | 11447 | 3834 | 2957 | 2876 | 3847 | 10030 |
|   | 3657 | 8737 | 2532 | 19313 | 13162 | 19695 | 11283 | 21477 | 13270 | 11090 | 20277 | 5569 |
|   | 11224 | 1524 | 7689 | 5785 | 1443 | 1174 | 5378 | 3463 | 7893 | 2512 | 20456 | 11012 |
|   | 5357 | 17062 | 17203 | 17936 | 14894 | 10285 | 19219 | 19980 | 15015 | 19783 | 22068 | 1918 |
|   | 19153 | 5369 | 14302 | 9654 | 16742 | 15180 | 4073 | 14772 | 14901 | 3954 | 13470 | 8012 |
|   | 15898 | 12241 | 11155 | 18311 | 11712 | 3109 | 18530 | 17791 | 1700 | 6065 | 18830 | 8838 |
|   | 7741 | 20399 | 7063 | 8515 | 13562 | 2024 | 8969 | 7647 | 12054 | 19078 | 2184 | 16655 |
|   | 8540 | 7852 | 16491 | 13169 | 20514 | 20202 | 7535 | 18320 | 11710 | 7747 | 15987 | 17730 |
|   | 7302 | 1993 | 2766 | 4031 | 5562 | 21493 | 10046 | 1799 | 4731 | 18131 | 8100 | 10005 |
|   | 7123 | 2520 | 10396 | 22156 | 9867 | 7052 | 11207 | 4505 | 21049 | 11504 | 21868 | 11614 |
|   | 5889 | 12118 | 13000 | 22505 | 2411 | 10176 | 6296 | 9619 | 18566 | 20017 | 11928 | 3767 |
|   | 11046 | 7551 | 2528 | 11302 | 21596 | 6991 | 7083 | 2350 | 736 | 10023 | 5402 | 21313 |
|   | 14934 | 14110 | 14248 | 11521 | 15498 | 3429 | 17829 | 15576 | 19218 | 22393 | 10506 | 19723 |
|   | 20354 | 6720 | 17694 | 8466 | 4273 | 4916 | 22208 | 20427 | 9107 | 15921 | 4439 | 10197 |
|   | 2338 | 16397 | 13942 | 15715 | 20725 | 18142 | 3311 | 2926 | 10795 | 3889 | 17244 | 10288 |
|   | 19160 | 8477 | 12011 | 3565 | 21062 | 9658 | 16357 | 6172 | 2617 | 1734 | 15245 | 22324 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 7974 | 4678 | 3698 | 3992 | 10876 | 20303 | 19258 | 17048 | 4272 | 20359 | 11598 | 8412 |
| | 6693 | 19116 | 5690 | 8276 | 912 | 4024 | 10472 | 12647 | 6733 | 5738 | 15800 | 21800 |
| | 3295 | 8590 | 20011 | 17717 | 4177 | 7227 | 20102 | 5504 | 13132 | 11762 | 15477 | 18479 |
| | 9793 | 17968 | 11404 | 21844 | 17913 | 17281 | 14938 | 1225 | 7663 | 13582 | 11349 | 16247 |
| | 19951 | 3778 | 8781 | 7268 | 10618 | 18594 | 14849 | 15471 | 22337 | 22454 | 4787 | 4244 |
| | 12088 | 1992 | 9332 | 15917 | 17106 | 13790 | 19542 | 19573 | 2089 | 1592 | 7878 | 12361 |
| | 19383 | 14253 | 17356 | 4238 | 9481 | 1439 | | | | | | |
| 522: | 14431 | 6239 | 11377 | 22466 | 13606 | 11763 | 4871 | 19242 | 19036 | 9779 | 970 | 4882 |
| | 15417 | 18050 | 2958 | 13661 | 18314 | 19970 | 8044 | 8672 | 8262 | 4077 | 12369 | 12815 |
| | 15194 | 7431 | 19112 | 585 | 5289 | 17307 | 6089 | 5537 | 5935 | 21766 | 1304 | 15168 |
| | 4356 | 6485 | 15400 | 19439 | 706 | 14453 | 1031 | 5411 | 11160 | 12131 | 10020 | 11249 |
| | 8415 | 21643 | 14449 | 14017 | 1963 | 10261 | 1703 | 1878 | 4023 | 12040 | 9720 | 17260 |
| | 21578 | 15343 | 11117 | 16514 | 14299 | 20222 | 12107 | 18114 | 13664 | 4184 | 14261 | 16823 |
| | 13551 | 22313 | 3921 | 1998 | 666 | 4628 | 20928 | 18508 | 9588 | 8794 | 5200 | 619 |
| | 4115 | 20171 | 1555 | 3070 | 5376 | 7843 | 10040 | 19791 | 19447 | 20093 | 16957 | 19231 |
| 523: | 5718 | 10805 | 6298 | 2166 | 20556 | 21748 | 9437 | 8027 | 3472 | 10338 | 7212 | 20501 |
| | 11491 | 4341 | 11669 | 9303 | 16917 | 8868 | 14506 | 2160 | 21476 | 17596 | 18688 | 9966 |
| | 15557 | 11767 | 2124 | 18956 | 7553 | 18747 | 18697 | 17873 | 7757 | 16320 | 22134 | 13292 |
| | 7913 | 9948 | 6980 | 17735 | 634 | 12444 | 16435 | 5350 | 17955 | 19423 | 15565 | 11353 |
| | 20128 | 13016 | 5239 | 860 | 22552 | 2379 | 6033 | 16520 | 21986 | 17573 | 5222 | 14074 |
| | 2603 | 19569 | 20484 | 2875 | 1313 | 5161 | 7288 | 21179 | 5370 | 19621 | 980 | 10087 |
| | 20381 | 3366 | 6986 | 21533 | 16164 | 20883 | 3426 | 1157 | 16729 | 6898 | 20593 | 17576 |
| | 9698 | 12169 | 10986 | 8048 | 17173 | 5809 | 21767 | 582 | 9317 | 13750 | 3110 | 18945 |
| | 19532 | 13594 | 14859 | 19926 | 14149 | 16203 | 18916 | 2694 | 2259 | 3885 | 16893 | 6833 |
| | 6096 | 16248 | 7576 | 1925 | 6278 | 10533 | 5649 | 20618 | 13912 | 17331 | 9831 | 9223 |
| | 1851 | 20107 | 18714 | | | | | | | | | |
| 524: | 5146 | 21711 | 9443 | 19434 | 17798 | 8271 | 15157 | 6680 | 1121 | 22072 | 17654 | 19028 |
| | 13218 | 6405 | 9244 | 5217 | 7137 | 8194 | 21221 | 12019 | 13471 | 17578 | 11153 | 9140 |
| | 11727 | 17633 | 3462 | 17166 | 6295 | 21753 | 828 | 13617 | 9059 | 2402 | 16458 | 7601 |
| | 13675 | 21744 | 12228 | 3556 | 9011 | 10297 | 8699 | 1058 | 17727 | 3732 | 888 | 19098 |
| | 19007 | 20328 | 22435 | 9743 | 8151 | 9884 | 5912 | 13874 | 1793 | 20963 | 14276 | 11662 |
| | 13913 | 18489 | 16461 | 9898 | 8731 | 15745 | 3973 | 880 | 2296 | 9092 | 18765 | 17370 |
| | 18888 | 13547 | 17231 | 13680 | 4367 | 14754 | 17832 | 2159 | 8925 | 6054 | 4836 | 21950 |
| | 16483 | 17585 | 20898 | 15188 | 9783 | 19045 | 2088 | 7805 | 5781 | 7540 | 21423 | 10626 |
| | 3232 | 3412 | 16951 | 12593 | 7133 | 7230 | 17422 | 10172 | 19629 | 20061 | 15226 | 16396 |
| | 13106 | 16858 | 12395 | 8064 | 18608 | 10913 | 18148 | 14559 | 11640 | 22231 | 949 | 3806 |
| | 922 | 6047 | 14424 | 20294 | 21512 | 2844 | 21750 | 10411 | 1285 | 598 | 9413 | 13278 |
| | 5979 | 15078 | 9781 | 11382 | 15932 | 16934 | 17171 | 3994 | 21427 | 3887 | 3113 | 10974 |
| | 15635 | 18526 | 5503 | 9904 | 16377 | 17644 | 12020 | 15507 | 18396 | 5802 | 16207 | 16206 |
| | 6951 | 13409 | 14980 | 12042 | 9197 | 20762 | 11969 | 14942 | 19111 | 1373 | 9467 | 797 |
| | 8518 | 2947 | 13489 | 6590 | 10901 | 7185 | 7646 | 6204 | 6548 | 8825 | 7264 | 13425 |
| | 13837 | 10201 | 11983 | 19803 | 21421 | 11553 | 9049 | 3356 | 19634 | 16334 | 3944 | 7749 |
| | 20163 | 662 | 8190 | 6651 | 20724 | 22285 | 8240 | 12389 | 5598 | 11233 | 14315 | 15485 |
| | 11282 | 20624 | 12145 | 12327 | 13242 | 17891 | 1217 | 8203 | 12727 | 22111 | 8826 | 9668 |
| | 20863 | 11483 | 21587 | | | | | | | | | |
| 525: | 6387 | 20127 | 15922 | 6468 | 22478 | 5164 | 14961 | 7042 | 16305 | 2182 | 16677 | 7733 |
| | 8221 | 13250 | 4225 | 10787 | 11039 | 2823 | 13281 | 6380 | 6264 | 6360 | 20082 | 1398 |
| | 14175 | 14977 | 21194 | 5933 | 9986 | 10799 | 2049 | 7444 | 4924 | 15193 | 2703 | 12215 |
| | 13851 | 836 | 5401 | 12967 | 18193 | 18801 | 1103 | 3308 | 20749 | 18446 | 18404 | 15606 |
| | 19308 | 7496 | 14462 | 10044 | 21187 | 16900 | 8754 | 16101 | 22544 | 1746 | 5089 | 13111 |
| | 9288 | 15179 | 4423 | 14999 | 11584 | 15673 | 5028 | 18076 | 21294 | 12622 | 21553 | 14776 |
| | 12325 | 6837 | 10013 | 20597 | 20543 | 11805 | 18067 | 18468 | 4428 | 3795 | 8921 | 3661 |
| | 8624 | 4476 | 13323 | 11313 | 7963 | 22062 | 20636 | 18513 | 1030 | 8805 | 22083 | 5807 |
| | 3830 | 19568 | 5055 | 4025 | 10497 | 21824 | 10898 | 19772 | 590 | 10473 | 8226 | 20982 |
| | 6273 | 21435 | 16209 | 9607 | 18881 | 15700 | 11596 | 15700 | 10735 | 19808 | 17961 | 19021 |
| | 1837 | 21662 | 20927 | 1365 | 7598 | 21243 | 15848 | 17757 | 8577 | 12564 | 9707 | 7488 |
| | 9892 | 1675 | 13967 | 1620 | 3282 | 2358 | 18278 | 15275 | 15531 | 18220 | 21540 | 22120 |
| | 14812 | 13263 | 6574 | 14679 | 2574 | 16215 | 1945 | 10259 | 15499 | 11627 | 12347 | 2605 |
| | 6895 | 7286 | 10483 | 2487 | 10289 | 3346 | 7293 | 9601 | 10220 | 7996 | 4547 | 4237 |
| | 7808 | 7341 | 5250 | 14483 | | | | | | | | |
| 526: | 8075 | 16099 | 8242 | 429 | 13036 | 10217 | 18174 | 535 | 533 | 507 | 306 | 11062 |
| | 15313 | 16399 | 14594 | 314 | 3820 | 5717 | 20464 | 15374 | 18461 | 18690 | 9504 | 8137 |
| | 11945 | 3327 | 4030 | 1064 | 15390 | 4708 | 6367 | 19001 | 8581 | 6859 | 18172 | 3305 |
| | 18107 | 12112 | 13896 | 2465 | 12130 | 19906 | 4949 | 17359 | 14379 | 13607 | 10705 | 15889 |
| | 16978 | 8246 | 16554 | 18467 | 9002 | 9780 | 17882 | 21655 | 20242 | 9063 | 5705 | 9204 |
| | 9915 | 11991 | 16148 | 15840 | 14589 | 6171 | 20389 | 6007 | 14898 | 1840 | 4491 | 7812 |
| | 8977 | 13027 | 6371 | 15170 | 21310 | 12535 | 9755 | 2819 | 3052 | 12267 | 8377 | 3804 |
| | 7983 | 22167 | 21674 | 22450 | 891 | 13549 | 7113 | 14532 | 9354 | 7858 | 8394 | 2044 |
| | 9345 | 2341 | 6836 | 19148 | 17763 | 286 | 18665 | 2645 | 14240 | 13516 | 9032 | 15489 |
| | 8304 | 7822 | 9993 | 17083 | 7310 | 5481 | 11010 | 1093 | 7789 | 21306 | 21699 | 11113 |
| | 8956 | 18128 | 7880 | 3416 | 6279 | 2857 | 11961 | 19154 | 10481 | 11542 | 21609 | 21506 |
| | 3533 | 6663 | 3391 | 4677 | 18511 | 4730 | 696 | 9569 | 17797 | 18687 | 7097 | 20259 |
| | 15252 | 13221 | 3261 | 14692 | 22502 | 14915 | 21157 | 20371 | 3563 | 12591 | 16308 | 7626 |
| | 16130 | 21296 | 2832 | 830 | 14553 | 6434 | 18295 | 17956 | 20230 | 10392 | 12043 | 21065 |
| | 20779 | 1281 | 17745 | 3289 | 3754 | 5487 | 8587 | 11548 | 12578 | 2882 | 5552 | 16586 |
| | 7955 | 1768 | 22518 | 12705 | 15449 | 988 | 20859 | 11129 | 6547 | 9854 | 11376 | 6669 |
| | 5359 | 9132 | 10964 | 19776 | 1879 | 22087 | 13137 | 13752 | 17298 | 3333 | 20301 | 19370 |

TABLE 16-continued

Sequence IDs for homolog proteins
Seq ID NO: homolog Seq ID NOs

|  | | | | | | | | | | | |
|---|---|---|---|---|---|---|---|---|---|---|---|
| | 15830 | 2425 | 6946 | 19538 | 14273 | 15340 | 6427 | 17165 | 15603 | 12419 | 10809 | 8003 |
| | 13658 | 14568 | 12544 | 17630 | 2371 | 4694 | 12396 | 15369 | 16597 | 3697 | 10741 | 13396 |
| | 21621 | 16662 | 8841 | 11120 | 14081 | 13456 | 21472 | 7487 | 12898 | 12787 | 8692 | 9484 |
| | 15204 | 6565 | 11203 | 14320 | 2978 | 9294 | 7482 | 9493 | 1277 | 4952 | 7813 | 7306 |
| | 12296 | 12021 | 6645 | 9286 | 22489 | 13745 | 16653 | 19069 | 7780 | 15219 | 16969 | 19357 |
| | 14762 | 10802 | 10479 | 16663 | 3678 | 16713 | 7751 | 13703 | 3630 | 4691 | 9472 | 10709 |
| | 8542 | 7060 | 6112 | 22457 | 21974 | 20476 | 7333 | 6482 | 14526 | 7151 | 644 | 835 |
| | 10655 | 12264 | 17372 | 10889 | 6281 | 10965 | 15558 | 5973 | 1482 | 22476 | 19408 | 9637 |
| | 5773 | 5016 | 20819 | 18982 | 19997 | 4572 | 640 | 19168 | 8691 | 17905 | 2970 | 2132 |
| | 20312 | 4655 | 16568 | 21093 | 13882 | 5730 | 7976 | 7079 | 13035 | 3505 | 2800 | 12522 |
| | 8939 | 2155 | 3206 | 2017 | 15587 | 6277 | 1297 | 1423 | 18728 | 305 | 509 | 12545 |
| | 2037 | 11704 | 9571 | 21379 | 13089 | 11197 | 13107 | 22367 | 17943 | 2420 | 7599 | 5997 |
| | 372 | 1801 | 21374 | 16528 | 8722 | 16672 | | | | | | |
| 527: | 3642 | 15482 | 8461 | 18796 | 11646 | 4433 | 18911 | 12512 | 19895 | 14727 | 7891 | 5229 |
| | 8941 | 8192 | 671 | 3621 | 19293 | 20133 | 7775 | 16444 | 5601 | 9047 | 7456 | 1332 |
| | 15241 | 20870 | 3570 | 13126 | 6335 | 14830 | 17816 | 4052 | 1048 | 11934 | 7415 | 16817 |
| | 11466 | 15006 | 17149 | 16740 | 13546 | 20225 | 18675 | 12360 | 11085 | 4464 | 12955 | 7636 |
| | 18831 | 17524 | 21731 | 2244 | 8988 | 9012 | 18649 | 8617 | 6285 | 18612 | 1053 | 1455 |
| | 4829 | 16779 | 15889 | 18827 | 14953 | 12980 | 10447 | 1034 | 15656 | 2581 | 22412 | 4354 |
| | 10756 | 21138 | 3468 | 6872 | 6990 | 15371 | 16865 | 14170 | 14485 | 16553 | 7703 | 21199 |
| | 6847 | 729 | 14001 | 18779 | 7182 | 2836 | 8312 | 3038 | 18069 | 16737 | 4357 | 10422 |
| | 3567 | 6722 | 22039 | 3264 | 5085 | 20829 | 6719 | 2934 | 10564 | 14973 | 13027 | 2205 |
| | 9393 | 19576 | 7148 | 2665 | 6959 | 16605 | 4997 | 17039 | 7857 | 4310 | 11556 | 19590 |
| | 12715 | 6725 | 8377 | 3489 | 3770 | 22024 | 3546 | 20586 | 5189 | 20926 | 2245 | 1604 |
| | 7700 | 18947 | 5485 | 22116 | 21537 | 11706 | 18715 | 21536 | 17691 | 17398 | 2949 | 3079 |
| | 6290 | 961 | 6042 | 4750 | 8302 | 20882 | 5852 | 13136 | 16392 | 2643 | 14077 | 9240 |
| | 11996 | 3702 | 14090 | 19402 | 7233 | 5546 | 10148 | 20680 | 8638 | 3269 | 15282 | 9663 |
| | 15009 | 15604 | 8648 | 14392 | 18782 | 10570 | 6318 | 19862 | 13514 | 13217 | 3980 | 5231 |
| | 11578 | 4812 | 18337 | 3004 | 3073 | 8249 | 18941 | 9036 | 3233 | 864 | 15080 | 19930 |
| | 6746 | 1476 | 10866 | 20483 | 19942 | 7450 | 762 | 21276 | 3235 | 15320 | 22462 | 11955 |
| | 1562 | 13099 | 7710 | 9136 | 7251 | 16129 | 19467 | 10892 | 10630 | 13600 | 12857 | 14732 |
| | 4581 | 18096 | 3518 | 12368 | 1009 | 17283 | 4039 | 6864 | 5773 | 6063 | 15842 | 16851 |
| | 18149 | 7977 | 14608 | 4572 | 10553 | 4514 | 11848 | 18068 | 17157 | 12223 | 18597 | 15178 |
| | 10550 | 11835 | 16242 | 11778 | 20884 | 14445 | 5068 | 7404 | 1516 | 6277 | 17663 |
| | 17662 | 21513 | 5526 | 14789 | 7565 | 21347 | 1238 | 10660 | 18496 | 16381 | 20827 | 19639 |
| 528: | 22368 | 2262 | 4500 | 18087 | 11171 | 3257 | 5531 | 17538 | 11849 | 9017 | 9287 | 9644 |
| | 19677 | 20195 | 3911 | 3945 | 21129 | 6446 | | | | | | |
| 529: | 18280 | 2326 | 4826 | 11407 | 11186 | 16051 | 1917 | 13113 | 10636 | 10206 | 19238 | 18366 |
| | 6941 | 11986 | 7683 | 16587 | 14340 | 18850 | 6892 | 3404 | 17954 | 20223 | 11450 | 10435 |
| | 19074 | 13384 | 7518 | 15985 | 8336 | 5383 | 3907 | 13379 | 12855 | 14509 | 12217 | 3398 |
| 530: | 1719 | 15257 | 12828 | 16494 | 8849 | 18495 | 10061 | 1831 | 11005 | 20446 | 21892 | 17075 |
| | 9052 | 1023 | 10386 | 2348 | 6364 | 14482 | 15814 | 7746 | 9263 | 3529 | 9935 | 10786 |
| | 20919 | 12407 | 11705 | 8493 | 5095 | 8481 | 6104 | 3104 | 14770 | 19267 | 1032 | 17399 |
| | 8085 | 17728 | 7344 | 673 | 15714 | 3361 | 5103 | 21218 | 15350 | 7539 | 761 | 19758 |
| | 16925 | 17515 | 8371 | 9594 | 13769 | 16744 | 17772 | 4420 | 8605 | 6819 | 6628 | 9541 |
| | 19100 | 13982 | 7360 | 20665 | 9903 | 5639 | 8487 | 13488 | 9666 | 5511 | 11106 | 17709 |
| | 5021 | 19088 | 20007 | 12811 | 14758 | 15329 | 7823 | 21543 | 20508 | 1178 | 5558 | 16935 |
| | 1252 | 7312 | 20192 | 18963 | 5305 | 19575 | 17193 | 1262 | 3577 | 20951 | 2711 | 18829 |
| | 9159 | 6009 | 6176 | 17751 | 9694 | 17992 | 12429 | 15448 | 4598 | 18452 | 7077 | 10597 |
| | 16197 | 705 | 8820 | 11971 | 19192 | 1370 | 996 | 1578 | 21971 | 6312 | 17349 | 2736 |
| | 3936 | 10254 | 10398 | 22265 | 20083 | 15853 | 14066 | 5564 | 9113 | 3087 | 1078 | 7435 |
| | 14028 | 16372 | 9321 | 18704 | 8983 | 21564 | 9660 | 11558 | 17282 | 12695 | 19057 | 13847 |
| | 17094 | 11400 | 7613 | 2232 | 17213 | 17103 | 19378 | 6072 | 14868 | 8879 | 6825 | 12193 |
| | 1427 | 3275 | 9458 | 15007 | 6271 | 4411 | 4190 | 12430 | 16366 | 20438 | 15680 | 10929 |
| | 4035 | 20030 | 4556 | 17229 | 4660 | 597 | 1587 | 15707 | 4334 | 22484 | 21035 | 8211 |
| | 16251 | 13133 | 11295 | 2966 | 14058 | 5665 | 6592 | 8738 | 6102 | 13087 | 3436 | 12074 |
| | 14546 | 13772 | 20692 | 10970 | 19345 | 13509 | 5329 | 19187 | 16282 | 9968 | 21671 | 9048 |
| | 8976 | 7492 | 21462 | 19662 | 8457 | 8317 | 18846 | 12864 | 10746 | 4141 | 8673 | 21010 |
| | 10417 | 4329 | 7895 | 998 | 10132 | 8852 | 14795 | 5620 | 6695 | 13781 | 19165 | 7258 |
| | 20895 | 4154 | 7359 | 12259 | 11737 | 12704 | 21606 | 3865 | 5520 | 6932 | 12901 | 20940 |
| | 15027 | 3236 | 4907 | 20734 | 15492 | 10607 | 2472 | 15046 | 8506 | 18724 | 11671 | 15259 |
| | 15936 | 7889 | 5596 | 2053 | 6905 | 8323 | 16351 | 10263 | 15826 | 21160 | 19461 | 17456 |
| | 3953 | 3584 | 4314 | 6428 | 14221 | 4758 | 5800 | 22365 | 17678 | 16252 | 14893 | 17154 |
| | 19437 | 16453 | 21224 | 9572 | 16225 | 9367 | 1899 | 8751 | 8426 | 12483 | 4441 | 20592 |
| | 6867 | 2168 | 16928 | 13225 | 22460 | 20208 | 12970 | 2591 | 5304 | 13498 | 21581 | 4699 |
| | 21894 | 1461 | 5860 | 21622 | 18703 | 2500 | 7014 | 15116 | 596 | 14962 | 5517 | 13693 |
| | 21739 | 19681 | 11533 | 3338 | 3956 | 11364 | 17988 | | | | | |
| 531: | 15910 | 22524 | 13589 | 1006 | 11575 | 20349 | 18523 | 10911 | 13067 | 10217 | 9609 | 5233 |
| | 4966 | 9015 | 21390 | 18461 | 9866 | 21665 | 7323 | 5049 | 9997 | 5240 | 6367 | 19001 |
| | 2814 | 21443 | 1880 | 1396 | 3615 | 13867 | 7787 | 22538 | 13411 | 13344 | 1205 | 18398 |
| | 13083 | 17485 | 1550 | 757 | 11281 | 11029 | 21967 | 827 | 1873 | 21174 | 14091 | 5281 |
| | 885 | 7332 | 8229 | 21103 | 4400 | 1012 | 15883 | 7812 | 7121 | 16424 | 1339 | 1866 |
| | 3474 | 11617 | 19918 | 14296 | 1352 | 17699 | 12367 | 3388 | 20896 | 20167 | 6697 | 19989 |
| | 9358 | 15375 | 4618 | 11468 | 13543 | 3097 | 15540 | 19380 | 14287 | 5051 | 11086 | 12824 |
| | 13271 | 15196 | 6303 | 4194 | 1182 | 15803 | 1842 | 19299 | 2857 | 17664 | 21589 | 11961 |
| | 19154 | 12506 | 21814 | 6334 | 21437 | 20936 | 11195 | 20933 | 21506 | 22069 | 5476 | 3533 |
| | 19583 | 7949 | 4677 | 18511 | 4730 | 696 | 9569 | 17797 | 18687 | 7097 | 20259 | 15252 |

TABLE 16-continued

Sequence IDs for homolog proteins
Seq ID NO: homolog Seq ID NOs

|   | | | | | | | | | | | |
|---|---|---|---|---|---|---|---|---|---|---|---|
| | 13221 | 13305 | 450 | 22502 | 14915 | 21157 | 6730 | 2195 | 19855 | 10324 | 11089 | 1744 |
| | 19917 | 16130 | 21296 | 2832 | 830 | 14553 | 6434 | 18295 | 17956 | 829 | 476 | 12043 |
| | 2457 | 13959 | 12384 | 5220 | 3209 | 19341 | 5731 | 10908 | 4395 | 21843 | 14568 | 17630 |
| | 2371 | 4694 | 12396 | 15369 | 13051 | 16597 | 3697 | 10741 | 16309 | 4927 | 13396 | 21621 |
| | 8841 | 16662 | 11120 | 14081 | 19449 | 21259 | 15204 | 6565 | 18317 | 14304 | 4952 | 7813 |
| | 7306 | 12296 | 12021 | 6645 | 21386 | 16505 | 9286 | 22489 | 3622 | 14762 | 18330 | 10802 |
| | 10479 | 16663 | 3678 | 16713 | 7751 | 13703 | 3630 | 4691 | 9472 | 10709 | 8542 | 7060 |
| | 6112 | 22457 | 21974 | 20476 | 7333 | 6482 | 14526 | 7151 | 2644 | 835 | 10655 | 12264 |
| | 9315 | 2786 | 16253 | 9488 | 5634 | 17372 | 3836 | 7637 | 4946 | 18143 | 11559 | 18362 |
| | 12059 | 10889 | 5190 | 13207 | 16465 | 17346 | 3323 | 5354 | 5825 | 2210 | 19147 | 9333 |
| | 13177 | 20541 | 3458 | 1240 | 15787 | 20099 | 9282 | 11480 | 4994 | 14011 | 1145 | 19545 |
| | 802 | 17144 | 13420 | 13439 | 14301 | 1357 | 10965 | 15558 | 22251 | 22565 | 810 | 7570 |
| | 2692 | 15666 | 13168 | 10912 | 20574 | 4894 | 2526 | 18982 | 4020 | 19796 | 2984 | 11522 |
| | 11245 | 21570 | 8695 | 16749 | 17392 | 2132 | 20312 | 4655 | 16568 | 21093 | 13882 | 5730 |
| | 7976 | 7079 | 13035 | 2800 | 16658 | 18348 | 16408 | 4157 | 8112 | 5264 | 305 | 12545 |
| | 2037 | 11704 | 9571 | 21379 | 3712 | 7685 | 4483 | 18456 | 22341 | 3397 | 11197 | 13107 |
| | 675 | 16006 | 20604 | 18536 | | | | | | | | |
| 532: | 15542 | 3190 | 1006 | 429 | 7236 | 21108 | 10856 | 10217 | 1694 | 1170 | 507 | 478 |
| | 7946 | 4963 | 10952 | 8465 | 18461 | 9739 | 1850 | 5240 | 2382 | 6367 | 19001 | 19407 |
| | 14319 | 21808 | 15520 | 1498 | 14212 | 14282 | 19450 | 526 | 3987 | 18034 | 12939 | 14517 |
| | 22533 | 14740 | 7812 | 18725 | 15422 | 12515 | 6665 | 8294 | 20640 | 9749 | 7933 | 18742 |
| | 10601 | 1528 | 14184 | 8297 | 11430 | 21253 | 7897 | 4901 | 7308 | 16574 | 19527 | 9882 |
| | 8330 | 6186 | 16730 | 3076 | 15579 | 16073 | 19400 | 17335 | 2857 | 17664 | 21589 | 11961 |
| | 19154 | 6997 | 3197 | 21437 | 4440 | 11195 | 20933 | 21506 | 3533 | 4677 | 18511 | 4730 |
| | 696 | 9569 | 17797 | 18687 | 7097 | 20259 | 2920 | 15252 | 13221 | 3452 | 14930 | 450 |
| | 11335 | 20777 | 12713 | 22502 | 14915 | 21157 | 14054 | 10864 | 5059 | 21184 | 8816 | 9146 |
| | 14653 | 14579 | 20371 | 3563 | 12591 | 16308 | 7626 | 4212 | 19798 | 19458 | 5691 | 18292 |
| | 7706 | 5100 | 4540 | 16130 | 21296 | 2832 | 830 | 14553 | 6434 | 18295 | 17956 | 829 |
| | 476 | 12043 | 13241 | 11023 | 4301 | 9298 | 2269 | 1306 | 13291 | 17064 | 20779 | 5613 |
| | 1281 | 17745 | 11486 | 9723 | 16586 | 7955 | 12705 | 15449 | 988 | 20859 | 1768 | 11129 |
| | 6547 | 22518 | 5552 | 9854 | 11376 | 6669 | 5359 | 9132 | 10964 | 1879 | 22087 | 13137 |
| | 17298 | 3333 | 13752 | 20301 | 19370 | 2425 | 20461 | 6946 | 19538 | 14273 | 15340 | 6427 |
| | 17165 | 15603 | 12419 | 10809 | 8003 | 13658 | 14064 | 14568 | 17630 | 2371 | 4694 | 12396 |
| | 15369 | 16597 | 3697 | 10741 | 12482 | 16309 | 4927 | 13396 | 21621 | 8841 | 16662 | 11120 |
| | 14081 | 15751 | 4903 | 21508 | 18755 | 14599 | 6384 | 8692 | 9484 | 15204 | 6565 | 14320 |
| | 2978 | 9294 | 7482 | 9493 | 1277 | 4952 | 7813 | 7306 | 12296 | 12021 | 6645 | 9286 |
| | 22489 | 13745 | 16653 | 19069 | 7780 | 15219 | 16969 | 14762 | 18330 | 10802 | 10479 | 16663 |
| | 3678 | 16713 | 7751 | 13703 | 3630 | 4691 | 9472 | 10709 | 8542 | 7060 | 6112 | 22457 |
| | 21974 | 20476 | 7333 | 6482 | 14526 | 7151 | 2644 | 835 | 10655 | 12264 | 9315 | 2786 |
| | 16253 | 9488 | 5634 | 17372 | 1733 | 20453 | 21787 | 16624 | 7001 | 20828 | 13302 | 10357 |
| | 4549 | 788 | 10490 | 19133 | 12318 | 5515 | 9280 | 22095 | 18903 | 3706 | 15256 | 18593 |
| | 5764 | 11115 | 12583 | 11568 | 13613 | 2331 | 5136 | 8073 | 15998 | 5630 | 11304 | 19137 |
| | 5817 | 5580 | 3044 | 18341 | 8588 | 5857 | 12540 | 2454 | 4970 | 16919 | 17445 | 2401 |
| | 11869 | 6193 | 21516 | 10889 | 5190 | 13207 | 16465 | 9673 | 11625 | 9771 | 2283 | 11716 |
| | 19554 | 905 | 7481 | 12401 | 19686 | 13656 | 22135 | 9553 | 18575 | 9584 | 12794 | 5644 |
| | 21399 | 20485 | 9218 | 18691 | 3350 | 18263 | 4846 | 544 | 19667 | 9933 | 4140 | 1318 |
| | 20418 | 11128 | 20105 | 16734 | 2376 | 15699 | 7061 | 4232 | 15357 | 14036 | 5339 | 7107 |
| | 19030 | 7165 | 21370 | 12103 | 4848 | 13211 | 22530 | 15360 | 12863 | 9975 | 6398 | 14067 |
| | 16683 | 21170 | 1924 | 890 | 8155 | 15866 | 10131 | 7187 | 4332 | 1235 | 20330 | 12927 |
| | 7088 | 5099 | 2302 | 12424 | 8303 | 17466 | 14322 | 11383 | 2282 | 15956 | 3414 | 12982 |
| | 18548 | 15665 | 10961 | 21084 | 10824 | 18440 | 16819 | 3730 | 13940 | 18821 | 14864 | 1818 |
| | 19607 | 7969 | 6546 | 16771 | 5441 | 8459 | 18266 | 5000 | 15749 | 13014 | 14274 | 8444 |
| | 4707 | 13097 | 15930 | 11872 | 2621 | 7158 | 6942 | 18502 | 5408 | 10837 | 21928 | 13800 |
| | 5188 | 19614 | 16117 | 4719 | 1833 | 13499 | 3107 | 21492 | 12503 | 21929 | 7921 | 1429 |
| | 14398 | 22189 | 6439 | 12993 | 12307 | 19714 | 6650 | 18994 | 747 | 5932 | 18630 | 6683 |
| | 1921 | 15651 | 5594 | 6958 | 13597 | 19763 | 10097 | 14124 | 14687 | 1094 | 5780 | 7770 |
| | 7688 | 15110 | 5797 | 7907 | 21169 | 3329 | 12627 | 4065 | 19882 | 22067 | 19211 | 2061 |
| | 7038 | 8909 | 16914 | 13129 | 19881 | 11720 | 16317 | 1551 | 13235 | 14888 | 1201 | 20264 |
| | 7800 | 7526 | 2209 | 5887 | 15285 | 10798 | 15317 | 10223 | 11351 | 10105 | 10661 | 15014 |
| | 2908 | 16412 | 22277 | 19851 | 12003 | 19616 | 11003 | 7768 | 6166 | 21613 | 4620 | 13850 |
| | 16231 | 7016 | 2717 | 20541 | 3458 | 1240 | 15787 | 20099 | 9282 | 11480 | 4994 | 937 |
| | 16775 | 18459 | 14476 | 9221 | 17450 | 6281 | 18662 | 7992 | 9661 | 19875 | 11156 | 3619 |
| | 14086 | 20948 | 16946 | 3456 | 6143 | 786 | 6709 | 5954 | 17926 | 20839 | 22351 | 13277 |
| | 11255 | 5140 | 4283 | 9455 | 4818 | 14459 | 5187 | 16668 | 10965 | 15558 | 17215 | 14289 |
| | 11685 | 4388 | 14119 | 18982 | 2984 | 11245 | 304 | 477 | 427 | 18112 | 965 | 2900 |
| | 2132 | 20312 | 4655 | 16568 | 21093 | 13882 | 5730 | 7976 | 7079 | 13035 | 5498 | 2800 |
| | 19337 | 9600 | 307 | 12545 | 2037 | 11704 | 9571 | 21379 | 3712 | 7685 | 4483 | 18456 |
| | 22341 | 11197 | 13107 | 16006 | 7623 | | | | | | | |
| 533: | 6090 | 1006 | 429 | 10217 | 10250 | 19910 | 18933 | 314 | 18461 | 5240 | 6367 | 19001 |
| | 16913 | 19119 | 526 | 3693 | 7812 | 13179 | 534 | 300 | 531 | 2857 | 17664 | 21589 |
| | 11961 | 19154 | 21437 | 11195 | 20933 | 21506 | 3533 | 4677 | 18511 | 4730 | 696 | 9569 |
| | 17797 | 18687 | 7097 | 20259 | 15252 | 13221 | 450 | 11335 | 20777 | 12713 | 22502 | 14915 |
| | 21157 | 20371 | 3563 | 12591 | 16308 | 7626 | 4212 | 19798 | 19458 | 5691 | 18292 | 16130 |
| | 21296 | 2832 | 830 | 14553 | 6434 | 18295 | 17956 | 829 | 476 | 12043 | 20779 | 1281 |
| | 17745 | 16586 | 7955 | 12705 | 15449 | 988 | 20859 | 1768 | 11129 | 6547 | 22518 | 5552 |
| | 9854 | 11376 | 6669 | 5359 | 9132 | 10964 | 1879 | 22087 | 13137 | 17298 | 3333 | 13752 |
| | 20301 | 19370 | 2425 | 6946 | 19538 | 14273 | 15603 | 15340 | 6427 | 17165 | 12419 | 10809 |

TABLE 16-continued

Sequence IDs for homolog proteins
Seq ID NO: homolog Seq ID NOs

|  | | | | | | | | | | | | |
|---|---|---|---|---|---|---|---|---|---|---|---|
|  | 8003 | 13658 | 14064 | 4221 | 7387 | 13284 | 20981 | 2316 | 3116 | 8418 | 3386 | 6508 |
|  | 18217 | 3578 | 22249 | 992 | 13442 | 3471 | 14855 | 19949 | 5277 | 19885 | 2816 | 10917 |
|  | 9436 | 18538 | 18659 | 12816 | 12308 | 15943 | 2515 | 20364 | 14701 | 8193 | 17579 | 22076 |
|  | 8890 | 2649 | 9329 | 21073 | 8376 | 15177 | 10882 | 859 | 5990 | 9814 | 16053 | 5209 |
|  | 3144 | 13848 | 22428 | 19076 | 5454 | 17056 | 14918 | 4088 | 11270 | 5837 | 9604 | 22455 |
|  | 19840 | 12234 | 1149 | 801 | 953 | 9960 | 21301 | 1656 | 3755 | 12278 | 22119 | 21098 |
|  | 1005 | 10264 | 13037 | 11702 | 20954 | 5581 | 5063 | 1118 | 6454 | 20632 | 1696 | 19474 |
|  | 14911 | 9381 | 4111 | 13374 | 2932 | 3071 | 18551 | 22362 | 1431 | 12923 | 6509 | 19229 |
|  | 14012 | 5372 | 12362 | 17380 | 20272 | 16391 | 13395 | 5132 | 901 | 9540 | 19228 | 11589 |
|  | 13306 | 3179 | 14568 | 17630 | 2371 | 4694 | 12396 | 15369 | 11784 | 16597 | 3697 | 10741 |
|  | 16309 | 4927 | 13396 | 21621 | 8841 | 16662 | 11120 | 14081 | 8692 | 9484 | 15204 | 6565 |
|  | 14320 | 2978 | 9294 | 7482 | 9493 | 1277 | 4952 | 7813 | 7306 | 12296 | 12021 | 6645 |
|  | 9286 | 22489 | 13745 | 16653 | 19069 | 7780 | 15219 | 16969 | 14762 | 18330 | 10280 | 10802 |
|  | 10479 | 16663 | 3678 | 16713 | 7751 | 13703 | 3630 | 4691 | 9472 | 10709 | 8542 | 7060 |
|  | 6112 | 22457 | 21974 | 20476 | 7333 | 6482 | 14526 | 7151 | 2644 | 835 | 10655 | 12264 |
|  | 9315 | 2786 | 16253 | 9488 | 5634 | 17372 | 788 | 9280 | 22095 | 18903 | 3706 | 15256 |
|  | 18593 | 5764 | 11115 | 12583 | 11568 | 13613 | 2331 | 5136 | 8073 | 15998 | 5630 | 11304 |
|  | 19137 | 5817 | 5580 | 18341 | 8588 | 12540 | 2454 | 4970 | 17445 | 2401 | 11869 | 6193 |
|  | 21516 | 2447 | 10889 | 5190 | 13207 | 16465 | 9673 | 9771 | 11716 | 18575 | 9584 | 12794 |
|  | 21399 | 20485 | 9218 | 18691 | 3350 | 18263 | 4846 | 544 | 19667 | 9933 | 4140 | 1318 |
|  | 20418 | 11128 | 20105 | 16734 | 2376 | 15699 | 7061 | 4232 | 15357 | 14036 | 5339 | 7107 |
|  | 19030 | 7165 | 21370 | 12103 | 4848 | 13211 | 22530 | 15360 | 12863 | 9975 | 6398 | 14067 |
|  | 16683 | 21170 | 1924 | 890 | 8155 | 15866 | 10131 | 7187 | 4332 | 1235 | 20330 | 12927 |
|  | 7088 | 5099 | 2302 | 12424 | 8303 | 17466 | 14322 | 11383 | 2282 | 15956 | 3414 | 12982 |
|  | 18548 | 15665 | 10961 | 21084 | 10824 | 18440 | 16819 | 3730 | 13940 | 18821 | 14864 | 1818 |
|  | 19607 | 7969 | 6546 | 16771 | 5441 | 8459 | 18266 | 5000 | 15749 | 13014 | 14274 | 8444 |
|  | 4707 | 13097 | 15930 | 11872 | 2621 | 7158 | 6942 | 18502 | 5408 | 10837 | 21928 | 13800 |
|  | 5188 | 19614 | 16117 | 4719 | 1833 | 13499 | 3107 | 21492 | 12503 | 21929 | 7921 | 1429 |
|  | 14398 | 22189 | 747 | 6439 | 12993 | 12307 | 19714 | 6650 | 18994 | 5932 | 18630 | 6683 |
|  | 1921 | 15651 | 5594 | 6958 | 13597 | 19763 | 10097 | 4065 | 14124 | 14687 | 1094 | 5780 |
|  | 7770 | 7688 | 15110 | 5797 | 7907 | 21169 | 3329 | 12627 | 19882 | 22067 | 19211 | 2061 |
|  | 7038 | 8909 | 16914 | 13129 | 19881 | 16317 | 1551 | 13235 | 14888 | 1201 | 20264 | 7800 |
|  | 7526 | 2209 | 5887 | 10223 | 10798 | 15317 | 11351 | 10105 | 10661 | 15014 | 2908 | 16412 |
|  | 22277 | 19851 | 12003 | 19616 | 11003 | 7768 | 6166 | 4620 | 16231 | 13850 | 7016 | 2717 |
|  | 20886 | 14522 | 5254 | 15519 | 20541 | 3458 | 1240 | 15787 | 20099 | 9282 | 11480 | 4994 |
|  | 6281 | 18662 | 7992 | 9661 | 19875 | 11156 | 3619 | 14086 | 20948 | 16946 | 3456 | 6143 |
|  | 786 | 6709 | 5954 | 17926 | 20839 | 22351 | 13277 | 15113 | 6368 | 7704 | 18694 | 3644 |
|  | 12154 | 3794 | 21257 | 21638 | 18386 | 18111 | 21498 | 10731 | 13776 | 5539 | 14530 | 20282 |
|  | 7762 | 9529 | 17675 | 15191 | 12380 | 14865 | 15825 | 2818 | 16442 | 5901 | 8220 | 18578 |
|  | 13297 | 2495 | 21913 | 4526 | 16085 | 10965 | 15558 | 18982 | 2984 | 11245 | 21040 | 477 |
|  | 11140 | 2132 | 20312 | 4655 | 16568 | 21093 | 13882 | 5730 | 7976 | 7079 | 13035 | 2800 |
|  | 15563 | 509 | 12545 | 2037 | 11704 | 9571 | 21379 | 3712 | 7685 | 4483 | 18456 | 22341 |
|  | 11197 | 13107 | 13802 | 16006 | 428 | | | | | | | |
| 534: | 6383 | 10450 | 1006 | 8266 | 17986 | 13269 | 9010 | 9822 | 18387 | 3735 | 10217 | 533 |
|  | 535 | 1774 | 16191 | 18891 | 13849 | 14706 | 571 | 8356 | 3340 | 18461 | 20284 | 20753 |
|  | 10192 | 13836 | 5240 | 2653 | 20833 | 3564 | 1870 | 11250 | 6367 | 19001 | 20137 | 15672 |
|  | 13176 | 20207 | 8314 | 4015 | 1887 | 8795 | 21466 | 7023 | 6876 | 8560 | 16477 |  |
|  | 13630 | 10793 | 4136 | 5249 | 17099 | 9152 | 2730 | 4724 | 8684 | 5821 | 3710 | 16562 |
|  | 22562 | 9500 | 21952 | 12129 | 1151 | 5863 | 2635 | 13579 | 5947 | 9543 | 6219 | 4851 |
|  | 7812 | 10216 | 19130 | 12258 | 1950 | 8843 | 1084 | 2519 | 12495 | 7141 | 1845 | 6128 |
|  | 9067 | 2618 | 1308 | 1202 | 16045 | 2887 | 3970 | 22176 | 2992 | 14189 | 2020 | 3687 |
|  | 18669 | 17082 | 7279 | 10946 | 10754 | 10583 | 4481 | 915 | 16903 | 18701 | 14442 | 11182 |
|  | 12710 | 8108 | 4737 | 8174 | 21990 | 14565 | 20445 | 20022 | 9861 | 2888 | 17080 | 6216 |
|  | 3441 | 9629 | 4034 | 4019 | 17401 | 1207 | 22219 | 1481 | 5143 | 2857 | 17664 | 21589 |
|  | 11961 | 19154 | 12425 | 21437 | 17489 | 11195 | 20933 | 21506 | 3533 | 12843 | 4677 | 18511 |
|  | 4730 | 696 | 9569 | 17797 | 18687 | 7097 | 20259 | 20966 | 15252 | 13221 | 11335 | 20777 |
|  | 12713 | 22502 | 14915 | 21157 | 13596 | 7735 | 6111 | 14062 | 20371 | 3563 | 12591 | 16308 |
|  | 7626 | 21483 | 4212 | 19798 | 19458 | 5691 | 18292 | 16130 | 21296 | 2832 | 830 | 14553 |
|  | 4632 | 6434 | 18295 | 17956 | 829 | 12043 | 1189 | 3932 | 18731 | 6845 | 21360 | 6772 |
|  | 19039 | 21673 | 20779 | 1281 | 16128 | 14568 | 17630 | 2371 | 4694 | 12396 | 15369 | 14260 |
|  | 13396 | 21621 | 8841 | 16662 | 11120 | 14081 | 6657 | 8692 | 9484 | 14065 | 2540 | 15204 |
|  | 6565 | 14320 | 2978 | 9294 | 7482 | 9493 | 1277 | 4952 | 7813 | 7306 | 12296 | 12021 |
|  | 6645 | 9286 | 22489 | 19908 | 893 | 14762 | 18330 | 10802 | 10479 | 16663 | 3678 | 16713 |
|  | 7751 | 13703 | 3630 | 4691 | 9472 | 10709 | 8542 | 7060 | 6112 | 22457 | 21974 | 20476 |
|  | 7333 | 6482 | 14526 | 7151 | 2644 | 835 | 10655 | 12264 | 9315 | 2786 | 16253 | 9488 |
|  | 5634 | 17372 | 2081 | 12643 | 15099 | 7425 | 15838 | 10094 | 788 | 3348 | 9280 | 22095 |
|  | 18903 | 3706 | 15256 | 18593 | 5764 | 11115 | 12583 | 5630 | 11568 | 13613 | 2331 | 5136 |
|  | 8073 | 15998 | 11304 | 19137 | 5817 | 4430 | 5580 | 8588 | 18341 | 12540 | 2454 | 4970 |
|  | 17445 | 2401 | 10889 | 5190 | 13207 | 16465 | 11291 | 16479 | 21467 | 4263 | 2705 | 9673 |
|  | 20541 | 3458 | 1240 | 15787 | 20099 | 9282 | 11480 | 4994 | 2798 | 5475 | 1814 | 2683 |
|  | 8435 | 4345 | 3627 | 15897 | 9366 | 6281 | 20716 | 18662 | 7992 | 9661 | 19875 | 11156 |
|  | 21818 | 3619 | 14086 | 20948 | 16946 | 3456 | 6143 | 786 | 6709 | 5954 | 17926 | 20839 |
|  | 13891 | 10965 | 15558 | 15276 | 3513 | 17600 | 11426 | 1123 | 16786 | 5326 | 17407 | 18982 |
|  | 2984 | 19817 | 11245 | 5838 | 21039 | 15310 | 2132 | 20312 | 4655 | 16568 | 21093 | 13882 |
|  | 5730 | 7976 | 7079 | 13035 | 2800 | 16353 | 4982 | 22032 | 3731 | 7388 | 13436 | 8698 |
|  | 509 | 12545 | 2037 | 11704 | 9571 | 21379 | 3712 | 7685 | 4483 | 18456 | 22341 | 15886 |

TABLE 16-continued

Sequence IDs for homolog proteins
Seq ID NO: homolog Seq ID NOs

|  | | | | | | | | | | | |
|---|---|---|---|---|---|---|---|---|---|---|---|
|  | 11197 | 13107 | 5444 | 16006 | 9573 | 20805 | 372 | 19913 | 9499 | 18057 | 7973 | 22459 |
|  | 21704 | 8464 | | | | | | | | | | |
| 535: | 9382 | 1006 | 429 | 10217 | 2438 | 9883 | 314 | 18461 | 5240 | 6367 | 19001 | 16674 |
|  | 12484 | 526 | 11896 | 7812 | 9819 | 2857 | 17664 | 21589 | 11961 | 19154 | 21437 | 11195 |
|  | 20933 | 21506 | 3533 | 4677 | 18511 | 4730 | 696 | 9569 | 17797 | 18687 | 7097 | 20259 |
|  | 15252 | 13221 | 450 | 11335 | 20777 | 12713 | 22502 | 14915 | 21157 | 20371 | 3563 | 12591 |
|  | 16308 | 7626 | 4212 | 19798 | 19458 | 5691 | 18292 | 16130 | 21296 | 2832 | 830 | 14553 |
|  | 6434 | 18295 | 17956 | 829 | 476 | 12043 | 20779 | 1281 | 17745 | 16586 | 7955 | 12705 |
|  | 15449 | 988 | 20859 | 1768 | 11129 | 6547 | 22518 | 5552 | 9854 | 11376 | 6669 | 5359 |
|  | 9132 | 10964 | 1879 | 22087 | 13137 | 17298 | 3333 | 13752 | 20301 | 19370 | 2425 | 6946 |
|  | 19538 | 14273 | 15340 | 6427 | 17165 | 15603 | 12419 | 10809 | 8003 | 13658 | 14064 | 4221 |
|  | 7387 | 13284 | 20981 | 2316 | 3116 | 8418 | 3386 | 6508 | 18217 | 3578 | 22249 | 992 |
|  | 14855 | 13442 | 3471 | 19949 | 5277 | 19885 | 2816 | 10917 | 9436 | 18538 | 18659 | 12816 |
|  | 12308 | 15943 | 2515 | 20364 | 14701 | 8193 | 17579 | 22076 | 8890 | 2649 | 9329 | 21073 |
|  | 8376 | 15177 | 10882 | 859 | 5990 | 9814 | 16053 | 5209 | 3144 | 13848 | 22428 | 19076 |
|  | 5454 | 17056 | 14918 | 4088 | 11270 | 5837 | 9604 | 22455 | 19840 | 12234 | 1149 | 801 |
|  | 953 | 9960 | 21301 | 1656 | 3755 | 12278 | 22119 | 21098 | 1005 | 10264 | 13037 | 11702 |
|  | 20954 | 5581 | 5063 | 1118 | 6454 | 20632 | 1696 | 19474 | 14911 | 9381 | 4111 | 13374 |
|  | 2932 | 3071 | 18551 | 22362 | 1431 | 12923 | 6509 | 19229 | 14012 | 5372 | 12362 | 17380 |
|  | 20272 | 16391 | 13395 | 5132 | 901 | 9540 | 19228 | 14568 | 17630 | 2371 | 4694 | 12396 |
|  | 15369 | 16597 | 3697 | 10741 | 16309 | 4927 | 13396 | 21621 | 8841 | 16662 | 11120 | 14081 |
|  | 8692 | 9484 | 15204 | 6565 | 14320 | 2978 | 9294 | 7482 | 9493 | 1277 | 4952 | 7813 |
|  | 7306 | 12296 | 12021 | 6645 | 9286 | 22489 | 13745 | 16653 | 19069 | 7780 | 15219 | 16969 |
|  | 14762 | 18330 | 10802 | 10479 | 16663 | 3678 | 16713 | 7751 | 13703 | 3630 | 4691 | 9472 |
|  | 10709 | 8542 | 7060 | 6112 | 22457 | 21974 | 20476 | 7333 | 6482 | 14526 | 7151 | 2644 |
|  | 835 | 10655 | 12264 | 9315 | 2786 | 16253 | 9488 | 5634 | 17372 | 788 | 9280 | 22095 |
|  | 18903 | 3706 | 15256 | 18593 | 5764 | 11115 | 12583 | 11568 | 13613 | 2331 | 5136 | 8073 |
|  | 15998 | 5630 | 11304 | 19137 | 5817 | 5580 | 8588 | 18341 | 12540 | 2454 | 4970 | 17445 |
|  | 2401 | 11869 | 6193 | 21516 | 10889 | 5190 | 13207 | 16465 | 9673 | 9771 | 11716 | 18575 |
|  | 9584 | 12794 | 21399 | 20485 | 9218 | 18691 | 3350 | 18263 | 4846 | 544 | 19667 | 9933 |
|  | 4140 | 1318 | 20418 | 11128 | 20105 | 16734 | 2376 | 15699 | 7061 | 4232 | 15357 | 14036 |
|  | 5339 | 7107 | 19030 | 7165 | 21370 | 12103 | 4848 | 13211 | 22530 | 15360 | 12863 | 9975 |
|  | 6398 | 14067 | 16683 | 21170 | 1924 | 890 | 8155 | 15866 | 10131 | 7187 | 4332 | 1235 |
|  | 20330 | 12927 | 7088 | 5099 | 2302 | 12424 | 8303 | 17466 | 14322 | 11383 | 2282 | 15956 |
|  | 3414 | 12982 | 18548 | 15665 | 10961 | 21084 | 10824 | 18440 | 16819 | 3730 | 13940 | 18821 |
|  | 14864 | 1818 | 19607 | 7969 | 6546 | 16771 | 5441 | 8459 | 18266 | 5000 | 15749 | 13014 |
|  | 14274 | 8444 | 4707 | 13097 | 15930 | 11872 | 2621 | 7158 | 6942 | 18502 | 5408 | 10837 |
|  | 21928 | 13800 | 5188 | 19614 | 16117 | 4719 | 1833 | 13499 | 3107 | 21492 | 12503 | 21929 |
|  | 7921 | 1429 | 14398 | 22189 | 6439 | 12993 | 12307 | 19714 | 6650 | 18994 | 747 | 5932 |
|  | 18630 | 6683 | 1921 | 15651 | 5594 | 6958 | 13597 | 19763 | 10097 | 14124 | 14687 | 1094 |
|  | 5780 | 7770 | 7688 | 15110 | 5797 | 7907 | 21169 | 3329 | 19882 | 12627 | 4065 | 22067 |
|  | 19211 | 2061 | 7038 | 8909 | 16914 | 13129 | 19881 | 16317 | 1551 | 13235 | 14888 | 1201 |
|  | 20264 | 7800 | 7526 | 2209 | 5887 | 10798 | 15317 | 10223 | 11351 | 10105 | 10661 | 15014 |
|  | 2908 | 16412 | 22277 | 19851 | 12003 | 19616 | 11003 | 7768 | 6166 | 4620 | 13850 | 16231 |
|  | 7016 | 2717 | 20541 | 3458 | 1240 | 15787 | 20099 | 9282 | 11480 | 4994 | 6281 | 18662 |
|  | 7992 | 9661 | 19875 | 11156 | 3619 | 14086 | 20948 | 16946 | 3456 | 6143 | 786 | 6709 |
|  | 5954 | 17926 | 20839 | 22351 | 13277 | 15113 | 6368 | 7704 | 18694 | 3644 | 12154 | 3794 |
|  | 21257 | 21638 | 18386 | 18111 | 21498 | 10731 | 13776 | 5539 | 14530 | 20282 | 7762 | 9529 |
|  | 17675 | 15191 | 12380 | 14865 | 15825 | 2818 | 16442 | 5901 | 8220 | 18578 | 13297 | 2495 |
|  | 21913 | 4526 | 16085 | 10965 | 15558 | 18982 | 2984 | 11245 | 16474 | 304 | 477 | 427 |
|  | 5067 | 2132 | 20312 | 4655 | 16568 | 21093 | 13882 | 5730 | 7976 | 7079 | 13035 | 2800 |
|  | 20416 | 509 | 307 | 305 | 12545 | 2037 | 11704 | 9571 | 21379 | 3712 | 7685 | 4483 |
|  | 18456 | 22341 | 11197 | 13107 | 13268 | 16006 | 428 | | | | | |
| 536: | 8250 | 5293 | 17519 | 10969 | 8775 | 16532 | 10286 | 11811 | 5689 | 2871 | 680 | 20415 |
|  | 14104 | 16888 | 17043 | 10273 | 6777 | 22396 | 602 | 4866 | 12333 | 9909 | 22327 | 4344 |
|  | 9005 | 16476 | 2573 | 10616 | 19638 | 15657 | 8950 | 4378 | 2657 | 3364 | 21708 | 985 |
|  | 6316 | 8776 | 2238 | 13856 | 1099 | 10466 | 19656 | 6879 | 9313 | 19604 | 12069 | 8122 |
|  | 21385 | 16087 | 20487 | 1424 | 14078 | 2427 | 4175 | 7418 | 9385 | 16892 | 15809 | 3499 |
|  | 16714 | 5768 | 6322 | 13627 | 19469 | 8252 | 19551 | 14976 | 12742 | 10499 | 11322 | 9597 |
|  | 3569 | 9336 | 20132 | 5283 | 22127 | 10381 | 3149 | 7067 | 13886 | 7478 | 3897 | 20869 |
|  | 19398 | 13086 | 4191 | 3669 | 20800 | 6799 | 8453 | 17539 | 21956 | 5724 | 13878 | 16687 |
|  | 1797 | | | | | | | | | | | |
| 537: | 12225 | 7991 | 19769 | 20707 | 6346 | 21228 | 18920 | 15677 | 22007 | 17216 | 1246 | 1299 |
|  | 3482 | 8428 | 4864 | 1869 | 18259 | 5076 | 18894 | 10621 | 1194 | 21241 | 4280 | 10372 |
|  | 9939 | 3461 | 22101 | 14388 | 9687 | 1934 | 3266 | 19426 | 6888 | 17781 | 1697 | 1251 |
|  | 15687 | 11467 | 11444 | 7248 | 4960 | 3598 | 18026 | 17460 | 7270 | 18737 | 20522 | 18581 |
|  | 16569 | 13403 | 4999 | 20923 | 3253 | 12847 | 6541 | 12065 | 13811 | 442 | 18246 | 10039 |
|  | 21176 | 20831 | 13532 | 19077 | 10287 | 9635 | 12724 | 898 | 4347 | 11482 | 12691 | 8702 |
|  | 12055 | 8006 | 14571 | 19675 | 16542 | 21229 | 14891 | 11459 | 15395 | 15872 | 9301 | 10051 |
|  | 6843 | 5509 | 11707 | 10865 | 18908 | 12031 | 9844 | 20469 | 4041 | 4623 | 22346 | 1849 |
|  | 12095 | 14281 | 3840 | 16733 | 15322 | 21786 | 17305 | 10611 | 1428 | 7631 | 22045 | 6676 |
|  | 5894 | 8015 | 21902 | 14896 | 17330 | 3090 | 15122 | 7759 | 6196 | 16678 | 475 | 20224 |
|  | 3032 | 21119 | 21396 | 1165 | 20759 | 22152 | 18157 | 1337 | 3062 | 12222 | 10847 | 14596 |
|  | 3679 | 21087 | 17626 | 3743 | 10092 | 21220 | 22333 | 4831 | 6340 | 2684 | 14394 | 17353 |
|  | 12317 | 2073 | 22147 | 10166 | 9664 | 11412 | 21185 | 7389 | 11862 | 11526 | 9220 | 2983 |
|  | 5429 | 13258 | 10529 | 12270 | 6868 | 5672 | 2355 | 11711 | 9314 | 17713 | 6624 | 12386 |
|  | 17898 | 3480 | 10028 | 20275 | 1292 | 12254 | 17594 | 20642 | 4853 | 10383 | 4591 | 8186 |

TABLE 16-continued

Sequence IDs for homolog proteins
Seq ID NO: homolog Seq ID NOs

|  | 16379 | 15333 | 9201 | 15765 | 17720 | 5294 | 9934 | 7376 | 4038 | 2297 | 1916 | 7144 |
|---|---|---|---|---|---|---|---|---|---|---|---|---|
|  | 16736 | 10304 | 3319 | 3762 | 20614 | 11341 | 10440 | 4734 | 9677 | 12289 | 20772 | 4271 |
|  | 19954 | 22175 | 3020 | 19748 | 16083 | 8948 | 19737 | 22114 | 2955 | 21137 | 3274 | 1408 |
|  | 6780 | 10848 | 7124 | 14060 | 11449 | 17939 | 4794 | 16058 | 21761 | 10251 | 4961 | 19141 |
|  | 1661 | 9701 | 6223 | 5983 | 18048 | 10670 | 17196 | 1709 | 4904 | 12196 | 630 | 8403 |
|  | 8582 | 6184 | 18819 | 3380 | 9202 | 16022 | 17350 | 12703 | 15237 | 17792 | 4597 | 11159 |
|  | 1072 | 20441 | 15476 | 15612 | 17341 | 12261 | 21044 | 4892 | 1108 | 1406 | 22046 | 18198 |
|  | 6967 | 20318 | 12469 | 22123 | 7645 | 10452 | 1264 | 712 | 14602 | 6109 | 14712 | 22157 |
|  | 7745 | 16695 | 11050 | 22271 | 21574 |  |  |  |  |  |  |  |
| 538: | 8633 | 21066 | 20486 | 15659 | 19893 | 20341 | 18625 | 7202 | 9210 | 15561 | 8243 | 19452 |
|  | 10486 | 9599 | 20104 | 5911 | 17836 | 3744 | 3313 | 22371 | 13393 | 8083 | 14598 | 8878 |
|  | 4121 | 11696 | 16024 | 6949 | 9760 | 18073 | 21021 | 1691 | 3955 | 13639 | 14076 | 5677 |
|  | 2739 | 10860 | 20215 | 14300 | 10639 | 13585 | 11393 | 3392 | 7331 | 2940 | 4631 | 3646 |
|  | 14037 | 5709 | 8396 | 7169 | 3234 | 9515 | 13640 | 21141 | 9848 | 13213 | 16854 | 10018 |
|  | 17683 | 4171 | 20607 | 15041 | 2557 | 19483 | 17558 | 19443 | 20760 | 13774 | 16065 | 5097 |
|  | 13747 | 713 | 8505 | 18788 | 18352 | 817 | 5302 | 8167 | 10335 | 22171 | 13497 | 18845 |
|  | 11474 | 8093 | 22332 | 17185 | 18392 | 15387 | 7019 | 17613 | 13932 | 22281 | 9232 | 21810 |
|  | 19046 | 14214 | 6221 | 10362 | 21188 | 12117 | 2909 | 9179 | 16519 | 21842 | 14950 | 5628 |
|  | 5467 | 18729 | 7240 | 8434 | 11000 | 2806 | 17205 | 1863 | 9645 | 18886 | 6782 | 20838 |
|  | 7708 | 6070 | 7788 | 22286 | 19842 | 16891 | 9527 | 18008 | 7791 | 11889 | 5849 | 2006 |
|  | 3823 | 12758 | 17857 | 15410 | 11552 | 11047 | 5550 | 18384 | 903 | 18870 | 12346 | 18758 |
|  | 1298 | 11723 | 11231 | 13187 | 11334 | 10943 | 11898 | 11754 | 4492 | 6688 | 19935 | 13184 |
|  | 13651 | 1487 | 20841 | 6884 | 6464 | 8803 | 16050 | 6362 | 1430 | 1363 | 10992 | 6297 |
|  | 3031 | 2620 | 18570 | 22021 | 21438 | 13674 | 22415 | 1440 | 6599 | 17348 | 16403 | 2064 |
|  | 5725 | 621 | 12956 | 13371 | 3689 | 813 | 8410 | 17547 | 5880 | 7069 | 7272 | 13965 |
|  | 9296 | 18273 | 16456 | 7801 | 2112 | 17834 | 8758 | 7378 | 19838 | 6388 | 10579 | 19671 |
|  | 16279 | 806 | 14835 | 2530 | 4277 | 795 | 12076 | 5622 | 13454 | 3935 | 4559 | 18529 |
|  | 18155 | 19209 | 15646 | 5247 | 6539 | 16369 | 5499 | 21300 | 14158 | 12126 | 17163 | 16184 |
|  | 993 | 21342 | 16623 | 17172 | 10687 | 11363 | 1456 | 21186 | 21282 | 21603 | 10623 | 6475 |
|  | 17459 | 18745 | 21602 | 9996 | 3042 | 16551 | 1505 | 5224 | 5300 | 3833 | 4119 | 10925 |
|  | 11838 | 21509 | 15409 | 13868 | 11753 | 16835 | 13881 | 7206 | 18880 | 6510 | 4201 | 3942 |
|  | 968 | 5155 | 13073 | 10765 | 5458 | 12673 | 3180 | 3108 | 15770 | 908 | 21482 | 5413 |
|  | 18381 | 14279 | 4351 | 15582 | 22158 | 16937 | 12412 | 13635 | 14711 | 5969 | 9888 | 21962 |
|  | 11801 | 16194 | 10513 | 4703 | 11781 | 15593 | 17383 | 18258 | 9184 | 7699 | 9109 | 1971 |
|  | 18780 | 3171 | 11419 | 10405 | 631 | 15583 | 21710 | 7483 | 5744 | 22254 | 12810 | 13894 |
|  | 20089 | 6909 | 5948 | 3120 | 15669 | 17412 | 19244 | 2016 | 16850 | 22002 | 7260 | 14202 |
|  | 3293 | 4461 | 2271 | 14582 | 18598 | 17872 | 1569 | 18470 | 5671 | 8965 | 4082 | 7327 |
|  | 22511 | 15167 | 1160 | 15734 | 5450 | 19432 | 14387 | 14587 | 3176 | 8359 | 18160 | 11357 |
|  | 15085 | 6948 | 5337 | 2567 | 10321 | 22182 | 10881 | 10168 | 18477 | 12537 | 19015 | 20260 |
|  | 2170 | 18422 | 2440 | 3225 | 5484 | 1260 | 1822 | 7532 | 19248 | 7693 | 4353 | 10441 |
|  | 2660 | 5734 | 10038 | 19976 | 3453 | 19019 | 1674 | 12312 | 16581 | 10232 | 3727 | 1523 |
|  | 2140 | 22432 | 20580 | 9947 | 19324 | 20180 | 1384 | 2325 | 18901 | 10198 | 20110 | 9744 |
|  | 9208 | 3182 | 14144 | 18875 | 14329 | 929 | 22054 | 2752 | 4524 | 986 | 977 | 21117 |
|  | 9567 | 9679 | 12352 | 20957 | 4772 | 12912 | 19652 | 11510 | 5608 | 21827 | 13765 | 8183 |
|  | 14331 | 13670 | 20503 | 12206 | 21116 | 22320 | 844 | 2226 | 21795 | 13733 | 11051 | 20995 |
|  | 2615 | 7715 | 4478 | 2290 | 12549 | 15082 | 2491 | 2301 | 14182 | 15076 | 1227 | 10071 |
|  | 3792 | 13186 | 4722 | 1595 | 10880 | 11269 | 8528 | 3213 | 14537 | 4257 | 8761 | 17108 |
|  |  | 4834 | 2651 | 19705 | 3355 | 7552 | 6681 |  |  |  |  |  |

Example 3 Consensus Sequence Build

ClustalW program was selected for multiple sequence alignments of the amino acid sequence of SEQ ID NO: 379 and 10 homologs. Three major factors affecting the sequence alignments dramatically are (1) protein weight matrices; (2) gap open penalty; (3) gap extension penalty. Protein weight matrices available for ClustalW program include Blosum, Pam and Gonnet series. Those parameters with gap open penalty and gap extension penalty were extensively tested.

On the basis of the test results, Blosum weight matrix, gap open penalty of 10 and gap extension penalty of 1 were chosen for multiple sequence alignment. Attached are the sequences of SEQ ID NO: 379, its homologs and the consensus sequence SEQ ID NO: 22569 at the end. The symbols for consensus sequence are (1) uppercase letters for 100% identity in all positions of multiple sequence alignment output; (2) lowercase letters for >=70% identity; symbol; (3) "X" indicated <70% identity; (4) dashes "-" meaning that gaps were in >=70% sequences.

```
SEQ ID NO
   2406    ------------------------MGSNGGSSNNNNNKVLEKPGQDQLVQQQQQQQE-
  15414    ------------------------MGSNGGSSNNNNNKVLEKPGQDQLVQQQHPQE-
    587    ---------------------------------MMGRVMEKPSQDLLQQQQQ-----
   9696    ---------------------------------MMGRVMEKPSQDLLQQQQQ-----
   5895    ---------------------------------MMGRVMEKPSQDLLQQQQQ-----
  17251    MFGNGNCDVDNEKTIITSSKWTQSEIDDHKVSMASSTGNRVMEKPGQELLQQQQQ-----
  19549    -------------------------------------MEKQGQELLQQHHQQQQQQ
    379    ------------------------------------MQSKNMIVASSHQQQQQQQPQQPQP
  21357    ---------MGLSSKQVSSSGLDWKQTLLEAQNLELPKPNLMRKQQQQQQQQQQQTONSE
  17711    ---------MGLSSKQVSSSGLDWKQTLLEAQNLELPKPNLMRKQQQQQQQQQQQTQPNSE
```

```
13715      ---------------------------------LTLTKCCMQRGSHFRSRSGSQEARS
consensus  -------------------------xxxxxxxxxxxxxxxxxxxxqxxxqqqqxxxxxx
22569

APKCPRCDSSNTKFCYYNNYSLSQPRHECKACKRYWTRGGTLRNVPVGCCCRRNKRVKRP
APKCPRCDSSNTKFCYYNNYSLSQPRHFCKACKRYWTRGGTLRNVPVGGGCRRNKRVERP
ALKCPRCESSNTKFCYYNNYSLSQPRHFCKACKRYWTRGGTLRNVPVGGGCRKNKRVKRP
ALKCPRCESSNTKFCYYNNYSLSQPRHFCKACKRYWTRGGTLRNVPVGGGCRKNKRVKRP
ALKCPRCESSNTKFCYYNNYSLSQPRHFCKACKRYWTRGGTLRNVPVGGGCRKNKRVKRP
ALRCPRCDSSNTKFCYYNNYSLTQPRHFCKACKRYWTRGGTLRNVPVGGGCRKNKRLKRP
ALKCPRCDSSNTKFCYYNNYSLSQPRHFCKACKRYWTRGGTLRNVPVGGGYRRNNKRSTS
QLKCPRCDSSNTKFCYYNNYSLSQPRHFCKACKRYWTRGGTLRNVPVGGSYRKNKRVKRP
SLKCPRCDSTNTKFCYYNNYNKSQPRHFCRACKRHWTKGGTLRNVPVGG-GRKNKRVKKS
SLKCPRCDSTNTKFCYYNNYNKSQPRHFCRACKRHWTKGGTLRNVPVGG-GRKNKRVRKS
GSSMSRCNSMDTKFCYYNNYNVNQPRHFCKNCQRYWTAGGSMRNVPVGAGRRKNKHTGSV
xlkcpRCxSsnTKFCYYNNYslsQPRHFCkaCkRyWTrGGtlRNVPVGggxRkNkrvxxx LITTNPSSAAIDTAASNNSSN-SSSAPLQPPIDTASTS--------------NHINPLFY
ITSPCSAAIDTASNSSNSSSAPTAAASLQPQIDTASTS--------------NHINPLFY
TNHGDSSSSAANSPSSSNSNPPSQPHLDNIIASSSTTN------------HINNISPFFY
TNHGDSSSSAANSPSSSNSNPPSQPHIDNIIASSSTTN------------HINNISPFFY
TNHGDSSSSAANSPSSSNSNPPSQPHIDNIIASSSTTN------------HINNISPFFY
TYPCSNNNNIDFSASPSSSTPSSVVANPNPPSQSQQQQQQQQHHSFDIAATSNHINTMLY
SSNGPTSTTTLIKRPISTIETATTSNSSSPSSTHSSTS--------------NHMNPMFY
STATTTTASTVSTTNSSSPNNPHQISHFSSMN--------------------HHPLFY
ITPITTSSTTTTPITTATSTCTATVTTSIGNNNNNMDAMLG----------CYSHMTIQT
ITTPITTSSTTTHQSQPPLQLALPQSQPQLATTTTTWMLCW----------VVIAT----
YRHTVITRDSLASLQVDGPDLVDHKPLSPEKVNGTILKEG--------------PDAPLC
xxxxxxxxxxxxxxxxxxxxxxxxxxxxxxxxxxxxxxx----------xxxxxxxxxy GLPSSS-SDVNLPLFSRFGSRISSS----GEDLQLNNALGLGESSGVLSNEASDNNGYR-
GLPSSS-SDVNLPLFSRFGSRISSS----GFDLQLNNALGLGESSRVLSNEASDNNRYR-
GG-----DVMSSVPFPRFNLHSQLN------------ALGLGFSTGVSENGFSTSNNN--
GG-----DVMSSVPFPRFNLHSQLN------------ALGLGFSTGVSENGFSTSNNN--
GG-----DVMSSVPFPRFNLHSQLN------------ALGLGESTGVSENGESTSNNN--
GGNSCH-DVMNPPFSTRFNSTTRVSNPASGYDNLPQNGLGLGLGFSSGILMSAAGGEVNLNH
GLSSTNNPCDPNLPFSRFNITSRLSTSSGYDLQPQMNFFGLGFSSGFENNGYTNGFNTS-
GLSDHMSSCNNNLPMIPSRFSDSSK-----------TCSSSGLESEFLSSGFSSLSALG-
PLADDQKNMSSSLYQALIRPPPLLLQQQNLLNTRELEGKDFGIGIGNGNNGIFPSSTLAL
ESMASILNLGEQNLSSQLDFTAGAE-----------NREETSCSSACKPVKKKDITQHN-
gxxxxxxxxxxxxxxxxxxxxxxxxx----xxxxxxxxxxxgxsxxxxxxxxxxxxxxx- -------------NWFGSNNTLLSSYTSTTSTTTPAMSSLLSSSLLQQKFMTDGVD----
SG-------------FGSNNMLLSSYTSTT-TTTPAMSSLLLQQKFISGGLKNDAD----
------------SFFSAYNSMFGSSSSSTCAPSTPVMASLLSSTLLQQNLMGGGG---GG
------------SFFSAYNSMFGSSSSSTCAPSTPVMASLLSCTLLQQNFMGGGG---GG
------------SFFSAYNSMFGSSSSSTCAPSTPVMASLLSSTLLQQKLMSGGG---GG
HHHHHHDEGSYRNGFSTSNNNNYSSIFGSSSTTTPVMASLLSSTLLQQKFMGTGGGIKGG
----------------NNNYDSIFSSSTSASNNTSVMPSVLSSTLLQHKFFDDGLK----
--------LGLPHQMSHDHTINGSFINNSTTNKPFLLSGLFGSSMSSSSTLLQHP-----
P-------------IPHQSQSLLFPFSASSRSFDTNPCSVVSTSLRSSNVYNYGED----
------------------------------------------------------------
------------------------------------------------------------
------------xxxxxxxxxxxxxxxxxxxxxxxxxsxxxxxxxxxxxxxxxx---xx --------STNTFQHGLGLTPLEQLQMASDHSSEAGMVALKDVKVELGQNNRLEWNNGAA
--------SSNTFQHGLSLTSLEQLQIASDHSSEAGMVALKDVKVELGQNNRLEWNGGA
VKGRDHDQGDNTFHGLAPLQGLRVEGDSNNNIGSKEVKGEGQNRFEWSNNNNNNNNNGGG
VKGRDHDQGDNTFHGLAPLQGLRVEGDSNNNIGSKEVKGEGQNRFEWSNNNNNNNNNGGG
EGEEVVIMIKVATLSMAWHRYKGCKWKGIIIIVIILAQKK--------------------
GGGGGGDDDPFHHHQEMDSKEVKLGEGLQNRLDQWNMNNLNGNGGAVFQNQMENMGLSDN
----------YGSDAGSNGAFQDLQFGSKMQNQMEHIGGFYDPASSIYLNATSSSAIGVW
----------HKPMNNGGDMLGQSHLQTLASLQDLHVGGNNEDMKYKEGKLDQISGNING
---------QFKAIEEPTINSTTATIVPSTGGTNNTHHPWEIAAATSGVGLGTSSNSNYW
xxxxxxxxxxxxxxxxxxxxxxxxxxxxxxxxxxxxxxxxxxxxxxxxxxxxxxxxxxx CQSQIQHVGLYDPSLYWNNSAATALGVWNDQAANIGSSVTSLI
FQSQIQHVGLYDPLLYWNN-SATALGVWNDQAANIGSSVTSLI
GQNQMEHVGLSDPNSLYWN-TATGLGAWSDQPNNIGPSVTSLI
GQNQMEHVGLSDPNSLYWN-TATGLGAWSDQPN-IGPSVTSLI
-------------------------------------------
NASLYWNNNHNNSNNNTSA-TATGLSSVWSTDQPGSNSVSSLI
NDQGANNIGSSVTSLI---------------------------
FMSSSSSLDPSNYNNMWNNASVVNGAWLDPTNNNVGSSLTSLI
NWEDEDSLVSTDLKDPWDDSDIKP-------------------
-------------------------------------------
-------------------------------------------
xxxxxxxxxxxxxxxxxxx-xxxxxxxxxxxxxxxxxxxxxxx
```

Example 4 Corn Transformation Construct

GATEWAY™ destination vectors (available from Invitrogen Life Technologies, Carlsbad, Calif.) are constructed for insertion of trait-improving DNA for corn transformation. The elements of each destination vector are summarized in Table 17 below and include a selectable marker transcription region and a DNA insertion transcription region. The selectable marker transcription region comprises a Cauliflower Mosaic Virus 35S promoter operably linked to a gene encoding neomycin phosphotransferase II (nptII) followed by both the 3' region of the *Agrobacterium tumefaciens* nopaline synthase gene (nos) and the 3' region of the potato proteinase inhibitor II (pinII) gene. The DNA insertion transcription region comprises a rice actin 1 promoter, a rice actin 1 exon 1 intron1 enhancer, an att-flanked insertion site and the 3' region of the potato pinII gene. Following standard procedures provided by Invitrogen the att-flanked insertion region is replaced by recombination with trait-improving DNA, in a sense orientation for expression of a trait-improving protein and in a gene suppression orientation (i.e., either anti-sense orientation or in a sense- and anti-sense orientation) for a trait-improving suppression of a protein. Although the vector with trait-improving DNA inserted at the att-flanked insertion region is useful for plant transformation by direct DNA delivery, such as microprojectile bombardment, it is preferable to bombard target plant tissue with tandem transcription units that have been cut from the vector. For *Agrobacterium*-mediated transformation of plants the vector also comprises T-DNA borders from *Agrobacterium* flanking the transcription units.

Vectors for *Agrobacterium*-mediated transformation are prepared with each of the trait-improving genes having a sequence of SEQ ID NO:1 through SEQ ID NO:269 with the DNA solely in sense orientation for expression of the encoded, cognate trait-improving protein and in a gene suppression orientation for suppression of the cognate protein. Each vector is transformed into corn callus which is propagated into a plant that is grown to produce transgenic seed for each transgenic event. Progeny plants are self-pollinated to produce seed which is selected for homozygous seed. Homozygous seed is used for producing inbred plants, for introgressing the trait into elite lines, and for crossing to make hybrid seed. The progeny transgenic plants comprising the trait-improving DNA with a sequence of SEQ ID NO: 1 through SEQ ID NO: 269 have one or more improved traits identified by agronomic trait screening including, but not limited to, enhanced nitrogen use efficiency, increased yield, enhanced water use efficiency, growth under cold stress and enhanced oil, starch and protein levels. Transgenic corn including inbred and hybrids are also produced with DNA from each of the identified homologs of DNA of SEQ ID NO: 1 through SEQ ID NO: 269 to provide transgenic seeds and plants which are identified from total transgenic events by screening for the improved agronomic trait. Transgenic corn plants are also produced where the trait-improving DNA is transcribed by each of the promoters from the group selected from, a maize globulin 1 promoter, a maize oleosin promoter, a glutelin 1 promoter, an aldolase promoter, a zein Z27 promoter, a pyruvate orthophosphate dikinase (PPDK) promoter, a soybean 7S alpha promoter, a peroxiredoxin antioxidant (Per1) promoter and a CaMV 35S promoter.

Seed produced by the plants is provided to growers to enable production of corn crops with improved traits associated with the trait-improving DNA.

TABLE 17

| FUNCTION | ELEMENT | REFERENCE |
|---|---|---|
| DNA insertion transcription region | Rice actin 1 promoter | U.S. Pat. No. 5,641,876 |
| | Rice actin 1 exon 1, intron 1 enhancer | U.S. Pat. No. 5,641,876 |
| DNA insertion transcription region (att-flanked insertin region) | AttR1 | GATEWAY ™Cloning Technology Instruction Manual |
| | CmR gene | GATEWAY ™Cloning Technology Instruction Manual |
| | ccdA, ccdB genes | GATEWAY ™Cloning Technology Instruction Manual |
| | attR2 | GATEWAY ™Cloning Technology Instruction Manual |
| DNA insertion transcription region | Potato pinII 3' region | An et al., (1989) Plant Cell 1: 115-122 |
| selectable marker transcription region | CaMV 35S promoter | U.S. Pat. No. 5,858,742 |
| | nptII selectable marker | U.S. Pat. No. 5,858,742 |
| | nos 3region | U.S. Pat. No. 5,858,742 |
| | PinII 3' region | An et al., (1989) Plant Cell 1: 115-122 |
| E. coli maintenance region | ColE1 origin of replication | |
| | F1 origin of replication | |
| | Bla ampicillin resistance | |

Example 5 Soybean Transformation Construct

Constructs for use in transformation of soybean are prepared by restriction enzyme based cloning into a common expression vector. Elements of an exemplary common expression vector are shown in Table 18 below and include a selectable marker expression cassette and a gene of interest expression cassette. The selectable marker expression cassette comprises *Arabidopsis* act 7 gene (AtAct7) promoter with intron and 5'UTR, the transit peptide of *Arabidopsis* EPSPS, the synthetic CP4 coding region with dicot preferred codon usage and a 3' UTR of the nopaline synthase gene. The gene of interest expression cassette comprises a Cauliflower Mosaic Virus 35S promoter operably linked to a trait-improving gene in a sense orientation for expression of a trait-improving protein and in a gene suppression orientation (i.e., either anti-sense orientation or in a sense- and anti-sense orientation for a trait-improving suppression of a protein.

Vectors similar to that described above are constructed for use in *Agrobacterium* mediated soybean transformation systems, with each of the trait-improving DNA having a sequence of SEQ ID NO:1 though SEQ ID NO:269 and the respective identified homologs with the DNA in sense orientation for expression of the encoded, cognate protein and in a gene suppression arrangement for suppression of the cognate protein. Each vector is transformed into soybean embryo tissue to produce transgenic events which are grown into plants that produce progeny transgenic plants and seed for screening to identify the transgenic soybean plants of this invention that exhibit the enhanced agronomic trait imparted by DNA with a sequence of SEQ ID NO:1 through SEQ ID NO:269 or a respective homolog. The transgenic soybean plants of this invention are identified by agronomic trait screening including, but not limited to, enhanced nitrogen use efficiency, increased yield, enhanced water use efficiency, growth under cold stress and enhanced oil, starch and protein levels. Transgenic soybean plants are also produced where the trait-improving DNA is transcribed by a napin promoter and *Arabidopsis* SSU promoter.

Seed produced by the plants is provided to growers to enable production of soybean crops with improved traits associated with the trait-improving DNA.

Example 6 Cotton Transformation

Vectors similar to that described above for soybean transformation are constructed for use in *Agrobacterium* mediated cotton transformation systems, with each of the trait-improving DNA having a sequence of SEQ ID NO:1 though SEQ ID NO:269 and the respective identified homologs with the DNA in sense orientation for expression of the encoded, cognate protein and in a gene suppression arrangement for suppression of the cognate protein. Each vector is transformed into cotton embryo tissue to produce transgenic events which are grown into plants that produce progeny transgenic plants and seed for screening to identify the transgenic soybean plants of this invention that exhibit the enhanced agronomic trait imparted by DNA with a sequence of SEQ ID NO:1 through SEQ ID NO:269 or a respective homolog. The transgenic cotton plants of this invention are identified by agronomic trait screening including, but not limited to, enhanced nitrogen use efficiency, increased yield, enhanced water use efficiency, growth under cold stress and enhanced oil, starch and protein levels. Transgenic cotton plants are also produced where the trait-improving DNA is transcribed by a napin promoter and *Arabidopsis* SSU promoter.

Seed produced by the plants is provided to growers to enable production of cotton crops with improved traits associated with the trait-improving DNA.

TABLE 18

| Function | Element | Reference |
| --- | --- | --- |
| Agro transformation | B-ARGtu.right border | Depicker, A. et al (1982) Mol Appl Genet 1: 561-573 |
| Antibiotic resistance | CR-Ec.aadA-SPC/STR | |
| Repressor of primers from the ColE1 plasmid | CR-Ec.rop | |
| Origin of replication | OR-Ec.oriV-RK2 | |
| Agro transformation | B-ARGtu.left border | Barker, R. F. et al (1983) Plant Mol Biol 2: 335-350 |
| Plant selectable marker expression cassette | *Arabidopsis* act 7 gene (AtAct7) promoter with intron and 5'UTR | McDowell et al., (1996) Plant Physiol. 111: 699-711. |
| | 5' UTR of *Arabidopsis* act 7 gene | |
| | Intron in 5'UTR of AtAct7 | |
| | Transit peptide region of *Arabidopsis* EPSPS | Klee, H. J. et al (1987) MGG 210: 437-442 |
| | Synthetic CP4 coding region with dicot preferred codon usage | |
| | A 3' UTR of the nopaline synthase gene of *Agrobacterium tumefaciens* Ti plasmid | U.S. Pat. No. 5,858,742 |
| Plant gene of interest expression cassette | Promoter for 35S RNA from CaMV containing a duplication of the −90 to −350 region | U.S. Pat. No. 5,322,938 |
| | Gene of interest insertion site | |
| | Cotton E6 3' end | GenBank accession U30508 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10301643B2). An electronic copy of the "Sequence Listing" will also be available from the USPTO upon request and payment of the fee set forth in 37 CFR 1.19(b)(3).

We claim:

1. A method of producing a crop comprising growing transgenic seed for a crop, wherein the genome of said transgenic seed comprises a recombinant DNA comprising a nucleotide sequence encoding a protein having an amino acid sequence with at least 99% amino acid sequence identity to the amino acid sequence of SEQ ID NO: 505 and having the function of the protein of SEQ ID NO: 505, thereby producing a population of transgenic plants, and selecting from the population transgenic plants a transgenic plant which expresses said protein encoded by said nucleotide sequence and having an enhanced trait as compared to a control plant of the same plant species lacking said recombinant DNA in their nuclei, wherein said enhanced trait is selected from the group of enhanced traits consisting of enhanced cold tolerance, enhanced heat tolerance, enhanced resistance to salt exposure, enhanced yield and enhanced nitrogen use efficiency.

2. The method according to claim 1, wherein transgenic plants grown from said transgenic seed exhibit increased yield as compared to a control plant of the same species lacking said recombinant DNA.

3. The method according to claim 1, wherein said selected transgenic plant exhibits increased yield as compared to a control plant of the same species lacking said recombinant DNA when said selected transgenic plant is grown in a yield-limiting environment of low nitrogen availability.

4. The method according to claim 1, wherein said selected transgenic plant exhibits increased yield as compared to a control plant of the same species lacking said recombinant DNA when said selected transgenic plant is grown in a yield-limiting environment of water deficit stress.

5. The method of claim 2, wherein the protein has the amino acid sequence of SEQ ID NO: 505.

6. The method according to claim 1, wherein said selected transgenic plant exhibits increased yield as compared to a control plant of the same species lacking said recombinant DNA when said selected transgenic plant is grown in a yield-limiting environment of high salinity stress.

7. The method according to claim 1, wherein said selected transgenic plant exhibits increased yield as compared to a control plant of the same species lacking said recombinant DNA when said selected transgenic plant is grown in a yield-limiting environment of cold stress.

* * * * *